United States Patent
Grogan et al.

(10) Patent No.: US 10,047,158 B2
(45) Date of Patent: Aug. 14, 2018

(54) ANTI-TIGIT ANTIBODIES AND METHODS OF USE

(71) Applicant: Genentech, Inc., South San Francisco, CA (US)

(72) Inventors: Jane L. Grogan, San Francisco, CA (US); Robert J. Johnston, San Francisco, CA (US); Yan Wu, Foster City, CA (US); Wei-Ching Liang, Foster City, CA (US); Patrick Lupardus, Redwood City, CA (US); Mahesh Yadav, San Bruno, CA (US); Dhaya Seshasayee, Cupertino, CA (US); Meredith Hazen, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/895,741

(22) Filed: Feb. 13, 2018

(65) Prior Publication Data

US 2018/0186875 A1    Jul. 5, 2018

Related U.S. Application Data

(62) Division of application No. 15/274,603, filed on Sep. 23, 2016.

(60) Provisional application No. 62/369,299, filed on Aug. 1, 2016, provisional application No. 62/233,230, filed on Sep. 25, 2015.

(51) Int. Cl.
| | |
|---|---|
| *C07K 16/00* | (2006.01) |
| *C07K 16/28* | (2006.01) |
| *A61K 38/17* | (2006.01) |
| *A61K 45/06* | (2006.01) |
| *A61K 39/395* | (2006.01) |
| *C07K 16/30* | (2006.01) |
| *A61K 39/00* | (2006.01) |

(52) U.S. Cl.
CPC ............ *C07K 16/28* (2013.01); *A61K 38/177* (2013.01); *A61K 39/39558* (2013.01); *A61K 45/06* (2013.01); *C07K 16/2818* (2013.01); *C07K 16/2827* (2013.01); *C07K 16/2878* (2013.01); *C07K 16/3061* (2013.01); *A61K 2039/505* (2013.01); *A61K 2039/507* (2013.01); *C07K 2317/24* (2013.01); *C07K 2317/33* (2013.01); *C07K 2317/34* (2013.01); *C07K 2317/55* (2013.01); *C07K 2317/56* (2013.01); *C07K 2317/567* (2013.01); *C07K 2317/70* (2013.01); *C07K 2317/75* (2013.01); *C07K 2317/76* (2013.01); *C07K 2317/90* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 5,364,934 A | 11/1994 | Drayna et al. |
| 5,750,345 A | 5/1998 | Bowie |
| 5,989,811 A | 11/1999 | Veltri et al. |
| 6,518,033 B1 | 2/2003 | Gromeier et al. |
| 7,193,069 B2 | 3/2007 | Isogai et al. |
| 7,282,570 B2 | 10/2007 | Goddard et al. |
| 8,431,350 B2 | 4/2013 | Baldwin et al. |
| 8,728,474 B2 | 5/2014 | Honjo et al. |
| 9,499,596 B2 | 11/2016 | Clark et al. |
| RE46,534 E | 9/2017 | Baldwin et al. |
| 9,873,740 B2 | 1/2018 | Grogan et al. |
| 2004/0005560 A1 | 1/2004 | Isogai et al. |
| 2004/0101876 A1 | 5/2004 | Mintz et al. |
| 2004/0121343 A1 | 6/2004 | Buechler et al. |
| 2004/0121370 A1 | 6/2004 | Baldwin et al. |
| 2004/0219521 A1 | 11/2004 | Tang et al. |
| 2004/0258678 A1 | 12/2004 | Bodary et al. |
| 2006/0105376 A1 | 5/2006 | Isogai et al. |
| 2006/0199181 A1 | 9/2006 | Bodary et al. |
| 2007/0041985 A1 | 2/2007 | Unger et al. |
| 2007/0054360 A1 | 3/2007 | Gao et al. |
| 2007/0243584 A1 | 10/2007 | West |
| 2007/0254339 A1 | 11/2007 | West et al. |
| 2008/0038264 A1 | 2/2008 | Bodary et al. |
| 2008/0050809 A1 | 2/2008 | Abuin et al. |
| 2009/0156495 A1 | 6/2009 | Gao et al. |
| 2009/0181024 A1 | 7/2009 | Baldwin et al. |
| 2009/0258013 A1 | 10/2009 | Clark et al. |
| 2010/0075377 A1 | 3/2010 | West et al. |
| 2010/0316646 A1 | 12/2010 | Gao et al. |
| 2011/0104170 A1 | 5/2011 | Baldwin et al. |
| 2012/0219540 A1 | 8/2012 | Gao et al. |

(Continued)

FOREIGN PATENT DOCUMENTS

| | | |
|---|---|---|
| CN | 101035807 A | 9/2007 |
| CN | 103073644 A | 5/2013 |

(Continued)

OTHER PUBLICATIONS

International Preliminary Report on Patentability for International Patent Application No. PCT/US2016/053368, dated Mar. 27, 2018 (10 pages).
"FDA approves new, targeted treatment for bladder cancer," <http://www.fda.gov/NewsEvents/Newsroom/PressAnnouncements/ucm501762.htm>, retrieved on Sep. 19, 2016, dated May 18, 2016 (3 pages).
"VSTM3_HUMAN," <http://www.uniprot.org/uniprot/Q495A1.txt?version=27>, retrieved on Apr. 28, 2017 (2 pages).
Abbas et al., "Immune response in silico (IRIS): immune-specific genes identified from a compendium of microarray expression data," Genes Immun. 6(4):319-31 (2005).

(Continued)

*Primary Examiner* — Lei Yao
(74) *Attorney, Agent, or Firm* — Clark & Elbing LLP; Karen L. Elbing

(57) ABSTRACT

The invention provides anti-TIGIT (T-cell immunoreceptor with Ig and ITIM domains) antibodies and methods of using the same.

30 Claims, 24 Drawing Sheets
(12 of 24 Drawing Sheet(s) Filed in Color)

(56) References Cited

U.S. PATENT DOCUMENTS

| | | |
|---|---|---|
| 2013/0095102 A1 | 4/2013 | Levin et al. |
| 2013/0251720 A1 | 9/2013 | Clark et al. |
| 2014/0186380 A1 | 7/2014 | Gurney et al. |
| 2014/0341902 A1 | 11/2014 | Maecker et al. |
| 2015/0216970 A1 | 8/2015 | Grogan et al. |
| 2016/0152720 A1 | 6/2016 | Kim et al. |
| 2017/0037127 A1 | 2/2017 | Grogan et al. |
| 2017/0044256 A1 | 2/2017 | Grogan et al. |
| 2017/0088613 A1 | 3/2017 | Grogan et al. |
| 2017/0143825 A1 | 5/2017 | Grogan |
| 2017/0145093 A1 | 5/2017 | Clark et al. |

FOREIGN PATENT DOCUMENTS

| | | |
|---|---|---|
| EP | 1516629 B1 | 4/2013 |
| GB | 2408508 A | 6/2005 |
| JP | 2006-508649 A | 3/2006 |
| JP | 2006-521082 A | 9/2006 |
| WO | WO-99/63063 A1 | 12/1999 |
| WO | WO-00/53758 A2 | 9/2000 |
| WO | WO-00/58334 A1 | 10/2000 |
| WO | WO-01/05972 A1 | 1/2001 |
| WO | WO-01/29221 A2 | 4/2001 |
| WO | WO-01/75116 A2 | 10/2001 |
| WO | WO-01/75166 A2 | 10/2001 |
| WO | WO-01/94413 A2 | 12/2001 |
| WO | WO-03/054152 A2 | 7/2003 |
| WO | WO-03/068943 A2 | 8/2003 |
| WO | WO-03/072035 A2 | 9/2003 |
| WO | WO-2004/024068 A2 | 3/2004 |
| WO | WO-2004/024072 A2 | 3/2004 |
| WO | WO-2004/074324 A2 | 9/2004 |
| WO | WO-2005/052005 A1 | 6/2005 |
| WO | WO-2006/042240 A2 | 4/2006 |
| WO | WO-2006/121168 A1 | 11/2006 |
| WO | WO-2006/124667 A2 | 11/2006 |
| WO | WO-2007/124383 A2 | 11/2007 |
| WO | WO-2009/126688 A2 | 10/2009 |
| WO | WO-2010/077634 A1 | 7/2010 |
| WO | WO-2011/066342 A2 | 6/2011 |
| WO | WO-2013/019906 A1 | 2/2013 |
| WO | WO-2013/119202 A1 | 8/2013 |
| WO | WO-2014/089113 A1 | 6/2014 |
| WO | WO-2014/116846 A2 | 7/2014 |
| WO | WO-2015/009856 A2 | 1/2015 |
| WO | WO-2015/037005 A1 | 3/2015 |
| WO | WO-2015/153513 A1 | 10/2015 |
| WO | WO-2015/153514 A1 | 10/2015 |
| WO | WO-2016/011264 A1 | 1/2016 |
| WO | WO-2016/073282 A1 | 5/2016 |

OTHER PUBLICATIONS

Aebersold et al., "Perspective: a program to improve protein biomarker discovery for cancer," J Proteome Res. 4(4):1104-9 (2005).

Ahn et al., "Dendritic cells partially abrogate the regulatory activity of CD4+CD25+ T cells present in the human peripheral blood," Int Immunol. 19(3):227-37 (2007).

Baury et al., "Identification of secreted CD155 isoforms," Biochem Biophys Res Commun. 309(1):175-82 (2003).

Beers et al., Neurologic Disorders. The Merck Manual of Diagnosis and Therapy. Beers & Berkow, 1474-6 (1999).

Bergers et al., "Extrinsic regulators of epithelial tumor progression: metalloproteinases," Curr Opin Genet Dev. 10(1):120-7 (2000).

Blackburn et al., "Coregulation of CD8+ T cell exhaustion during chronic viral infection by multiple inhibitory receptors," available in PMC Jul. 1, 2009, published in final edited form as: Nat Immunol. 10(1):29-37 (2009) (22 pages).

Blalock et al., "Harnessing the power of gene microarrays for the study of brain aging and Alzheimer's disease: statistical reliability and functional correlation," Ageing Res Rev. 4(4):481-512 (2005).

Bolton, "Recent advances in the pharmacological control of experimental allergic encephalomyelitis (EAE) and the implications for multiple sclerosis treatment," Mult Scler. 1(3):143-9 (1995).

Bottino et al., "Identification of PVR (CD155) and Nectin-2 (CD112) as cell surface ligands for the human DNAM-1 (CD226) activating molecule," J Exp Med. 198(4):557-67 (2003).

Bruder et al., "Neuropilin-1: a surface marker of regulatory T cells," Eur J Immunol. 34(3):623-30 (2004).

Burshtyn et al., "A novel phosphotyrosine motif with a critical amino acid at position −2 for the SH2 domain-mediated activation of the tyrosine phosphatase SHP-1," J Biol Chem. 272(20):13066-72 (1997).

Butte et al., "Programmed death-1 ligand 1 interacts specifically with the B7-1 costimulatory molecule to inhibit T cell responses," Immunity. 27(1):111-22 (2007).

Caldas et al., "Humanization of the anti-CD18 antibody 6.7: An unexpected effect of a framework residue in binding to antigen," Mol Immunol. 39(15):941-52 (2003).

Callahan et al., "Anti-CTLA-4 antibody therapy: immune monitoring during clinical development of a novel immunotherapy," Semin Oncol. 37(5):473-84 (2010).

Casset et al., "A peptide mimetic of an anti-CD4 monoclonal antibody by rational design," Biochem Biophys Res Commun. 307(1):198-205 (2003).

Chan et al., "Receptors that interact with nectin and nectin-like proteins in the immunosurveillance and immunotherapy of cancer," Curr Opin Immunol. 24(2):246-51 (2012).

Chang et al., "Loop-sequence features and stability determinants in antibody variable domains by high-throughput experiments," Structure. 22(1):9-21 (2014).

Chien et al., "Significant structural and functional change of an antigen-binding site by a distant amino acid substitution: proposal of a structural mechanism," Proc Natl Acad Sci U S A. 86(14):5532-6 (1989).

Chin et al., "Immune intervention with monoclonal antibodies targeting CD152 (CTLA-4) for autoimmune and malignant diseases," Chang Gung Med J. 31(1):1-15 (2008).

Comps-Agrar et al., "TIGIT mediated T cell exhaustion in cancer is dependent on TIGIT/CD226 interaction (TUM2P.907)," Immunology 2014 Meeting Abstracts, J Immunol. 192(Suppl 1):71.31 (2014) (5 pages).

Correale et al., "Patterns of cytokine secretion by autoreactive proteolipid protein-specific T cell clones during the course of multiple sclerosis," J Immunol. 154(6):2959-68 (1995).

Danisch et al., "CD226 interaction with CD155 impacts on retention and negative selection of CD8 positive thymocytes as well as T cell differentiation to follicular helper cells in Peyer's Patches," Immunobiology. 218(2):152-8 (2013).

Dardalhon et al., "CD226 is specifically expressed on the surface of Th1 cells and regulates their expansion and effector functions," J Immunol. 175(3):1558-65 (2005).

De Pascalis et al., "Grafting of "abbreviated" complementarity-determining regions containing specificity-determining residues essential for ligand contact to engineer a less immunogenic humanized monoclonal antibody," J Immunol. 169(6):3076-84 (2002).

Dennis, "Cancer: off by a whisker," Nature. 442(7104):739-41 (2006).

Dong et al., "Crystal structure of the V domain of human Nectin-like molecule-1/Syncam3/Tsll1/Igsf4b, a neural tissue-specific immunoglobulin-like cell-cell adhesion molecule," J Biol Chem. 281(15):10610-7 (2006).

Edgar, "T cell immunodeficiency," J Clin Pathol. 61(9):988-93 (2008).

Elder et al., "Growth factor and proto-oncogene expression in psoriasis," J Invest Dermatol. 95(5 Suppl):7S-9S (1990).

Fallarino et al., "Modulation of tryptophan catabolism by regulatory T cells," Nat Immunol. 4(12):1206-12 (2003).

Fehérvari et al., "Development and function of CD25+CD4+ regulatory T cells," Curr Opin Immunol. 16(2):203-8 (2004).

Finch et al., "Analysis of the cellular basis of keratinocyte growth factor overexpression in inflammatory bowel disease," Gut. 45(6):848-55 (1999).

(56) References Cited

OTHER PUBLICATIONS

Flies et al., "Blockade of the B7-H1/PD-1 pathway for cancer immunotherapy," Yale J Biol Med. 84(4):409-21 (2011).
Foks et al., "Agonistic anti-TIGIT treatment inhibits T cell responses in LDLr deficient mice without affecting atherosclerotic lesion development," PLoS One. 8(12):e83134 (2013) (7 pages).
Fuchs et al., "Cutting edge: CD96 (tactile) promotes NK cell-target cell adhesion by interacting with the poliovirus receptor (CD155)," J Immunol. 172(7):3994-8 (2004).
Fuchs et al., "The role of NK cell recognition of nectin and nectin-like proteins in tumor immunosurveillance," Semin Cancer Biol. 16(5):359-66 (2006).
Giusti et al. "Somatic diversification of S107 from an antiphosphocholine to an anti-DNA autoantibody is due to a single base change in its heavy chain variable region," Proc Natl Acad Sci U S A. 84(9):2926-30 (1987).
Goding et al., "Restoring immune function of tumor-specific CD4+ T cells during recurrence of melanoma," J Immunol. 190(9):4899-909 (2013).
Greenwald et al., "The B7 family revisited," Annu Rev Immunol. 23:515-48 (2005).
Grogan et al., "TIGIT inhibits CD8+ T cell effector function during chronic viral infection and cancer (TUM7P.933)," J Immunol. 192(Suppl 1):203.15 (2014) (1 page) (Abstract Only).
Guo et al., "PD-1 blockade and OX40 triggering synergistically protects against tumor growth in a murine model of ovarian cancer," PLoS One. 9(2):e89350 (2014) (10 pages).
Gura, "Systems for identifying new drugs are often faulty," Science. 278(5340):1041-2 (1997).
Güssow et al., "Humanization of monoclonal antibodies," Methods Enzymol. 203:99-121 (1991).
He et al., "Complexes of poliovirus serotypes with their common cellular receptor, CD155," J Virol. 77(8):4827-35 (2003).
Holm et al., "Functional mapping and single chain construction of the anti-cytokeratin 8 monoclonal antibody TS1," Mol Immunol. 44(6):1075-84 (2007).
Hori et al., "Control of regulatory T cell development by the transcription factor Foxp3," Science. 299(5609):1057-61 (2003).
Hou et al., "Recombinant soluble CD226 protein directly inhibits cancer cell proliferation in vitro," Int Immunopharmacol. 19(1):119-26 (2014).
Huang, "Structural chemistry and therapeutic intervention of protein-protein interactions in immune response, human immunodeficiency virus entry, and apoptosis," Pharmacol Ther. 86(3):201-15 (2000).
Inoue et al., "Cancer-associated fibroblast suppresses killing activity of natural killer cells through downregulation of poliovirus receptor (PVR/CD155), a ligand of activating NK receptor," Int J Oncol. 49(4):1297-304 (2016).
Inozume et al., "CD155 is highly expressed by melanoma tissues and it suppresses the activation of melanoma specific CTLs via interaction with TIGIT," Journal of Dermatological Science. 69(2):e67-e68, Abstract P10-01 (2013) (2 pages).
Inozume et al., "Development of a novel immunotherapy for melanoma which inhibits interaction between CD155 on melanoma cells and TIGIT on activated CTL," J Invest Dermatol. 133:S3 (2013) (1 page) (Abstract Only).
Inozume et al., "Melanoma Cells Control Antimelanoma CTL Responses via Interaction between TIGIT and CD155 in the Effector Phase," J Invest Dermatol. 136(1):255-63 (2016).
Issekutz et al., "Treatment of established adjuvant arthritis in rats with monoclonal antibody to CD18 and very late activation antigen-4 integrins suppresses neutrophil and T-lymphocyte migration to the joints and improves clinical disease," Immunology. 88(4):569-76 (1996).
Janeway et al., B-cell heterogeneity. Immunobiology, 3rd edition. Garland Publications Inc., 5:23-26, 8:3, and 9:23-9:27 (1997).
Jiang et al. "A novel peptide isolated from a phage display peptide library with trastuzumab can mimic antigen epitope of HER-2," J Biol Chem. 280(6):4656-62 (2005).
Jiang et al., "Disruption of E-cadherin-mediated adhesion induces a functionally distinct pathway of dendritic cell maturation," Immunity. 27(4):610-24 (2007).
Jin et al., "Cooperation of Tim-3 and PD-1 in CD8 T-cell exhaustion during chronic viral infection," Proc Natl Acad Sci U S A. 107(33):14733-8 (2010).
Johnston et al., "The immunoreceptor TIGIT regulates antitumor and antiviral CD8(+) T cell effector function," Cancer Cell. 26(6):923-37 (2014).
Joller et al., "Cutting edge: TIGIT has T cell-intrinsic inhibitory functions," J Immunol. 186(3)1338-42 (2011).
Joller et al., "Immune checkpoints in CNS autoimmunity," available in PMC Jul. 1, 2013, published in final edited form as: Immunol Rev. 248(1):122-39 (2012) (28 pages).
Ju et al., "Immunoglobulin-like transcripts ILT2, ILT3 and ILT7 are expressed by human dendritic cells and down-regulated following activation," Gene. 331:159-64 (2004).
Kashiwada et al., "Immunoreceptor tyrosine-based inhibitory motif of the IL-4 receptor associates with SH2-containing phosphatases and regulates IL-4-induced proliferation," J Immunol. 167(11):6382-7 (2001).
Kelland, "'Of mice and men': values and liabilities of the athymic nude mouse model in anticancer drug development," Eur J Cancer. 40(6):827-36 (2004).
Kisseleva et al., "Signaling through the JAK/STAT pathway, recent advances and future challenges," Gene. 285(1-2):1-24 (2002).
Kruisbeek et al., Proliferative Assays for T Cell Function. Current Protocols in Immunology. John Wiley & Sons, Inc. 3.12.1-3.12.14 (1991) (26 pages).
Kurtulus et al., "Mechanisms of TIGIT-driven immune suppression in cancer," J Immunother Cancer. 2(Suppl 3): O13 (2014) (1 page).
Lee et al., "Macrophage PD-L1 strikes back: PD-1/PD-L1 interaction drives macrophages toward regulatory subsets," Adv Biosci Biotechnol. 4:19-29 (2013).
Levin et al., "Identification and characterization of Vsig9 as an inhibitory member of the CD28 family," Keystone Symposia on Molecular and Cellular Biology: Tolerance in Transplantation and Autoimmunity, Jan. 29-Feb. 3, Keystone, Colorado. 74, Abstract 217 (2008).
Levin et al., "Vstm3 is a member of the CD28 family and an important modulator of T-cell function," available in PMC Aug. 5, 2013, published in final edited form as: Eur J Immunol. 41(4):902-15 (2011) (22 pages).
Liebman, "Biomedical informatics: the future for drug development," Drug Discov Today. 7(20 Suppl):S197-203 (2002).
Linsley et al., "Immunosuppression in vivo by a soluble form of the CTLA-4 T cell activation molecule," Science. 257(5071):792-5 (1992).
Luo et al., "Delayed-type hypersensitivity," Curr Protoc Immunolog. Chapter 4:Unit 4.5 (1993) (5 pages).
MacCallum et al., "Antibody-antigen interactions: contact analysis and binding site topography," J Mol Biol. 262(5):732-45 (1996).
Maier et al., "The adhesion receptor CD155 determines the magnitude of humoral immune responses against orally ingested antigens," Eur J Immunol. 37(8):2214-25 (2007).
Mariuzza et al., "The structural basis of antigen-antibody recognition," Annu Rev Biophys Biophys Chem. 16:139-59 (1987).
Martinet et al., "Balancing natural killer cell activation through paired receptors," Nat Rev Immunol. 15(4):243-54 (2015).
McHugh et al., "CD4(+)CD25(+) immunoregulatory T cells: gene expression analysis reveals a functional role for the glucocorticoid-induced TNF receptor," Immunity. 16(2):311-23 (2002).
Melero et al., "Evolving synergistic combinations of targeted immunotherapies to combat cancer," Nat Rev Cancer. 15(8):457-72 (2015).
Morales-Kastresana et al., "Combined immunostimulatory monoclonal antibodies extend survival in an aggressive transgenic hepatocellular carcinoma mouse model," Clin Cancer Res. 19(22):6151-62 (2013).
NCBI Blast for Accession No. gi256600228. Retrieved on Jun. 17, 2004 (1 page).
NCBI Blast for Accession No. gi57997171. Retrieved on Nov. 20, 2003 (1 page).

(56) References Cited

OTHER PUBLICATIONS

NCBI Blast for Accession No. Q8N877. Retrieved on Aug. 6, 2014 (2 pages).
NCBI Blast for Accession No. AL833175 GI:21733802. Retrieved on Aug. 6, 2014 (3 pages).
Nickoloff et al., "Severe combined immunodeficiency mouse and human psoriatic skin chimeras. Validation of a new animal model," Am J Pathol. 146(3):580-8 (1995).
Nobis et al., "Production of a monoclonal antibody against an epitope on HeLa cells that is the functional poliovirus binding site," J Gen Virol. 66(Pt 12):2563-9 (1985).
Ota et al., "Complete sequencing and characterization of 21,243 full-length human cDNAs," Nat Genet. 36(1):40-5 (2004).
Pende et al., "Expression of the DNAM-1 ligands, Nectin-2 (CD112) and poliovirus receptor (CD155), on dendritic cells: relevance for natural killer-dendritic cell interaction," Blood. 107(5):2030-6 (2006).
Qiu et al., "CD155 is involved in negative selection and is required to retain terminally maturing CD8 T cells in thymus," J Immunol. 184(4):1681-9 (2010).
Qu et al., "Loss of CD155 expression predicts poor prognosis in hepatocellular carcinoma," Histopathology. 66(5):706-14 (2015) Abstract only (2 pages).
Read et al., "Cytotoxic T lymphocyte-associated antigen 4 plays an essential role in the function of CD25(+)CD4(+) regulatory cells that control intestinal inflammation," J Exp Med. 192(2):295-302 (2000).
Redmond et al., "Combined targeting of co-stimulatory (OX40) and co-inhibitory (CTLA-4) pathways elicits potent effector T cells capable of driving robust antitumor immunity," available in PMC Feb. 1, 2015, published in final edited form as: Cancer Immunol Res. 2(2):142-53 (2014) (20 pages).
Reymond et al., "DNAM-1 and PVR regulate monocyte migration through endothelial junctions," J Exp Med. 199(10):1331-41 (2004).
Riemer et al., "Matching of trastuzumab (Herceptin) epitope mimics onto the surface of Her-2/neu—a new method of epitope definition," Mol Immunol. 42(9):1121-4 (2005).
Rosenblatt et al., "Targetting the PD-L1/PD-1 axis holds promise in the treatment of malignancy," Transl Cancer Res. 1(4):283-6 (2012).
Rosloniec et al., Collagen-Induced Arthritis. Current Protocols in Immunology. Coligan, Kruisbeek, Margulies, Shevach, Strober. 15.5.1-15.5.24 (1996).
Rudikoff et al., "Single amino acid substitution altering antigen-binding specificity," Proc Natl Acad Sci U S A. 79(6):1979-83 (1982).
Saijo, "What are the reasons for negative phase III trials of molecular-target-based drugs?" Cancer Sci. 95(10):772-6 (2004).
Sakaguchi et al., "Immunologic self-tolerance maintained by activated T cells expressing IL-2 receptor alpha-chains (CD25). Breakdown of a single mechanism of self-tolerance causes various autoimmune diseases," J Immunol. 155(3):1151-64 (1995).
Sakisaka et al., "Biology and pathology of nectins and nectin-like molecules," Curr Opin Cell Biol. 16(5):513-21 (2004).
Sakuishi et al., "Targeting Tim-3 and PD-1 pathways to reverse T cell exhaustion and restore anti-tumor immunity," J Exp Med. 207(10):2187-94 (2010).
Satoh-Horikawa et al., "Nectin-3, a new member of immunoglobulin-like cell adhesion molecules that shows homophilic and heterophilic cell-cell adhesion activities," J Biol Chem. 275(14):10291-9 (2000).
Schaerli et al., "CXC chemokine receptor 5 expression defines follicular homing T cells with B cell helper function," J Exp Med. 192(11):1553-62 (2000).
Schneider, "A rational approach to maximize success rate in target discovery," Arch Pharm (Weinheim). 337(12):625-33 (2004).
Sequence Alignment with U.S. Appl. No. 14/236,064, filed Jan. 29, 2014 (2 pages).
Serra et al., "CD40 ligation releases immature dendritic cells from the control of regulatory CD4+CD25+ T cells," Immunity. 19(6):877-89 (2003).
Seth et al., "The poliovirus receptor/CD155 is a potential modulator of the T cell response," Immunobiology. 210(6-8):542 (2005).
Shimizu et al., "Stimulation of CD25(+)CD4(+) regulatory T cells through GITR breaks immunological self-tolerance," Nat Immunol. 3(2):135-42 (2002).
Sicotte et al., "Onset of multiple sclerosis associated with anti-TNF therapy," Neurology. 57(10):1885-8 (2001).
Skolnick et al., "From genes to protein structure and function: novel applications of computational approaches in the genomic era," Trends Biotechnol. 18(1):34-9 (2000).
Smith, "Drug target validation: Hitting the target," Nature. 422(6929):341-7 (2003).
Stancovski et al., "Mechanistic aspects of the opposing effects of monoclonal antibodies to the ERBB2 receptor on tumor growth," Proc Natl Acad Sci U S A. 88(19):8691-5 (1991).
Stanietsky et al., "Mouse TIGIT inhibits NK-cell cytotoxicity upon interaction with PVR," Eur J Immunol. 43(8):2138-50 (2013).
Tahara-Hanaoka et al., "Functional characterization of DNAM-1 (CD226) interaction with its ligands PVR (CD155) and nectin-2 (PRR-2/CD112)," Int Immunol. 16(4):533-8 (2004).
Takahashi et al., "Immunologic self-tolerance maintained by CD25(+)CD4(+) regulatory T cells constitutively expressing cytotoxic T lymphocyte-associated antigen 4," J Exp Med. 192(2):303-9 (2000).
Tarbell et al., "CD25+ CD4+ T cells, expanded with dendritic cells presenting a single autoantigenic peptide, suppress autoimmune diabetes," J Exp Med. 199(11):1467-77 (2004).
Thaventhiran et al., "T cell co-inhibitory receptors: functions and signalling mechanisms," J Clin Cell Immunol. S12:004 (2012) (12 pages).
Thornton et al., "CD4+CD25+ immunoregulatory T cells suppress polyclonal T cell activation in vitro by inhibiting interleukin 2 production," J Exp Med. 188(2):287-96 (1998).
Vajdos et al., "Comprehensive functional maps of the antigen-binding site of an anti-ErbB2 antibody obtained with shotgun scanning mutagenesis," J Mol Biol. 320(2):415-28 (2002).
Velten et al., "A gene signature of inhibitory MHC receptors identifies a BDCA3(+) subset of IL-10-induced dendritic cells with reduced allostimulatory capacity in vitro," Eur J Immunol. 34(10):2800-11 (2004).
Vinuesa et al., "Follicular B helper T cells in antibody responses and autoimmunity," Nat Rev Immunol. 5(11):853-65 (2005).
Wang et al., "Regulatory T cells and cancer," Curr Opin Immunol. 19(2):217-23 (2007).
Whisstock et al., "Prediction of protein function from protein sequence and structure," Q Rev Biophys. 36(3):307-40 (2003).
Wiesmann et al., "Nerve growth factor: structure and function," Cell Mol Life Sci. 58(5-6):748-59 (2001).
Winkler et al., "Changing the antigen binding specificity by single point mutations of an anti-p24 (HIV-1) antibody," J Immunol. 165(8):4505-14 (2000).
Wolchok et al., "Nivolumab plus ipilimumab in advanced melanoma," N Engl J Med. 369(2):122-33 (2013).
Wu et al., "Humanization of a murine monoclonal antibody by simultaneous optimization of framework and CDR residues," J Mol Biol. 294(1):151-62 (1999).
Xia et al., "Suppression of interleukin-12 production through endogenously secreted interleukin-10 in activated dendritic cells: involvement of activation of extracellular signal-regulated protein kinase," Scand J Immunol. 58(1):23-32 (2003).
Xiao et al., "RGMb is a novel binding partner for PD-L2 and its engagement with PD-L2 promotes respiratory tolerance," J Exp Med. 211(5):943-59 (2014).
Xu et al., "A novel interface consisting of homologous immunoglobulin superfamily members with multiple functions," Cell Mol Immunol. 7(1):11-9 (2010).
Yamashita-Kanemaru et al., "CD155 (PVR/Necl5) mediates a costimulatory signal in CD4+ T cells and regulates allergic inflammation," J Immunol. 194(12):5644-53 (2015).

(56) References Cited

OTHER PUBLICATIONS

Yamazaki et al., "Effective expansion of alloantigen-specific Foxp3+ CD25+ CD4+ regulatory T cells by dendritic cells during the mixed leukocyte reaction," Proc Natl Acad Sci USA. 103(8):2758-63 (2006).
Yu et al., "Rationalization and design of the complementarity determining region sequences in an antibody-antigen recognition interface," PLoS One. 7(3):e33340 (2012) (15 pages).
Yu et al., "Simultaneous inhibition of two regulatory T-cell subsets enhanced Interleukin-15 efficacy in a prostate tumor model," Proc Natl Acad Sci USA. 109(16):6187-92 (2012).
Yu et al., "The surface protein TIGIT suppresses T cell activation by promoting the generation of mature immunoregulatory dendritic cells" Nat Immunol. 10(1):48-57 (2009).
Zhan et al., "From monoclonal antibodies to small molecules: the development of inhibitors targeting the PD-1/PD-L1 pathway," Drug Discov Today. 21(6):1027-36 (2016).
Zheng et al., "Human Cancer Immunotherapy with PD-1/PD-L1 Blockade," Biomark Cancer. 7(Suppl 2):15-8 (2015).
Zhou et al., "Coexpression of Tim-3 and PD-1 identifies a CD8+ T-cell exhaustion phenotype in mice with disseminated acute myelogenous leukemia," Blood. 117(17):4501-10 (2011).
Ziegler, "FOXP3: not just for regulatory T cells anymore," Eur J Immunol. 37(1):21-3 (2007).
Communication pursuant to Article 94(3) for European Patent Application No. 14750063.1, dated Oct. 18, 2017 (9 pages).
English Translation of Office Action for Chinese Application No. 200980121734.2, dated Sep. 22, 2013 (2 pages).
Examination Report for Australian Application No. 2009233708, dated Sep. 6, 2013 (3 pages).
International Preliminary Report on Patentability for International Patent Application No. PCT/US2015/040770, dated Jan. 17, 2017 (11 pages).
International Search Report and Written Opinion for International Application No. PCT/US2009/039868, dated Oct. 23, 2009 (25 pages).
International Search Report and Written Opinion for International Application No. PCT/US2014/046896, dated Mar. 2, 2015 (21 pages).
International Search Report and Written Opinion for International Patent Application No. PCT/US2015/040770, dated Oct. 16, 2015 (13 pages).
International Search Report and Written Opinion for International Patent Application No. PCT/US2015/058087, dated Apr. 8, 2016 (22 pages).
International Search Report and Written Opinion for International Patent Application No. PCT/US2016/053368, dated Mar. 31, 2017 (19 pages).
Invitation to Pay Additional Fees for International Patent Application No. PCT/US2015/058087, dated Jan. 27, 2016 (10 pages).
Invitation to Pay Additional Fees for International Patent Application No. PCT/US2016/053368, dated Feb. 2, 2017 (8 pages).
Notice of Preliminary Rejection for Korean Patent Application No. 10-2010-7025044, dated Nov. 13, 2015 (6 pages).
Office Action for U.S. Appl. No. 14/228,172, dated Feb. 12, 2015 (14 pages).
Office Action for U.S. Appl. No. 14/228,173, dated Mar. 11, 2015 (18 pages).
Office Action for U.S. Appl. No. 14/333,375, dated Sep. 23, 2016 (27 pages).
Office Action for U.S. Appl. No. 14/699,845, dated Jun. 9, 2016 (11 pages).
Search Report for Singaporean Patent Application No. 11201600310Q, dated Mar. 9, 2017 (5 pages).
Search Report for Singaporean Patent Application No. 11201700258V, dated Jan. 18, 2018 (3 pages).
Written Opinion for Singaporean Patent Application No. 11201600310Q, dated Apr. 6, 2017 (10 pages).
Written Opinion for Singaporean Patent Application No. 11201700258V, dated Jan. 18, 2018 (6 pages).

Figures 1D-1E
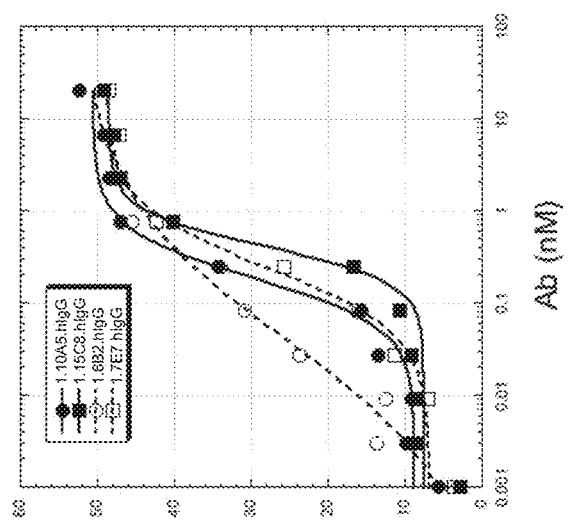
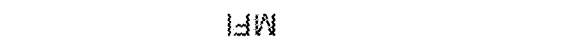
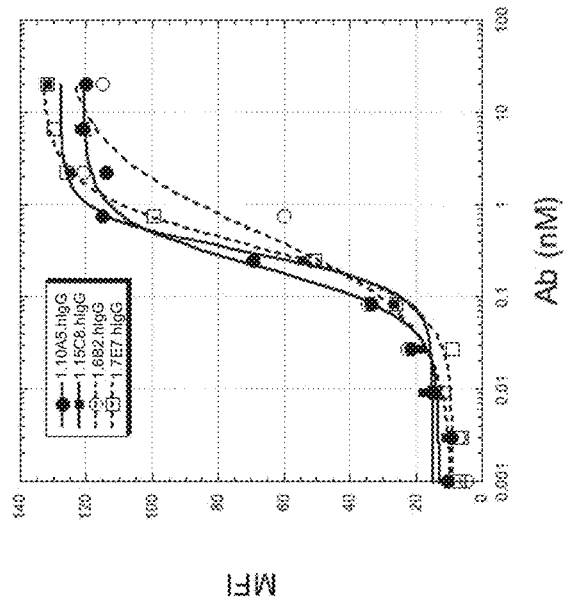

Figure 3D

| anti-TIGIT | Block ELISA Human PVR-Fc:Bio-TIGIT-AviFlag IC50, nM | Block ELISA Cyno PVR-Fc:Bio-TIGIT-AviFlag IC50, nM | Block ELISA Mouse PVR-Fc:TIGIT-His IC50, nM |
|---|---|---|---|
| 10A7Fab | 21.2 | >133 | 20.9 |
| 10A7 mIgG2a | 12.9 | 55.7 | 12.6 |
| 4.1D3.Q1E Fab | 6.9 | 1.5 | >133 |
| 4.1D3.Q1E huIgG1 | 6.9 | 2.6 | >133 |
| xCSF1 Fab control | >133 | >133 | >133 |

Figure 5B

| Anti-TIGIT Variants | AUC$_{INF}$ (day·µg/mL) | CL (mL/day/kg) | C$_{max}$ (ug/mL) |
|---|---|---|---|
| Anti-gD | 3480 ± 1450 | 3.19 ± 1.18 | 216 ± 26.7 |
| 1A5.N297G | 735 ± 166 | 14.1 ± 2.85 | 376 ± 168 |
| SD h1.6B2.L1H1 | 512 ± 88.7 | 19.9 ± 3.75 | 246 ± 22.1 |
| OMT 4.1D3.Q1E | 1200 ± 88.5 | 8.39 ± 0.64 | 214 ± 11.1 |
| OMT 7.4A3.C96S.Q1E | 973 ± 128 | 10.4 ± 1.44 | 218 ± 18.5 |
| OMT 4.1A4.C96S.Q1E | 1016 ± 123 | 9.93 ± 1.21 | 206 ± 22.9 |

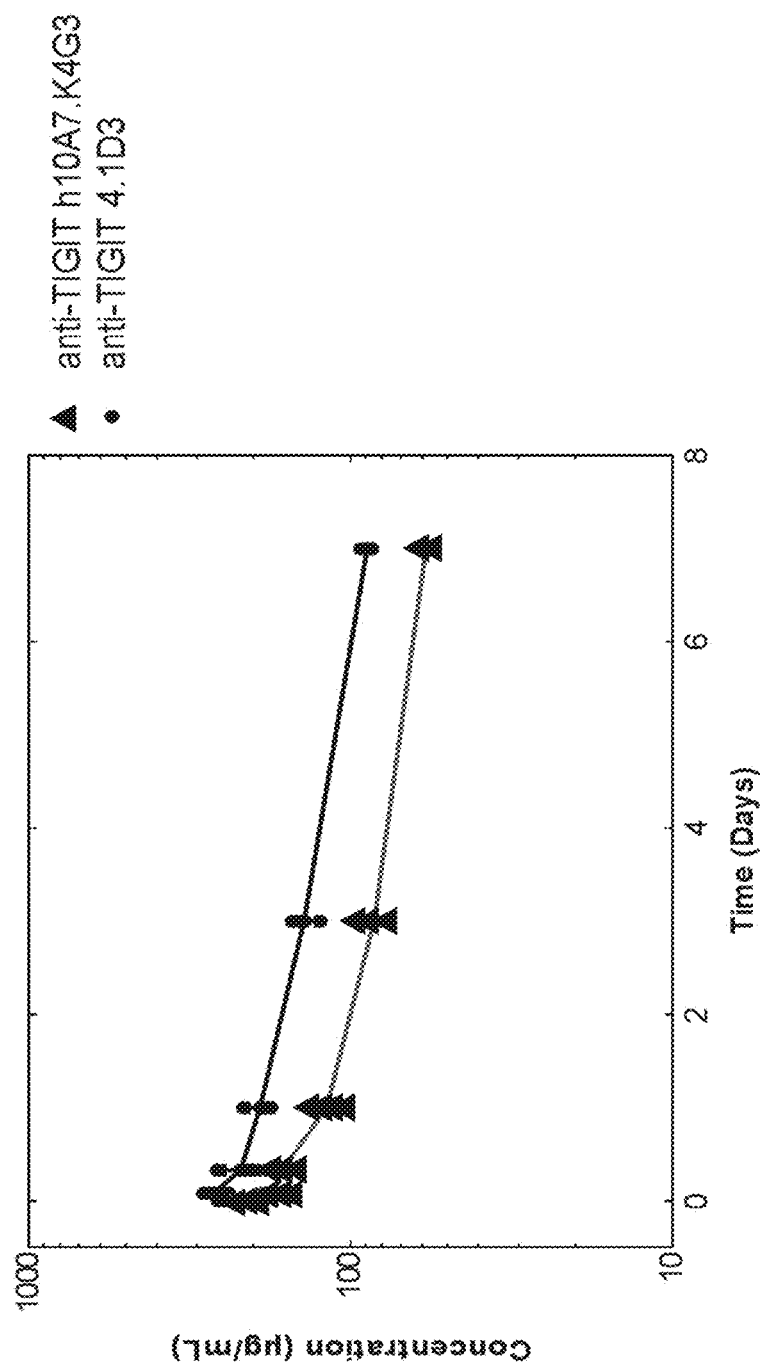

Figure 5D

| | $AUC_{D0-7}$ (day*ug/mL) |
|---|---|
| | Mean (SD) |
| anti-TIGIT h10A7.K4G3 | 641 (SD, 34) |
| anti-TIGIT 4.1D3 | 1,006 (SD, 49) |

| hTIGIT mutants | Binding affinity KD (nM) [N=2] | | | | | | |
|---|---|---|---|---|---|---|---|
| | Chimeric 10A7 | h1A5.L2H8 | 4.1D3 | 7.4A3.C96S | 4.1A4.C96S | h6B2.L2H5 | h7E7.L5aH9a |
| WT | 44.7 ± 20.1 | 4.4 ± 0.9 | 0.5 ± 0.03 | 1.8 ± 1.1 | 30.8 ± 0.9 | 0.7 ± 0.1 | 0.4 ± 0.1 |
| Q53A | 32.0 ± 5.7 | 5.1 ± 1.7 | 0.8 ± 0.3 | >100 | >500 | 0.9 ± 0.1 | 0.8 ± 0.1 |
| Q56A | 29.5 ± 5.0 | >500 | 2.7 ± 0.9 | 23.7 ± 11.4 | 1.4 ± 0.1 | 1.3 ± 0.1 | 2.1 ± 0.3 |
| E60A | 40.3 ± 8.6 | >500 | 6.1 ± 0.4 | 4.8 ± 1.5 | 7.8 ± 0.1 | 2.4 ± 0.3 | 0.7 ± 0.1 |
| L65A | 10.6 ± 2.3 | 50.6 ± 4.0 | 8.8 ± 1.1 | 3.9 ± 1.6 | 42.8 ± 2.9 | 3.0 ± 0.8 | 1.0 ± 0.4 |
| I68A | 17.1 ± 3.5 | >500 | 10.5 ± 0.2 | 4.9 ± 1.8 | 28.6 ± 2.6 | 11.5 ± 1.1 | 0.9 ± 0.3 |
| N70A | 24.3 ± 5.7 | 13.2 ± 3.5 | 1.7 ± 0.8 | 10.7 ± 8.7 | >500 | 2.8 ± 0.1 | 1.6 ± 0.6 |
| L73A | >500 | 41.0 ± 8.3 | 1.3 ± 0.8 | 6.4 ± 4.9 | 82.9 ± 8.9 | >100 | 44.9 ± 5.9 |
| H76A | >500 | 22.3 ± 5.4 | 0.7 ± 0.3 | 4.2 ± 1.9 | 44.5 ± 10.0 | 1.3 ± 0.1 | 1.0 ± 0.1 |
| H111A | 53.3 ± 4.5 | 12.6 ± 3.7 | 1.9 ± 1.4 | 151.2 ± 75.3 | 85.0 ± 7.6 | 1.8 ± 0.6 | 1.8 ± 0.6 |
| Y113A | 55.5 ± 16.4 | >500 | 2.8 ± 1.5 | >100 | >500 | 2.5 ± 0.6 | 3.0 ± 1.1 |
| T117A | 36.4 ± 6.4 | 22.7 ± 1.1 | 0.7 ± 0.4 | 3.3 ± 1.6 | 37.9 ± 4.3 | 1.1 ± 0.1 | 0.8 ± 0.1 |

B

| hTIGIT mutants | Binding affinity drop vs. WT [N=2] | | | | | | |
|---|---|---|---|---|---|---|---|
| | Chimeric 10A7 | h1A5.L2H8 | 4.1D3 | 7.4A3.C96S | 4.1A4.C96S | h6B2.L2H5 | h7E7.L5aH9a |
| WT | 1.0 | 1.0 | 1.0 | 1.0 | 1.0 | 1.0 | 1.0 |
| Q53A | 0.7 | 1.2 | 1.6 | 55 | 16.2 | 1.3 | 2.0 |
| Q56A | 0.7 | 113.6 | 5.4 | 13.2 | 0.1 | 1.9 | 5.3 |
| E60A | 0.9 | 113.6 | 12.2 | 2.7 | 0.3 | 3.4 | 1.8 |
| L65A | 0.2 | 11.5 | 17.6 | 2.2 | 1.4 | 4.3 | 2.5 |
| I68A | 0.4 | 113.6 | 21.0 | 2.7 | 0.9 | 16.4 | 2.3 |
| N70A | 0.5 | 3.0 | 3.4 | 5.9 | 16.2 | 4.0 | 4.0 |
| L73A | 11.2 | 9.3 | 2.6 | 3.6 | 2.7 | 142.9 | 112.2 |
| H76A | 11.2 | 5.1 | 1.4 | 2.3 | 1.4 | 1.9 | 2.5 |
| H111A | 0.7 | 2.9 | 3.8 | 83.0 | 2.8 | 2.6 | 4.5 |
| Y113A | 1.2 | 113.6 | 5.6 | 55 | 16.2 | 3.6 | 7.5 |
| T117A | 0.8 | 5.2 | 1.4 | 1.8 | 1.2 | 1.6 | 2.0 |

Key: ≥10 fold drop; 1-10 fold drop

Fab 1A5/TIGIT

A  Fab 10A7/TIGIT

B

```
                         SEQUENCE LISTING

<160> NUMBER OF SEQ ID NOS: 354

<210> SEQ ID NO 1
<211> LENGTH: 7
<212> TYPE: PRT
<213> ORGANISM: Homo sapiens

<400> SEQUENCE: 1

Ser Asn Ser Ala Ala Trp Asn
1               5

<210> SEQ ID NO 2
<211> LENGTH: 18
<212> TYPE: PRT
<213> ORGANISM: Homo sapiens

<400> SEQUENCE: 2

Lys Thr Tyr Tyr Arg Phe Lys Trp Tyr Ser Asp Tyr Ala Val Ser Val
1               5                   10                  15

Lys Gly

<210> SEQ ID NO 3
<211> LENGTH: 14
<212> TYPE: PRT
<213> ORGANISM: Homo sapiens

<400> SEQUENCE: 3

Glu Ser Thr Thr Tyr Asp Leu Leu Ala Gly Pro Phe Asp Tyr
1               5                   10

<210> SEQ ID NO 4
<211> LENGTH: 17
<212> TYPE: PRT
<213> ORGANISM: Homo sapiens

<400> SEQUENCE: 4

Lys Ser Ser Gln Thr Val Leu Tyr Ser Ser Asn Asn Lys Lys Tyr Leu
1               5                   10                  15

Ala

<210> SEQ ID NO 5
<211> LENGTH: 7
<212> TYPE: PRT
<213> ORGANISM: Homo sapiens

<400> SEQUENCE: 5

Trp Ala Ser Thr Arg Glu Ser
1               5

<210> SEQ ID NO 6
```

-continued

```
<211> LENGTH: 9
<212> TYPE: PRT
<213> ORGANISM: Homo sapiens

<400> SEQUENCE: 6

Gln Gln Tyr Tyr Ser Thr Pro Phe Thr
1               5

<210> SEQ ID NO 7
<211> LENGTH: 23
<212> TYPE: PRT
<213> ORGANISM: Homo sapiens

<400> SEQUENCE: 7

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 8
<211> LENGTH: 15
<212> TYPE: PRT
<213> ORGANISM: Homo sapiens

<400> SEQUENCE: 8

Trp Tyr Gln Gln Lys Pro Gly Gln Pro Pro Asn Leu Leu Ile Tyr
1               5                   10                  15

<210> SEQ ID NO 9
<211> LENGTH: 32
<212> TYPE: PRT
<213> ORGANISM: Homo sapiens

<400> SEQUENCE: 9

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 10
<211> LENGTH: 10
<212> TYPE: PRT
<213> ORGANISM: Homo sapiens

<400> SEQUENCE: 10

Phe Gly Pro Gly Thr Lys Val Glu Ile Lys
1               5                   10

<210> SEQ ID NO 11
<211> LENGTH: 30
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa is Gln or Glu

<400> SEQUENCE: 11

Xaa Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 12
```

```
<211> LENGTH: 14
<212> TYPE: PRT
<213> ORGANISM: Homo sapiens

<400> SEQUENCE: 12

Trp Ile Arg Gln Ser Pro Ser Arg Gly Leu Glu Trp Leu Gly
1               5                   10

<210> SEQ ID NO 13
<211> LENGTH: 32
<212> TYPE: PRT
<213> ORGANISM: Homo sapiens

<400> SEQUENCE: 13

Arg Ile Thr Ile Asn Pro Asp Thr Ser Lys Asn Gln Phe Ser Leu Gln
1               5                   10                  15

Leu Asn Ser Val Thr Pro Glu Asp Thr Ala Val Phe Tyr Cys Thr Arg
            20                  25                  30

<210> SEQ ID NO 14
<211> LENGTH: 11
<212> TYPE: PRT
<213> ORGANISM: Homo sapiens

<400> SEQUENCE: 14

Trp Gly Gln Gly Thr Leu Val Thr Val Ser Ser
1               5                   10

<210> SEQ ID NO 15
<211> LENGTH: 30
<212> TYPE: PRT
<213> ORGANISM: Homo sapiens

<400> SEQUENCE: 15

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 16
<211> LENGTH: 30
<212> TYPE: PRT
<213> ORGANISM: Homo sapiens

<400> SEQUENCE: 16

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser
            20                  25                  30

<210> SEQ ID NO 17
<211> LENGTH: 5
<212> TYPE: PRT
<213> ORGANISM: Homo sapiens

<400> SEQUENCE: 17

Ser Tyr Pro Met Asn
1               5

<210> SEQ ID NO 18
<211> LENGTH: 17
<212> TYPE: PRT
<213> ORGANISM: Homo sapiens
```

```
<400> SEQUENCE: 18

Trp Ile Asn Thr Asn Thr Gly Asn Pro Thr Tyr Val Gln Gly Phe Thr
1               5                   10                  15

Gly

<210> SEQ ID NO 19
<211> LENGTH: 13
<212> TYPE: PRT
<213> ORGANISM: Homo sapiens

<400> SEQUENCE: 19

Thr Gly Gly His Thr Tyr Asp Ser Tyr Ala Phe Asp Val
1               5                   10

<210> SEQ ID NO 20
<211> LENGTH: 11
<212> TYPE: PRT
<213> ORGANISM: Homo sapiens

<400> SEQUENCE: 20

Arg Ala Ser Gln Val Ile Ser Ser Ser Leu Ala
1               5                   10

<210> SEQ ID NO 21
<211> LENGTH: 7
<212> TYPE: PRT
<213> ORGANISM: Homo sapiens

<400> SEQUENCE: 21

Ala Ala Ser Thr Leu Gln Ser
1               5

<210> SEQ ID NO 22
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Xaa is Cys, Ser, or Tyr

<400> SEQUENCE: 22

Gln His Leu His Gly Tyr Pro Xaa Asn
1               5

<210> SEQ ID NO 23
<211> LENGTH: 9
<212> TYPE: PRT
<213> ORGANISM: Homo sapiens

<400> SEQUENCE: 23

Gln His Leu His Gly Tyr Pro Ser Asn
1               5

<210> SEQ ID NO 24
<211> LENGTH: 30
<212> TYPE: PRT
<213> ORGANISM: Homo sapiens

<400> SEQUENCE: 24

Glu Val Gln Leu Val Gln Ser Gly Ser Asp Leu Lys Lys Pro Gly Ala
1               5                   10                  15

Ser Val Arg Val Ser Cys Lys Ala Ser Gly Tyr Thr Phe Thr
            20                  25                  30
```

<210> SEQ ID NO 25
<211> LENGTH: 14
<212> TYPE: PRT
<213> ORGANISM: Homo sapiens

<400> SEQUENCE: 25

Trp Val Arg Gln Ala Pro Gly His Gly Leu Glu Trp Met Gly
1               5                   10

<210> SEQ ID NO 26
<211> LENGTH: 32
<212> TYPE: PRT
<213> ORGANISM: Homo sapiens

<400> SEQUENCE: 26

Arg Phe Val Phe Ser Leu Asp Thr Ser Val Asn Thr Ala Tyr Leu Gln
1               5                   10                  15

Ile Ser Ser Leu Lys Ala Glu Asp Thr Ala Val Tyr Phe Cys Ala Arg
            20                  25                  30

<210> SEQ ID NO 27
<211> LENGTH: 11
<212> TYPE: PRT
<213> ORGANISM: Homo sapiens

<400> SEQUENCE: 27

Trp Gly Gln Gly Thr Met Val Thr Val Ser Ser
1               5                   10

<210> SEQ ID NO 28
<211> LENGTH: 9
<212> TYPE: PRT
<213> ORGANISM: Homo sapiens

<400> SEQUENCE: 28

Gln His Leu His Gly Tyr Pro Cys Asn
1               5

<210> SEQ ID NO 29
<211> LENGTH: 30
<212> TYPE: PRT
<213> ORGANISM: Homo sapiens

<400> SEQUENCE: 29

Gln Val Gln Leu Val Gln Ser Gly Ser Asp Leu Lys Lys Pro Gly Ala
1               5                   10                  15

Ser Val Arg Val Ser Cys Lys Ala Ser Gly Tyr Thr Phe Thr
            20                  25                  30

<210> SEQ ID NO 30
<211> LENGTH: 23
<212> TYPE: PRT
<213> ORGANISM: Homo sapiens

<400> SEQUENCE: 30

Asp Ile Gln Leu Thr Gln Ser Pro Thr Phe Leu Ser Ala Ser Val Gly
1               5                   10                  15

Asp Arg Val Thr Ile Thr Cys
            20

<210> SEQ ID NO 31
<211> LENGTH: 15

<212> TYPE: PRT
<213> ORGANISM: Homo sapiens

<400> SEQUENCE: 31

Trp Tyr Gln Gln Asn Pro Gly Lys Ala Pro Lys Leu Leu Ile Tyr
1               5                   10                  15

<210> SEQ ID NO 32
<211> LENGTH: 32
<212> TYPE: PRT
<213> ORGANISM: Homo sapiens

<400> SEQUENCE: 32

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Val Thr Tyr Tyr Cys
                20                  25                  30

<210> SEQ ID NO 33
<211> LENGTH: 10
<212> TYPE: PRT
<213> ORGANISM: Homo sapiens

<400> SEQUENCE: 33

Phe Gly Gln Gly Thr Lys Val Glu Ile Lys
1               5                   10

<210> SEQ ID NO 34
<211> LENGTH: 126
<212> TYPE: PRT
<213> ORGANISM: Homo sapiens

<400> SEQUENCE: 34

Glu Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

Ser Ala Ala Trp Asn Trp Ile Arg Gln Ser Pro Ser Arg Gly Leu Glu
            35                  40                  45

Trp Leu Gly Lys Thr Tyr Tyr Arg Phe Lys Trp Tyr Ser Asp Tyr Ala
    50                  55                  60

Val Ser Val Lys Gly Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Phe Tyr Cys Thr Arg Glu Ser Thr Thr Tyr Asp Leu Leu Ala Gly Pro
            100                 105                 110

Phe Asp Tyr Trp Gly Gln Gly Thr Leu Val Thr Val Ser Ser
        115                 120                 125

<210> SEQ ID NO 35
<211> LENGTH: 126
<212> TYPE: PRT
<213> ORGANISM: Homo sapiens

<400> SEQUENCE: 35

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
                20                  25                  30

```
Ser Ala Ala Trp Asn Trp Ile Arg Gln Ser Pro Ser Arg Gly Leu Glu
         35                  40                  45

Trp Leu Gly Lys Thr Tyr Tyr Arg Phe Lys Trp Tyr Ser Asp Tyr Ala
 50                  55                  60

Val Ser Val Lys Gly Arg Ile Thr Ile Asn Pro Asp Thr Ser Lys Asn
 65                  70                  75                  80

Gln Phe Ser Leu Gln Leu Asn Ser Val Thr Pro Glu Asp Thr Ala Val
                 85                  90                  95

Phe Tyr Cys Thr Arg Glu Ser Thr Thr Tyr Asp Leu Leu Ala Gly Pro
             100                 105                 110

Phe Asp Tyr Trp Gly Gln Gly Thr Leu Val Thr Val Ser Ser
         115                 120                 125
```

<210> SEQ ID NO 36
<211> LENGTH: 113
<212> TYPE: PRT
<213> ORGANISM: Homo sapiens

<400> SEQUENCE: 36

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Thr Val Leu Tyr Ser
                 20                  25                  30

Ser Asn Asn Lys Lys Tyr Leu Ala Trp Tyr Gln Gln Lys Pro Gly Gln
             35                  40                  45

Pro Pro Asn Leu Leu Ile Tyr Trp Ala Ser Thr Arg Glu Ser Gly Val
         50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Ser Thr Pro Phe Thr Phe Gly Pro Gly Thr Lys Val Glu Ile
             100                 105                 110

Lys
```

<210> SEQ ID NO 37
<211> LENGTH: 122
<212> TYPE: PRT
<213> ORGANISM: Homo sapiens

<400> SEQUENCE: 37

```
Glu Val Gln Leu Val Gln Ser Gly Ser Asp Leu Lys Lys Pro Gly Ala
 1               5                  10                  15

Ser Val Arg Val Ser Cys Lys Ala Ser Gly Tyr Thr Phe Thr Ser Tyr
                 20                  25                  30

Pro Met Asn Trp Val Arg Gln Ala Pro Gly His Gly Leu Glu Trp Met
             35                  40                  45

Gly Trp Ile Asn Thr Asn Thr Gly Asn Pro Thr Tyr Val Gln Gly Phe
         50                  55                  60

Thr Gly Arg Phe Val Phe Ser Leu Asp Thr Ser Val Asn Thr Ala Tyr
 65                  70                  75                  80

Leu Gln Ile Ser Ser Leu Lys Ala Glu Asp Thr Ala Val Tyr Phe Cys
                 85                  90                  95

Ala Arg Thr Gly Gly His Thr Tyr Asp Ser Tyr Ala Phe Asp Val Trp
             100                 105                 110

Gly Gln Gly Thr Met Val Thr Val Ser Ser
```

<210> SEQ ID NO 38
<211> LENGTH: 107
<212> TYPE: PRT
<213> ORGANISM: Homo sapiens

<400> SEQUENCE: 38

Asp Ile Gln Leu Thr Gln Ser Pro Thr Phe Leu Ser Ala Ser Val Gly
1               5                   10                  15

Asp Arg Val Thr Ile Thr Cys Arg Ala Ser Gln Val Ile Ser Ser Ser
            20                  25                  30

Leu Ala Trp Tyr Gln Gln Asn Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Val Thr Tyr Tyr Cys Gln His Leu His Gly Tyr Pro Ser
                85                  90                  95

Asn Phe Gly Gln Gly Thr Lys Val Glu Ile Lys
            100                 105

<210> SEQ ID NO 39
<211> LENGTH: 122
<212> TYPE: PRT
<213> ORGANISM: Homo sapiens

<400> SEQUENCE: 39

Gln Val Gln Leu Val Gln Ser Gly Ser Asp Leu Lys Lys Pro Gly Ala
1               5                   10                  15

Ser Val Arg Val Ser Cys Lys Ala Ser Gly Tyr Thr Phe Thr Ser Tyr
            20                  25                  30

Pro Met Asn Trp Val Arg Gln Ala Pro Gly His Gly Leu Glu Trp Met
        35                  40                  45

Gly Trp Ile Asn Thr Asn Thr Gly Asn Pro Thr Tyr Val Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Phe Cys
                85                  90                  95

Ala Arg Thr Gly Gly His Thr Tyr Asp Ser Tyr Ala Phe Asp Val Trp
            100                 105                 110

Gly Gln Gly Thr Met Val Thr Val Ser Ser
        115                 120

<210> SEQ ID NO 40
<211> LENGTH: 107
<212> TYPE: PRT
<213> ORGANISM: Homo sapiens

<400> SEQUENCE: 40

Asp Ile Gln Leu Thr Gln Ser Pro Thr Phe Leu Ser Ala Ser Val Gly
1               5                   10                  15

Asp Arg Val Thr Ile Thr Cys Arg Ala Ser Gln Val Ile Ser Ser Ser
            20                  25                  30

Leu Ala Trp Tyr Gln Gln Asn Pro Gly Lys Ala Pro Lys Leu Leu Ile
        35                  40                  45

```
Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Val Thr Tyr Tyr Cys Gln His Leu His Gly Tyr Pro Cys
                85                  90                  95

Asn Phe Gly Gln Gly Thr Lys Val Glu Ile Lys
                100                 105

<210> SEQ ID NO 41
<211> LENGTH: 5
<212> TYPE: PRT
<213> ORGANISM: Homo sapiens

<400> SEQUENCE: 41

Asn Tyr Pro Met Asn
1               5

<210> SEQ ID NO 42
<211> LENGTH: 17
<212> TYPE: PRT
<213> ORGANISM: Homo sapiens

<400> SEQUENCE: 42

Trp Ile Asn Thr Asn Thr Gly Ser Pro Ala Tyr Ala Gln Asp Phe Thr
1               5                   10                  15

Glu

<210> SEQ ID NO 43
<211> LENGTH: 11
<212> TYPE: PRT
<213> ORGANISM: Homo sapiens

<400> SEQUENCE: 43

Thr Ala Ile Thr Ser Val Tyr His Phe Asp Tyr
1               5                   10

<210> SEQ ID NO 44
<211> LENGTH: 11
<212> TYPE: PRT
<213> ORGANISM: Homo sapiens

<400> SEQUENCE: 44

Arg Ala Ser Gln Gly Ile Ser Ser Tyr Leu Ala
1               5                   10

<210> SEQ ID NO 45
<211> LENGTH: 7
<212> TYPE: PRT
<213> ORGANISM: Homo sapiens

<400> SEQUENCE: 45

Gly Ala Thr Thr Leu Gln Ser
1               5

<210> SEQ ID NO 46
<211> LENGTH: 9
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Xaa is Cys, Ser, or Tyr
```

```
<400> SEQUENCE: 46

Gln Lys Leu Asn Ser His Pro Xaa Ser
1               5

<210> SEQ ID NO 47
<211> LENGTH: 9
<212> TYPE: PRT
<213> ORGANISM: Homo sapiens

<400> SEQUENCE: 47

Gln Lys Leu Asn Ser His Pro Cys Ser
1               5

<210> SEQ ID NO 48
<211> LENGTH: 9
<212> TYPE: PRT
<213> ORGANISM: Homo sapiens

<400> SEQUENCE: 48

Gln Lys Leu Asn Ser His Pro Ser Ser
1               5

<210> SEQ ID NO 49
<211> LENGTH: 9
<212> TYPE: PRT
<213> ORGANISM: Homo sapiens

<400> SEQUENCE: 49

Gln Lys Leu Asn Ser His Pro Tyr Ser
1               5

<210> SEQ ID NO 50
<211> LENGTH: 30
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: Xaa is Glu or Gln

<400> SEQUENCE: 50

Xaa Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr
            20                  25                  30

<210> SEQ ID NO 51
<211> LENGTH: 14
<212> TYPE: PRT
<213> ORGANISM: Homo sapiens

<400> SEQUENCE: 51

Trp Val Arg Gln Ala Pro Gly Arg Gly Leu Glu Trp Met Gly
1               5                   10

<210> SEQ ID NO 52
<211> LENGTH: 32
<212> TYPE: PRT
<213> ORGANISM: Homo sapiens

<400> SEQUENCE: 52

Arg Phe Val Phe Ser Leu Asp Thr Ser Val Thr Thr Ala Tyr Leu Gln
1               5                   10                  15
```

Ile Ser Ser Leu Lys Ala Glu Asp Thr Ala Val Tyr Tyr Cys Ala Arg
            20                  25                  30

<210> SEQ ID NO 53
<211> LENGTH: 11
<212> TYPE: PRT
<213> ORGANISM: Homo sapiens

<400> SEQUENCE: 53

Trp Gly Gln Gly Thr Leu Val Thr Val Ser Ser
1               5                   10

<210> SEQ ID NO 54
<211> LENGTH: 30
<212> TYPE: PRT
<213> ORGANISM: Homo sapiens

<400> SEQUENCE: 54

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr
            20                  25                  30

<210> SEQ ID NO 55
<211> LENGTH: 30
<212> TYPE: PRT
<213> ORGANISM: Homo sapiens

<400> SEQUENCE: 55

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr
            20                  25                  30

<210> SEQ ID NO 56
<211> LENGTH: 23
<212> TYPE: PRT
<213> ORGANISM: Homo sapiens

<400> SEQUENCE: 56

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 57
<211> LENGTH: 15
<212> TYPE: PRT
<213> ORGANISM: Homo sapiens

<400> SEQUENCE: 57

Trp Tyr Gln Gln Lys Pro Gly Lys Ala Pro Arg Val Leu Ile Tyr
1               5                   10                  15

<210> SEQ ID NO 58
<211> LENGTH: 32
<212> TYPE: PRT
<213> ORGANISM: Homo sapiens

<400> SEQUENCE: 58

Gly Val Pro Ser Arg Phe Ser Gly Ser Glu Ser Gly Thr Glu Phe Thr
1               5                   10                  15

Leu Thr Ile Ser Ser Leu Gln Pro Glu Asp Leu Ala Thr Tyr Tyr Cys

<210> SEQ ID NO 59
<211> LENGTH: 10
<212> TYPE: PRT
<213> ORGANISM: Homo sapiens

<400> SEQUENCE: 59

Phe Gly Gln Gly Thr Lys Val Glu Ile Lys
1               5                   10

<210> SEQ ID NO 60
<211> LENGTH: 120
<212> TYPE: PRT
<213> ORGANISM: Homo sapiens

<400> SEQUENCE: 60

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr Asn Tyr
            20                  25                  30

Pro Met Asn Trp Val Arg Gln Ala Pro Gly Arg Gly Leu Glu Trp Met
        35                  40                  45

Gly Trp Ile Asn Thr Asn Thr Gly Ser Pro Ala Tyr Ala Gln Asp Phe
    50                  55                  60

Thr Glu Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Ala Ile Thr Ser Val Tyr His Phe Asp Tyr Trp Gly Gln
            100                 105                 110

Gly Thr Leu Val Thr Val Ser Ser
        115                 120

<210> SEQ ID NO 61
<211> LENGTH: 107
<212> TYPE: PRT
<213> ORGANISM: Homo sapiens

<400> SEQUENCE: 61

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Arg Val Leu Ile
        35                  40                  45

Tyr Gly Ala Thr Thr Leu Gln Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Leu Ala Thr Tyr Tyr Cys Gln Lys Leu Asn Ser His Pro Cys
                85                  90                  95

Ser Phe Gly Gln Gly Thr Lys Val Glu Ile Lys
            100                 105

<210> SEQ ID NO 62
<211> LENGTH: 120
<212> TYPE: PRT
<213> ORGANISM: Homo sapiens

<400> SEQUENCE: 62

Glu Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Leu Thr Asn Tyr
            20                  25                  30

Pro Met Asn Trp Val Arg Gln Ala Pro Gly Arg Gly Leu Glu Trp Met
        35                  40                  45

Gly Trp Ile Asn Thr Asn Thr Gly Ser Pro Ala Tyr Ala Gln Asp Phe
    50                  55                  60

Thr Glu Arg Phe Val Phe Ser Leu Asp Thr Ser Val Thr Thr Ala Tyr
65                  70                  75                  80

Leu Gln Ile Ser Ser Leu Lys Ala Glu Asp Thr Ala Val Tyr Tyr Cys
                85                  90                  95

Ala Arg Thr Ala Ile Thr Ser Val Tyr His Phe Asp Tyr Trp Gly Gln
            100                 105                 110

Gly Thr Leu Val Thr Val Ser Ser
        115                 120

<210> SEQ ID NO 63
<211> LENGTH: 107
<212> TYPE: PRT
<213> ORGANISM: Homo sapiens

<400> SEQUENCE: 63

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Arg Val Leu Ile
        35                  40                  45

Tyr Gly Ala Thr Thr Leu Gln Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

Glu Asp Leu Ala Thr Tyr Tyr Cys Gln Lys Leu Asn Ser His Pro Ser
                85                  90                  95

Ser Phe Gly Gln Gly Thr Lys Val Glu Ile Lys
            100                 105

<210> SEQ ID NO 64
<211> LENGTH: 107
<212> TYPE: PRT
<213> ORGANISM: Homo sapiens

<400> SEQUENCE: 64

Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Arg Val Leu Ile
        35                  40                  45

Tyr Gly Ala Thr Thr Leu Gln Ser Gly Val Pro Ser Arg Phe Ser Gly
    50                  55                  60

Ser Glu Ser Gly Thr Glu Phe Thr Leu Thr Ile Ser Ser Leu Gln Pro
65                  70                  75                  80

```
Glu Asp Leu Ala Thr Tyr Tyr Cys Gln Lys Leu Asn Ser His Pro Tyr
                85                  90                  95

Ser Phe Gly Gln Gly Thr Lys Val Glu Ile Lys
        100                 105
```

<210> SEQ ID NO 65
<211> LENGTH: 9
<212> TYPE: PRT
<213> ORGANISM: Homo sapiens

<400> SEQUENCE: 65

```
Gln His Leu His Gly Tyr Pro Tyr Asn
1               5
```

<210> SEQ ID NO 66
<211> LENGTH: 122
<212> TYPE: PRT
<213> ORGANISM: Homo sapiens

<400> SEQUENCE: 66

```
Glu Val Gln Leu Val Gln Ser Gly Ser Asp Leu Lys Lys Pro Gly Ala
1               5                   10                  15

Ser Val Arg Val Ser Cys Lys Ala Ser Gly Tyr Thr Phe Thr Ser Tyr
            20                  25                  30

Pro Met Asn Trp Val Arg Gln Ala Pro Gly His Gly Leu Glu Trp Met
        35                  40                  45

Gly Trp Ile Asn Thr Asn Thr Gly Asn Pro Thr Tyr Val Gln Gly Phe
    50                  55                  60

Thr Gly Arg Phe Val Phe Ser Leu Asp Thr Ser Val Asn Thr Ala Tyr
65                  70                  75                  80

Leu Gln Ile Ser Ser Leu Lys Ala Glu Asp Thr Ala Val Tyr Phe Cys
                85                  90                  95

Ala Arg Thr Gly Gly His Thr Tyr Asp Ser Tyr Ala Phe Asp Val Trp
            100                 105                 110

Gly Gln Gly Thr Met Val Thr Val Ser Ser
        115                 120
```

<210> SEQ ID NO 67
<211> LENGTH: 107
<212> TYPE: PRT
<213> ORGANISM: Homo sapiens

<400> SEQUENCE: 67

```
Asp Ile Gln Leu Thr Gln Ser Pro Thr Phe Leu Ser Ala Ser Val Gly
1               5                   10                  15

Asp Arg Val Thr Ile Thr Cys Arg Ala Ser Gln Val Ile Ser Ser Ser
            20                  25                  30

Leu Ala Trp Tyr Gln Gln Asn Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Val Thr Tyr Tyr Cys Gln His Leu His Gly Tyr Pro Tyr
                85                  90                  95

Asn Phe Gly Gln Gly Thr Lys Val Glu Ile Lys
        100                 105
```

```
<210> SEQ ID NO 68
<211> LENGTH: 7
<212> TYPE: PRT
<213> ORGANISM: Rattus norvegicus

<400> SEQUENCE: 68

Thr Tyr Gly Met Gly Val Ser
1               5

<210> SEQ ID NO 69
<211> LENGTH: 16
<212> TYPE: PRT
<213> ORGANISM: Rattus norvegicus

<400> SEQUENCE: 69

Ser Ile Trp Trp Asn Gly Asn Thr Tyr Tyr Asn Pro Ser Leu Lys Ser
1               5                   10                  15

<210> SEQ ID NO 70
<211> LENGTH: 11
<212> TYPE: PRT
<213> ORGANISM: Rattus norvegicus

<400> SEQUENCE: 70

Thr Gly Gly Ala Val Ile Thr Trp Phe Ala Tyr
1               5                   10

<210> SEQ ID NO 71
<211> LENGTH: 11
<212> TYPE: PRT
<213> ORGANISM: Rattus norvegicus

<400> SEQUENCE: 71

Lys Ala Ser Gln Ser Val Gly Lys Asn Ile Ala
1               5                   10

<210> SEQ ID NO 72
<211> LENGTH: 7
<212> TYPE: PRT
<213> ORGANISM: Rattus norvegicus

<400> SEQUENCE: 72

Tyr Ala Ser Asn Arg Tyr Thr
1               5

<210> SEQ ID NO 73
<211> LENGTH: 9
<212> TYPE: PRT
<213> ORGANISM: Rattus norvegicus

<400> SEQUENCE: 73

Gln His Ile Tyr Asn Ser Pro Tyr Pro
1               5

<210> SEQ ID NO 74
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Glu or Gln
<220> FEATURE:
<221> NAME/KEY: MOD_RES
<222> LOCATION: (3)..(3)
```

```
<223> OTHER INFORMATION: Xaa is Ser or Thr
<220> FEATURE:
<221> NAME/KEY: MOD_RES
<222> LOCATION: (10)..(10)
<223> OTHER INFORMATION: Xaa is Ala or Gly
<220> FEATURE:
<221> NAME/KEY: MOD_RES
<222> LOCATION: (11)..(11)
<223> OTHER INFORMATION: Xaa is Ile or Leu
<220> FEATURE:
<221> NAME/KEY: MOD_RES
<222> LOCATION: (12)..(12)
<223> OTHER INFORMATION: Xaa is Leu or Val
<220> FEATURE:
<221> NAME/KEY: MOD_RES
<222> LOCATION: (13)..(13)
<223> OTHER INFORMATION: Xaa is Lys or Gln
<220> FEATURE:
<221> NAME/KEY: MOD_RES
<222> LOCATION: (15)..(15)
<223> OTHER INFORMATION: Xaa is Ser or Thr
<220> FEATURE:
<221> NAME/KEY: MOD_RES
<222> LOCATION: (16)..(16)
<223> OTHER INFORMATION: Xaa is His or Gln
<220> FEATURE:
<221> NAME/KEY: MOD_RES
<222> LOCATION: (19)..(19)
<223> OTHER INFORMATION: Xaa is Ser or Thr
<220> FEATURE:
<221> NAME/KEY: MOD_RES
<222> LOCATION: (23)..(23)
<223> OTHER INFORMATION: Xaa is Ser or Thr

<400> SEQUENCE: 74

Xaa Val Xaa Leu Lys Glu Ser Gly Pro Xaa Xaa Xaa Xaa Pro Xaa Xaa
1               5                   10                  15

Thr Leu Xaa Leu Thr Cys Xaa Phe Ser Gly Phe Ser Leu Ser
            20                  25                  30

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Pro or Ser
<220> FEATURE:
<221> NAME/KEY: MOD_RES
<222> LOCATION: (7)..(7)
<223> OTHER INFORMATION: Xaa is Glu or Gly
<220> FEATURE:
<221> NAME/KEY: MOD_RES
<222> LOCATION: (9)..(9)
<223> OTHER INFORMATION: Xaa is Ala or Gly

<400> SEQUENCE: 75

Trp Ile Arg Gln Pro Xaa Xaa Lys Xaa Leu Glu Trp Leu Ala
1               5                   10

<210> SEQ ID NO 76
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Ile or Val
<220> FEATURE:
```

-continued

```
<221> NAME/KEY: MOD_RES
<222> LOCATION: (5)..(5)
<223> OTHER INFORMATION: Xaa is Ser or Thr
<220> FEATURE:
<221> NAME/KEY: MOD_RES
<222> LOCATION: (8)..(8)
<223> OTHER INFORMATION: Xaa is Ala or Thr
<220> FEATURE:
<221> NAME/KEY: MOD_RES
<222> LOCATION: (10)..(10)
<223> OTHER INFORMATION: Xaa is Lys or Asn
<220> FEATURE:
<221> NAME/KEY: MOD_RES
<222> LOCATION: (11)..(11)
<223> OTHER INFORMATION: Xaa is Asp or Asn
<220> FEATURE:
<221> NAME/KEY: MOD_RES
<222> LOCATION: (13)..(13)
<223> OTHER INFORMATION: Xaa is Ala or Val
<220> FEATURE:
<221> NAME/KEY: MOD_RES
<222> LOCATION: (14)..(14)
<223> OTHER INFORMATION: Xaa is Phe or Val
<220> FEATURE:
<221> NAME/KEY: MOD_RES
<222> LOCATION: (16)..(16)
<223> OTHER INFORMATION: Xaa is Asn or Thr
<220> FEATURE:
<221> NAME/KEY: MOD_RES
<222> LOCATION: (17)..(17)
<223> OTHER INFORMATION: Xaa is Met or Val
<220> FEATURE:
<221> NAME/KEY: MOD_RES
<222> LOCATION: (19)..(19)
<223> OTHER INFORMATION: Xaa is Asn or Ser
<220> FEATURE:
<221> NAME/KEY: MOD_RES
<222> LOCATION: (20)..(20)
<223> OTHER INFORMATION: Xaa is Met or Val
<220> FEATURE:
<221> NAME/KEY: MOD_RES
<222> LOCATION: (22)..(22)
<223> OTHER INFORMATION: Xaa is Pro or Thr
<220> FEATURE:
<221> NAME/KEY: MOD_RES
<222> LOCATION: (23)..(23)
<223> OTHER INFORMATION: Xaa is Thr or Val

<400> SEQUENCE: 76

Arg Leu Thr Xaa Xaa Lys Asp Xaa Ser Xaa Xaa Gln Xaa Xaa Leu Xaa
1               5                   10                  15

Xaa Thr Xaa Xaa Asp Xaa Xaa Asp Thr Ala Thr Tyr Tyr Cys Ala His
            20                  25                  30

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Trp Gly Gln Gly Thr Leu Val Thr Val Ser Ser
1               5                   10

<210> SEQ ID NO 78
<211> LENGTH: 30
<212> TYPE: PRT
<213> ORGANISM: Rattus norvegicus

<400> SEQUENCE: 78

Gln Val Ser Leu Lys Glu Ser Gly Pro Gly Ile Leu Gln Pro Ser His
1               5                   10                  15
```

```
Thr Leu Ser Leu Thr Cys Ser Phe Ser Gly Phe Ser Leu Ser
            20                  25                  30

<210> SEQ ID NO 79
<211> LENGTH: 14
<212> TYPE: PRT
<213> ORGANISM: Rattus norvegicus

<400> SEQUENCE: 79

Trp Ile Arg Gln Pro Ser Glu Lys Gly Leu Glu Trp Leu Ala
1               5                   10

<210> SEQ ID NO 80
<211> LENGTH: 32
<212> TYPE: PRT
<213> ORGANISM: Rattus norvegicus

<400> SEQUENCE: 80

Arg Leu Thr Val Ser Lys Asp Ala Ser Asn Asp Gln Ala Phe Leu Asn
1               5                   10                  15

Val Thr Ser Val Asp Thr Thr Asp Thr Ala Thr Tyr Tyr Cys Ala His
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Synthetic Construct

<400> SEQUENCE: 81

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser
            20                  25                  30

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

<400> SEQUENCE: 82

Trp Ile Arg Gln Pro Pro Gly Lys Ala Leu Glu Trp Leu Ala
1               5                   10

<210> SEQ ID NO 83
<211> LENGTH: 32
<212> TYPE: PRT
<213> ORGANISM: Artificial Sequence
<220> FEATURE:
<223> OTHER INFORMATION: Synthetic Construct

<400> SEQUENCE: 83

Arg Leu Thr Val Thr Lys Asp Ala Ser Lys Asn Gln Ala Val Leu Thr
1               5                   10                  15

Met Thr Asn Met Asp Pro Val Asp Thr Ala Thr Tyr Tyr Cys Ala His
            20                  25                  30

<210> SEQ ID NO 84
<211> LENGTH: 32
<212> TYPE: PRT
<213> ORGANISM: Artificial Sequence
```

-continued

```
<220> FEATURE:
<223> OTHER INFORMATION: Synthetic Construct

<400> SEQUENCE: 84

Arg Leu Thr Ile Thr Lys Asp Ala Ser Lys Asn Gln Ala Val Leu Thr
1               5                   10                  15

Met Thr Asn Met Asp Pro Val Asp Thr Ala Thr Tyr Tyr Cys Ala His
            20                  25                  30

<210> SEQ ID NO 85
<211> LENGTH: 32
<212> TYPE: PRT
<213> ORGANISM: Artificial Sequence
<220> FEATURE:
<223> OTHER INFORMATION: Synthetic Construct

<400> SEQUENCE: 85

Arg Leu Thr Val Thr Lys Asp Thr Ser Lys Asn Gln Ala Val Leu Thr
1               5                   10                  15

Met Thr Asn Met Asp Pro Val Asp Thr Ala Thr Tyr Tyr Cys Ala His
            20                  25                  30

<210> SEQ ID NO 86
<211> LENGTH: 32
<212> TYPE: PRT
<213> ORGANISM: Artificial Sequence
<220> FEATURE:
<223> OTHER INFORMATION: Synthetic Construct

<400> SEQUENCE: 86

Arg Leu Thr Val Thr Lys Asp Ala Ser Lys Asn Gln Val Val Leu Thr
1               5                   10                  15

Met Thr Asn Met Asp Pro Val Asp Thr Ala Thr Tyr Tyr Cys Ala His
            20                  25                  30

<210> SEQ ID NO 87
<211> LENGTH: 32
<212> TYPE: PRT
<213> ORGANISM: Artificial Sequence
<220> FEATURE:
<223> OTHER INFORMATION: Synthetic Construct

<400> SEQUENCE: 87

Arg Leu Thr Ile Thr Lys Asp Thr Ser Lys Asn Gln Val Val Leu Thr
1               5                   10                  15

Met Thr Asn Met Asp Pro Val Asp Thr Ala Thr Tyr Tyr Cys Ala His
            20                  25                  30

<210> SEQ ID NO 88
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Asp or Asn
<220> FEATURE:
<221> NAME/KEY: MOD_RES
<222> LOCATION: (3)..(3)
<223> OTHER INFORMATION: Xaa is Gln or Val
<220> FEATURE:
<221> NAME/KEY: MOD_RES
<222> LOCATION: (9)..(9)
<223> OTHER INFORMATION: Xaa is Lys or Ser
<220> FEATURE:
```

```
<221> NAME/KEY: MOD_RES
<222> LOCATION: (11)..(11)
<223> OTHER INFORMATION: Xaa is Leu or Met
<220> FEATURE:
<221> NAME/KEY: MOD_RES
<222> LOCATION: (13)..(13)
<223> OTHER INFORMATION: Xaa is Ala or Ile
<220> FEATURE:
<221> NAME/KEY: MOD_RES
<222> LOCATION: (21)..(21)
<223> OTHER INFORMATION: Xaa is Ile or Met
<220> FEATURE:
<221> NAME/KEY: MOD_RES
<222> LOCATION: (22)..(22)
<223> OTHER INFORMATION: Xaa is Asn or Thr

<400> SEQUENCE: 88

Xaa Ile Xaa Met Thr Gln Ser Pro Xaa Ser Xaa Ser Xaa Ser Val Gly
1               5                  10                  15

Asp Arg Val Thr Xaa Xaa Cys
            20

<210> SEQ ID NO 89
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Lys or Gln
<220> FEATURE:
<221> NAME/KEY: MOD_RES
<222> LOCATION: (9)..(9)
<223> OTHER INFORMATION: Xaa is Ala or Ser

<400> SEQUENCE: 89

Trp Tyr Gln Gln Lys Pro Gly Xaa Xaa Pro Lys Leu Leu Ile Tyr
1               5                  10                  15

<210> SEQ ID NO 90
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Asp or Ser
<220> FEATURE:
<221> NAME/KEY: MOD_RES
<222> LOCATION: (7)..(7)
<223> OTHER INFORMATION: Xaa is Ser or Thr
<220> FEATURE:
<221> NAME/KEY: MOD_RES
<222> LOCATION: (9)..(9)
<223> OTHER INFORMATION: Xaa is Gly or Ser
<220> FEATURE:
<221> NAME/KEY: MOD_RES
<222> LOCATION: (17)..(17)
<223> OTHER INFORMATION: Xaa is Phe or Leu
<220> FEATURE:
<221> NAME/KEY: MOD_RES
<222> LOCATION: (20)..(20)
<223> OTHER INFORMATION: Xaa is Asn or Ser
<220> FEATURE:
<221> NAME/KEY: MOD_RES
<222> LOCATION: (21)..(21)
<223> OTHER INFORMATION: Xaa is Ser or Thr
<220> FEATURE:
<221> NAME/KEY: MOD_RES
<222> LOCATION: (22)..(22)
```

```
<223> OTHER INFORMATION: Xaa is Leu or Val
<220> FEATURE:
<221> NAME/KEY: MOD_RES
<222> LOCATION: (24)..(24)
<223> OTHER INFORMATION: Xaa is Ala or Pro
<220> FEATURE:
<221> NAME/KEY: MOD_RES
<222> LOCATION: (27)..(27)
<223> OTHER INFORMATION: Xaa is Ala or Ile
<220> FEATURE:
<221> NAME/KEY: MOD_RES
<222> LOCATION: (29)..(29)
<223> OTHER INFORMATION: Xaa is Phe or Thr
<220> FEATURE:
<221> NAME/KEY: MOD_RES
<222> LOCATION: (30)..(30)
<223> OTHER INFORMATION: Xaa is Phe or Tyr

<400> SEQUENCE: 90

Gly Val Pro Xaa Arg Phe Xaa Gly Xaa Gly Ser Gly Thr Asp Phe Thr
1               5                   10                  15

Xaa Thr Ile Xaa Xaa Xaa Gln Xaa Glu Asp Xaa Ala Xaa Xaa Tyr Cys
            20                  25                  30

<210> SEQ ID NO 91
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Gln or Thr
<220> FEATURE:
<221> NAME/KEY: MOD_RES
<222> LOCATION: (7)..(7)
<223> OTHER INFORMATION: Xaa is Leu or Val

<400> SEQUENCE: 91

Phe Gly Xaa Gly Thr Lys Xaa Glu Ile Lys
1               5                   10

<210> SEQ ID NO 92
<211> LENGTH: 23
<212> TYPE: PRT
<213> ORGANISM: Rattus norvegicus

<400> SEQUENCE: 92

Asn Ile Val Met Thr Gln Ser Pro Lys Ser Met Ser Ile Ser Val Gly
1               5                   10                  15

Asp Arg Val Thr Met Asn Cys
            20

<210> SEQ ID NO 93
<211> LENGTH: 15
<212> TYPE: PRT
<213> ORGANISM: Rattus norvegicus

<400> SEQUENCE: 93

Trp Tyr Gln Gln Lys Pro Gly Gln Ser Pro Lys Leu Leu Ile Tyr
1               5                   10                  15

<210> SEQ ID NO 94
<211> LENGTH: 32
<212> TYPE: PRT
<213> ORGANISM: Rattus norvegicus

<400> SEQUENCE: 94
```

Gly Val Pro Asp Arg Phe Thr Gly Gly Ser Gly Thr Asp Phe Thr
1               5                   10                  15

Leu Thr Ile Asn Thr Val Gln Ala Glu Asp Ala Ala Phe Phe Tyr Cys
            20                  25                  30

<210> SEQ ID NO 95
<211> LENGTH: 10
<212> TYPE: PRT
<213> ORGANISM: Rattus norvegicus

<400> SEQUENCE: 95

Phe Gly Thr Gly Thr Lys Leu Glu Ile Lys
1               5                   10

<210> SEQ ID NO 96
<211> LENGTH: 23
<212> TYPE: PRT
<213> ORGANISM: Artificial Sequence
<220> FEATURE:
<223> OTHER INFORMATION: Synthetic Construct

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 97
<211> LENGTH: 15
<212> TYPE: PRT
<213> ORGANISM: Artificial Sequence
<220> FEATURE:
<223> OTHER INFORMATION: Synthetic Construct

<400> SEQUENCE: 97

Trp Tyr Gln Gln Lys Pro Gly Lys Ser Pro Lys Leu Leu Ile Tyr
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Synthetic Construct

<400> SEQUENCE: 98

Trp Tyr Gln Gln Lys Pro Gly Lys Ala Pro Lys Leu Leu Ile Tyr
1               5                   10                  15

<210> SEQ ID NO 99
<211> LENGTH: 32
<212> TYPE: PRT
<213> ORGANISM: Artificial Sequence
<220> FEATURE:
<223> OTHER INFORMATION: Synthetic Construct

<400> SEQUENCE: 99

Gly Val Pro Ser Arg Phe Ser Gly Ser Gly Ser Gly Thr Asp Phe Thr
1               5                   10                  15

Phe Thr Ile Ser Ser Leu Gln Pro Glu Asp Ile Ala Thr Tyr Tyr Cys
            20                  25                  30

<210> SEQ ID NO 100
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 100

Phe Gly Gln Gly Thr Lys Val Glu Ile Lys
1               5                   10

<210> SEQ ID NO 101
<211> LENGTH: 121
<212> TYPE: PRT
<213> ORGANISM: Rattus norvegicus

<400> SEQUENCE: 101

Gln Val Ser Leu Lys Glu Ser Gly Pro Gly Ile Leu Gln Pro Ser His
1               5                   10                  15

Thr Leu Ser Leu Thr Cys Ser Phe Ser Gly Phe Ser Leu Ser Thr Tyr
                20                  25                  30

Gly Met Gly Val Ser Trp Ile Arg Gln Pro Ser Glu Lys Gly Leu Glu
            35                  40                  45

Trp Leu Ala Ser Ile Trp Trp Asn Gly Asn Thr Tyr Tyr Asn Pro Ser
    50                  55                  60

Leu Lys Ser Arg Leu Thr Val Ser Lys Asp Ala Ser Asn Asp Gln Ala
65                  70                  75                  80

Phe Leu Asn Val Thr Ser Val Asp Thr Thr Asp Thr Ala Thr Tyr Tyr
                85                  90                  95

Cys Ala His Thr Gly Gly Ala Val Ile Thr Trp Phe Ala Tyr Trp Gly
            100                 105                 110

Gln Gly Thr Leu Val Thr Val Ser Ser
        115                 120

<210> SEQ ID NO 102
<211> LENGTH: 107
<212> TYPE: PRT
<213> ORGANISM: Rattus norvegicus

<400> SEQUENCE: 102

Asn Ile Val Met Thr Gln Ser Pro Lys Ser Met Ser Ile Ser Val Gly
1               5                   10                  15

Asp Arg Val Thr Met Asn Cys Lys Ala Ser Gln Ser Val Gly Lys Asn
                20                  25                  30

Ile Ala Trp Tyr Gln Gln Lys Pro Gly Gln Ser Pro Lys Leu Leu Ile
            35                  40                  45

Tyr Tyr Ala Ser Asn Arg Tyr Thr Gly Val Pro Asp Arg Phe Thr Gly
    50                  55                  60

Gly Gly Ser Gly Thr Asp Phe Thr Leu Thr Ile Asn Thr Val Gln Ala
65                  70                  75                  80

Glu Asp Ala Ala Phe Phe Tyr Cys Gln His Ile Tyr Asn Ser Pro Tyr
                85                  90                  95

Pro Phe Gly Thr Gly Thr Lys Leu Glu Ile Lys
            100                 105

<210> SEQ ID NO 103
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 103

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Ser Trp Ile Arg Gln Pro Pro Gly Lys Ala Leu Glu
        35                  40                  45

Trp Leu Ala Ser Ile Trp Trp Asn Gly Asn Thr Tyr Tyr Asn Pro Ser
    50                  55                  60

Leu Lys Ser Arg Leu Thr Val Thr Lys Asp Ala Ser Lys Asn Gln Ala
65                  70                  75                  80

Val Leu Thr Met Thr Asn Met Asp Pro Val Asp Thr Ala Thr Tyr Tyr
                85                  90                  95

Cys Ala His Thr Gly Gly Ala Val Ile Thr Trp Phe Ala Tyr Trp Gly
            100                 105                 110

Gln Gly Thr Leu Val Thr Val Ser Ser
        115                 120

<210> SEQ ID NO 104
<211> LENGTH: 121
<212> TYPE: PRT
<213> ORGANISM: Artificial Sequence
<220> FEATURE:
<223> OTHER INFORMATION: Synthetic Construct

<400> SEQUENCE: 104

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Ser Trp Ile Arg Gln Pro Pro Gly Lys Ala Leu Glu
        35                  40                  45

Trp Leu Ala Ser Ile Trp Trp Asn Gly Asn Thr Tyr Tyr Asn Pro Ser
    50                  55                  60

Leu Lys Ser Arg Leu Thr Ile Thr Lys Asp Ala Ser Lys Asn Gln Ala
65                  70                  75                  80

Val Leu Thr Met Thr Asn Met Asp Pro Val Asp Thr Ala Thr Tyr Tyr
                85                  90                  95

Cys Ala His Thr Gly Gly Ala Val Ile Thr Trp Phe Ala Tyr Trp Gly
            100                 105                 110

Gln Gly Thr Leu Val Thr Val Ser Ser
        115                 120

<210> SEQ ID NO 105
<211> LENGTH: 121
<212> TYPE: PRT
<213> ORGANISM: Artificial Sequence
<220> FEATURE:
<223> OTHER INFORMATION: Synthetic Construct

<400> SEQUENCE: 105

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Ser Trp Ile Arg Gln Pro Pro Gly Lys Ala Leu Glu
        35                  40                  45

-continued

Trp Leu Ala Ser Ile Trp Trp Asn Gly Asn Thr Tyr Tyr Asn Pro Ser
         50                  55                  60

Leu Lys Ser Arg Leu Thr Val Thr Lys Asp Thr Ser Lys Asn Gln Ala
 65                  70                  75                  80

Val Leu Thr Met Thr Asn Met Asp Pro Val Asp Thr Ala Thr Tyr Tyr
                 85                  90                  95

Cys Ala His Thr Gly Gly Ala Val Ile Thr Trp Phe Ala Tyr Trp Gly
                100                 105                 110

Gln Gly Thr Leu Val Thr Val Ser Ser
            115                 120

<210> SEQ ID NO 106
<211> LENGTH: 121
<212> TYPE: PRT
<213> ORGANISM: Artificial Sequence
<220> FEATURE:
<223> OTHER INFORMATION: Synthetic Construct

<400> SEQUENCE: 106

Glu Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Tyr
                 20                  25                  30

Gly Met Gly Val Ser Trp Ile Arg Gln Pro Pro Gly Lys Ala Leu Glu
             35                  40                  45

Trp Leu Ala Ser Ile Trp Trp Asn Gly Asn Thr Tyr Tyr Asn Pro Ser
 50                  55                  60

Leu Lys Ser Arg Leu Thr Val Thr Lys Asp Ala Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Thr Gly Gly Ala Val Ile Thr Trp Phe Ala Tyr Trp Gly
                100                 105                 110

Gln Gly Thr Leu Val Thr Val Ser Ser
            115                 120

<210> SEQ ID NO 107
<211> LENGTH: 121
<212> TYPE: PRT
<213> ORGANISM: Artificial Sequence
<220> FEATURE:
<223> OTHER INFORMATION: Synthetic Construct

<400> SEQUENCE: 107

Glu Val Thr Leu Lys Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Tyr
                 20                  25                  30

Gly Met Gly Val Ser Trp Ile Arg Gln Pro Pro Gly Lys Ala Leu Glu
             35                  40                  45

Trp Leu Ala Ser Ile Trp Trp Asn Gly Asn Thr Tyr Tyr Asn Pro Ser
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala His Thr Gly Gly Ala Val Ile Thr Trp Phe Ala Tyr Trp Gly
                100                 105                 110

```
Gln Gly Thr Leu Val Thr Val Ser Ser
        115                 120

<210> SEQ ID NO 108
<211> LENGTH: 107
<212> TYPE: PRT
<213> ORGANISM: Artificial Sequence
<220> FEATURE:
<223> OTHER INFORMATION: Synthetic Construct

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Gly Lys Asn
            20                  25                  30

Ile Ala Trp Tyr Gln Gln Lys Pro Gly Lys Ser Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Ile Tyr Asn Ser Pro Tyr
                85                  90                  95

Pro Phe Gly Gln Gly Thr Lys Val Glu Ile Lys
            100                 105

<210> SEQ ID NO 109
<211> LENGTH: 107
<212> TYPE: PRT
<213> ORGANISM: Artificial Sequence
<220> FEATURE:
<223> OTHER INFORMATION: Synthetic Construct

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Gly Lys Asn
            20                  25                  30

Ile Ala Trp Tyr Gln Gln Lys Pro Gly Lys Ala Pro Lys Leu Leu Ile
        35                  40                  45

Tyr Tyr Ala Ser Asn Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln His Ile Tyr Asn Ser Pro Tyr
                85                  90                  95

Pro Phe Gly Gln Gly Thr Lys Val Glu Ile Lys
            100                 105

<210> SEQ ID NO 110
<211> LENGTH: 7
<212> TYPE: PRT
<213> ORGANISM: Rattus norvegicus

<400> SEQUENCE: 110

Thr Tyr Gly Met Gly Val Ser
1               5

<210> SEQ ID NO 111
```

```
<211> LENGTH: 16
<212> TYPE: PRT
<213> ORGANISM: Rattus norvegicus

<400> SEQUENCE: 111

Ser Ile Trp Trp Asn Gly Asn Thr Tyr Tyr Asn Pro Ser Leu Arg Ser
1               5                   10                  15

<210> SEQ ID NO 112
<211> LENGTH: 11
<212> TYPE: PRT
<213> ORGANISM: Rattus norvegicus

<400> SEQUENCE: 112

Thr Gly Gly Ala Val Ile Thr Trp Phe Ala Tyr
1               5                   10

<210> SEQ ID NO 113
<211> LENGTH: 11
<212> TYPE: PRT
<213> ORGANISM: Rattus norvegicus

<400> SEQUENCE: 113

Lys Ala Ser Gln Ser Val Gly Lys Asn Ile Ala
1               5                   10

<210> SEQ ID NO 114
<211> LENGTH: 7
<212> TYPE: PRT
<213> ORGANISM: Rattus norvegicus

<400> SEQUENCE: 114

Tyr Ala Ser Asn Arg Tyr Thr
1               5

<210> SEQ ID NO 115
<211> LENGTH: 9
<212> TYPE: PRT
<213> ORGANISM: Rattus norvegicus

<400> SEQUENCE: 115

Gln His Ile Tyr Asn Ser Pro Tyr Pro
1               5

<210> SEQ ID NO 116
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Glu or Gln
<220> FEATURE:
<221> NAME/KEY: MOD_RES
<222> LOCATION: (3)..(3)
<223> OTHER INFORMATION: Xaa is Ser or Thr
<220> FEATURE:
<221> NAME/KEY: MOD_RES
<222> LOCATION: (10)..(10)
<223> OTHER INFORMATION: Xaa is Ala or Gly
<220> FEATURE:
<221> NAME/KEY: MOD_RES
<222> LOCATION: (11)..(11)
<223> OTHER INFORMATION: Xaa is Ile or Leu
<220> FEATURE:
<221> NAME/KEY: MOD_RES
<222> LOCATION: (12)..(12)
```

```
<223> OTHER INFORMATION: Xaa is Leu or Val
<220> FEATURE:
<221> NAME/KEY: MOD_RES
<222> LOCATION: (13)..(13)
<223> OTHER INFORMATION: Xaa is Lys or Gln
<220> FEATURE:
<221> NAME/KEY: MOD_RES
<222> LOCATION: (15)..(15)
<223> OTHER INFORMATION: Xaa is Ser or Thr
<220> FEATURE:
<221> NAME/KEY: MOD_RES
<222> LOCATION: (16)..(16)
<223> OTHER INFORMATION: Xaa is His or Gln
<220> FEATURE:
<221> NAME/KEY: MOD_RES
<222> LOCATION: (19)..(19)
<223> OTHER INFORMATION: Xaa is Ser or Thr
<220> FEATURE:
<221> NAME/KEY: MOD_RES
<222> LOCATION: (23)..(23)
<223> OTHER INFORMATION: Xaa is Ser or Thr

<400> SEQUENCE: 116

Xaa Val Xaa Leu Lys Glu Ser Gly Pro Xaa Xaa Xaa Xaa Pro Xaa Xaa
1               5                   10                  15

Thr Leu Xaa Leu Thr Cys Xaa Phe Ser Gly Phe Ser Leu Thr
            20                  25                  30

<210> SEQ ID NO 117
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Pro or Ser
<220> FEATURE:
<221> NAME/KEY: MOD_RES
<222> LOCATION: (7)..(7)
<223> OTHER INFORMATION: Xaa is Glu or Gly
<220> FEATURE:
<221> NAME/KEY: MOD_RES
<222> LOCATION: (9)..(9)
<223> OTHER INFORMATION: Xaa is Ala or Gly

<400> SEQUENCE: 117

Trp Ile Arg Gln Pro Xaa Xaa Lys Xaa Leu Glu Trp Leu Ala
1               5                   10

<210> SEQ ID NO 118
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Ile or Val
<220> FEATURE:
<221> NAME/KEY: MOD_RES
<222> LOCATION: (5)..(5)
<223> OTHER INFORMATION: Xaa is Ser or Thr
<220> FEATURE:
<221> NAME/KEY: MOD_RES
<222> LOCATION: (10)..(10)
<223> OTHER INFORMATION: Xaa is Lys or Asn
<220> FEATURE:
<221> NAME/KEY: MOD_RES
<222> LOCATION: (11)..(11)
<223> OTHER INFORMATION: Xaa is Asp or Asn
<220> FEATURE:
```

```
<221> NAME/KEY: MOD_RES
<222> LOCATION: (13)..(13)
<223> OTHER INFORMATION: Xaa is Ala or Val
<220> FEATURE:
<221> NAME/KEY: MOD_RES
<222> LOCATION: (14)..(14)
<223> OTHER INFORMATION: Xaa is Phe or Val
<220> FEATURE:
<221> NAME/KEY: MOD_RES
<222> LOCATION: (16)..(16)
<223> OTHER INFORMATION: Xaa is Asn or Thr
<220> FEATURE:
<221> NAME/KEY: MOD_RES
<222> LOCATION: (17)..(17)
<223> OTHER INFORMATION: Xaa is Met or Val
<220> FEATURE:
<221> NAME/KEY: MOD_RES
<222> LOCATION: (19)..(19)
<223> OTHER INFORMATION: Xaa is Asn or Ser
<220> FEATURE:
<221> NAME/KEY: MOD_RES
<222> LOCATION: (20)..(20)
<223> OTHER INFORMATION: Xaa is Met or Val
<220> FEATURE:
<221> NAME/KEY: MOD_RES
<222> LOCATION: (22)..(22)
<223> OTHER INFORMATION: Xaa is Pro or Thr
<220> FEATURE:
<221> NAME/KEY: MOD_RES
<222> LOCATION: (23)..(23)
<223> OTHER INFORMATION: Xaa is Thr or Val

<400> SEQUENCE: 118

Arg Leu Thr Xaa Xaa Lys Asp Thr Ser Xaa Xaa Gln Xaa Xaa Leu Xaa
1               5                   10                  15

Xaa Thr Xaa Xaa Asp Xaa Xaa Asp Thr Ala Thr Tyr Tyr Cys Ala His
            20                  25                  30

<210> SEQ ID NO 119
<211> LENGTH: 11
<212> TYPE: PRT
<213> ORGANISM: Artificial Sequence
<220> FEATURE:
<223> OTHER INFORMATION: Synthetic Construct

<400> SEQUENCE: 119

Trp Gly Gln Gly Thr Leu Val Thr Val Ser Ser
1               5                   10

<210> SEQ ID NO 120
<211> LENGTH: 30
<212> TYPE: PRT
<213> ORGANISM: Rattus norvegicus

<400> SEQUENCE: 120

Gln Val Ser Leu Lys Glu Ser Gly Pro Gly Ile Leu Gln Pro Ser His
1               5                   10                  15

Thr Leu Ser Leu Thr Cys Ser Phe Ser Gly Phe Ser Leu Thr
            20                  25                  30

<210> SEQ ID NO 121
<211> LENGTH: 14
<212> TYPE: PRT
<213> ORGANISM: Rattus norvegicus

<400> SEQUENCE: 121

Trp Ile Arg Gln Pro Ser Glu Lys Gly Leu Glu Trp Leu Ala
1               5                   10
```

```
<210> SEQ ID NO 122
<211> LENGTH: 32
<212> TYPE: PRT
<213> ORGANISM: Rattus norvegicus

<400> SEQUENCE: 122

Arg Leu Thr Val Ser Lys Asp Thr Ser Asn Asp Gln Ala Phe Leu Asn
1               5                   10                  15

Val Thr Ser Val Asp Thr Thr Asp Thr Ala Thr Tyr Tyr Cys Ala His
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Synthetic Construct

<400> SEQUENCE: 123

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr
            20                  25                  30

<210> SEQ ID NO 124
<211> LENGTH: 14
<212> TYPE: PRT
<213> ORGANISM: Artificial Sequence
<220> FEATURE:
<223> OTHER INFORMATION: Synthetic Construct

<400> SEQUENCE: 124

Trp Ile Arg Gln Pro Pro Gly Lys Ala Leu Glu Trp Leu Ala
1               5                   10

<210> SEQ ID NO 125
<211> LENGTH: 32
<212> TYPE: PRT
<213> ORGANISM: Artificial Sequence
<220> FEATURE:
<223> OTHER INFORMATION: Synthetic Construct

<400> SEQUENCE: 125

Arg Leu Thr Val Thr Lys Asp Thr Ser Lys Asn Gln Ala Val Leu Thr
1               5                   10                  15

Met Thr Asn Met Asp Pro Val Asp Thr Ala Thr Tyr Tyr Cys Ala His
            20                  25                  30

<210> SEQ ID NO 126
<211> LENGTH: 32
<212> TYPE: PRT
<213> ORGANISM: Artificial Sequence
<220> FEATURE:
<223> OTHER INFORMATION: Synthetic Construct

<400> SEQUENCE: 126

Arg Leu Thr Ile Thr Lys Asp Thr Ser Lys Asn Gln Ala Val Leu Thr
1               5                   10                  15

Met Thr Asn Met Asp Pro Val Asp Thr Ala Thr Tyr Tyr Cys Ala His
            20                  25                  30

<210> SEQ ID NO 127
<211> LENGTH: 32
<212> TYPE: PRT
<213> ORGANISM: Artificial Sequence
```

```
<220> FEATURE:
<223> OTHER INFORMATION: Synthetic Construct

<400> SEQUENCE: 127

Arg Leu Thr Val Thr Lys Asp Thr Ser Lys Asn Gln Val Val Leu Thr
1               5                   10                  15

Met Thr Asn Met Asp Pro Val Asp Thr Ala Thr Tyr Tyr Cys Ala His
            20                  25                  30

<210> SEQ ID NO 128
<211> LENGTH: 32
<212> TYPE: PRT
<213> ORGANISM: Artificial Sequence
<220> FEATURE:
<223> OTHER INFORMATION: Synthetic Construct

<400> SEQUENCE: 128

Arg Leu Thr Ile Thr Lys Asp Thr Ser Lys Asn Gln Val Val Leu Thr
1               5                   10                  15

Met Thr Asn Met Asp Pro Val Asp Thr Ala Thr Tyr Tyr Cys Ala His
            20                  25                  30

<210> SEQ ID NO 129
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Glu or Asn
<220> FEATURE:
<221> NAME/KEY: MOD_RES
<222> LOCATION: (9)..(9)
<223> OTHER INFORMATION: Xaa is Ala or Lys
<220> FEATURE:
<221> NAME/KEY: MOD_RES
<222> LOCATION: (10)..(10)
<223> OTHER INFORMATION: Xaa is Ser or Thr
<220> FEATURE:
<221> NAME/KEY: MOD_RES
<222> LOCATION: (11)..(11)
<223> OTHER INFORMATION: Xaa is Leu or Met
<220> FEATURE:
<221> NAME/KEY: MOD_RES
<222> LOCATION: (13)..(13)
<223> OTHER INFORMATION: Xaa is Ile or Val
<220> FEATURE:
<221> NAME/KEY: MOD_RES
<222> LOCATION: (15)..(15)
<223> OTHER INFORMATION: Xaa is Ile or Pro
<220> FEATURE:
<221> NAME/KEY: MOD_RES
<222> LOCATION: (17)..(17)
<223> OTHER INFORMATION: Xaa is Asp or Glu
<220> FEATURE:
<221> NAME/KEY: MOD_RES
<222> LOCATION: (19)..(19)
<223> OTHER INFORMATION: Xaa is Ala or Val
<220> FEATURE:
<221> NAME/KEY: MOD_RES
<222> LOCATION: (21)..(21)
<223> OTHER INFORMATION: Xaa is Leu or Met
<220> FEATURE:
<221> NAME/KEY: MOD_RES
<222> LOCATION: (22)..(22)
<223> OTHER INFORMATION: Xaa is Asn or Ser

<400> SEQUENCE: 129

Xaa Ile Val Met Thr Gln Ser Pro Xaa Xaa Xaa Ser Xaa Ser Xaa Gly
1               5                   10                  15
```

```
Xaa Arg Xaa Thr Xaa Xaa Cys
            20

<210> SEQ ID NO 130
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Pro or Thr
<220> FEATURE:
<221> NAME/KEY: MOD_RES
<222> LOCATION: (9)..(9)
<223> OTHER INFORMATION: Xaa is Ala or Ser
<220> FEATURE:
<221> NAME/KEY: MOD_RES
<222> LOCATION: (11)..(11)
<223> OTHER INFORMATION: Xaa is Gln or Arg

<400> SEQUENCE: 130

Trp Tyr Gln Gln Lys Xaa Gly Gln Xaa Pro Xaa Leu Leu Ile Tyr
1               5                   10                  15

<210> SEQ ID NO 131
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ile or Val
<220> FEATURE:
<221> NAME/KEY: MOD_RES
<222> LOCATION: (4)..(4)
<223> OTHER INFORMATION: Xaa is Ala or Asp
<220> FEATURE:
<221> NAME/KEY: MOD_RES
<222> LOCATION: (7)..(7)
<223> OTHER INFORMATION: Xaa is Ser or Thr
<220> FEATURE:
<221> NAME/KEY: MOD_RES
<222> LOCATION: (9)..(9)
<223> OTHER INFORMATION: Xaa is Gly or Ser
<220> FEATURE:
<221> NAME/KEY: MOD_RES
<222> LOCATION: (14)..(14)
<223> OTHER INFORMATION: Xaa is Asp or Glu
<220> FEATURE:
<221> NAME/KEY: MOD_RES
<222> LOCATION: (20)..(20)
<223> OTHER INFORMATION: Xaa is Asn or Ser
<220> FEATURE:
<221> NAME/KEY: MOD_RES
<222> LOCATION: (22)..(22)
<223> OTHER INFORMATION: Xaa is Leu or Val
<220> FEATURE:
<221> NAME/KEY: MOD_RES
<222> LOCATION: (24)..(24)
<223> OTHER INFORMATION: Xaa is Ala or Ser
<220> FEATURE:
<221> NAME/KEY: MOD_RES
<222> LOCATION: (27)..(27)
<223> OTHER INFORMATION: Xaa is Ala or Phe
<220> FEATURE:
<221> NAME/KEY: MOD_RES
<222> LOCATION: (29)..(29)
<223> OTHER INFORMATION: Xaa is Phe or Val
<220> FEATURE:
<221> NAME/KEY: MOD_RES
<222> LOCATION: (30)..(30)
```

<223> OTHER INFORMATION: Xaa is Phe or Tyr

<400> SEQUENCE: 131

Gly Xaa Pro Xaa Arg Phe Xaa Gly Xaa Gly Ser Gly Thr Xaa Phe Thr
1               5                   10                  15

Leu Thr Ile Xaa Ser Xaa Gln Xaa Glu Asp Xaa Ala Xaa Xaa Tyr Cys
            20                  25                  30

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Gln or Thr
<220> FEATURE:
<221> NAME/KEY: MOD_RES
<222> LOCATION: (7)..(7)
<223> OTHER INFORMATION: Xaa is Leu or Val

<400> SEQUENCE: 132

Phe Gly Xaa Gly Thr Lys Xaa Glu Ile Lys
1               5                   10

<210> SEQ ID NO 133
<211> LENGTH: 23
<212> TYPE: PRT
<213> ORGANISM: Rattus norvegicus

<400> SEQUENCE: 133

Asn Ile Val Met Thr Gln Ser Pro Lys Ser Met Ser Ile Ser Ile Gly
1               5                   10                  15

Asp Arg Val Thr Met Asn Cys
            20

<210> SEQ ID NO 134
<211> LENGTH: 15
<212> TYPE: PRT
<213> ORGANISM: Rattus norvegicus

<400> SEQUENCE: 134

Trp Tyr Gln Gln Lys Thr Gly Gln Ser Pro Gln Leu Leu Ile Tyr
1               5                   10                  15

<210> SEQ ID NO 135
<211> LENGTH: 32
<212> TYPE: PRT
<213> ORGANISM: Rattus norvegicus

<400> SEQUENCE: 135

Gly Val Pro Asp Arg Phe Thr Gly Gly Gly Ser Gly Thr Asp Phe Thr
1               5                   10                  15

Leu Thr Ile Asn Ser Val Gln Ala Glu Asp Ala Ala Phe Phe Tyr Cys
            20                  25                  30

<210> SEQ ID NO 136
<211> LENGTH: 10
<212> TYPE: PRT
<213> ORGANISM: Rattus norvegicus

<400> SEQUENCE: 136

Phe Gly Thr Gly Thr Lys Leu Glu Ile Lys
1               5                   10

<210> SEQ ID NO 137
<211> LENGTH: 23
<212> TYPE: PRT
<213> ORGANISM: Artificial Sequence
<220> FEATURE:
<223> OTHER INFORMATION: Synthetic Construct

<400> SEQUENCE: 137

Glu Ile Val Met Thr Gln Ser Pro Ala Thr Leu Ser Val Ser Pro Gly
1               5                   10                  15

Glu Arg Ala Thr Leu Ser Cys
            20

<210> SEQ ID NO 138
<211> LENGTH: 15
<212> TYPE: PRT
<213> ORGANISM: Artificial Sequence
<220> FEATURE:
<223> OTHER INFORMATION: Synthetic Construct

<400> SEQUENCE: 138

Trp Tyr Gln Gln Lys Pro Gly Gln Ser Pro Arg Leu Leu Ile Tyr
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: Synthetic Construct

<400> SEQUENCE: 139

Trp Tyr Gln Gln Lys Pro Gly Gln Ala Pro Arg Leu Leu Ile Tyr
1               5                   10                  15

<210> SEQ ID NO 140
<211> LENGTH: 32
<212> TYPE: PRT
<213> ORGANISM: Artificial Sequence
<220> FEATURE:
<223> OTHER INFORMATION: Synthetic Construct

<400> SEQUENCE: 140

Gly Val Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 141
<211> LENGTH: 32
<212> TYPE: PRT
<213> ORGANISM: Artificial Sequence
<220> FEATURE:
<223> OTHER INFORMATION: Synthetic Construct

<400> SEQUENCE: 141

Gly Ile Pro Ala Arg Phe Ser Gly Ser Gly Ser Gly Thr Glu Phe Thr
1               5                   10                  15

Leu Thr Ile Ser Ser Leu Gln Ser Glu Asp Phe Ala Val Tyr Tyr Cys
            20                  25                  30

<210> SEQ ID NO 142
<211> LENGTH: 10

```
<212> TYPE: PRT
<213> ORGANISM: Artificial Sequence
<220> FEATURE:
<223> OTHER INFORMATION: Synthetic Construct

<400> SEQUENCE: 142

Phe Gly Gln Gly Thr Lys Val Glu Ile Lys
1               5                   10

<210> SEQ ID NO 143
<211> LENGTH: 121
<212> TYPE: PRT
<213> ORGANISM: Rattus norvegicus

<400> SEQUENCE: 143

Gln Val Ser Leu Lys Glu Ser Gly Pro Gly Ile Leu Gln Pro Ser His
1               5                   10                  15

Thr Leu Ser Leu Thr Cys Ser Phe Ser Gly Phe Ser Leu Thr Thr Tyr
                20                  25                  30

Gly Met Gly Val Ser Trp Ile Arg Gln Pro Ser Glu Lys Gly Leu Glu
            35                  40                  45

Trp Leu Ala Ser Ile Trp Trp Asn Gly Asn Thr Tyr Tyr Asn Pro Ser
    50                  55                  60

Leu Arg Ser Arg Leu Thr Val Ser Lys Asp Thr Ser Asn Asp Gln Ala
65                  70                  75                  80

Phe Leu Asn Val Thr Ser Val Asp Thr Thr Asp Thr Ala Thr Tyr Tyr
                85                  90                  95

Cys Ala His Thr Gly Gly Ala Val Ile Thr Trp Phe Ala Tyr Trp Gly
            100                 105                 110

Gln Gly Thr Leu Val Thr Val Ser Ser
        115                 120

<210> SEQ ID NO 144
<211> LENGTH: 107
<212> TYPE: PRT
<213> ORGANISM: Rattus norvegicus

<400> SEQUENCE: 144

Asn Ile Val Met Thr Gln Ser Pro Lys Ser Met Ser Ile Ser Ile Gly
1               5                   10                  15

Asp Arg Val Thr Met Asn Cys Lys Ala Ser Gln Ser Val Gly Lys Asn
                20                  25                  30

Ile Ala Trp Tyr Gln Gln Lys Thr Gly Gln Ser Pro Gln Leu Leu Ile
            35                  40                  45

Tyr Tyr Ala Ser Asn Arg Tyr Thr Gly Val Pro Asp Arg Phe Thr Gly
    50                  55                  60

Gly Gly Ser Gly Thr Asp Phe Thr Leu Thr Ile Asn Ser Val Gln Ala
65                  70                  75                  80

Glu Asp Ala Ala Phe Phe Tyr Cys Gln His Ile Tyr Asn Ser Pro Tyr
                85                  90                  95

Pro Phe Gly Thr Gly Thr Lys Leu Glu Ile Lys
            100                 105

<210> SEQ ID NO 145
<211> LENGTH: 121
<212> TYPE: PRT
<213> ORGANISM: Artificial Sequence
<220> FEATURE:
<223> OTHER INFORMATION: Synthetic Construct
```

<400> SEQUENCE: 145

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Ser Trp Ile Arg Gln Pro Pro Gly Lys Ala Leu Glu
        35                  40                  45

Trp Leu Ala Ser Ile Trp Trp Asn Gly Asn Thr Tyr Tyr Asn Pro Ser
    50                  55                  60

Leu Arg Ser Arg Leu Thr Val Thr Lys Asp Thr Ser Lys Asn Gln Ala
65                  70                  75                  80

Val Leu Thr Met Thr Asn Met Asp Pro Val Asp Thr Ala Thr Tyr Tyr
                85                  90                  95

Cys Ala His Thr Gly Gly Ala Val Ile Thr Phe Ala Tyr Trp Gly
            100                 105                 110

Gln Gly Thr Leu Val Thr Val Ser Ser
            115                 120

<210> SEQ ID NO 146
<211> LENGTH: 121
<212> TYPE: PRT
<213> ORGANISM: Artificial Sequence
<220> FEATURE:
<223> OTHER INFORMATION: Synthetic Construct

<400> SEQUENCE: 146

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Ser Trp Ile Arg Gln Pro Pro Gly Lys Ala Leu Glu
        35                  40                  45

Trp Leu Ala Ser Ile Trp Trp Asn Gly Asn Thr Tyr Tyr Asn Pro Ser
    50                  55                  60

Leu Arg Ser Arg Leu Thr Ile Thr Lys Asp Thr Ser Lys Asn Gln Ala
65                  70                  75                  80

Val Leu Thr Met Thr Asn Met Asp Pro Val Asp Thr Ala Thr Tyr Tyr
                85                  90                  95

Cys Ala His Thr Gly Gly Ala Val Ile Thr Phe Ala Tyr Trp Gly
            100                 105                 110

Gln Gly Thr Leu Val Thr Val Ser Ser
            115                 120

<210> SEQ ID NO 147
<211> LENGTH: 121
<212> TYPE: PRT
<213> ORGANISM: Artificial Sequence
<220> FEATURE:
<223> OTHER INFORMATION: Synthetic Construct

<400> SEQUENCE: 147

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
            20                  25                  30

Gly Met Gly Val Ser Trp Ile Arg Gln Pro Pro Gly Lys Ala Leu Glu
        35                  40                  45

Trp Leu Ala Ser Ile Trp Trp Asn Gly Asn Thr Tyr Tyr Asn Pro Ser
    50                  55                  60

Leu Arg Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Thr Gly Gly Ala Val Ile Thr Trp Phe Ala Tyr Trp Gly
            100                 105                 110

Gln Gly Thr Leu Val Thr Val Ser Ser
            115                 120

<210> SEQ ID NO 148
<211> LENGTH: 121
<212> TYPE: PRT
<213> ORGANISM: Artificial Sequence
<220> FEATURE:
<223> OTHER INFORMATION: Synthetic Construct

<400> SEQUENCE: 148

Glu Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Thr Thr Tyr
                20                  25                  30

Gly Met Gly Val Ser Trp Ile Arg Gln Pro Pro Gly Lys Ala Leu Glu
            35                  40                  45

Trp Leu Ala Ser Ile Trp Trp Asn Gly Asn Thr Tyr Tyr Asn Pro Ser
    50                  55                  60

Leu Arg Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Thr Gly Gly Ala Val Ile Thr Trp Phe Ala Tyr Trp Gly
            100                 105                 110

Gln Gly Thr Leu Val Thr Val Ser Ser
            115                 120

<210> SEQ ID NO 149
<211> LENGTH: 107
<212> TYPE: PRT
<213> ORGANISM: Artificial Sequence
<220> FEATURE:
<223> OTHER INFORMATION: Synthetic Construct

<400> SEQUENCE: 149

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Gly Lys Asn
                20                  25                  30

Ile Ala Trp Tyr Gln Gln Lys Pro Gly Gln Ser Pro Arg Leu Leu Ile
            35                  40                  45

Tyr Tyr Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Ile Tyr Asn Ser Pro Tyr
                85                  90                  95

Pro Phe Gly Gln Gly Thr Lys Val Glu Ile Lys
            100                 105

<210> SEQ ID NO 150
<211> LENGTH: 107
<212> TYPE: PRT
<213> ORGANISM: Artificial Sequence
<220> FEATURE:
<223> OTHER INFORMATION: Synthetic Construct

<400> SEQUENCE: 150

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Gly Lys Asn
            20                  25                  30

Ile Ala Trp Tyr Gln Gln Lys Pro Gly Gln Ala Pro Arg Leu Leu Ile
        35                  40                  45

Tyr Tyr Ala Ser Asn Arg Tyr Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Ile Tyr Asn Ser Pro Tyr
                85                  90                  95

Pro Phe Gly Gln Gly Thr Lys Val Glu Ile Lys
            100                 105

<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Gly Lys Asn
            20                  25                  30

Ile Ala Trp Tyr Gln Gln Lys Pro Gly Gln Ser Pro Arg Leu Leu Ile
        35                  40                  45

Tyr Tyr Ala Ser Asn Arg Tyr Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Ile Tyr Asn Ser Pro Tyr
                85                  90                  95

Pro Phe Gly Gln Gly Thr Lys Val Glu Ile Lys
            100                 105

<210> SEQ ID NO 152
<211> LENGTH: 107
<212> TYPE: PRT
<213> ORGANISM: Artificial Sequence
<220> FEATURE:
<223> OTHER INFORMATION: Synthetic Construct

<400> SEQUENCE: 152

Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Ser Val Gly Lys Asn
            20                  25                  30

```
Ile Ala Trp Tyr Gln Gln Lys Pro Gly Gln Ala Pro Arg Leu Leu Ile
            35                  40                  45

Tyr Tyr Ala Ser Asn Arg Tyr Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln His Ile Tyr Asn Ser Pro Tyr
                 85                  90                  95

Pro Phe Gly Gln Gly Thr Lys Val Glu Ile Lys
            100                 105
```

<210> SEQ ID NO 153
<211> LENGTH: 5
<212> TYPE: PRT
<213> ORGANISM: Rattus norvegicus

<400> SEQUENCE: 153

```
Glu Tyr Ser Ile Tyr
 1               5
```

<210> SEQ ID NO 154
<211> LENGTH: 17
<212> TYPE: PRT
<213> ORGANISM: Rattus norvegicus

<400> SEQUENCE: 154

```
Arg Ile Asp Pro Lys Asn Gly Arg Thr Tyr Tyr Val Asp Lys Phe Lys
 1               5                  10                  15

Asn
```

<210> SEQ ID NO 155
<211> LENGTH: 8
<212> TYPE: PRT
<213> ORGANISM: Rattus norvegicus

<400> SEQUENCE: 155

```
Ile Tyr Gly Phe Tyr Phe Asp Phe
 1               5
```

<210> SEQ ID NO 156
<211> LENGTH: 11
<212> TYPE: PRT
<213> ORGANISM: Rattus norvegicus

<400> SEQUENCE: 156

```
Lys Gly Ser Gln Asn Val Asn Lys Tyr Leu Val
 1               5                  10
```

<210> SEQ ID NO 157
<211> LENGTH: 7
<212> TYPE: PRT
<213> ORGANISM: Rattus norvegicus

<400> SEQUENCE: 157

```
Asn Thr Asp Asn Leu Gln Ser
 1               5
```

<210> SEQ ID NO 158
<211> LENGTH: 8
<212> TYPE: PRT
<213> ORGANISM: Rattus norvegicus

<400> SEQUENCE: 158

Tyr Gln Tyr Asn Asn Gly Phe Thr
1               5

<210> SEQ ID NO 159
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Gln or Val
<220> FEATURE:
<221> NAME/KEY: MOD_RES
<222> LOCATION: (9)..(9)
<223> OTHER INFORMATION: Xaa is Ala or Pro
<220> FEATURE:
<221> NAME/KEY: MOD_RES
<222> LOCATION: (11)..(11)
<223> OTHER INFORMATION: Xaa is Leu or Val
<220> FEATURE:
<221> NAME/KEY: MOD_RES
<222> LOCATION: (12)..(12)
<223> OTHER INFORMATION: Xaa is Lys or Gln
<220> FEATURE:
<221> NAME/KEY: MOD_RES
<222> LOCATION: (13)..(13)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Leu or Val
<220> FEATURE:
<221> NAME/KEY: MOD_RES
<222> LOCATION: (25)..(25)
<223> OTHER INFORMATION: Xaa is Ser or Thr

<400> SEQUENCE: 159

Glu Val Gln Leu Xaa Gln Ser Gly Xaa Glu Xaa Xaa Xaa Pro Gly Ala
1               5                   10                  15

Ser Val Lys Xaa Ser Cys Lys Ala Xaa Gly Tyr Thr Phe Thr
            20                  25                  30

<210> SEQ ID NO 160
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Lys or Arg
<220> FEATURE:
<221> NAME/KEY: MOD_RES
<222> LOCATION: (5)..(5)
<223> OTHER INFORMATION: Xaa is Ala or Arg
<220> FEATURE:
<221> NAME/KEY: MOD_RES
<222> LOCATION: (7)..(7)
<223> OTHER INFORMATION: Xaa is Gly or Lys
<220> FEATURE:
<221> NAME/KEY: MOD_RES
<222> LOCATION: (9)..(9)
<223> OTHER INFORMATION: Xaa is Arg or Ser
<220> FEATURE:
<221> NAME/KEY: MOD_RES
<222> LOCATION: (12)..(12)
<223> OTHER INFORMATION: Xaa is Ile or Trp
<220> FEATURE:
<221> NAME/KEY: MOD_RES
<222> LOCATION: (13)..(13)
<223> OTHER INFORMATION: Xaa is Ile or Met

<400> SEQUENCE: 160

Trp Val Xaa Gln Xaa Pro Xaa Gln Xaa Leu Glu Xaa Xaa Gly
1               5                   10

<210> SEQ ID NO 161
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ala or Val
<220> FEATURE:
<221> NAME/KEY: MOD_RES
<222> LOCATION: (4)..(4)
<223> OTHER INFORMATION: Xaa is Ile or Leu
<220> FEATURE:
<221> NAME/KEY: MOD_RES
<222> LOCATION: (6)..(6)
<223> OTHER INFORMATION: Xaa is Ala or Arg
<220> FEATURE:
<221> NAME/KEY: MOD_RES
<222> LOCATION: (10)..(10)
<223> OTHER INFORMATION: Xaa is Ala or Ser
<220> FEATURE:
<221> NAME/KEY: MOD_RES
<222> LOCATION: (11)..(11)
<223> OTHER INFORMATION: Xaa is Asn or Ser
<220> FEATURE:
<221> NAME/KEY: MOD_RES
<222> LOCATION: (16)..(16)
<223> OTHER INFORMATION: Xaa is Glu or Gln
<220> FEATURE:
<221> NAME/KEY: MOD_RES
<222> LOCATION: (21)..(21)
<223> OTHER INFORMATION: Xaa is Arg or Thr
<220> FEATURE:
<221> NAME/KEY: MOD_RES
<222> LOCATION: (27)..(27)
<223> OTHER INFORMATION: Xaa is Thr or Val
<220> FEATURE:
<221> NAME/KEY: MOD_RES
<222> LOCATION: (29)..(29)
<223> OTHER INFORMATION: Xaa is Phe or Tyr
<220> FEATURE:
<221> NAME/KEY: MOD_RES
<222> LOCATION: (31)..(31)
<223> OTHER INFORMATION: Xaa is Ala or Thr

<400> SEQUENCE: 161

Arg Xaa Thr Xaa Thr Xaa Asp Thr Ser Xaa Xaa Thr Ala Tyr Met Xaa
1               5                   10                  15

Leu Ser Ser Leu Xaa Ser Glu Asp Thr Ala Xaa Tyr Xaa Cys Xaa Arg
                20                  25                  30

<210> SEQ ID NO 162
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Thr or Val
<220> FEATURE:
<221> NAME/KEY: MOD_RES
<222> LOCATION: (6)..(6)
<223> OTHER INFORMATION: Xaa is Leu or Met
<220> FEATURE:
<221> NAME/KEY: MOD_RES
<222> LOCATION: (9)..(9)
<223> OTHER INFORMATION: Xaa is Ala or Val

<400> SEQUENCE: 162

Trp Gly Gln Gly Xaa Xaa Val Thr Xaa Ser Ser
1               5                   10

<210> SEQ ID NO 163
<211> LENGTH: 30
<212> TYPE: PRT
<213> ORGANISM: Rattus norvegicus

<400> SEQUENCE: 163

Glu Val Gln Leu Gln Gln Ser Gly Pro Glu Leu Gln Arg Pro Gly Ala
1               5                   10                  15

Ser Val Lys Leu Ser Cys Lys Ala Thr Gly Tyr Thr Phe Thr
            20                  25                  30

<210> SEQ ID NO 164
<211> LENGTH: 14
<212> TYPE: PRT
<213> ORGANISM: Rattus norvegicus

<400> SEQUENCE: 164

Trp Val Lys Gln Arg Pro Lys Gln Ser Leu Glu Ile Ile Gly
1               5                   10

<210> SEQ ID NO 165
<211> LENGTH: 32
<212> TYPE: PRT
<213> ORGANISM: Rattus norvegicus

<400> SEQUENCE: 165

Arg Ala Thr Leu Thr Ala Asp Thr Ser Ser Asn Thr Ala Tyr Met Gln
1               5                   10                  15

Leu Ser Ser Leu Thr Ser Glu Asp Thr Ala Thr Tyr Phe Cys Thr Arg
            20                  25                  30

<210> SEQ ID NO 166
<211> LENGTH: 11
<212> TYPE: PRT
<213> ORGANISM: Rattus norvegicus

<400> SEQUENCE: 166

Trp Gly Gln Gly Val Met Val Thr Ala Ser Ser
1               5                   10

<210> SEQ ID NO 167
<211> LENGTH: 30
<212> TYPE: PRT
<213> ORGANISM: Artificial Sequence
<220> FEATURE:
<223> OTHER INFORMATION: Synthetic Construct

<400> SEQUENCE: 167

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 168
<211> LENGTH: 14
<212> TYPE: PRT
<213> ORGANISM: Artificial Sequence

```
<220> FEATURE:
<223> OTHER INFORMATION: Synthetic Construct

<400> SEQUENCE: 168

Trp Val Arg Gln Ala Pro Gly Gln Arg Leu Glu Ile Ile Gly
1               5                   10

<210> SEQ ID NO 169
<211> LENGTH: 14
<212> TYPE: PRT
<213> ORGANISM: Artificial Sequence
<220> FEATURE:
<223> OTHER INFORMATION: Synthetic Construct

<400> SEQUENCE: 169

Trp Val Arg Gln Ala Pro Gly Gln Arg Leu Glu Trp Ile Gly
1               5                   10

<210> SEQ ID NO 170
<211> LENGTH: 14
<212> TYPE: PRT
<213> ORGANISM: Artificial Sequence
<220> FEATURE:
<223> OTHER INFORMATION: Synthetic Construct

<400> SEQUENCE: 170

Trp Val Arg Gln Ala Pro Gly Gln Arg Leu Glu Ile Met Gly
1               5                   10

<210> SEQ ID NO 171
<211> LENGTH: 14
<212> TYPE: PRT
<213> ORGANISM: Artificial Sequence
<220> FEATURE:
<223> OTHER INFORMATION: Synthetic Construct

<400> SEQUENCE: 171

Trp Val Arg Gln Ala Pro Gly Gln Arg Leu Glu Trp Met Gly
1               5                   10

<210> SEQ ID NO 172
<211> LENGTH: 32
<212> TYPE: PRT
<213> ORGANISM: Artificial Sequence
<220> FEATURE:
<223> OTHER INFORMATION: Synthetic Construct

<400> SEQUENCE: 172

Arg Ala Thr Leu Thr Ala Asp Thr Ser Ala Ser Thr Ala Tyr Met Glu
1               5                   10                  15

Leu Ser Ser Leu Arg Ser Glu Asp Thr Ala Val Tyr Phe Cys Thr Arg
                20                  25                  30

<210> SEQ ID NO 173
<211> LENGTH: 32
<212> TYPE: PRT
<213> ORGANISM: Artificial Sequence
<220> FEATURE:
<223> OTHER INFORMATION: Synthetic Construct

<400> SEQUENCE: 173

Arg Val Thr Leu Thr Ala Asp Thr Ser Ala Ser Thr Ala Tyr Met Glu
1               5                   10                  15

Leu Ser Ser Leu Arg Ser Glu Asp Thr Ala Val Tyr Phe Cys Thr Arg
                20                  25                  30
```

<210> SEQ ID NO 174
<211> LENGTH: 32
<212> TYPE: PRT
<213> ORGANISM: Artificial Sequence
<220> FEATURE:
<223> OTHER INFORMATION: Synthetic Construct

<400> SEQUENCE: 174

Arg Ala Thr Ile Thr Ala Asp Thr Ser Ala Ser Thr Ala Tyr Met Glu
1               5                   10                  15

Leu Ser Ser Leu Arg Ser Glu Asp Thr Ala Val Tyr Phe Cys Thr Arg
                20                  25                  30

<210> SEQ ID NO 175
<211> LENGTH: 32
<212> TYPE: PRT
<213> ORGANISM: Artificial Sequence
<220> FEATURE:
<223> OTHER INFORMATION: Synthetic Construct

<400> SEQUENCE: 175

Arg Ala Thr Leu Thr Arg Asp Thr Ser Ala Ser Thr Ala Tyr Met Glu
1               5                   10                  15

Leu Ser Ser Leu Arg Ser Glu Asp Thr Ala Val Tyr Phe Cys Thr Arg
                20                  25                  30

<210> SEQ ID NO 176
<211> LENGTH: 32
<212> TYPE: PRT
<213> ORGANISM: Artificial Sequence
<220> FEATURE:
<223> OTHER INFORMATION: Synthetic Construct

<400> SEQUENCE: 176

Arg Ala Thr Leu Thr Ala Asp Thr Ser Ala Ser Thr Ala Tyr Met Glu
1               5                   10                  15

Leu Ser Ser Leu Arg Ser Glu Asp Thr Ala Val Tyr Tyr Cys Thr Arg
                20                  25                  30

<210> SEQ ID NO 177
<211> LENGTH: 32
<212> TYPE: PRT
<213> ORGANISM: Artificial Sequence
<220> FEATURE:
<223> OTHER INFORMATION: Synthetic Construct

<400> SEQUENCE: 177

Arg Ala Thr Leu Thr Ala Asp Thr Ser Ala Ser Thr Ala Tyr Met Glu
1               5                   10                  15

Leu Ser Ser Leu Arg Ser Glu Asp Thr Ala Val Tyr Phe Cys Ala Arg
                20                  25                  30

<210> SEQ ID NO 178
<211> LENGTH: 32
<212> TYPE: PRT
<213> ORGANISM: Artificial Sequence
<220> FEATURE:
<223> OTHER INFORMATION: Synthetic Construct

<400> SEQUENCE: 178

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
                20                  25                  30

<210> SEQ ID NO 179
<211> LENGTH: 11
<212> TYPE: PRT
<213> ORGANISM: Artificial Sequence
<220> FEATURE:
<223> OTHER INFORMATION: Synthetic Construct

<400> SEQUENCE: 179

Trp Gly Gln Gly Thr Leu Val Thr Val Ser Ser
1               5                   10

<210> SEQ ID NO 180
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Asp or Asn
<220> FEATURE:
<221> NAME/KEY: MOD_RES
<222> LOCATION: (3)..(3)
<223> OTHER INFORMATION: Xaa is His or Gln
<220> FEATURE:
<221> NAME/KEY: MOD_RES
<222> LOCATION: (10)..(10)
<223> OTHER INFORMATION: Xaa is Phe or Leu
<220> FEATURE:
<221> NAME/KEY: MOD_RES
<222> LOCATION: (21)..(21)
<223> OTHER INFORMATION: Xaa is Ile or Leu
<220> FEATURE:
<221> NAME/KEY: MOD_RES
<222> LOCATION: (22)..(22)
<223> OTHER INFORMATION: Xaa is Ser or Thr

<400> SEQUENCE: 180

Xaa Ile Xaa Leu Thr Gln Ser Pro Ser Xaa Leu Ser Ala Ser Val Gly
1               5                   10                  15

Asp Arg Val Thr Xaa Xaa Cys
            20

<210> SEQ ID NO 181
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Leu or Pro
<220> FEATURE:
<221> NAME/KEY: MOD_RES
<222> LOCATION: (8)..(8)
<223> OTHER INFORMATION: Xaa is Glu or Lys

<400> SEQUENCE: 181

Trp Tyr Gln Gln Lys Xaa Gly Xaa Ala Pro Lys Leu Leu Ile Tyr
1               5                   10                  15

<210> SEQ ID NO 182
<211> LENGTH: 32
<212> TYPE: PRT
<213> ORGANISM: Artificial Sequence
<220> FEATURE:
<223> OTHER INFORMATION: Synthetic Construct
<220> FEATURE:

```
<221> NAME/KEY: MOD_RES
<222> LOCATION: (2)..(2)
<223> OTHER INFORMATION: Xaa is Ile or Val
<220> FEATURE:
<221> NAME/KEY: MOD_RES
<222> LOCATION: (14)..(14)
<223> OTHER INFORMATION: Xaa is Asp or Glu
<220> FEATURE:
<221> NAME/KEY: MOD_RES
<222> LOCATION: (15)..(15)
<223> OTHER INFORMATION: Xaa is Phe or Tyr
<220> FEATURE:
<221> NAME/KEY: MOD_RES
<222> LOCATION: (27)..(27)
<223> OTHER INFORMATION: Xaa is Ala or Phe
<220> FEATURE:
<221> NAME/KEY: MOD_RES
<222> LOCATION: (31)..(31)
<223> OTHER INFORMATION: Xaa is Phe or Tyr

<400> SEQUENCE: 182

Gly Xaa Pro Ser Arg Phe Ser Gly Ser Gly Ser Gly Thr Xaa Xaa Thr
1               5                   10                  15

Leu Thr Ile Ser Ser Leu Gln Pro Glu Asp Xaa Ala Thr Tyr Xaa Cys
            20                  25                  30

<210> SEQ ID NO 183
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Gln or Ser
<220> FEATURE:
<221> NAME/KEY: MOD_RES
<222> LOCATION: (7)..(7)
<223> OTHER INFORMATION: Xaa is Leu or Val

<400> SEQUENCE: 183

Phe Gly Xaa Gly Thr Lys Xaa Glu Ile Lys
1               5                   10

<210> SEQ ID NO 184
<211> LENGTH: 23
<212> TYPE: PRT
<213> ORGANISM: Rattus norvegicus

<400> SEQUENCE: 184

Asn Ile His Leu Thr Gln Ser Pro Ser Leu Leu Ser Ala Ser Val Gly
1               5                   10                  15

Asp Arg Val Thr Leu Ser Cys
            20

<210> SEQ ID NO 185
<211> LENGTH: 15
<212> TYPE: PRT
<213> ORGANISM: Rattus norvegicus

<400> SEQUENCE: 185

Trp Tyr Gln Gln Lys Leu Gly Glu Ala Pro Lys Leu Leu Ile Tyr
1               5                   10                  15

<210> SEQ ID NO 186
<211> LENGTH: 32
<212> TYPE: PRT
<213> ORGANISM: Rattus norvegicus
```

<400> SEQUENCE: 186

Gly Ile Pro Ser Arg Phe Ser Gly Ser Gly Ser Gly Thr Asp Tyr Thr
1               5                   10                  15

Leu Thr Ile Ser Ser Leu Gln Pro Glu Asp Ala Ala Thr Tyr Phe Cys
            20                  25                  30

<210> SEQ ID NO 187
<211> LENGTH: 10
<212> TYPE: PRT
<213> ORGANISM: Rattus norvegicus

<400> SEQUENCE: 187

Phe Gly Ser Gly Thr Lys Leu Glu Ile Lys
1               5                   10

<210> SEQ ID NO 188
<211> LENGTH: 23
<212> TYPE: PRT
<213> ORGANISM: Artificial Sequence
<220> FEATURE:
<223> OTHER INFORMATION: Synthetic Construct

<400> SEQUENCE: 188

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 189
<211> LENGTH: 15
<212> TYPE: PRT
<213> ORGANISM: Artificial Sequence
<220> FEATURE:
<223> OTHER INFORMATION: Synthetic Construct

<400> SEQUENCE: 189

Trp Tyr Gln Gln Lys Pro Gly Lys Ala Pro Lys Leu Leu Ile Tyr
1               5                   10                  15

<210> SEQ ID NO 190
<211> LENGTH: 32
<212> TYPE: PRT
<213> ORGANISM: Artificial Sequence
<220> FEATURE:
<223> OTHER INFORMATION: Synthetic Construct

<400> SEQUENCE: 190

Gly Ile Pro Ser Arg Phe Ser Gly Ser Gly Ser Gly Thr Glu Tyr Thr
1               5                   10                  15

Leu Thr Ile Ser Ser Leu Gln Pro Glu Asp Phe Ala Thr Tyr Phe Cys
            20                  25                  30

<210> SEQ ID NO 191
<211> LENGTH: 32
<212> TYPE: PRT
<213> ORGANISM: Artificial Sequence
<220> FEATURE:
<223> OTHER INFORMATION: Synthetic Construct

<400> SEQUENCE: 191

Gly Val Pro Ser Arg Phe Ser Gly Ser Gly Ser Gly Thr Glu Tyr Thr
1               5                   10                  15

Leu Thr Ile Ser Ser Leu Gln Pro Glu Asp Phe Ala Thr Tyr Phe Cys

```
                20                  25                  30

<210> SEQ ID NO 192
<211> LENGTH: 32
<212> TYPE: PRT
<213> ORGANISM: Artificial Sequence
<220> FEATURE:
<223> OTHER INFORMATION: Seq_193

<400> SEQUENCE: 192

Gly Ile Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Phe Cys
            20                  25                  30

<210> SEQ ID NO 193
<211> LENGTH: 32
<212> TYPE: PRT
<213> ORGANISM: Artificial Sequence
<220> FEATURE:
<223> OTHER INFORMATION: Synthetic Construct

<400> SEQUENCE: 193

Gly Ile Pro Ser Arg Phe Ser Gly Ser Gly Ser Gly Thr Glu Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 194
<211> LENGTH: 32
<212> TYPE: PRT
<213> ORGANISM: Artificial Sequence
<220> FEATURE:
<223> OTHER INFORMATION: Synthetic Construct

<400> SEQUENCE: 194

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Phe Ala Thr Tyr Tyr Cys
            20                  25                  30

<210> SEQ ID NO 195
<211> LENGTH: 32
<212> TYPE: PRT
<213> ORGANISM: Artificial Sequence
<220> FEATURE:
<223> OTHER INFORMATION: Synthetic Construct

<400> SEQUENCE: 195

Gly Val Pro Ser Arg Phe Ser Gly Ser Gly Ser Gly Thr Glu Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 196
<211> LENGTH: 10
<212> TYPE: PRT
<213> ORGANISM: Artificial Sequence
<220> FEATURE:
<223> OTHER INFORMATION: Synthetic Construct

<400> SEQUENCE: 196

Phe Gly Gln Gly Thr Lys Val Glu Ile Lys
1               5                   10
```

<210> SEQ ID NO 197
<211> LENGTH: 117
<212> TYPE: PRT
<213> ORGANISM: Rattus norvegicus

<400> SEQUENCE: 197

Glu Val Gln Leu Gln Gln Ser Gly Pro Glu Leu Gln Arg Pro Gly Ala
1               5                   10                  15

Ser Val Lys Leu Ser Cys Lys Ala Thr Gly Tyr Thr Phe Thr Glu Tyr
                20                  25                  30

Ser Ile Tyr Trp Val Lys Gln Arg Pro Lys Gln Ser Leu Glu Ile Ile
            35                  40                  45

Gly Arg Ile Asp Pro Lys Asn Gly Arg Thr Tyr Tyr Val Asp Lys Phe
        50                  55                  60

Lys Asn Arg Ala Thr Leu Thr Ala Asp Thr Ser Ser Asn Thr Ala Tyr
65                  70                  75                  80

Met Gln Leu Ser Ser Leu Thr Ser Glu Asp Thr Ala Thr Tyr Phe Cys
                85                  90                  95

Thr Arg Ile Tyr Gly Phe Tyr Phe Asp Phe Trp Gly Gln Gly Val Met
                100                 105                 110

Val Thr Ala Ser Ser
            115

<210> SEQ ID NO 198
<211> LENGTH: 106
<212> TYPE: PRT
<213> ORGANISM: Rattus norvegicus

<400> SEQUENCE: 198

Asn Ile His Leu Thr Gln Ser Pro Ser Leu Leu Ser Ala Ser Val Gly
1               5                   10                  15

Asp Arg Val Thr Leu Ser Cys Lys Gly Ser Gln Asn Val Asn Lys Tyr
                20                  25                  30

Leu Val Trp Tyr Gln Gln Lys Leu Gly Glu Ala Pro Lys Leu Leu Ile
            35                  40                  45

Tyr Asn Thr Asp Asn Leu Gln Ser Gly Ile Pro Ser Arg Phe Ser Gly
        50                  55                  60

Ser Gly Ser Gly Thr Asp Tyr Thr Leu Thr Ile Ser Ser Leu Gln Pro
65                  70                  75                  80

Glu Asp Ala Ala Thr Tyr Phe Cys Tyr Gln Tyr Asn Asn Gly Phe Thr
                85                  90                  95

Phe Gly Ser Gly Thr Lys Leu Glu Ile Lys
                100                 105

<210> SEQ ID NO 199
<211> LENGTH: 117
<212> TYPE: PRT
<213> ORGANISM: Artificial Sequence
<220> FEATURE:
<223> OTHER INFORMATION: Synthetic Construct

<400> SEQUENCE: 199

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Ser Ile Tyr Trp Val Arg Gln Ala Pro Gly Gln Arg Leu Glu Ile Ile
            35                  40                  45

Gly Arg Ile Asp Pro Lys Asn Gly Arg Thr Tyr Tyr Val Asp Lys Phe
        50                  55                  60

Lys Asn Arg Ala Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Thr Arg Ile Tyr Gly Phe Tyr Phe Asp Phe Trp Gly Gln Gly Thr Leu
                100                 105                 110

Val Thr Val Ser Ser
            115

<210> SEQ ID NO 200
<211> LENGTH: 117
<212> TYPE: PRT
<213> ORGANISM: Artificial Sequence
<220> FEATURE:
<223> OTHER INFORMATION: Synthetic Construct

<400> SEQUENCE: 200

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Tyr
                 20                  25                  30

Ser Ile Tyr Trp Val Arg Gln Ala Pro Gly Gln Arg Leu Glu Trp Ile
                 35                  40                  45

Gly Arg Ile Asp Pro Lys Asn Gly Arg Thr Tyr Tyr Val Asp Lys Phe
        50                  55                  60

Lys Asn Arg Ala Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Thr Arg Ile Tyr Gly Phe Tyr Phe Asp Phe Trp Gly Gln Gly Thr Leu
                100                 105                 110

Val Thr Val Ser Ser
            115

<210> SEQ ID NO 201
<211> LENGTH: 117
<212> TYPE: PRT
<213> ORGANISM: Artificial Sequence
<220> FEATURE:
<223> OTHER INFORMATION: Synthetic Construct

<400> SEQUENCE: 201

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu Tyr
                 20                  25                  30

Ser Ile Tyr Trp Val Arg Gln Ala Pro Gly Gln Arg Leu Glu Ile Met
                 35                  40                  45

Gly Arg Ile Asp Pro Lys Asn Gly Arg Thr Tyr Tyr Val Asp Lys Phe
        50                  55                  60

Lys Asn Arg Ala Thr Leu Thr Ala Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Thr Arg Ile Tyr Gly Phe Tyr Phe Asp Phe Trp Gly Gln Gly Thr Leu

Val Thr Val Ser Ser
        115

<210> SEQ ID NO 202
<211> LENGTH: 117
<212> TYPE: PRT
<213> ORGANISM: Artificial Sequence
<220> FEATURE:
<223> OTHER INFORMATION: Synthetic Construct

<400> SEQUENCE: 202

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ser Ile Tyr Trp Val Arg Gln Ala Pro Gly Gln Arg Leu Glu Ile Ile
        35                  40                  45

Gly Arg Ile Asp Pro Lys Asn Gly Arg Thr Tyr Tyr Val Asp Lys Phe
    50                  55                  60

Lys Asn Arg Val Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ile Tyr Gly Phe Tyr Phe Asp Phe Trp Gly Gln Gly Thr Leu
            100                 105                 110

Val Thr Val Ser Ser
        115

<210> SEQ ID NO 203
<211> LENGTH: 117
<212> TYPE: PRT
<213> ORGANISM: Artificial Sequence
<220> FEATURE:
<223> OTHER INFORMATION: Synthetic Construct

<400> SEQUENCE: 203

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ser Ile Tyr Trp Val Arg Gln Ala Pro Gly Gln Arg Leu Glu Ile Ile
        35                  40                  45

Gly Arg Ile Asp Pro Lys Asn Gly Arg Thr Tyr Tyr Val Asp Lys Phe
    50                  55                  60

Lys Asn Arg Ala Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ile Tyr Gly Phe Tyr Phe Asp Phe Trp Gly Gln Gly Thr Leu
            100                 105                 110

Val Thr Val Ser Ser
        115

<210> SEQ ID NO 204
<211> LENGTH: 117
<212> TYPE: PRT
<213> ORGANISM: Artificial Sequence
<220> FEATURE:

<223> OTHER INFORMATION: Synthetic Construct

<400> SEQUENCE: 204

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Ser Ile Tyr Trp Val Arg Gln Ala Pro Gly Gln Arg Leu Glu Ile Ile
            35                  40                  45

Gly Arg Ile Asp Pro Lys Asn Gly Arg Thr Tyr Tyr Val Asp Lys Phe
    50                  55                  60

Lys Asn Arg Ala Thr Leu Thr Arg Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ile Tyr Gly Phe Tyr Phe Asp Phe Trp Gly Gln Gly Thr Leu
                100                 105                 110

Val Thr Val Ser Ser
            115

<210> SEQ ID NO 205
<211> LENGTH: 117
<212> TYPE: PRT
<213> ORGANISM: Artificial Sequence
<220> FEATURE:
<223> OTHER INFORMATION: Synthetic Construct

<400> SEQUENCE: 205

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Ser Ile Tyr Trp Val Arg Gln Ala Pro Gly Gln Arg Leu Glu Ile Ile
            35                  40                  45

Gly Arg Ile Asp Pro Lys Asn Gly Arg Thr Tyr Tyr Val Asp Lys Phe
    50                  55                  60

Lys Asn Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Ile Tyr Gly Phe Tyr Phe Asp Phe Trp Gly Gln Gly Thr Leu
                100                 105                 110

Val Thr Val Ser Ser
            115

<210> SEQ ID NO 206
<211> LENGTH: 117
<212> TYPE: PRT
<213> ORGANISM: Artificial Sequence
<220> FEATURE:
<223> OTHER INFORMATION: Synthetic Construct

<400> SEQUENCE: 206

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Ser Ile Tyr Trp Val Arg Gln Ala Pro Gly Gln Arg Leu Glu Ile Ile

```
                    35                  40                  45
Gly Arg Ile Asp Pro Lys Asn Gly Arg Thr Tyr Tyr Val Asp Lys Phe
        50                  55                  60

Lys Asn Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ile Tyr Gly Phe Tyr Phe Asp Phe Trp Gly Gln Gly Thr Leu
            100                 105                 110

Val Thr Val Ser Ser
        115

<210> SEQ ID NO 207
<211> LENGTH: 117
<212> TYPE: PRT
<213> ORGANISM: Artificial Sequence
<220> FEATURE:
<223> OTHER INFORMATION: Synthetic Construct

<400> SEQUENCE: 207

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Ser Ile Tyr Trp Val Arg Gln Ala Pro Gly Gln Arg Leu Glu Trp Met
            35                  40                  45

Gly Arg Ile Asp Pro Lys Asn Gly Arg Thr Tyr Tyr Val Asp Lys Phe
        50                  55                  60

Lys Asn Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Phe Tyr Phe Asp Phe Trp Gly Gln Gly Thr Leu
            100                 105                 110

Val Thr Val Ser Ser
        115

<210> SEQ ID NO 208
<211> LENGTH: 106
<212> TYPE: PRT
<213> ORGANISM: Artificial Sequence
<220> FEATURE:
<223> OTHER INFORMATION: Synthetic Construct

<400> SEQUENCE: 208

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
                20                  25                  30

Leu Val Trp Tyr Gln Gln Lys Pro Gly Lys Ala Pro Lys Leu Leu Ile
            35                  40                  45

Tyr Asn Thr Asp Asn Leu Gln Ser Gly Ile Pro Ser Arg Phe Ser Gly
        50                  55                  60

Ser Gly Ser Gly Thr Glu Tyr Thr Leu Thr Ile Ser Ser Leu Gln Pro
65                  70                  75                  80

Glu Asp Phe Ala Thr Tyr Phe Cys Tyr Gln Tyr Asn Asn Gly Phe Thr
                85                  90                  95
```

Phe Gly Gln Gly Thr Lys Val Glu Ile Lys
            100                 105

<210> SEQ ID NO 209
<211> LENGTH: 106
<212> TYPE: PRT
<213> ORGANISM: Artificial Sequence
<220> FEATURE:
<223> OTHER INFORMATION: Synthetic Construct

<400> SEQUENCE: 209

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Asn Thr Asp Asn Leu Gln Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Phe Cys Tyr Gln Tyr Asn Asn Gly Phe Thr
                85                  90                  95

Phe Gly Gln Gly Thr Lys Val Glu Ile Lys
            100                 105

<210> SEQ ID NO 210
<211> LENGTH: 106
<212> TYPE: PRT
<213> ORGANISM: Artificial Sequence
<220> FEATURE:
<223> OTHER INFORMATION: Synthetic Construct

<400> SEQUENCE: 210

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Asn Thr Asp Asn Leu Gln Ser Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Tyr Gln Tyr Asn Asn Gly Phe Thr
                85                  90                  95

Phe Gly Gln Gly Thr Lys Val Glu Ile Lys
            100                 105

<210> SEQ ID NO 211
<211> LENGTH: 106
<212> TYPE: PRT
<213> ORGANISM: Artificial Sequence
<220> FEATURE:
<223> OTHER INFORMATION: Synthetic Construct

<400> SEQUENCE: 211

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr

```
            20                  25                  30
Leu Val Trp Tyr Gln Gln Lys Pro Gly Lys Ala Pro Lys Leu Leu Ile
        35                  40                  45

Tyr Asn Thr Asp Asn Leu Gln Ser Gly Ile Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Phe Thr
                85                  90                  95

Phe Gly Gln Gly Thr Lys Val Glu Ile Lys
            100                 105

<210> SEQ ID NO 212
<211> LENGTH: 106
<212> TYPE: PRT
<213> ORGANISM: Artificial Sequence
<220> FEATURE:
<223> OTHER INFORMATION: Synthetic Construct

<400> SEQUENCE: 212

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Asn Thr Asp Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Tyr Gln Tyr Asn Asn Gly Phe Thr
                85                  90                  95

Phe Gly Gln Gly Thr Lys Val Glu Ile Lys
            100                 105

<210> SEQ ID NO 213
<211> LENGTH: 117
<212> TYPE: PRT
<213> ORGANISM: Artificial Sequence
<220> FEATURE:
<223> OTHER INFORMATION: Synthetic Construct

<400> SEQUENCE: 213

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Ser Ile Tyr Trp Val Arg Gln Ala Pro Gly Gln Arg Leu Glu Ile Met
        35                  40                  45

Gly Arg Ile Asp Pro Lys Asn Gly Arg Thr Tyr Tyr Val Asp Lys Phe
    50                  55                  60

Lys Asn Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Tyr Gly Phe Tyr Phe Asp Phe Trp Gly Gln Gly Thr Leu
            100                 105                 110
```

Val Thr Val Ser Ser
        115

<210> SEQ ID NO 214
<211> LENGTH: 106
<212> TYPE: PRT
<213> ORGANISM: Artificial Sequence
<220> FEATURE:
<223> OTHER INFORMATION: Synthetic Construct

<400> SEQUENCE: 214

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Asn Thr Asp Asn Leu Gln Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Phe Thr
                85                  90                  95

Phe Gly Gln Gly Thr Lys Val Glu Ile Lys
            100                 105

<210> SEQ ID NO 215
<211> LENGTH: 5
<212> TYPE: PRT
<213> ORGANISM: Rattus norvegicus

<400> SEQUENCE: 215

Glu His Ser Ile Tyr
1               5

<210> SEQ ID NO 216
<211> LENGTH: 17
<212> TYPE: PRT
<213> ORGANISM: Rattus norvegicus

<400> SEQUENCE: 216

Arg Ile Asp Pro Lys Asn Gly Arg Thr Tyr Phe Val Asp Lys Phe Lys
1               5                   10                  15

Asn

<210> SEQ ID NO 217
<211> LENGTH: 8
<212> TYPE: PRT
<213> ORGANISM: Rattus norvegicus

<400> SEQUENCE: 217

Ile Asp Gly Phe Tyr Phe Asp Phe
1               5

<210> SEQ ID NO 218
<211> LENGTH: 11
<212> TYPE: PRT
<213> ORGANISM: Rattus norvegicus

<400> SEQUENCE: 218

Lys Gly Ser Gln Asn Val Asn Lys Tyr Leu Val
1               5                   10

<210> SEQ ID NO 219
<211> LENGTH: 7
<212> TYPE: PRT
<213> ORGANISM: Rattus norvegicus

<400> SEQUENCE: 219

Ser Thr Asp Asn Leu Gln Ser
1               5

<210> SEQ ID NO 220
<211> LENGTH: 8
<212> TYPE: PRT
<213> ORGANISM: Rattus norvegicus

<400> SEQUENCE: 220

Tyr Gln Tyr Asn Asn Gly Phe Thr
1               5

<210> SEQ ID NO 221
<211> LENGTH: 30
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Gln or Val
<220> FEATURE:
<221> NAME/KEY: MOD_RES
<222> LOCATION: (9)..(9)
<223> OTHER INFORMATION: Xaa is Ala or Pro
<220> FEATURE:
<221> NAME/KEY: MOD_RES
<222> LOCATION: (11)..(11)
<223> OTHER INFORMATION: Xaa is Leu or Val
<220> FEATURE:
<221> NAME/KEY: MOD_RES
<222> LOCATION: (12)..(12)
<223> OTHER INFORMATION: Xaa is Lys or Gln
<220> FEATURE:
<221> NAME/KEY: MOD_RES
<222> LOCATION: (13)..(13)
<223> OTHER INFORMATION: Xaa is Lys or Arg
<220> FEATURE:
<221> NAME/KEY: MOD_RES
<222> LOCATION: (20)..(20)
<223> OTHER INFORMATION: Xaa is Leu or Val

<400> SEQUENCE: 221

Glu Val Gln Leu Xaa Gln Ser Gly Xaa Glu Xaa Xaa Xaa Pro Gly Ala
1               5                   10                  15

Ser Val Lys Xaa Ser Cys Lys Ala Ser Gly Tyr Thr Phe Thr
            20                  25                  30

<210> SEQ ID NO 222
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Leu or Val
<220> FEATURE:
<221> NAME/KEY: MOD_RES
<222> LOCATION: (3)..(3)
<223> OTHER INFORMATION: Xaa is Lys or Arg
<220> FEATURE:

```
<221> NAME/KEY: MOD_RES
<222> LOCATION: (5)..(5)
<223> OTHER INFORMATION: Xaa is Ala or Arg
<220> FEATURE:
<221> NAME/KEY: MOD_RES
<222> LOCATION: (7)..(7)
<223> OTHER INFORMATION: Xaa is Gly or Lys
<220> FEATURE:
<221> NAME/KEY: MOD_RES
<222> LOCATION: (9)..(9)
<223> OTHER INFORMATION: Xaa is Arg or Ser
<220> FEATURE:
<221> NAME/KEY: MOD_RES
<222> LOCATION: (12)..(12)
<223> OTHER INFORMATION: Xaa is Ile or Trp
<220> FEATURE:
<221> NAME/KEY: MOD_RES
<222> LOCATION: (13)..(13)
<223> OTHER INFORMATION: Xaa is Ile or Met

<400> SEQUENCE: 222

Trp Xaa Xaa Gln Xaa Pro Xaa Gln Xaa Leu Glu Xaa Xaa Gly
1               5                   10

<210> SEQ ID NO 223
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ala or Val
<220> FEATURE:
<221> NAME/KEY: MOD_RES
<222> LOCATION: (4)..(4)
<223> OTHER INFORMATION: Xaa is Ile or Leu
<220> FEATURE:
<221> NAME/KEY: MOD_RES
<222> LOCATION: (6)..(6)
<223> OTHER INFORMATION: Xaa is Arg or Thr
<220> FEATURE:
<221> NAME/KEY: MOD_RES
<222> LOCATION: (7)..(7)
<223> OTHER INFORMATION: Xaa is Asp or Asn
<220> FEATURE:
<221> NAME/KEY: MOD_RES
<222> LOCATION: (10)..(10)
<223> OTHER INFORMATION: Xaa is Ala or Ser
<220> FEATURE:
<221> NAME/KEY: MOD_RES
<222> LOCATION: (11)..(11)
<223> OTHER INFORMATION: Xaa is Asn or Ser
<220> FEATURE:
<221> NAME/KEY: MOD_RES
<222> LOCATION: (16)..(16)
<223> OTHER INFORMATION: Xaa is Glu or Gln
<220> FEATURE:
<221> NAME/KEY: MOD_RES
<222> LOCATION: (21)..(21)
<223> OTHER INFORMATION: Xaa is Arg or Thr
<220> FEATURE:
<221> NAME/KEY: MOD_RES
<222> LOCATION: (27)..(27)
<223> OTHER INFORMATION: Xaa is Ile or Val
<220> FEATURE:
<221> NAME/KEY: MOD_RES
<222> LOCATION: (29)..(29)
<223> OTHER INFORMATION: Xaa is Phe or Tyr

<400> SEQUENCE: 223

Arg Xaa Thr Xaa Thr Xaa Xaa Thr Ser Xaa Xaa Thr Ala Tyr Met Xaa
1               5                   10                  15

Leu Ser Ser Leu Xaa Ser Glu Asp Thr Ala Xaa Tyr Xaa Cys Ala Arg
```

<210> SEQ ID NO 224
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Thr or Val
<220> FEATURE:
<221> NAME/KEY: MOD_RES
<222> LOCATION: (6)..(6)
<223> OTHER INFORMATION: Xaa is Leu or Met
<220> FEATURE:
<221> NAME/KEY: MOD_RES
<222> LOCATION: (9)..(9)
<223> OTHER INFORMATION: Xaa is Ala or Val

<400> SEQUENCE: 224

Trp Gly Gln Gly Xaa Xaa Val Thr Xaa Ser Ser
1               5                   10

<210> SEQ ID NO 225
<211> LENGTH: 30
<212> TYPE: PRT
<213> ORGANISM: Rattus norvegicus

<400> SEQUENCE: 225

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr
            20                  25                  30

<210> SEQ ID NO 226
<211> LENGTH: 14
<212> TYPE: PRT
<213> ORGANISM: Rattus norvegicus

<400> SEQUENCE: 226

Trp Leu Lys Gln Arg Pro Lys Gln Ser Leu Glu Ile Ile Gly
1               5                   10

<210> SEQ ID NO 227
<211> LENGTH: 32
<212> TYPE: PRT
<213> ORGANISM: Rattus norvegicus

<400> SEQUENCE: 227

Arg Ala Thr Leu Thr Thr Asn Thr Ser Ser Asn Thr Ala Tyr Met Gln
1               5                   10                  15

Leu Ser Ser Leu Thr Ser Glu Asp Thr Ala Ile Tyr Phe Cys Ala Arg
            20                  25                  30

<210> SEQ ID NO 228
<211> LENGTH: 11
<212> TYPE: PRT
<213> ORGANISM: Rattus norvegicus

<400> SEQUENCE: 228

Trp Gly Gln Gly Val Met Val Thr Ala Ser Ser
1               5                   10

<210> SEQ ID NO 229

```
<211> LENGTH: 30
<212> TYPE: PRT
<213> ORGANISM: Artificial Sequence
<220> FEATURE:
<223> OTHER INFORMATION: Synthetic Construct

<400> SEQUENCE: 229

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 230
<211> LENGTH: 14
<212> TYPE: PRT
<213> ORGANISM: Artificial Sequence
<220> FEATURE:
<223> OTHER INFORMATION: Synthetic Construct

<400> SEQUENCE: 230

Trp Leu Arg Gln Ala Pro Gly Gln Arg Leu Glu Ile Ile Gly
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Synthetic Construct

<400> SEQUENCE: 231

Trp Val Arg Gln Ala Pro Gly Gln Arg Leu Glu Ile Ile Gly
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Synthetic Construct

<400> SEQUENCE: 232

Trp Leu Arg Gln Ala Pro Gly Gln Arg Leu Glu Trp Ile Gly
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Synthetic Construct

<400> SEQUENCE: 233

Trp Leu Arg Gln Ala Pro Gly Gln Arg Leu Glu Ile Met Gly
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Synthetic Construct

<400> SEQUENCE: 234

Trp Val Arg Gln Ala Pro Gly Gln Arg Leu Glu Trp Met Gly
1               5                   10
```

<210> SEQ ID NO 235
<211> LENGTH: 32
<212> TYPE: PRT
<213> ORGANISM: Artificial Sequence
<220> FEATURE:
<223> OTHER INFORMATION: Synthetic Construct

<400> SEQUENCE: 235

Arg Ala Thr Leu Thr Thr Asp Thr Ser Ala Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 236
<211> LENGTH: 32
<212> TYPE: PRT
<213> ORGANISM: Artificial Sequence
<220> FEATURE:
<223> OTHER INFORMATION: Synthetic Construct

<400> SEQUENCE: 236

Arg Val Thr Leu Thr Thr Asp Thr Ser Ala Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 237
<211> LENGTH: 32
<212> TYPE: PRT
<213> ORGANISM: Artificial Sequence
<220> FEATURE:
<223> OTHER INFORMATION: Synthetic Construct

<400> SEQUENCE: 237

Arg Ala Thr Ile Thr Thr Asp Thr Ser Ala Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 238
<211> LENGTH: 32
<212> TYPE: PRT
<213> ORGANISM: Artificial Sequence
<220> FEATURE:
<223> OTHER INFORMATION: Synthetic Construct

<400> SEQUENCE: 238

Arg Ala Thr Leu Thr Arg Asp Thr Ser Ala Ser Thr Ala Tyr Met Glu
1               5                   10                  15

Leu Ser Ser Leu Arg Ser Glu Asp Thr Ala Val Tyr Phe Cys Ala Arg
            20                  25                  30

<210> SEQ ID NO 239
<211> LENGTH: 32
<212> TYPE: PRT
<213> ORGANISM: Artificial Sequence
<220> FEATURE:
<223> OTHER INFORMATION: Synthetic Construct

<400> SEQUENCE: 239

Arg Ala Thr Leu Thr Thr Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 240
<211> LENGTH: 32
<212> TYPE: PRT
<213> ORGANISM: Artificial Sequence
<220> FEATURE:
<223> OTHER INFORMATION: Synthetic Construct

<400> SEQUENCE: 240

Arg Val Thr Ile Thr Arg Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 241
<211> LENGTH: 32
<212> TYPE: PRT
<213> ORGANISM: Artificial Sequence
<220> FEATURE:
<223> OTHER INFORMATION: Synthetic Construct

<400> SEQUENCE: 241

Arg Ala Thr Ile Thr Thr Asp Thr Ser Ala Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 242
<211> LENGTH: 11
<212> TYPE: PRT
<213> ORGANISM: Artificial Sequence
<220> FEATURE:
<223> OTHER INFORMATION: Synthetic Construct

<400> SEQUENCE: 242

Trp Gly Gln Gly Thr Leu Val Thr Val Ser Ser
1               5                   10

<210> SEQ ID NO 243
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Asp or Asn
<220> FEATURE:
<221> NAME/KEY: MOD_RES
<222> LOCATION: (3)..(3)
<223> OTHER INFORMATION: Xaa is His or Gln
<220> FEATURE:
<221> NAME/KEY: MOD_RES
<222> LOCATION: (10)..(10)
<223> OTHER INFORMATION: Xaa is Phe or Leu
<220> FEATURE:
<221> NAME/KEY: MOD_RES
<222> LOCATION: (21)..(21)
<223> OTHER INFORMATION: Xaa is Ile or Leu
<220> FEATURE:
<221> NAME/KEY: MOD_RES
<222> LOCATION: (22)..(22)
<223> OTHER INFORMATION: Xaa is Ser or Thr

<400> SEQUENCE: 243

Xaa Ile Xaa Leu Thr Gln Ser Pro Ser Xaa Leu Ser Ala Ser Val Gly
1               5                   10                  15

Asp Arg Val Thr Xaa Xaa Cys
            20

<210> SEQ ID NO 244
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Leu or Pro
<220> FEATURE:
<221> NAME/KEY: MOD_RES
<222> LOCATION: (8)..(8)
<223> OTHER INFORMATION: Xaa is Glu or Lys

<400> SEQUENCE: 244

Trp Tyr Gln Gln Lys Xaa Gly Xaa Ala Pro Lys Leu Leu Ile Tyr
1               5                   10                  15

<210> SEQ ID NO 245
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ile or Val
<220> FEATURE:
<221> NAME/KEY: MOD_RES
<222> LOCATION: (14)..(14)
<223> OTHER INFORMATION: Xaa is Asp or Glu
<220> FEATURE:
<221> NAME/KEY: MOD_RES
<222> LOCATION: (15)..(15)
<223> OTHER INFORMATION: Xaa is Phe or Tyr
<220> FEATURE:
<221> NAME/KEY: MOD_RES
<222> LOCATION: (27)..(27)
<223> OTHER INFORMATION: Xaa is Ala or Phe
<220> FEATURE:
<221> NAME/KEY: MOD_RES
<222> LOCATION: (31)..(31)
<223> OTHER INFORMATION: Xaa is Phe or Tyr

<400> SEQUENCE: 245

Gly Xaa Pro Ser Arg Phe Ser Gly Ser Gly Ser Gly Thr Xaa Xaa Thr
1               5                   10                  15

Leu Thr Ile Ser Ser Leu Gln Pro Glu Asp Xaa Ala Thr Tyr Xaa Cys
            20                  25                  30

<210> SEQ ID NO 246
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Gln or Ser
<220> FEATURE:
<221> NAME/KEY: MOD_RES
<222> LOCATION: (7)..(7)
<223> OTHER INFORMATION: Xaa is Leu or Val

<400> SEQUENCE: 246

Phe Gly Xaa Gly Thr Lys Xaa Glu Ile Lys

```
<210> SEQ ID NO 247
<211> LENGTH: 23
<212> TYPE: PRT
<213> ORGANISM: Rattus norvegicus

<400> SEQUENCE: 247

Asn Ile His Leu Thr Gln Ser Pro Ser Leu Leu Ser Ala Ser Val Gly
1               5                   10                  15

Asp Arg Val Thr Leu Ser Cys
            20

<210> SEQ ID NO 248
<211> LENGTH: 15
<212> TYPE: PRT
<213> ORGANISM: Rattus norvegicus

<400> SEQUENCE: 248

Trp Tyr Gln Gln Lys Leu Gly Glu Ala Pro Lys Leu Leu Ile Tyr
1               5                   10                  15

<210> SEQ ID NO 249
<211> LENGTH: 32
<212> TYPE: PRT
<213> ORGANISM: Rattus norvegicus

<400> SEQUENCE: 249

Gly Ile Pro Ser Arg Phe Ser Gly Ser Gly Ser Gly Thr Asp Tyr Thr
1               5                   10                  15

Leu Thr Ile Ser Ser Leu Gln Pro Glu Asp Ala Ala Thr Tyr Phe Cys
            20                  25                  30

<210> SEQ ID NO 250
<211> LENGTH: 10
<212> TYPE: PRT
<213> ORGANISM: Rattus norvegicus

<400> SEQUENCE: 250

Phe Gly Ser Gly Thr Lys Leu Glu Ile Lys
1               5                   10

<210> SEQ ID NO 251
<211> LENGTH: 23
<212> TYPE: PRT
<213> ORGANISM: Artificial Sequence
<220> FEATURE:
<223> OTHER INFORMATION: Synthetic Construct

<400> SEQUENCE: 251

Asp Ile Gln Leu Thr Gln Ser Pro Ser Phe Leu Ser Ala Ser Val Gly
1               5                   10                  15

Asp Arg Val Thr Ile Thr Cys
            20

<210> SEQ ID NO 252
<211> LENGTH: 15
<212> TYPE: PRT
<213> ORGANISM: Artificial Sequence
<220> FEATURE:
<223> OTHER INFORMATION: Synthetic Construct

<400> SEQUENCE: 252

Trp Tyr Gln Gln Lys Pro Gly Lys Ala Pro Lys Leu Leu Ile Tyr
```

<210> SEQ ID NO 253
<211> LENGTH: 32
<212> TYPE: PRT
<213> ORGANISM: Artificial Sequence
<220> FEATURE:
<223> OTHER INFORMATION: Synthetic Construct

<400> SEQUENCE: 253

Gly Ile Pro Ser Arg Phe Ser Gly Ser Gly Ser Gly Thr Glu Tyr Thr
 1               5                  10                  15
Leu Thr Ile Ser Ser Leu Gln Pro Glu Asp Phe Ala Thr Tyr Phe Cys
            20                  25                  30

<210> SEQ ID NO 254
<211> LENGTH: 32
<212> TYPE: PRT
<213> ORGANISM: Artificial Sequence
<220> FEATURE:
<223> OTHER INFORMATION: Synthetic Construct

<400> SEQUENCE: 254

Gly Val Pro Ser Arg Phe Ser Gly Ser Gly Ser Gly Thr Glu Tyr Thr
 1               5                  10                  15
Leu Thr Ile Ser Ser Leu Gln Pro Glu Asp Phe Ala Thr Tyr Phe Cys
            20                  25                  30

<210> SEQ ID NO 255
<211> LENGTH: 32
<212> TYPE: PRT
<213> ORGANISM: Artificial Sequence
<220> FEATURE:
<223> OTHER INFORMATION: Synthetic Construct

<400> SEQUENCE: 255

Gly Ile Pro Ser Arg Phe Ser Gly Ser Gly Ser Gly Thr Glu Phe Thr
 1               5                  10                  15
Leu Thr Ile Ser Ser Leu Gln Pro Glu Asp Phe Ala Thr Tyr Phe Cys
            20                  25                  30

<210> SEQ ID NO 256
<211> LENGTH: 32
<212> TYPE: PRT
<213> ORGANISM: Artificial Sequence
<220> FEATURE:
<223> OTHER INFORMATION: Synthetic Construct

<400> SEQUENCE: 256

Gly Ile Pro Ser Arg Phe Ser Gly Ser Gly Ser Gly Thr Glu Tyr Thr
 1               5                  10                  15
Leu Thr Ile Ser Ser Leu Gln Pro Glu Asp Phe Ala Thr Tyr Tyr Cys
            20                  25                  30

<210> SEQ ID NO 257
<211> LENGTH: 32
<212> TYPE: PRT
<213> ORGANISM: Artificial Sequence
<220> FEATURE:
<223> OTHER INFORMATION: Synthetic Construct

<400> SEQUENCE: 257

Gly Val Pro Ser Arg Phe Ser Gly Ser Gly Ser Gly Thr Glu Phe Thr
 1               5                  10                  15

Leu Thr Ile Ser Ser Leu Gln Pro Glu Asp Phe Ala Thr Tyr Tyr Cys
            20                  25                  30

<210> SEQ ID NO 258
<211> LENGTH: 32
<212> TYPE: PRT
<213> ORGANISM: Artificial Sequence
<220> FEATURE:
<223> OTHER INFORMATION: Synthetic Construct

<400> SEQUENCE: 258

Gly Val Pro Ser Arg Phe Ser Gly Ser Gly Ser Gly Thr Glu Tyr Thr
1               5                   10                  15

Leu Thr Ile Ser Ser Leu Gln Pro Glu Asp Phe Ala Thr Tyr Tyr Cys
            20                  25                  30

<210> SEQ ID NO 259
<211> LENGTH: 10
<212> TYPE: PRT
<213> ORGANISM: Artificial Sequence
<220> FEATURE:
<223> OTHER INFORMATION: Synthetic Construct

<400> SEQUENCE: 259

Phe Gly Gln Gly Thr Lys Val Glu Ile Lys
1               5                   10

<210> SEQ ID NO 260
<211> LENGTH: 117
<212> TYPE: PRT
<213> ORGANISM: Rattus norvegicus

<400> SEQUENCE: 260

Glu Val Gln Leu Gln Gln Ser Gly Pro Glu Leu Gln Arg Pro Gly Ala
1               5                   10                  15

Ser Val Lys Leu Ser Cys Lys Ala Ser Gly Tyr Thr Phe Thr Glu His
            20                  25                  30

Ser Ile Tyr Trp Leu Lys Gln Arg Pro Lys Gln Ser Leu Glu Ile Ile
        35                  40                  45

Gly Arg Ile Asp Pro Lys Asn Gly Arg Thr Tyr Phe Val Asp Lys Phe
    50                  55                  60

Lys Asn Arg Ala Thr Leu Thr Thr Asn Thr Ser Ser Asn Thr Ala Tyr
65                  70                  75                  80

Met Gln Leu Ser Ser Leu Thr Ser Glu Asp Thr Ala Ile Tyr Phe Cys
                85                  90                  95

Ala Arg Ile Asp Gly Phe Tyr Phe Asp Phe Trp Gly Gln Gly Val Met
            100                 105                 110

Val Thr Ala Ser Ser
        115

<210> SEQ ID NO 261
<211> LENGTH: 106
<212> TYPE: PRT
<213> ORGANISM: Rattus norvegicus

<400> SEQUENCE: 261

Asn Ile His Leu Thr Gln Ser Pro Ser Leu Leu Ser Ala Ser Val Gly
1               5                   10                  15

Asp Arg Val Thr Leu Ser Cys Lys Gly Ser Gln Asn Val Asn Lys Tyr
            20                  25                  30

Leu Val Trp Tyr Gln Gln Lys Leu Gly Glu Ala Pro Lys Leu Leu Ile

```
                    35                  40                  45
Tyr Ser Thr Asp Asn Leu Gln Ser Gly Ile Pro Ser Arg Phe Ser Gly
                50                  55                  60

Ser Gly Ser Gly Thr Asp Tyr Thr Leu Thr Ile Ser Ser Leu Gln Pro
 65                  70                  75                  80

Glu Asp Ala Ala Thr Tyr Phe Cys Tyr Gln Tyr Asn Asn Gly Phe Thr
                    85                  90                  95

Phe Gly Ser Gly Thr Lys Leu Glu Ile Lys
                100                 105
```

<210> SEQ ID NO 262
<211> LENGTH: 117
<212> TYPE: PRT
<213> ORGANISM: Artificial Sequence
<220> FEATURE:
<223> OTHER INFORMATION: Synthetic Construct

<400> SEQUENCE: 262

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu His
                20                  25                  30

Ser Ile Tyr Trp Leu Arg Gln Ala Pro Gly Gln Arg Leu Glu Ile Ile
            35                  40                  45

Gly Arg Ile Asp Pro Lys Asn Gly Arg Thr Tyr Phe Val Asp Lys Phe
    50                  55                  60

Lys Asn Arg Ala Thr Leu Thr Thr Asp Thr Ser Ala Ser Thr Ala Tyr
 65                  70                  75                  80

Met Glu Leu Ser Ser Leu Arg Ser Glu Asp Thr Ala Val Tyr Phe Cys
                    85                  90                  95

Ala Arg Ile Asp Gly Phe Tyr Phe Asp Phe Trp Gly Gln Gly Thr Leu
                100                 105                 110

Val Thr Val Ser Ser
            115
```

<210> SEQ ID NO 263
<211> LENGTH: 117
<212> TYPE: PRT
<213> ORGANISM: Artificial Sequence
<220> FEATURE:
<223> OTHER INFORMATION: Synthetic Construct

<400> SEQUENCE: 263

```
Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu His
                20                  25                  30

Ser Ile Tyr Trp Val Arg Gln Ala Pro Gly Gln Arg Leu Glu Ile Ile
            35                  40                  45

Gly Arg Ile Asp Pro Lys Asn Gly Arg Thr Tyr Phe Val Asp Lys Phe
    50                  55                  60

Lys Asn Arg Ala Thr Leu Thr Thr Asp Thr Ser Ala Ser Thr Ala Tyr
 65                  70                  75                  80

Met Glu Leu Ser Ser Leu Arg Ser Glu Asp Thr Ala Val Tyr Phe Cys
                    85                  90                  95

Ala Arg Ile Asp Gly Phe Tyr Phe Asp Phe Trp Gly Gln Gly Thr Leu
                100                 105                 110
```

Val Thr Val Ser Ser
        115

<210> SEQ ID NO 264
<211> LENGTH: 117
<212> TYPE: PRT
<213> ORGANISM: Artificial Sequence
<220> FEATURE:
<223> OTHER INFORMATION: Synthetic Construct

<400> SEQUENCE: 264

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ser Ile Tyr Trp Leu Arg Gln Ala Pro Gly Gln Arg Leu Glu Trp Ile
        35                  40                  45

Gly Arg Ile Asp Pro Lys Asn Gly Arg Thr Tyr Phe Val Asp Lys Phe
    50                  55                  60

Lys Asn Arg Ala Thr Leu Thr Thr Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ile Asp Gly Phe Tyr Phe Asp Phe Trp Gly Gln Gly Thr Leu
            100                 105                 110

Val Thr Val Ser Ser
        115

<210> SEQ ID NO 265
<211> LENGTH: 117
<212> TYPE: PRT
<213> ORGANISM: Artificial Sequence
<220> FEATURE:
<223> OTHER INFORMATION: Synthetic Construct

<400> SEQUENCE: 265

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ser Ile Tyr Trp Leu Arg Gln Ala Pro Gly Gln Arg Leu Glu Ile Met
        35                  40                  45

Gly Arg Ile Asp Pro Lys Asn Gly Arg Thr Tyr Phe Val Asp Lys Phe
    50                  55                  60

Lys Asn Arg Ala Thr Leu Thr Thr Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ile Asp Gly Phe Tyr Phe Asp Phe Trp Gly Gln Gly Thr Leu
            100                 105                 110

Val Thr Val Ser Ser
        115

<210> SEQ ID NO 266
<211> LENGTH: 117
<212> TYPE: PRT
<213> ORGANISM: Artificial Sequence
<220> FEATURE:
<223> OTHER INFORMATION: Synthetic Construct

<400> SEQUENCE: 266

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ser Ile Tyr Trp Leu Arg Gln Ala Pro Gly Gln Arg Leu Glu Ile Ile
        35                  40                  45

Gly Arg Ile Asp Pro Lys Asn Gly Arg Thr Tyr Phe Val Asp Lys Phe
50                  55                  60

Lys Asn Arg Val Thr Leu Thr Thr Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ile Asp Gly Phe Tyr Phe Asp Phe Trp Gly Gln Gly Thr Leu
            100                 105                 110

Val Thr Val Ser Ser
            115

<210> SEQ ID NO 267
<211> LENGTH: 117
<212> TYPE: PRT
<213> ORGANISM: Artificial Sequence
<220> FEATURE:
<223> OTHER INFORMATION: Synthetic Construct

<400> SEQUENCE: 267

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ser Ile Tyr Trp Leu Arg Gln Ala Pro Gly Gln Arg Leu Glu Ile Ile
        35                  40                  45

Gly Arg Ile Asp Pro Lys Asn Gly Arg Thr Tyr Phe Val Asp Lys Phe
50                  55                  60

Lys Asn Arg Ala Thr Ile Thr Thr Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Ile Asp Gly Phe Tyr Phe Asp Phe Trp Gly Gln Gly Thr Leu
            100                 105                 110

Val Thr Val Ser Ser
            115

<210> SEQ ID NO 268
<211> LENGTH: 117
<212> TYPE: PRT
<213> ORGANISM: Artificial Sequence
<220> FEATURE:
<223> OTHER INFORMATION: Synthetic Construct

<400> SEQUENCE: 268

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ser Ile Tyr Trp Leu Arg Gln Ala Pro Gly Gln Arg Leu Glu Ile Ile
        35                  40                  45

-continued

Gly Arg Ile Asp Pro Lys Asn Gly Arg Thr Tyr Phe Val Asp Lys Phe
        50                  55                  60

Lys Asn Arg Ala Thr Leu Thr Arg Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Ile Asp Gly Phe Tyr Phe Asp Phe Trp Gly Gln Gly Thr Leu
            100                 105                 110

Val Thr Val Ser Ser
            115

<210> SEQ ID NO 269
<211> LENGTH: 117
<212> TYPE: PRT
<213> ORGANISM: Artificial Sequence
<220> FEATURE:
<223> OTHER INFORMATION: Synthetic Construct

<400> SEQUENCE: 269

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu His
             20                  25                  30

Ser Ile Tyr Trp Leu Arg Gln Ala Pro Gly Gln Arg Leu Glu Ile Ile
         35                  40                  45

Gly Arg Ile Asp Pro Lys Asn Gly Arg Thr Tyr Phe Val Asp Lys Phe
        50                  55                  60

Lys Asn Arg Ala Thr Leu Thr Thr Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ile Asp Gly Phe Tyr Phe Asp Phe Trp Gly Gln Gly Thr Leu
            100                 105                 110

Val Thr Val Ser Ser
            115

<210> SEQ ID NO 270
<211> LENGTH: 117
<212> TYPE: PRT
<213> ORGANISM: Artificial Sequence
<220> FEATURE:
<223> OTHER INFORMATION: Synthetic Construct

<400> SEQUENCE: 270

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Glu His
             20                  25                  30

Ser Ile Tyr Trp Val Arg Gln Ala Pro Gly Gln Arg Leu Glu Trp Met
         35                  40                  45

Gly Arg Ile Asp Pro Lys Asn Gly Arg Thr Tyr Phe Val Asp Lys Phe
        50                  55                  60

Lys Asn Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ile Asp Gly Phe Tyr Phe Asp Phe Trp Gly Gln Gly Thr Leu
            100                 105                 110

Val Thr Val Ser Ser
        115

<210> SEQ ID NO 271
<211> LENGTH: 106
<212> TYPE: PRT
<213> ORGANISM: Artificial Sequence
<220> FEATURE:
<223> OTHER INFORMATION: Synthetic Construct

<400> SEQUENCE: 271

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Ser Thr Asp Asn Leu Gln Ser Gly Ile Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Phe Cys Tyr Gln Tyr Asn Asn Gly Phe Thr
                85                  90                  95

Phe Gly Gln Gly Thr Lys Val Glu Ile Lys
            100                 105

<210> SEQ ID NO 272
<211> LENGTH: 106
<212> TYPE: PRT
<213> ORGANISM: Artificial Sequence
<220> FEATURE:
<223> OTHER INFORMATION: Synthetic Construct

<400> SEQUENCE: 272

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Ser Thr Asp Asn Leu Gln Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Phe Cys Tyr Gln Tyr Asn Asn Gly Phe Thr
                85                  90                  95

Phe Gly Gln Gly Thr Lys Val Glu Ile Lys
            100                 105

<210> SEQ ID NO 273
<211> LENGTH: 106
<212> TYPE: PRT
<213> ORGANISM: Artificial Sequence
<220> FEATURE:
<223> OTHER INFORMATION: Synthetic Construct

<400> SEQUENCE: 273

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Ser Thr Asp Asn Leu Gln Ser Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Tyr Gln Tyr Asn Asn Gly Phe Thr
                85                  90                  95

Phe Gly Gln Gly Thr Lys Val Glu Ile Lys
            100                 105

<210> SEQ ID NO 274
<211> LENGTH: 106
<212> TYPE: PRT
<213> ORGANISM: Artificial Sequence
<220> FEATURE:
<223> OTHER INFORMATION: Synthetic Construct

<400> SEQUENCE: 274

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Ser Thr Asp Asn Leu Gln Ser Gly Ile Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Phe Thr
                85                  90                  95

Phe Gly Gln Gly Thr Lys Val Glu Ile Lys
            100                 105

<210> SEQ ID NO 275
<211> LENGTH: 106
<212> TYPE: PRT
<213> ORGANISM: Artificial Sequence
<220> FEATURE:
<223> OTHER INFORMATION: Synthetic Construct

<400> SEQUENCE: 275

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Ser Thr Asp Asn Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Tyr Gln Tyr Asn Asn Gly Phe Thr
                85                  90                  95

Phe Gly Gln Gly Thr Lys Val Glu Ile Lys
            100                 105

```
<210> SEQ ID NO 276
<211> LENGTH: 117
<212> TYPE: PRT
<213> ORGANISM: Artificial Sequence
<220> FEATURE:
<223> OTHER INFORMATION: Synthetic Construct

<400> SEQUENCE: 276

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu His
            20                  25                  30

Ser Ile Tyr Trp Leu Arg Gln Ala Pro Gly Gln Arg Leu Glu Ile Met
        35                  40                  45

Gly Arg Ile Asp Pro Lys Asn Gly Arg Thr Tyr Phe Val Asp Lys Phe
    50                  55                  60

Lys Asn Arg Ala Thr Ile Thr Thr Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ile Asp Gly Phe Tyr Phe Asp Phe Trp Gly Gln Gly Thr Leu
            100                 105                 110

Val Thr Val Ser Ser
        115

<210> SEQ ID NO 277
<211> LENGTH: 106
<212> TYPE: PRT
<213> ORGANISM: Artificial Sequence
<220> FEATURE:
<223> OTHER INFORMATION: Synthetic Construct

<400> SEQUENCE: 277

Asp Ile Gln Leu Thr Gln Ser Pro Ser Phe Leu Ser Ala Ser Val Gly
1               5                   10                  15

Asp Arg Val Thr Ile Thr Cys Lys Gly Ser Gln Asn Val Asn Lys Tyr
            20                  25                  30

Leu Val Trp Tyr Gln Gln Lys Pro Gly Lys Ala Pro Lys Leu Leu Ile
        35                  40                  45

Tyr Ser Thr Asp Asn Leu Gln Ser Gly Val Pro Ser Arg Phe Ser Gly
    50                  55                  60

Ser Gly Ser Gly Thr Glu Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Phe Thr
                85                  90                  95

Phe Gly Gln Gly Thr Lys Val Glu Ile Lys
            100                 105

<210> SEQ ID NO 278
<211> LENGTH: 5
<212> TYPE: PRT
<213> ORGANISM: Artificial Sequence
<220> FEATURE:
<223> OTHER INFORMATION: Synthetic Construct

<400> SEQUENCE: 278

Asp Ser Tyr Met Ser
1               5
```

```
<210> SEQ ID NO 279
<211> LENGTH: 5
<212> TYPE: PRT
<213> ORGANISM: Artificial Sequence
<220> FEATURE:
<223> OTHER INFORMATION: Synthetic Construct

<400> SEQUENCE: 279

Asp Ala Tyr Met Ser
1               5

<210> SEQ ID NO 280
<211> LENGTH: 5
<212> TYPE: PRT
<213> ORGANISM: Artificial Sequence
<220> FEATURE:
<223> OTHER INFORMATION: Synthetic Construct

<400> SEQUENCE: 280

Glu Ser Tyr Met Ser
1               5

<210> SEQ ID NO 281
<211> LENGTH: 17
<212> TYPE: PRT
<213> ORGANISM: Artificial Sequence
<220> FEATURE:
<223> OTHER INFORMATION: Synthetic Construct

<400> SEQUENCE: 281

Asp Met Tyr Pro Asp Asn Gly Asp Ser Ser Tyr Asn Gln Lys Phe Arg
1               5                   10                  15

Glu

<210> SEQ ID NO 282
<211> LENGTH: 17
<212> TYPE: PRT
<213> ORGANISM: Artificial Sequence
<220> FEATURE:
<223> OTHER INFORMATION: Synthetic Construct

<400> SEQUENCE: 282

Asp Met Tyr Pro Asp Asn Ala Asp Ser Ser Tyr Asn Gln Lys Phe Arg
1               5                   10                  15

Glu

<210> SEQ ID NO 283
<211> LENGTH: 17
<212> TYPE: PRT
<213> ORGANISM: Artificial Sequence
<220> FEATURE:
<223> OTHER INFORMATION: Synthetic Construct

<400> SEQUENCE: 283

Asp Met Tyr Pro Asp Asn Ala Asp Ala Ser Tyr Asn Gln Lys Phe Arg
1               5                   10                  15

Glu

<210> SEQ ID NO 284
<211> LENGTH: 17
<212> TYPE: PRT
<213> ORGANISM: Artificial Sequence
<220> FEATURE:
<223> OTHER INFORMATION: Synthetic Construct
```

```
<400> SEQUENCE: 284

Asp Met Tyr Pro Asp Asn Gly Asp Ala Ser Tyr Asn Gln Lys Phe Arg
1               5                   10                  15

Glu

<210> SEQ ID NO 285
<211> LENGTH: 17
<212> TYPE: PRT
<213> ORGANISM: Artificial Sequence
<220> FEATURE:
<223> OTHER INFORMATION: Synthetic Construct

<400> SEQUENCE: 285

Asp Met Tyr Pro Asp Ser Gly Asp Ser Ser Tyr Asn Gln Lys Phe Arg
1               5                   10                  15

Glu

<210> SEQ ID NO 286
<211> LENGTH: 17
<212> TYPE: PRT
<213> ORGANISM: Artificial Sequence
<220> FEATURE:
<223> OTHER INFORMATION: Synthetic Construct

<400> SEQUENCE: 286

Asp Met Tyr Pro Asp Asn Gly Ser Ser Ser Tyr Asn Gln Lys Phe Arg
1               5                   10                  15

Glu

<210> SEQ ID NO 287
<211> LENGTH: 8
<212> TYPE: PRT
<213> ORGANISM: Artificial Sequence
<220> FEATURE:
<223> OTHER INFORMATION: Synthetic Construct

<400> SEQUENCE: 287

Ala Pro Arg Trp Tyr Phe Ser Val
1               5

<210> SEQ ID NO 288
<211> LENGTH: 8
<212> TYPE: PRT
<213> ORGANISM: Artificial Sequence
<220> FEATURE:
<223> OTHER INFORMATION: Synthetic Construct

<400> SEQUENCE: 288

Ala Pro Arg Trp Tyr Phe Ser Ala
1               5

<210> SEQ ID NO 289
<211> LENGTH: 8
<212> TYPE: PRT
<213> ORGANISM: Artificial Sequence
<220> FEATURE:
<223> OTHER INFORMATION: Synthetic Construct

<400> SEQUENCE: 289

Ala Pro Arg Trp Tyr Phe Ala Val
1               5

<210> SEQ ID NO 290
<211> LENGTH: 11
```

```
<212> TYPE: PRT
<213> ORGANISM: Artificial Sequence
<220> FEATURE:
<223> OTHER INFORMATION: Synthetic Construct

<400> SEQUENCE: 290

Arg Ala Ser Gln Asp Ile Ser Asn Tyr Leu Asn
1               5                   10

<210> SEQ ID NO 291
<211> LENGTH: 7
<212> TYPE: PRT
<213> ORGANISM: Artificial Sequence
<220> FEATURE:
<223> OTHER INFORMATION: Synthetic Construct

<400> SEQUENCE: 291

Tyr Thr Ser Arg Leu Arg Ser
1               5

<210> SEQ ID NO 292
<211> LENGTH: 9
<212> TYPE: PRT
<213> ORGANISM: Artificial Sequence
<220> FEATURE:
<223> OTHER INFORMATION: Synthetic Construct

<400> SEQUENCE: 292

Gln Gln Gly His Thr Leu Pro Pro Thr
1               5

<210> SEQ ID NO 293
<211> LENGTH: 9
<212> TYPE: PRT
<213> ORGANISM: Artificial Sequence
<220> FEATURE:
<223> OTHER INFORMATION: Synthetic Construct

<400> SEQUENCE: 293

Gln Gln Gly His Thr Leu Pro Ala Thr
1               5

<210> SEQ ID NO 294
<211> LENGTH: 9
<212> TYPE: PRT
<213> ORGANISM: Artificial Sequence
<220> FEATURE:
<223> OTHER INFORMATION: Synthetic Construct

<400> SEQUENCE: 294

Gln Gln Gly His Thr Ala Pro Pro Thr
1               5

<210> SEQ ID NO 295
<211> LENGTH: 9
<212> TYPE: PRT
<213> ORGANISM: Artificial Sequence
<220> FEATURE:
<223> OTHER INFORMATION: Synthetic Construct

<400> SEQUENCE: 295

Gln Gln Gly Ala Thr Leu Pro Pro Thr
1               5

<210> SEQ ID NO 296
<211> LENGTH: 9
<212> TYPE: PRT
```

<210> SEQ ID NO 296
<211> LENGTH: 9
<212> TYPE: PRT
<213> ORGANISM: Artificial Sequence
<220> FEATURE:
<223> OTHER INFORMATION: Synthetic Construct

<400> SEQUENCE: 296

Gln Gln Gly His Ala Leu Pro Pro Thr
1               5

<210> SEQ ID NO 297
<211> LENGTH: 9
<212> TYPE: PRT
<213> ORGANISM: Artificial Sequence
<220> FEATURE:
<223> OTHER INFORMATION: Synthetic Construct

<400> SEQUENCE: 297

Gln Gln Ala His Thr Leu Pro Pro Thr
1               5

<210> SEQ ID NO 298
<211> LENGTH: 9
<212> TYPE: PRT
<213> ORGANISM: Artificial Sequence
<220> FEATURE:
<223> OTHER INFORMATION: Synthetic Construct

<400> SEQUENCE: 298

Gln Gln Gly His Thr Leu Ala Pro Thr
1               5

<210> SEQ ID NO 299
<211> LENGTH: 9
<212> TYPE: PRT
<213> ORGANISM: Artificial Sequence
<220> FEATURE:
<223> OTHER INFORMATION: Synthetic Construct

<400> SEQUENCE: 299

Gln Ala Gly His Thr Leu Pro Pro Thr
1               5

<210> SEQ ID NO 300
<211> LENGTH: 117
<212> TYPE: PRT
<213> ORGANISM: Artificial Sequence
<220> FEATURE:
<223> OTHER INFORMATION: Synthetic Construct

<400> SEQUENCE: 300

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 301
<211> LENGTH: 117
<212> TYPE: PRT
<213> ORGANISM: Artificial Sequence
<220> FEATURE:
<223> OTHER INFORMATION: Synthetic Construct

<400> SEQUENCE: 301

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 302
<211> LENGTH: 117
<212> TYPE: PRT
<213> ORGANISM: Artificial Sequence
<220> FEATURE:
<223> OTHER INFORMATION: Synthetic Construct

<400> SEQUENCE: 302

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Leu Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 303
<211> LENGTH: 117
<212> TYPE: PRT
<213> ORGANISM: Artificial Sequence
<220> FEATURE:
<223> OTHER INFORMATION: Synthetic Construct

<400> SEQUENCE: 303

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 304
<211> LENGTH: 117
<212> TYPE: PRT
<213> ORGANISM: Artificial Sequence
<220> FEATURE:
<223> OTHER INFORMATION: Synthetic Construct

<400> SEQUENCE: 304

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 305
<211> LENGTH: 117
<212> TYPE: PRT
<213> ORGANISM: Artificial Sequence
<220> FEATURE:
<223> OTHER INFORMATION: Synthetic Construct

<400> SEQUENCE: 305

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
        50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 306
<211> LENGTH: 117
<212> TYPE: PRT
<213> ORGANISM: Artificial Sequence
<220> FEATURE:
<223> OTHER INFORMATION: Synthetic Construct

<400> SEQUENCE: 306

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
        50                  55                  60

Arg Glu Arg Val Thr Ile Thr Val Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 307
<211> LENGTH: 117
<212> TYPE: PRT
<213> ORGANISM: Artificial Sequence
<220> FEATURE:
<223> OTHER INFORMATION: Synthetic Construct

<400> SEQUENCE: 307

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ala
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 308
<211> LENGTH: 117
<212> TYPE: PRT
<213> ORGANISM: Artificial Sequence
<220> FEATURE:
<223> OTHER INFORMATION: Synthetic Construct

<400> SEQUENCE: 308

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 309
<211> LENGTH: 117
<212> TYPE: PRT
<213> ORGANISM: Artificial Sequence
<220> FEATURE:
<223> OTHER INFORMATION: Synthetic Construct

<400> SEQUENCE: 309

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Ala Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 310
<211> LENGTH: 117
<212> TYPE: PRT
<213> ORGANISM: Artificial Sequence
<220> FEATURE:
<223> OTHER INFORMATION: Synthetic Construct

<400> SEQUENCE: 310

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Ala Asp Ala Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 311
<211> LENGTH: 117
<212> TYPE: PRT
<213> ORGANISM: Artificial Sequence
<220> FEATURE:
<223> OTHER INFORMATION: Synthetic Construct

<400> SEQUENCE: 311

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

Gly Asp Met Tyr Pro Asp Asn Gly Asp Ala Ser Tyr Asn Gln Lys Phe
        50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
                100                 105                 110

Val Thr Val Ser Ser
            115

<210> SEQ ID NO 312
<211> LENGTH: 117
<212> TYPE: PRT
<213> ORGANISM: Artificial Sequence
<220> FEATURE:
<223> OTHER INFORMATION: Synthetic Construct

<400> SEQUENCE: 312

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
                20                  25                  30

Tyr Met Ser Trp Val Arg Gln Ala Pro Gly Gln Gly Leu Glu Trp Ile
            35                  40                  45

```
Gly Asp Met Tyr Pro Asp Ser Gly Asp Ser Ser Tyr Asn Gln Lys Phe
        50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 313
<211> LENGTH: 117
<212> TYPE: PRT
<213> ORGANISM: Artificial Sequence
<220> FEATURE:
<223> OTHER INFORMATION: Synthetic Construct

<400> SEQUENCE: 313

Glu Val Gln Leu Val Gln Ser Gly Ala Glu Val Lys Lys Pro Gly Ala
 1                   5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Ser Ser Tyr Asn Gln Lys Phe
        50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
                100                 105                 110

Val Thr Val Ser Ser
        115

<210> SEQ ID NO 314
<211> LENGTH: 117
<212> TYPE: PRT
<213> ORGANISM: Artificial Sequence
<220> FEATURE:
<223> OTHER INFORMATION: Synthetic Construct

<400> SEQUENCE: 314

Glu Val Gln Leu Val Gln Ser Gly Ala Glu Val Lys Lys Pro Gly Ala
 1                   5                  10                  15

Ser Val Lys Val Ser Cys Lys Ala Ser Gly Tyr Thr Phe Thr Asp Ala
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Ala Asp Ala Ser Tyr Asn Gln Lys Phe
        50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
```

Val Thr Val Ser Ser
        115

<210> SEQ ID NO 315
<211> LENGTH: 117
<212> TYPE: PRT
<213> ORGANISM: Artificial Sequence
<220> FEATURE:
<223> OTHER INFORMATION: Synthetic Construct

<400> SEQUENCE: 315

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 316
<211> LENGTH: 117
<212> TYPE: PRT
<213> ORGANISM: Artificial Sequence
<220> FEATURE:
<223> OTHER INFORMATION: Synthetic Construct

<400> SEQUENCE: 316

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 317
<211> LENGTH: 117
<212> TYPE: PRT
<213> ORGANISM: Artificial Sequence
<220> FEATURE:

<223> OTHER INFORMATION: Synthetic Construct

<400> SEQUENCE: 317

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 318
<211> LENGTH: 117
<212> TYPE: PRT
<213> ORGANISM: Artificial Sequence
<220> FEATURE:
<223> OTHER INFORMATION: Synthetic Construct

<400> SEQUENCE: 318

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Val Trp Gly Gln Gly Thr Leu
            100                 105                 110

Val Thr Val Ser Ser
        115

<210> SEQ ID NO 319
<211> LENGTH: 117
<212> TYPE: PRT
<213> ORGANISM: Artificial Sequence
<220> FEATURE:
<223> OTHER INFORMATION: Synthetic Construct

<400> SEQUENCE: 319

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile

```
                35                  40                  45

Gly Asp Met Tyr Pro Asp Asn Gly Asp Ser Ser Tyr Asn Gln Lys Phe
         50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 320
<211> LENGTH: 117
<212> TYPE: PRT
<213> ORGANISM: Artificial Sequence
<220> FEATURE:
<223> OTHER INFORMATION: Synthetic Construct

<400> SEQUENCE: 320

Glu Val Gln Leu Val Gln Ser Gly Ala Glu Val Lys Lys Pro Gly Ala
 1                5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Asp Ser Ser Tyr Asn Gln Lys Phe
         50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95

Val Leu Ala Pro Arg Trp Tyr Phe Ser Val Trp Gly Gln Gly Thr Leu
            100                 105                 110

Val Thr Val Ser Ser
            115

<210> SEQ ID NO 321
<211> LENGTH: 117
<212> TYPE: PRT
<213> ORGANISM: Artificial Sequence
<220> FEATURE:
<223> OTHER INFORMATION: Synthetic Construct

<400> SEQUENCE: 321

Glu Val Gln Leu Val Gln Ser Gly Ala Glu Val Lys Lys Pro Gly Ala
 1                5                  10                  15

Ser Val Lys Val Ser Cys Lys Ala Ser Gly Tyr Thr Phe Thr Asp Ser
                 20                  25                  30

Tyr Met Ser Trp Val Arg Gln Ala Pro Gly Gln Gly Leu Glu Trp Ile
             35                  40                  45

Gly Asp Met Tyr Pro Asp Asn Gly Asp Ser Ser Tyr Asn Gln Lys Phe
         50                  55                  60

Arg Glu Arg Val Thr Ile Thr Arg Asp Thr Ser Thr Ser Thr Ala Tyr
 65                  70                  75                  80

Leu Glu Leu Ser Ser Leu Arg Ser Glu Asp Thr Ala Val Tyr Tyr Cys
                 85                  90                  95
```

Val Leu Ala Pro Arg Trp Tyr Phe Ser Val Trp Gly Gln Gly Thr Leu
              100                 105                 110

Val Thr Val Ser Ser
        115

<210> SEQ ID NO 322
<211> LENGTH: 117
<212> TYPE: PRT
<213> ORGANISM: Artificial Sequence
<220> FEATURE:
<223> OTHER INFORMATION: Synthetic Construct

<400> SEQUENCE: 322

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ser Ala Trp Gly Gln Gly Thr Leu
              100                 105                 110

Val Thr Val Ser Ser
        115

<210> SEQ ID NO 323
<211> LENGTH: 117
<212> TYPE: PRT
<213> ORGANISM: Artificial Sequence
<220> FEATURE:
<223> OTHER INFORMATION: Synthetic Construct

<400> SEQUENCE: 323

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Leu Ala Pro Arg Trp Tyr Phe Ala Val Trp Gly Gln Gly Thr Leu
              100                 105                 110

Val Thr Val Ser Ser
        115

<210> SEQ ID NO 324
<211> LENGTH: 117
<212> TYPE: PRT
<213> ORGANISM: Artificial Sequence
<220> FEATURE:
<223> OTHER INFORMATION: Synthetic Construct

<400> SEQUENCE: 324

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Ala Leu Ala Pro Arg Trp Tyr Phe Ser Val Trp Gly Gln Gly Thr Leu
            100                 105                 110

Val Thr Val Ser Ser
        115

<210> SEQ ID NO 325
<211> LENGTH: 117
<212> TYPE: PRT
<213> ORGANISM: Artificial Sequence
<220> FEATURE:
<223> OTHER INFORMATION: Synthetic Construct

<400> SEQUENCE: 325

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Ser
            20                  25                  30

Tyr Met Ser Trp Val Arg Gln Ala Pro Gly Gln Gly Leu Glu Trp Ile
        35                  40                  45

Gly Asp Met Tyr Pro Asp Asn Gly Asp Ser Ser Tyr Asn Gln Lys Phe
    50                  55                  60

Arg Glu Arg Val Thr Ile Thr Arg Asp Thr Ser Thr Ser Thr Ala Tyr
65                  70                  75                  80

Leu Glu Leu Ser Ser Leu Arg Ser Glu Asp Thr Ala Val Tyr Tyr Cys
                85                  90                  95

Val Ala Ala Pro Arg Trp Tyr Phe Ser Val Trp Gly Gln Gly Thr Leu
            100                 105                 110

Val Thr Val Ser Ser
        115

<210> SEQ ID NO 326
<211> LENGTH: 107
<212> TYPE: PRT
<213> ORGANISM: Artificial Sequence
<220> FEATURE:
<223> OTHER INFORMATION: Synthetic Construct

<400> SEQUENCE: 326

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

```
Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
                100                 105

<210> SEQ ID NO 327
<211> LENGTH: 107
<212> TYPE: PRT
<213> ORGANISM: Artificial Sequence
<220> FEATURE:
<223> OTHER INFORMATION: Synthetic Construct

<400> SEQUENCE: 327

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
                100                 105

<210> SEQ ID NO 328
<211> LENGTH: 107
<212> TYPE: PRT
<213> ORGANISM: Artificial Sequence
<220> FEATURE:
<223> OTHER INFORMATION: Synthetic Construct

<400> SEQUENCE: 328

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
                 20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
                100                 105

<210> SEQ ID NO 329
```

```
<211> LENGTH: 107
<212> TYPE: PRT
<213> ORGANISM: Artificial Sequence
<220> FEATURE:
<223> OTHER INFORMATION: Synthetic Construct

<400> SEQUENCE: 329

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 330
<211> LENGTH: 107
<212> TYPE: PRT
<213> ORGANISM: Artificial Sequence
<220> FEATURE:
<223> OTHER INFORMATION: Synthetic Construct

<400> SEQUENCE: 330

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 331
<211> LENGTH: 107
<212> TYPE: PRT
<213> ORGANISM: Artificial Sequence
<220> FEATURE:
<223> OTHER INFORMATION: Synthetic Construct

<400> SEQUENCE: 331

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45
```

Tyr Tyr Thr Ser Arg Leu Arg Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
            100                 105

<210> SEQ ID NO 332
<211> LENGTH: 107
<212> TYPE: PRT
<213> ORGANISM: Artificial Sequence
<220> FEATURE:
<223> OTHER INFORMATION: Synthetic Construct

<400> SEQUENCE: 332

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Lys Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Pro
                85                  90                  95

Thr Phe Gly Gln Gly Thr Lys Val Glu Ile Lys
            100                 105

<210> SEQ ID NO 333
<211> LENGTH: 107
<212> TYPE: PRT
<213> ORGANISM: Artificial Sequence
<220> FEATURE:
<223> OTHER INFORMATION: Synthetic Construct

<400> SEQUENCE: 333

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 334
<211> LENGTH: 107
<212> TYPE: PRT
<213> ORGANISM: Artificial Sequence
<220> FEATURE:
<223> OTHER INFORMATION: Synthetic Construct

<400> SEQUENCE: 334

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 335
<211> LENGTH: 107
<212> TYPE: PRT
<213> ORGANISM: Artificial Sequence
<220> FEATURE:
<223> OTHER INFORMATION: Synthetic Construct

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 336
<211> LENGTH: 107
<212> TYPE: PRT
<213> ORGANISM: Artificial Sequence
<220> FEATURE:
<223> OTHER INFORMATION: Synthetic Construct

<400> SEQUENCE: 336

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 337
<211> LENGTH: 107
<212> TYPE: PRT
<213> ORGANISM: Artificial Sequence
<220> FEATURE:
<223> OTHER INFORMATION: Synthetic Construct

<400> SEQUENCE: 337

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 338
<211> LENGTH: 107
<212> TYPE: PRT
<213> ORGANISM: Artificial Sequence
<220> FEATURE:
<223> OTHER INFORMATION: Synthetic Construct

<400> SEQUENCE: 338

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
             20                  25                  30

Leu Asn Trp Tyr Gln Gln Lys Pro Gly Lys Ala Pro Lys Leu Leu Ile
         35                  40                  45

Tyr Tyr Thr Ser Arg Leu Arg Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly His Thr Leu Pro Pro
                 85                  90                  95

Thr Phe Gly Gln Gly Thr Lys Val Glu Ile Lys
            100                 105

<210> SEQ ID NO 339
<211> LENGTH: 107
<212> TYPE: PRT
<213> ORGANISM: Artificial Sequence
<220> FEATURE:
<223> OTHER INFORMATION: Synthetic Construct
```

-continued

<400> SEQUENCE: 339

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 340
<211> LENGTH: 107
<212> TYPE: PRT
<213> ORGANISM: Artificial Sequence
<220> FEATURE:
<223> OTHER INFORMATION: Synthetic Construct

<400> SEQUENCE: 340

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 341
<211> LENGTH: 107
<212> TYPE: PRT
<213> ORGANISM: Artificial Sequence
<220> FEATURE:
<223> OTHER INFORMATION: Synthetic Construct

<400> SEQUENCE: 341

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Ala
                85                  90                  95

Thr Phe Gly Gln Gly Thr Lys Val Glu Ile Lys
            100                 105

<210> SEQ ID NO 342
<211> LENGTH: 107
<212> TYPE: PRT
<213> ORGANISM: Artificial Sequence
<220> FEATURE:
<223> OTHER INFORMATION: Synthetic Construct

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Ala Pro Pro
                85                  90                  95

Thr Phe Gly Gln Gly Thr Lys Val Glu Ile Lys
            100                 105

<210> SEQ ID NO 343
<211> LENGTH: 107
<212> TYPE: PRT
<213> ORGANISM: Artificial Sequence
<220> FEATURE:
<223> OTHER INFORMATION: Synthetic Construct

<400> SEQUENCE: 343

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Thr Leu Pro Pro
                85                  90                  95

Thr Phe Gly Gln Gly Thr Lys Val Glu Ile Lys
            100                 105

<210> SEQ ID NO 344
<211> LENGTH: 107
<212> TYPE: PRT
<213> ORGANISM: Artificial Sequence
<220> FEATURE:
<223> OTHER INFORMATION: Synthetic Construct

<400> SEQUENCE: 344

Asp Ile Gln Met Thr Gln Ser Pro Ser Ser Leu Ser Ala Ser Val Gly

-continued

```
                1               5                  10                 15
            Asp Arg Val Thr Ile Thr Cys Arg Ala Ser Gln Asp Ile Ser Asn Tyr
                            20                 25                 30

Leu Asn Trp Tyr Gln Gln Lys Pro Gly Lys Ala Pro Lys Leu Leu Ile
                        35                 40                 45

Tyr Tyr Thr Ser Arg Leu Arg Ser Gly Val Pro Ser Arg Phe Ser Gly
                    50                 55                 60

Ser Gly Ser Gly Thr Asp Phe Thr Leu Thr Ile Ser Ser Leu Gln Pro
             65                 70                 75                 80

Glu Asp Phe Ala Thr Tyr Tyr Cys Gln Gln Gly His Ala Leu Pro Pro
                            85                 90                 95

Thr Phe Gly Gln Gly Thr Lys Val Glu Ile Lys
                            100                105

<210> SEQ ID NO 345
<211> LENGTH: 107
<212> TYPE: PRT
<213> ORGANISM: Artificial Sequence
<220> FEATURE:
<223> OTHER INFORMATION: Synthetic Construct

<400> SEQUENCE: 345

Asp Ile Gln Met Thr Gln Ser Pro Ser Ser Leu Ser Ala Ser Val Gly
             1               5                  10                 15

Asp Arg Val Thr Ile Thr Cys Arg Ala Ser Gln Asp Ile Ser Asn Tyr
                            20                 25                 30

Leu Asn Trp Tyr Gln Gln Lys Pro Gly Lys Ala Pro Lys Leu Leu Ile
                        35                 40                 45

Tyr Tyr Thr Ser Arg Leu Arg Ser Gly Val Pro Ser Arg Phe Ser Gly
                    50                 55                 60

Ser Gly Ser Gly Thr Asp Phe Thr Leu Thr Ile Ser Ser Leu Gln Pro
             65                 70                 75                 80

Glu Asp Phe Ala Thr Tyr Tyr Cys Gln Gln Ala His Thr Leu Pro Pro
                            85                 90                 95

Thr Phe Gly Gln Gly Thr Lys Val Glu Ile Lys
                            100                105

<210> SEQ ID NO 346
<211> LENGTH: 107
<212> TYPE: PRT
<213> ORGANISM: Artificial Sequence
<220> FEATURE:
<223> OTHER INFORMATION: Synthetic Construct

<400> SEQUENCE: 346

Asp Ile Gln Met Thr Gln Ser Pro Ser Ser Leu Ser Ala Ser Val Gly
             1               5                  10                 15

Asp Arg Val Thr Ile Thr Cys Arg Ala Ser Gln Asp Ile Ser Asn Tyr
                            20                 25                 30

Leu Asn Trp Tyr Gln Gln Lys Pro Gly Lys Ala Pro Lys Leu Leu Ile
                        35                 40                 45

Tyr Tyr Thr Ser Arg Leu Arg Ser Gly Val Pro Ser Arg Phe Ser Gly
                    50                 55                 60

Ser Gly Ser Gly Thr Asp Phe Thr Leu Thr Ile Ser Ser Leu Gln Pro
             65                 70                 75                 80

Glu Asp Phe Ala Thr Tyr Tyr Cys Gln Gln Gly His Thr Leu Ala Pro
                            85                 90                 95
```

Thr Phe Gly Gln Gly Thr Lys Val Glu Ile Lys
            100                 105

<210> SEQ ID NO 347
<211> LENGTH: 107
<212> TYPE: PRT
<213> ORGANISM: Artificial Sequence
<220> FEATURE:
<223> OTHER INFORMATION: Synthetic Construct

<400> SEQUENCE: 347

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly His Thr Leu Pro Pro
                85                  90                  95

Thr Phe Gly Gln Gly Thr Lys Val Glu Ile Lys
            100                 105

<210> SEQ ID NO 348
<211> LENGTH: 107
<212> TYPE: PRT
<213> ORGANISM: Artificial Sequence
<220> FEATURE:
<223> OTHER INFORMATION: Synthetic Construct

<400> SEQUENCE: 348

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu Arg Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 349
<211> LENGTH: 107
<212> TYPE: PRT
<213> ORGANISM: Artificial Sequence
<220> FEATURE:
<223> OTHER INFORMATION: Synthetic Construct

<400> SEQUENCE: 349

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr

```
                    20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 350
<211> LENGTH: 107
<212> TYPE: PRT
<213> ORGANISM: Artificial Sequence
<220> FEATURE:
<223> OTHER INFORMATION: Synthetic Construct

<400> SEQUENCE: 350

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105

<210> SEQ ID NO 351
<211> LENGTH: 107
<212> TYPE: PRT
<213> ORGANISM: Artificial Sequence
<220> FEATURE:
<223> OTHER INFORMATION: Synthetic Construct

<400> SEQUENCE: 351

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
            35                  40                  45

Tyr Tyr Thr Ser Arg Leu Arg Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly His Thr Leu Pro Pro
                85                  90                  95

Thr Phe Gly Gln Gly Thr Lys Val Glu Ile Lys
            100                 105
```

```
<210> SEQ ID NO 352
<211> LENGTH: 244
<212> TYPE: PRT
<213> ORGANISM: Homo sapiens

<400> SEQUENCE: 352

Met Arg Trp Cys Leu Leu Ile Trp Ala Gln Gly Leu Arg Gln Ala
1               5                   10                  15

Pro Leu Ala Ser Gly Met Met Thr Gly Thr Ile Glu Thr Thr Gly Asn
            20                  25                  30

Ile Ser Ala Glu Lys Gly Gly Ser Ile Ile Leu Gln Cys His Leu Ser
            35                  40                  45

Ser Thr Thr Ala Gln Val Thr Gln Val Asn Trp Glu Gln Gln Asp Gln
50                  55                  60

Leu Leu Ala Ile Cys Asn Ala Asp Leu Gly Trp His Ile Ser Pro Ser
65                  70                  75                  80

Phe Lys Asp Arg Val Ala Pro Gly Pro Gly Leu Gly Leu Thr Leu Gln
                85                  90                  95

Ser Leu Thr Val Asn Asp Thr Gly Glu Tyr Phe Cys Ile Tyr His Thr
            100                 105                 110

Tyr Pro Asp Gly Thr Tyr Thr Gly Arg Ile Phe Leu Glu Val Leu Glu
            115                 120                 125

Ser Ser Val Ala Glu His Gly Ala Arg Phe Gln Ile Pro Leu Leu Gly
        130                 135                 140

Ala Met Ala Ala Thr Leu Val Val Ile Cys Thr Ala Val Ile Val Val
145                 150                 155                 160

Val Ala Leu Thr Arg Lys Lys Lys Ala Leu Arg Ile His Ser Val Glu
                165                 170                 175

Gly Asp Leu Arg Arg Lys Ser Ala Gly Gln Glu Glu Trp Ser Pro Ser
            180                 185                 190

Ala Pro Ser Pro Pro Gly Ser Cys Val Gln Ala Glu Ala Ala Pro Ala
            195                 200                 205

Gly Leu Cys Gly Glu Gln Arg Gly Glu Asp Cys Ala Glu Leu His Asp
        210                 215                 220

Tyr Phe Asn Val Leu Ser Tyr Arg Ser Leu Gly Asn Cys Ser Phe Phe
225                 230                 235                 240

Thr Glu Thr Gly

<210> SEQ ID NO 353
<211> LENGTH: 223
<212> TYPE: PRT
<213> ORGANISM: Homo sapiens

<400> SEQUENCE: 353

Met Met Thr Gly Thr Ile Glu Thr Thr Gly Asn Ile Ser Ala Glu Lys
1               5                   10                  15

Gly Gly Ser Ile Ile Leu Gln Cys His Leu Ser Ser Thr Thr Ala Gln
            20                  25                  30

Val Thr Gln Val Asn Trp Glu Gln Gln Asp Gln Leu Leu Ala Ile Cys
            35                  40                  45

Asn Ala Asp Leu Gly Trp His Ile Ser Pro Ser Phe Lys Asp Arg Val
50                  55                  60

Ala Pro Gly Pro Gly Leu Gly Leu Thr Leu Gln Ser Leu Thr Val Asn
65                  70                  75                  80

Asp Thr Gly Glu Tyr Phe Cys Ile Tyr His Thr Tyr Pro Asp Gly Thr
```

```
                    85                  90                  95
Tyr Thr Gly Arg Ile Phe Leu Glu Val Leu Glu Ser Val Ala Glu
            100                 105                 110

His Gly Ala Arg Phe Gln Ile Pro Leu Gly Ala Met Ala Ala Thr
            115                 120                 125

Leu Val Val Ile Cys Thr Ala Val Val Val Ala Leu Thr Arg
130                 135                 140

Lys Lys Lys Ala Leu Arg Ile His Ser Val Glu Gly Asp Leu Arg Arg
145                 150                 155                 160

Lys Ser Ala Gly Gln Glu Glu Trp Ser Pro Ser Ala Pro Ser Pro Pro
                165                 170                 175

Gly Ser Cys Val Gln Ala Glu Ala Pro Ala Gly Leu Cys Gly Glu
            180                 185                 190

Gln Arg Gly Glu Asp Cys Ala Glu Leu His Asp Tyr Phe Asn Val Leu
            195                 200                 205

Ser Tyr Arg Ser Leu Gly Asn Cys Ser Phe Phe Thr Glu Thr Gly
    210                 215                 220

<210> SEQ ID NO 354
<211> LENGTH: 249
<212> TYPE: PRT
<213> ORGANISM: Homo sapiens

<400> SEQUENCE: 354

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Ala Ala Ile Leu Gly
            180                 185                 190

Leu Gly Leu Val Leu Gly Leu Leu Gly Pro Leu Ala Ile Leu Leu Ala
        195                 200                 205

Leu Tyr Leu Leu Arg Arg Asp Gln Arg Leu Pro Pro Asp Ala His Lys
210                 215                 220
```

Pro Pro Gly Gly Gly Ser Phe Arg Thr Pro Ile Gln Glu Glu Gln Ala
225                 230             235                 240

Asp Ala His Ser Thr Leu Ala Lys Ile
                245

ANTI-TIGIT ANTIBODIES AND METHODS OF USE

FIELD OF THE INVENTION

The present invention relates to anti-TIGIT (T-cell immunoreceptor with Ig and ITIM domains) antibodies and methods of using the same.

BACKGROUND OF THE INVENTION

Immune-related diseases (e.g., cancer) are the manifestation or consequence of complex biological pathways, which in normal physiology are critical for responding to insult or injury, initiating repair from insult or injury, and mounting innate and acquired defenses. Disease or pathology occurs when these normal physiological pathways cause additional insult or injury that is directly related to the intensity of the response (e.g., as a consequence of abnormal regulation or excessive stimulation) or as a reaction to self.

Although the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune-related diseases are known and have been extensively studied. Such diseases include cancer (neoplasia), immune-mediated inflammatory diseases, non-immune-mediated inflammatory diseases, infectious diseases, and immunodeficiency diseases.

T lymphocytes (T cells) are an important component of a mammalian immune response. T cells recognize antigens that are associated with a self-molecule encoded by genes within the major histocompatibility complex (MHC). The antigen may be displayed together with MHC molecules on the surface of antigen presenting cells (APCs), virus infected cells, cancer cells, grafts, etc. The T cell system eliminates these altered cells, which pose a health threat to the host mammal. T cells include helper T cells and cytotoxic T cells. Helper T cells proliferate extensively following recognition of an antigen-MHC complex on an APC. Helper T cells also secrete a variety of cytokines (i.e., lymphokines), which play a central role in the activation of B cells, cytotoxic T cells, and a variety of other cells that participate in the immune response.

Regulatory T cells (Treg) are a subset of helper T cells that play a critical role in inhibition of self-reactive immune responses and are often found in sites of chronic inflammation such as in tumor tissue. Tregs are defined phenotypically by high cell surface expression of CD25, CLTA4, GITR, and neuropilin-1 (NRP-1), and are under the control of the transcription factor FOXP3. Tregs perform their suppressive function on activated T cells through contact-dependent mechanisms and cytokine production. Tregs also modulate immune responses by direct interaction with ligands on dendritic cells (DCs), such as CD40L ligation and CTLA4 interaction with B7 molecules on DCs that elicits the induction of indoleamine 2,3-dioxygenase (IDO). DCs are professional APCs capable of inducing immunity or tolerance against self or non-self antigens. DC-expanded Tregs suppress alloreactivity responses in vitro, and when adoptively transferred, appropriate Tregs inhibited diabetes in NODscid mice or experimentally induced asthma. Specific interactions of ligands on DC with Tregs can also abrogate their suppressive function, such as engagement of GITR in mice, suggesting DC may have a pluralistic role in modulating Treg function.

The molecules CTLA4 and GITR are representative of ligands defined within the CD28-B7 and TNF-superfamilies of co-stimulatory/-inhibitory molecules, respectively. These molecules are highly expressed on Tregs but are typically upregulated on activated T cells. More recently, a protein designated TIGIT (for T-cell immunoreceptor with Ig and ITIM domains) was identified as a cell surface-bound protein specifically expressed in T cells that possessing an IgV domain, a transmembrane domain, and two putative immunoreceptor tyrosine inhibitory (ITIM) motifs. TIGIT was shown to be particularly expressed on Treg and memory T cell subsets, as well as NK cells. As there is an unmet need for new therapeutics and methods of treatment of immune-related disorders and particularly cancers, described herein are unexpectedly efficacious therapeutic compositions, such as the anti-TIGIT antibodies and compositions thereof, and methods of treatment of immune-related disorders and cancers, which involve modulating the interaction of TIGIT with its binding partners.

SUMMARY OF THE INVENTION

The present invention provides anti-TIGIT (T-cell immunoreceptor with Ig and ITIM domains) antibodies and variants thereof with improved properties, including, for example, binding affinity, cross-reactivity, pharmacokinetics, and/or expression. In particular, the present invention provides anti-TIGIT antibodies and variants thereof that possess, for example, high binding affinity to human TIGIT; cross-reactivity between human TIGIT, cynomolgus monkey (cyno) TIGIT, and/or rabbit TIGIT; desirable clearance properties in cyno; and biochemical and biophysical properties that confer the antibodies and variants thereof with high stability.

In one aspect, the invention features an antibody that specifically binds to human TIGIT, wherein the antibody binds to an epitope on human TIGIT comprising one or more of amino acid residues Ser78, Ser80, and Lys82 of human TIGIT. In one embodiment, the epitope comprises amino acid residues Ser80 and Lys82 of human TIGIT. In another embodiment, the epitope comprises amino acid residues Ser78, Ser80, and Lys82 of human TIGIT. In another embodiment, the epitope further comprises amino acid residue Ala67 of human TIGIT. In another embodiment, the epitope further comprises one or more additional amino acid residues selected from the group consisting of Glu60, Leu65, and Ile68 of human TIGIT. In another embodiment, the epitope further comprises one or more additional amino acid residues selected from the group consisting of Gln56, Asn70, Leu73, and His111 of human TIGIT. In another embodiment, the epitope further comprises one or more additional amino acid residues selected from the group consisting of Thr55, Asn58, Asp63, Gln64, His76, Ile77, and Pro79 of human TIGIT. In another embodiment, the epitope consists of amino acid residues Thr55, Gln56, Asn58, Glu60, Asp63, Gln64, Leu65, Ala67, Ile68, Asn70, Leu73, His76, Ile77, Ser78, Pro79, Ser80, Lys82, and His111 of human TIGIT.

In another aspect, the invention features an antibody that specifically binds to human TIGIT, wherein the antibody binds to an epitope on human TIGIT comprising one or more of amino acid residues Thr55, Ser80, and Lys82 of human TIGIT. In one embodiment, the epitope comprises amino acid residue Lys82 of human TIGIT. In another embodiment, the epitope comprises amino acid residues Thr55, Ser80, and Lys82 of human TIGIT. In another embodiment, the epitope further comprises amino acid residue Gln56 of human TIGIT. In another embodiment, the epitope further comprises amino acid residue Ile77 or Pro79 of human TIGIT. In another embodiment, the epitope further comprises amino acid residues Ile77 and Pro79 of human TIGIT. In another embodiment, the epitope further comprises amino acid residue Asn58 or Glu60 of human TIGIT. In another embodiment, the epitope further comprises amino acid residues Asn58 and Glu60 of human TIGIT. In another embodiment, the epitope further comprises one or more additional amino acid residues selected from the group consisting of Leu65, Ile68, Leu73, His76, Ser78, and His111 of human TIGIT. In another embodiment, the epitope further comprises amino acid residues Leu65, Ile68, Leu73, His76, Ser78, and His111 of human TIGIT. In yet another embodiment, the epitope consists of Thr55, Gln56, Asn58, Glu60, Leu65, Ile68, Leu73, His76, Ile77, Ser78, Pro79, Ser80, Lys82, and His111 of human TIGIT.

In another aspect, the invention features an antibody that specifically binds to human TIGIT, wherein the antibody comprises a paratope comprising one or more amino acid residues selected from the group consisting of heavy chain variable region amino acid residues Asn32, Tyr52, Arg52b, Phe53, Lys54, Tyr56, Asp58, Tyr99, Asp100, Leu100a, Leu100b, and Ala100c and light chain variable region amino acid residues Tyr27d, Tyr92, Ser93, Thr94, and Phe96. In one embodiment, the paratope consists of heavy chain variable region amino acid residues Asn32, Tyr52, Arg52b, Phe53, Lys54, Tyr56, Asp58, Tyr99, Asp100, Leu100a, Leu100b, and Ala100c and light chain variable region amino acid residues Tyr27d, Tyr92, Ser93, Thr94, and Phe96. In any of the above aspects, the antibody may be capable of binding to rabbit TIGIT.

In another aspect, the invention features an antibody that specifically binds to human TIGIT, wherein the antibody binds to an epitope on human TIGIT comprising one or more amino acid residues selected from the group consisting of Gln53, His111, and Tyr113 of human TIGIT. In some embodiments, the epitope further comprises Gln56 of human TIGIT. In some embodiments, the epitope further comprises Glu60, Leu65, Ile68, Asn70, Leu73, and His76 of human TIGIT.

In another aspect, the invention features an antibody that specifically binds to human TIGIT, wherein the antibody comprises the following six hypervariable regions (HVRs): an HVR-H1 comprising the amino acid sequence of SNSAAWN (SEQ ID NO: 1); an HVR-H2 comprising the amino acid sequence of KTYYRFKWYSDYAVSVKG (SEQ ID NO: 2); an HVR-H3 comprising the amino acid sequence of ESTTYDLLAGPFDY (SEQ ID NO: 3); an HVR-L1 comprising the amino acid sequence of KSSQTVLYSSNNKKYLA (SEQ ID NO: 4); an HVR-L2 comprising the amino acid sequence of WASTRES (SEQ ID NO: 5); and an HVR-L3 comprising the amino acid sequence of QQYYSTPFT (SEQ ID NO: 6). In some embodiments, the antibody further comprises the following light chain variable region framework regions (FRs): an FR-L1 comprising the amino acid sequence of DIVMTQSPDSLAVSLGERATINC (SEQ ID NO: 7); an FR-L2 comprising the amino acid sequence of WYQQKPGQPPNLLIY (SEQ ID NO: 8); an FR-L3 comprising the amino acid sequence of GVPDRFSGSGSGTDFTLTISSLQAEDVAVYYC (SEQ ID NO: 9); and an FR-L4 comprising the amino acid sequence of FGPGTKVEIK (SEQ ID NO: 10). In some embodiments, the antibody further comprises the following heavy chain variable region FRs: an FR-H1 comprising the amino acid sequence of X₁VQLQQSGPGLVKPSQTLSLTCAISGDSVS (SEQ ID NO: 11), wherein X₁ is Q or E; an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and an FR-H4 comprising the amino acid sequence of WGQGTLVTVSS (SEQ ID NO: 14). In some embodiments, the antibody further comprises the following heavy chain variable region FRs: an FR-H1 comprising the amino acid sequence of EVQLQQSGPGLVKPSQTLSLTCAISGDSVS (SEQ ID NO: 15); an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and an FR-H4 comprising the amino acid sequence of WGQGTLVTVSS (SEQ ID NO: 14). In some embodiments, the antibody further comprises the following heavy chain variable region FRs: an FR-H1 comprising the amino acid sequence of QVQLQQSGPGLVKPSQTLSLTCAISGDSVS (SEQ ID NO: 16); an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and an FR-H4 comprising the amino acid sequence of WGQGTLVTVSS (SEQ ID NO: 14). In some embodiments, the antibody is capable of binding to rabbit TIGIT.

In another aspect, the invention features an antibody that specifically binds to human TIGIT, wherein the antibody comprises the following six HVRs: an HVR-H1 comprising the amino acid sequence of SYPMN (SEQ ID NO: 17); an HVR-H2 comprising the amino acid sequence of WINTNTGNPTYVQGFTG (SEQ ID NO: 18); an HVR-H3 comprising the amino acid sequence of TGGHTYDSYAFDV (SEQ ID NO: 19); an HVR-L1 comprising the amino acid sequence of RASQVISSSLA (SEQ ID NO: 20); an HVR-L2 comprising the amino acid sequence of AASTLQS (SEQ ID NO: 21); and an HVR-L3 comprising the amino acid sequence of QHLHGYPX₁N (SEQ ID NO: 22), wherein X₁ is C or S. In some embodiments, the antibody comprises the following six HVRs: an HVR-H1 comprising the amino acid sequence of SYPMN (SEQ ID NO: 17); an HVR-H2 comprising the amino acid sequence of WINTNTGNPTYVQGFTG (SEQ ID NO: 18); an HVR-H3 comprising the amino acid sequence of TGGHTYDSYAFDV (SEQ ID NO: 19); an HVR-L1 comprising the amino acid sequence of RASQVISSSLA (SEQ ID NO: 20); an HVR-L2 comprising the amino acid sequence of AASTLQS (SEQ ID NO: 21); and an HVR-L3 comprising the amino acid sequence of QHLHGYPSN (SEQ ID NO: 23). In some embodiments, the antibody further comprises the following heavy chain variable region FRs: an FR-H1 comprising the amino acid sequence of EVQLVQSGSDLKKPGASVRVSCKASGYTFT (SEQ ID NO: 24); an FR-H2 comprising the amino acid sequence of WVRQAPGHGLEWMG (SEQ ID NO: 25); an FR-H3 comprising the amino acid sequence of RFVFSLDTSVNTAYLQISSLKAEDTAVYFCAR (SEQ ID NO: 26); and an FR-H4 comprising the amino acid sequence of WGQGTMVTVSS (SEQ ID NO: 27). In some embodiments, antibody comprises the following six HVRs: an HVR-H1 comprising the amino acid sequence of SYPMN (SEQ ID NO: 17); an HVR-H2 comprising the amino acid sequence of WINTNTGNPTYVQGFTG (SEQ ID NO: 18); an HVR-H3 comprising the amino acid sequence of TGGHTYDSYAFDV (SEQ ID NO: 19); an HVR-L1 comprising the amino acid sequence of RASQVISSSLA (SEQ ID NO:

20); an HVR-L2 comprising the amino acid sequence of AASTLQS (SEQ ID NO: 21); and an HVR-L3 comprising the amino acid sequence of QHLHGYPCN (SEQ ID NO: 28). In some embodiments, the antibody further comprises the following heavy chain variable region FRs: an FR-H1 comprising the amino acid sequence of QVQLVQSGSDLK-KPGASVRVSCKASGYTFT (SEQ ID NO: 29); an FR-H2 comprising the amino acid sequence of WVRQAPGH-GLEWMG (SEQ ID NO: 25); an FR-H3 comprising the amino acid sequence of RFVFSLDTSVNTAYLQISSL-KAEDTAVYFCAR (SEQ ID NO: 26); and an FR-H4 comprising the amino acid sequence of WGQGTMVTVSS (SEQ ID NO: 27). In some embodiments, the antibody further comprises the following light chain variable region FRs: an FR-L1 comprising the amino acid sequence of DIQLTQSPTFLSASVGDRVTITC (SEQ ID NO: 30); an FR-L2 comprising the amino acid sequence of WYQQN-PGKAPKLLIY (SEQ ID NO: 31); an FR-L3 comprising the amino acid sequence of GVPSRFSGSGSGTEFTLTISS-LQPEDFVTYYC (SEQ ID NO: 32); and an FR-L4 comprising the amino acid sequence of FGQGTKVEIK (SEQ ID NO: 33).

In another aspect, the invention features an antibody that specifically binds to human TIGIT, wherein the antibody comprises (a) a heavy chain variable region (VH) having at least 95% sequence identity to the amino acid sequence of SEQ ID NO: 34 or 35; (b) a light chain variable region (VL) having at least 95% sequence identity to the amino acid sequence of SEQ ID NO: 36; or (c) a heavy chain variable region as in (a) and a light chain variable region as in (b). In some embodiments, antibody comprises (a) a heavy chain variable region (VH) having at least 95% sequence identity to the amino acid sequence of SEQ ID NO: 34; (b) a light chain variable region (VL) having at least 95% sequence identity to the amino acid sequence of SEQ ID NO: 36; or (c) a heavy chain variable region as in (a) and a light chain variable region as in (b). In some embodiments, the antibody comprises (a) a heavy chain variable region (VH) having at least 95% sequence identity to the amino acid sequence of SEQ ID NO: 35; (b) a light chain variable region (VL) having at least 95% sequence identity to the amino acid sequence of SEQ ID NO: 36; or (c) a heavy chain variable region as in (a) and a light chain variable region as in (b). In some embodiments, the antibody is capable of binding to rabbit TIGIT.

In another aspect, the invention features an antibody that specifically binds to human TIGIT, wherein the antibody comprises (a) a heavy chain variable region (VH) having at least 95% sequence identity to the amino acid sequence of SEQ ID NO: 37; (b) a light chain variable region (VL) having at least 95% sequence identity to the amino acid sequence of SEQ ID NO: 38; or (c) a heavy chain variable region as in (a) and a light chain variable region as in (b).

In yet another aspect, the invention features an antibody that specifically binds to human TIGIT, wherein the antibody comprises (a) a heavy chain variable region (VH) having at least 95% sequence identity to the amino acid sequence of SEQ ID NO: 39; (b) a light chain variable region (VL) having at least 95% sequence identity to the amino acid sequence of SEQ ID NO: 40; or (c) a heavy chain variable region as in (a) and a light chain variable region as in (b).

In any one of the aspects described above, the antibody may be capable of binding to both human TIGIT and cynomolgus monkey (cyno) TIGIT, but not murine TIGIT. In some embodiments, the antibody binds human TIGIT with a Kd of about 10 nM or lower and cyno TIGIT with a Kd of about 10 nM or lower. In some embodiments, the antibody binds human TIGIT with a Kd of about 0.1 nM to about 1 nM and cyno TIGIT with a Kd of about 0.5 nM to about 1 nM. In some embodiments, the antibody binds human TIGIT with a Kd of about 0.1 nM or lower and cyno TIGIT with a Kd of about 0.5 nM or lower.

In any one of the aspects described above, the antibody may be an antagonist antibody or an agonist antibody.

In some embodiments, the antagonist antibody specifically binds TIGIT and inhibits or blocks TIGIT interaction with poliovirus receptor (PVR). In some embodiments, the antagonist antibody inhibits intracellular signaling mediated by TIGIT binding to PVR. In some embodiments, the antagonist antibody inhibits or blocks binding of human TIGIT to human PVR with an IC50 value of 10 nM or lower. In some embodiments, the antagonist antibody inhibits or blocks binding of human TIGIT to human PVR with an IC50 value of 1 nM to about 10 nM. In some embodiments, the antagonist antibody inhibits or blocks binding of cyno TIGIT to cyno PVR with an IC50 value of 50 nM or lower. In some embodiments, the antagonist antibody inhibits or blocks binding of cyno TIGIT to cyno PVR with an IC50 value of 1 nM to about 50 nM. In some embodiments, the antagonist antibody inhibits or blocks binding of cyno TIGIT to cyno PVR with an IC50 value of 1 nM to about 5 nM.

In some embodiments, the agonist antibody specifically binds TIGIT and stimulates the interaction of PVR with CD226 or CD96. In some embodiments, the agonist antibody specifically binds TIGIT and stimulates the interaction of PVR with CD226 and CD96. In some embodiments, the agonist antibody specifically binds TIGIT and stimulates the interaction of human PVR with human CD226 and human CD96.

In some embodiments, the agonist antibody specifically binds TIGIT and stimulates the interaction of cyno PVR with cyno CD226 and cyno CD96.

In another aspect, the invention features an isolated antibody that competes for binding to TIGIT with an antibody of any one of the above aspects.

In another aspect, the invention features an isolated antibody that binds to the same epitope as an antibody of any one of the above aspects.

In some embodiments of any one of the aspects described above, the antibody is monoclonal. In some embodiments, the antibody is human, humanized, or chimeric. In some embodiments, the antibody is a full-length antibody. In some embodiments, the antibody has a clearance following administration (e.g., injection, e.g., intravenous injection) of less than about 10 ml/kg/day (e.g., about 3 ml/kg/day to about 10 ml/kg/day). In some embodiments, the antibody antibody has a clearance of about 3 ml/kg/day to about 8 ml/kg/day. In some embodiments, administration of the antibody is to a mammal (e.g., a monkey, such as a cynomolgus monkey, or a human). In some embodiments, the antibody is an antibody fragment that binds TIGIT. In some embodiments, the antibody fragment is selected from the group consisting of Fab, Fab', Fab'-SH, Fv, single chain variable fragment (scFv), and (Fab')$_2$ fragments. In some embodiments, the antibody is an IgG class antibody. In some embodiments, the IgG class antibody is an IgG1 subclass antibody. In some embodiments, an antibody described herein can be for use as a medicament. In some embodiments, an antibody described herein may be for use in treating or delaying progression of a cancer in a subject in need thereof. In some embodiments, the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, mycoses fungoides, a merkel cell cancer, and a hematologic malignancy. In some embodiments, an antibody described herein may be for use in treating or delaying progression of multiple myeloma (MM). In some embodiments, an antibody described herein may be for use in treating or delaying progression of an immune-related disease in a subject in need thereof. In some embodiments, the immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, an antibody described herein may be for use in increasing, enhancing, or stimulating an immune response or function in a subject in need thereof.

In another aspect, the invention features a polynucleotide (e.g., an isolated polynucleotide) encoding any of the antibodies described herein. In another aspect, the invention features a vector (e.g., an expression vector) comprising the polynucleotide for expressing the antibody. In another aspect, the invention features host cells comprising the preceding polynucleotides and/or vectors. In some embodiments, the host cell is a eukaryotic (e.g., a mammalian cell). In some embodiments, the eukaryotic cell is a 293 cell, a Chinese hamster ovary (CHO) cell, a yeast cell, or a plant cell. In some embodiments, the host cell is a prokaryotic cell. In some embodiments, the prokaryotic cell is *E. coli*.

In another aspect, the invention features a method of producing any of the antibodies described herein, the method comprising culturing a host cell that comprises any of the preceding vectors (e.g., expression vectors) in a culture medium. In some embodiments, the method further comprises recovering the antibody from the host cell or the culture medium. In some embodiments, the host cell is a eukaryotic cell, for example, a mammalian cell, for example, a 293 cell, a Chinese hamster ovary (CHO) cell, a yeast cell, or a plant cell. In some embodiments, the host cell is a prokaryotic cell. In some embodiments, the prokaryotic cell is *E. coli*.

In another aspect, the invention features an immunoconjugate comprising any one of the antibodies described herein and an agent (e.g., a therapeutic agent, e.g., a cytotoxic agent).

In another aspect, the invention features a composition comprising an antibody described herein. In some embodiments, the composition further comprises a pharmaceutically acceptable carrier, excipient, or diluent. In some embodiments, the composition is for diagnostic use (e.g., to detect TIGIT expression levels, e.g., TIGIT protein expression levels). In some embodiments, the composition is a pharmaceutical composition. In some embodiments, the composition further comprises a PD-1 axis binding antagonist or an additional therapeutic agent.

In another aspect, the invention features the use of an antibody described herein in the manufacture of a medicament for treating or delaying progression of a cancer in a subject in need thereof. In some embodiments, the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, mycoses fungoides, a merkel cell cancer, and a hematologic malignancy. In some embodiments, the myeloma is MM. In some embodiments, the medicament is formulated for administration subcutaneously, intravenously, intramuscularly, topically, orally, transdermally, intraperitoneally, intraorbitally, by implantation, by inhalation, intrathecally, intraventricularly, or intranasally. In some embodiments, the subject is a human.

In another aspect, the invention features the use of an antibody described herein in the manufacture of a medicament for treating or delaying progression of an immune-related disease in a subject in need thereof. In some embodiments, the immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the medicament is formulated for administration subcutaneously, intravenously, intramuscularly, topically, orally, transdermally, intraperitoneally, intraorbitally, by implantation, by inhalation, intrathecally, intraventricularly, or intranasally. In some embodiments, the subject is a human.

In another aspect, the invention features the use of an antibody described herein in the manufacture of a medicament for increasing, enhancing, or stimulating an immune response or function in a subject in need thereof. In some embodiments, the medicament is formulated for administration subcutaneously, intravenously, intramuscularly, topically, orally, transdermally, intraperitoneally, intraorbitally, by implantation, by inhalation, intrathecally, intraventricularly, or intranasally. In some embodiments, the subject is a human.

In another aspect, the invention features a method for treating or delaying progression of a cancer in a subject, the method comprising administering to the subject an effective amount of any one or more (e.g., 1, 2, 3, 4, 5, or 6 or more) of the antibodies described herein, thereby treating or delaying the progression of the cancer in the subject. In some embodiments, the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, mycoses fungoides, a merkel cell cancer, and a hematologic malignancy. In some embodiments, the myeloma is MM.

In another aspect, the invention features a method for treating or delaying progression of an immune-related disease in a subject, the method comprising administering to the subject an effective amount of one or more (e.g., 1, 2, 3, 4, 5, or 6 or more) of the antibodies described herein, thereby treating or delaying the progression of the immune-related disease in the subject. In some embodiments, the immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity.

In another aspect, the invention features a method of increasing, enhancing, or stimulating an immune response or function in a subject, the comprising administering to the subject an effective amount of one or more (e.g., 1, 2, 3, 4, 5, or 6 or more) of the antibodies described herein, thereby increasing, enhancing, or stimulating an immune response or function in the subject. In some embodiments, the method further comprises administering to the subject a PD-1 axis binding antagonist. In some embodiments, the PD-1 axis binding antagonist is administered prior to or subsequent to the administration of the antibody. In some embodiments, the PD-1 axis binding antagonist is administered concurrently with the antibody. In some embodiments, the PD-1 axis binding antagonist is selected from the group consisting of a PD-1 binding antagonist, a PD-L1 binding antagonist, and a PD-L2 binding antagonist. In some embodiments, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist is an anti-PD-1 antibody. In some embodiments, the PD-1 binding antagonist is selected from the group consisting of MDX 1106 (nivolumab), MK-3475 (pembrolizumab), CT-011 (pidilizumab), MEDI-0680 (AMP-514), PDR001, REGN2810, and BGB-108. In some embodiments, the PD-1 axis binding antagonist is a PD-L1 binding antagonist. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an anti-PD-L1 antibody. In some embodiments, the anti-PD-L1 antibody is selected from the group consisting of: MPDL3280A (atezolizumab), YW243.55.S70, MDX-1105, MEDI4736 (durvalumab), and MSB0010718C (avelumab). In some embodiments, the antibody is MPDL3280A. In some embodiments, the PD-1 axis binding antagonist is a PD-L2 binding antagonist. In some embodiments, the PD-L2 binding antagonist is an anti-PD-L2 antibody. In some embodiments, the PD-L2 binding antagonist is an immunoadhesin.

In some embodiments, any one of the methods of treatment described above may further comprise administering to the subject an OX40 binding agonist. In some embodiments, the OX40 binding agonist is administered prior to or subsequent to the administration of the antibody and/or the PD-1 axis binding antagonist. In some embodiments, the OX40 binding agonist is administered concurrently with the antibody and/or the PD-1 axis binding antagonist. In some embodiments, the OX40 binding agonist is selected from the group consisting of an OX40 agonist antibody, an OX40L agonist fragment, an OX40 oligomeric receptor, and an OX40 immunoadhesin. In some embodiments, the OX40 agonist antibody depletes cells that express human OX40. In some embodiments, the cells that express human OX40 are CD4+ effector T cells. In some embodiments, the cells that express human OX40 are regulatory T (Treg) cells. In some embodiments, the depleting is by ADCC and/or phagocytosis. In some embodiments, the OX40 agonist antibody binds human OX40 with an affinity of less than or equal to about 1 nM. In some embodiments, the OX40 agonist antibody binds human OX40 with an affinity of less than or equal to about 0.45 nM. In some embodiments, the OX40 agonist antibody binds human OX40 with an affinity of less than or equal to about 0.4 nM. In some embodiments, the OX40 agonist antibody binds human OX40 with an EC50 of less than or equal to 0.3 µg/ml. In some embodiments, the OX40 agonist antibody binds human OX40 with an EC50 of less than or equal to 0.2 µg/ml. In some embodiments, the OX40 agonist antibody increases CD4+ effector T cell proliferation and/or increases cytokine production by the CD4+ effector T cell as compared to proliferation and/or cytokine production prior to treatment with the OX40 agonist antibody. In some embodiments, the OX40 agonist antibody increases memory T cell proliferation and/or cytokine production by a memory T cell. In some embodiments, the cytokine production is IFN-γ production. In some embodiments, the OX40 agonist antibody inhibits Treg function. In some embodiments, the OX40 agonist antibody inhibits Treg suppression of effector T cell function (e.g., effector T cell proliferation and/or cytokine production). In some embodiments, the effector T cell is a CD4+ effector T cell. In some embodiments, the OX40 agonist antibody increases OX40 signal transduction in a target cell that expresses OX40. In some embodiments, the OX40 signal transduction is detected by monitoring NFkB downstream signaling. In some embodiments, the the OX40 agonist antibody comprises a variant IgG1 Fc polypeptide comprising a mutation that eliminates binding to human effector cells and has diminished activity relative to the OX40 agonist antibody comprising a native sequence IgG1 Fc portion. In some embodiments, the OX40 agonist antibody comprises a variant IgG1 Fc polypeptide comprising a DANA mutation. In some embodiments, the OX40 agonist antibody comprises (a) a VH domain comprising (i) a HVR-H1 comprising the amino acid sequence of SEQ ID NO: 278, 279, or 280, (ii) a HVR-H2 comprising the amino acid sequence of SEQ ID NO: 281, 282, 283, 284, 285, or 286, and (iii) a HVR-H3 comprising an amino acid sequence selected from SEQ ID NO: 287, 288, or 289; and (b) a VL domain comprising (i) a HVR-L1 comprising the amino acid sequence of SEQ ID NO: 290, (ii) a HVR-L2 comprising the amino acid sequence of SEQ ID NO: 291, and (iii) a HVR-L3 comprising the amino acid sequence of SEQ ID NO: 292, 293, 294, 295, 296, 297, 298, or 299. In some embodiments, the OX40 agonist antibody comprises (a) HVR-H1 comprising the amino acid sequence of SEQ ID NO: 278; (b) HVR-H2 comprising the amino acid sequence of SEQ ID NO: 281; (c) HVR-H3 comprising the amino acid sequence of SEQ ID NO: 287; (d) HVR-L1 comprising the amino acid sequence of SEQ ID NO: 290; (e) HVR-L2 comprising the amino acid sequence of SEQ ID NO: 291; and (f) HVR-L3 comprising an amino acid sequence selected from SEQ ID NO: 292. In some embodiments, the OX40 agonist antibody comprises (a) HVR-H1 comprising the amino acid sequence of SEQ ID NO: 278; (b) HVR-H2 comprising the amino acid sequence of SEQ ID NO: 281; (c) HVR-H3 comprising the amino acid sequence of SEQ ID NO: 287; (d) HVR-L1 comprising the amino acid sequence of SEQ ID NO: 290; (e) HVR-L2 comprising the amino acid sequence of SEQ ID NO: 291; and (f) HVR-L3 comprising an amino acid sequence selected from SEQ ID NO: 297. In some embodiments, the OX40 agonist antibody comprises (a) HVR-H1 comprising the amino acid sequence of SEQ ID NO: 278; (b) HVR-H2 comprising the amino acid sequence of SEQ ID NO: 281; (c) HVR-H3 comprising the amino acid sequence of SEQ ID NO: 287; (d) HVR-L1 comprising the amino acid sequence of SEQ ID NO: 290; (e) HVR-L2 comprising the amino acid sequence of SEQ ID NO: 291; and (f) HVR-L3 comprising an amino acid sequence selected from SEQ ID NO: 298. In some embodiments, the OX40 agonist antibody comprises a VH sequence having at least 90% sequence identity to the amino acid sequence of any one of SEQ ID NOs: 300-325. In some embodiments, the OX40 agonist antibody comprises a VH sequence having at least 90% sequence identity to the amino acid sequence of SEQ ID NO: 300. In some embodiments, a total of 1 to 10 amino acids have been substituted, inserted, and/or deleted in SEQ ID NO: 300. In some embodiments, the OX40 agonist antibody comprises a VH comprising one, two, or three HVRs selected from: (a) HVR-H1 comprising the amino acid sequence of SEQ ID NO: 278, (b) HVR-H2 comprising the amino acid sequence of SEQ ID NO: 281, and (c) HVR-H3 comprising the amino acid sequence of SEQ ID NO: 287. In some embodiments, the OX40 agonist antibody comprises a VL sequence having at least 90% sequence identity to the amino acid sequence of any one of SEQ ID NOs: 326-351. In some embodiments, the OX40 agonist antibody comprises a VL having at least 90% sequence identity to the amino acid sequence of SEQ ID NO: 326. In some embodiments, a total of 1 to 10 amino acids have been substituted, inserted, and/or deleted in SEQ ID NO: 326. In some embodiments, the OX40 agonist antibody comprises a VL comprising one, two, or three HVRs selected from (a) HVR-L1 comprising the amino acid sequence of SEQ ID NO: 290; (b) HVR-L2 comprising the amino acid sequence of SEQ ID NO: 291; and (c) HVR-L3 comprising the amino acid sequence of SEQ ID NO: 292. In some embodiments, the OX40 agonist antibody comprises (a) a VH sequence of SEQ ID NO: 300; (b) a VL sequence of SEQ ID NO: 326; or (c) a VH sequence as in (a) and a VL sequence as in (b). In some embodiments, the OX40 agonist antibody comprises (a) a VH sequence of SEQ ID NO: 319; (b) a VL sequence of SEQ ID NO: 345; or (c) a VH sequence as in (a) and a VL sequence as in (b). In some embodiments, the OX40 agonist antibody comprises (a) a VH sequence of SEQ ID NO: 320; (b) a VL sequence of SEQ ID NO: 346; or (c) a VH sequence as in (a) and a VL sequence as in (b). In some embodiments, the OX40 agonist antibody is antibody L106, antibody ACT35, MEDI6469, or MEDI0562. In some embodiments, the OX40 agonist antibody is a full-length IgG1 antibody. In some embodiments, the OX40 immunoadhesin is a trimeric OX40-Fc protein.

In some embodiments, any one of the methods of treatment described above may further comprise administering to the subject an agent that decreases or inhibits one or more additional immune co-inhibitory receptors. In some embodiments, the one or more additional immune co-inhibitory receptor is selected from the group consisting of PD-1, CTLA-4, LAG3, TIM3, BTLA, VISTA, B7H4, and CD96. In some embodiments, any one of the methods of treatment described above may further comprise administering to the subject an additional therapeutic agent. In some embodiments, the additional therapeutic agent is a chemotherapeutic agent. In some embodiments, antibody is administered subcutaneously, intravenously, intramuscularly, topically, orally, transdermally, intraperitoneally, intraorbitally, by implantation, by inhalation, intrathecally, intraventricularly, or intranasally. In some embodiments, the subject is a human.

In another aspect, the invention features a kit comprising any one or more (e.g., 1, 2, 3, 4, 5, or 6 or more) of the antibodies described herein and package insert comprising instructions for using the antibody for treating or delaying progression of a cancer in a subject. In some embodiments, the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, mycoses fungoides, a merkel cell cancer, and a hematologic malignancy. In some embodiments, the subject is a human. In some embodiments, the myeloma is MM.

In another aspect, the invention features a kit comprising any one or more (e.g., 1, 2, 3, 4, 5, or 6 or more) of the antibodies described herein and a package insert comprising instructions for using the antibody for treating or delaying progression of an immune-related disease in a subject. In some embodiments, the immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the subject is a human.

In another aspect, the invention features a kit comprising any one or more (e.g., 1, 2, 3, 4, 5, or 6 or more) of the antibodies described herein and a package insert comprising instructions for increasing, enhancing, or stimulating an immune response or function in a subject. In some embodiments, the subject is a human.

BRIEF DESCRIPTION OF THE DRAWINGS

The application file contains at least one drawing executed in color. Copies of this patent or patent application with color drawings will be provided by the Office upon request and payment of the necessary fee.

FIG. 1D is a graph showing the results of the CHO-TIGIT binding assay depicted in FIG. 1A using human TIGIT-expressing CHO cells and the indicated SD-derived anti-TIGIT antibodies at varying concentrations, as analyzed by FACS.

FIG. 1E is a graph showing the results of the CHO-TIGIT binding assay depicted in FIG. 1A using cyno TIGIT-expressing CHO cells and the indicated SD-derived anti-TIGIT antibodies at varying concentrations, as analyzed by FACS.

FIG. 3D is a table showing the results of the blocking ELISA assays described in FIGS. 3A-3C.

FIG. 5B is a table showing the calculated clearance values for each antibody tested in the pharmacokinetic clearance experiments in FIG. 5A.

FIG. 5C is a graph showing the pharmacokinetic clearance of anti-TIGIT antibodies h10A7.K4G3 and 4.1D3 in cyno following 10 mg/kg intravenous administration as a function of serum concentration (μg/ml) over time (days; d0-d7).

FIG. 5D is a table showing the calculated clearance values for the anti-TIGIT antibodies h10A7.K4G3 and 4.1D3 tested in the pharmacokinetic clearance experiments in FIG. 5C.

FIG. 7A is a graph of showing the $K_D$ values (nM) for each of the identified anti-TIGIT antibodies for the indicated human TIGIT alanine scanning mutant.

FIG. 7B is a graph of showing the $K_D$ values (nM) for each of the identified anti-TIGIT antibodies for the indicated human TIGIT alanine scanning mutant, normalized against the wild-type human TIGIT target. Alanine scanning mutants of TIGIT that resulted in a 1- to 10-fold or greater than 10-fold drop in binding affinity are indicated by light gray and dark gray shading, respectively.

DETAILED DESCRIPTION OF THE INVENTION

I. General Techniques

Figures 1A, 1B, 1C:
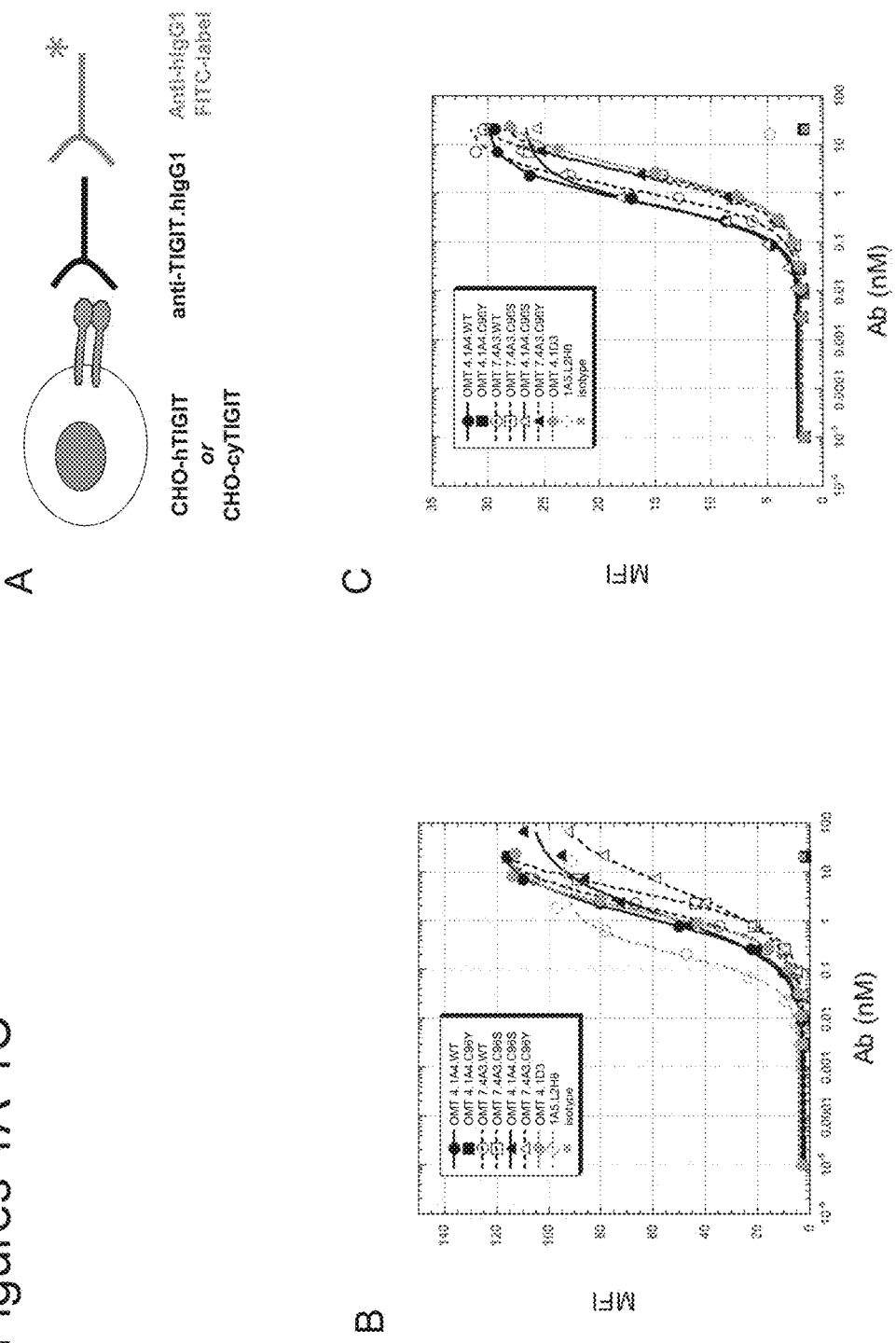
FIG. 1A is a schematic diagram of a CHO-TIGIT binding assay.
FIG. 1B is a graph showing the results of the CHO-TIGIT binding assay depicted in FIG. 1A using human TIGIT-expressing CHO cells and the indicated OMT-derived anti-TIGIT antibodies at varying concentrations, as analyzed by FACS.
FIG. 1C is a graph showing the results of the CHO-TIGIT binding assay depicted in FIG. 1A using cynomolgus monkey (cyno) TIGIT-expressing CHO cells and the indicated OMT-derived anti-TIGIT antibodies at varying concentrations, as analyzed by FACS.
Figure 2A:
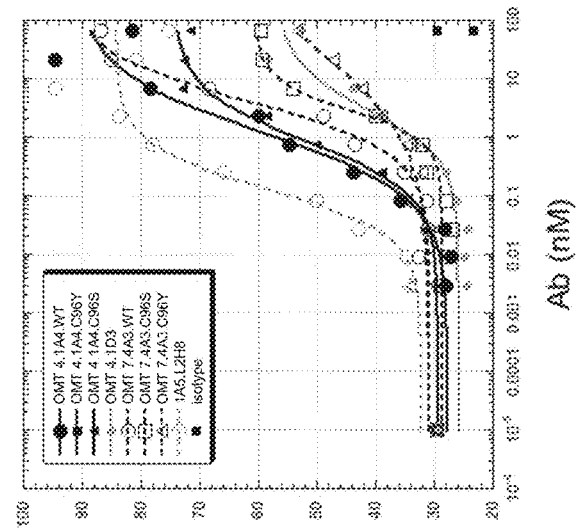
FIG. 2A is a graph showing the binding of the indicated OMT-derived anti-TIGIT antibodies to human CD4 T cells as a function of antibody concentration.
Figure 2B:
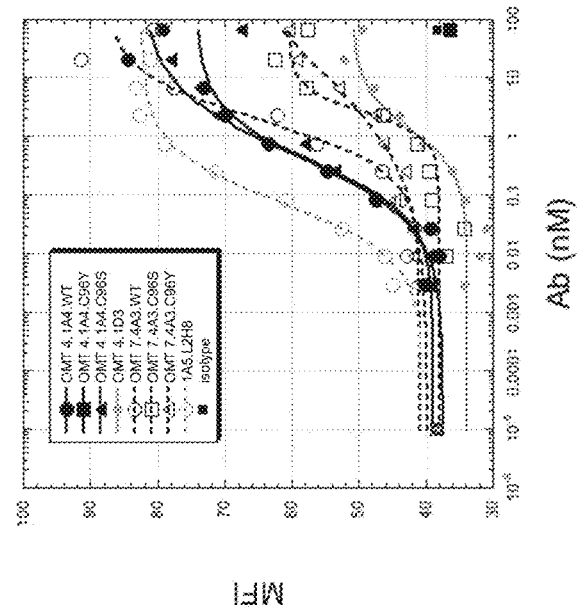
FIG. 2B is a graph showing the binding of the indicated OMT-derived anti-TIGIT antibodies to human CD8 T cells as a function of antibody concentration.
Figure 2C:
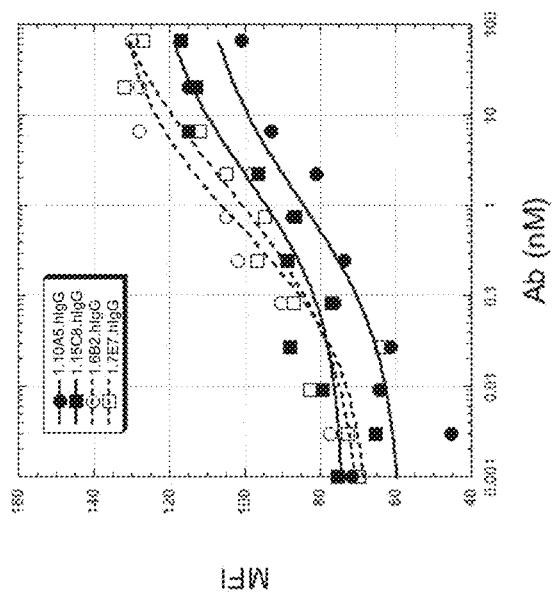
FIG. 2C is a graph showing the binding of the indicated SD-derived anti-TIGIT antibodies to human CD4 T cells as a function of antibody concentration.
Figure 2D:
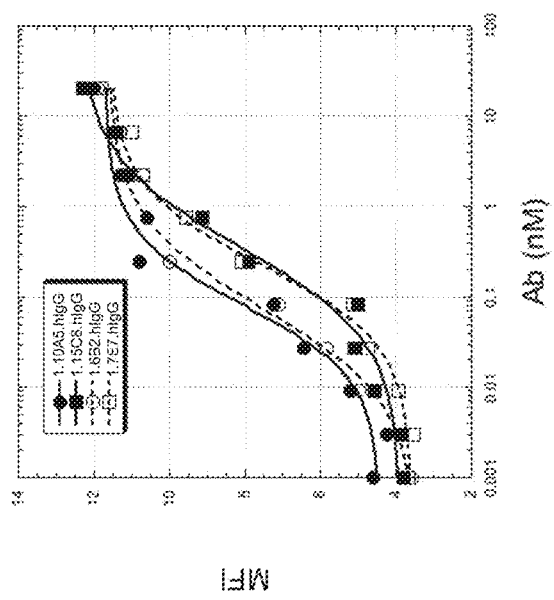
FIG. 2D is a graph showing the binding of the indicated SD-derived anti-TIGIT antibodies to human CD8 T cells as a function of antibody concentration.
Figures 3A, 3B, 3C:
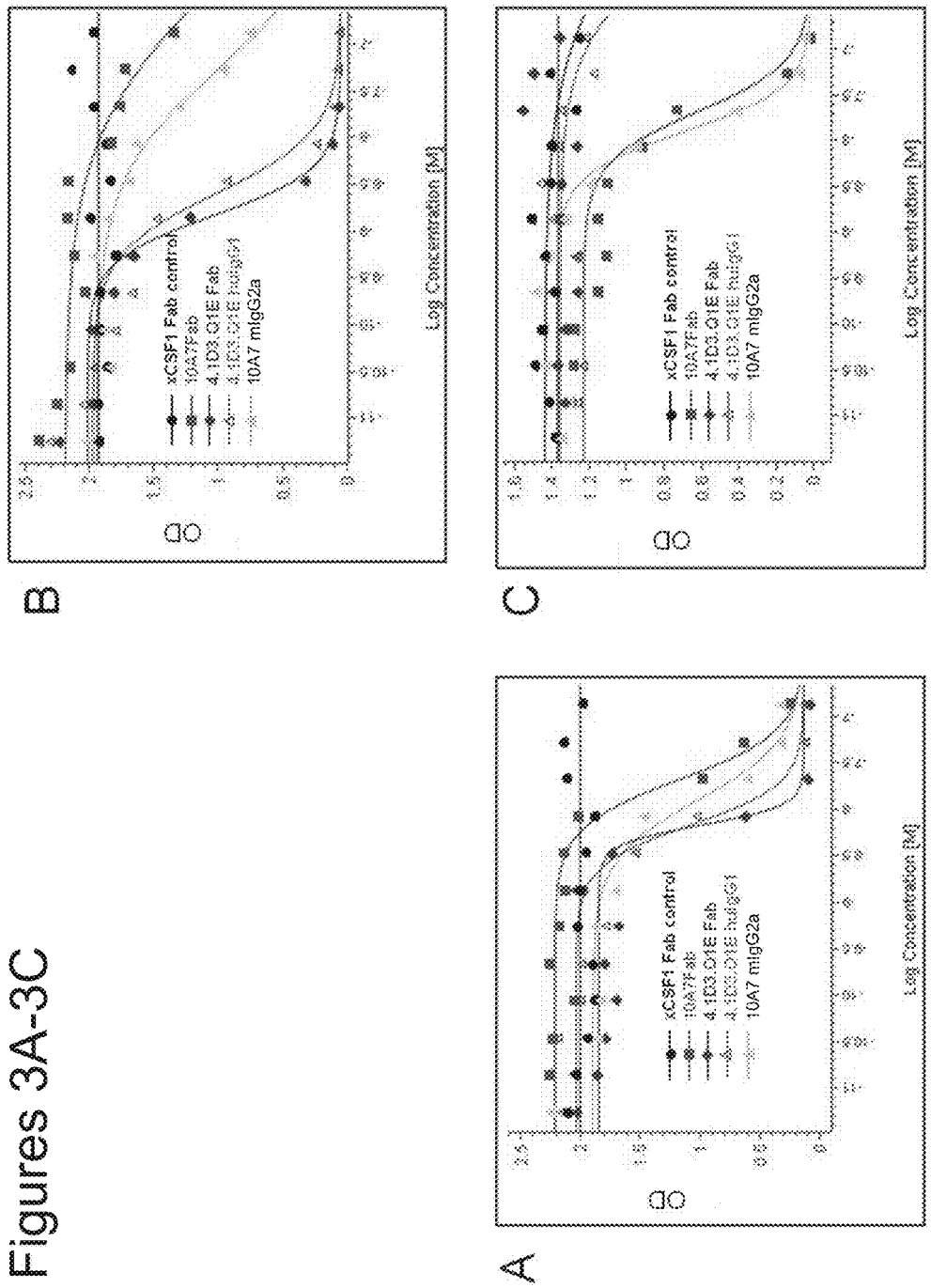
FIG. 3A is a graph showing the results of a blocking ELISA assay using human PVR-Fc fusion protein coated-plates, human TIGIT, and the indicated anti-TIGIT antibodies (10A7 and 4.1D3.Q1E in Fab or IgG format) or anti-CSF1 Fab control, as a function of antibody/Fab concentration.
FIG. 3B is a graph showing the results of a blocking ELISA assay using cyno PVR-Fc fusion protein coated-plates, cyno TIGIT, and the indicated anti-TIGIT antibodies (10A7 and 4.1D3.Q1E in Fab or IgG format) or anti-CSF1 Fab control, as a function of antibody/Fab concentration.
FIG. 3C is a graph showing the results of a blocking ELISA assay using murine PVR-Fc fusion protein coated-plates, murine TIGIT, and the indicated anti-TIGIT antibodies (10A7 and 4.1D3.Q1E in Fab or IgG format) or anti-CSF1 Fab control, as a function of antibody/Fab concentration.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

The term "TIGIT" or "T-cell immunoreceptor with Ig and ITIM domains" as used herein refers to any native TIGIT from any vertebrate source, including mammals such as primates (e.g., humans) and rodents (e.g., mice and rats), unless otherwise indicated. TIGIT is also known in the art as DKFZp667A205, FLJ39873, V-set and immunoglobulin domain-containing protein 9, V-set and transmembrane domain-containing protein 3, VSIG9, VSTM3, and WUCAM. The term encompasses "full-length," unprocessed TIGIT (e.g., full-length human TIGIT having the amino acid sequence of SEQ ID NO: 352), as well as any form of TIGIT that results from processing in the cell (e.g., processed human TIGIT without a signal sequence, having the amino acid sequence of SEQ ID NO: 353). The term also encompasses naturally occurring variants of TIGIT, e.g., splice variants or allelic variants. The amino acid sequence of an exemplary human TIGIT may be found under UniProt Accession Number Q495A1.

The terms "anti-TIGIT antibody" and "an antibody that specifically binds to TIGIT" refer to an antibody that is capable of binding TIGIT with sufficient affinity such that the antibody is useful as a diagnostic and/or therapeutic agent in targeting TIGIT. In one embodiment, the extent of binding of an anti-TIGIT antibody to an unrelated, non-TIGIT protein is less than about 10% of the binding of the antibody to TIGIT as measured, e.g., by a radioimmunoassay (RIA). In certain embodiments, an antibody that binds to TIGIT has a dissociation constant (Kd) of $\leq 1$ µM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g. from $10^{-8}$ M to $10^{-13}$ M, e.g., from $10^{-9}$ M to $10^{-13}$ M). In certain embodiments, an anti-TIGIT antibody binds to an epitope of TIGIT that is conserved among TIGIT from different species or an epitope on TIGIT that allows for cross-species reactivity, such as an epitope comprising amino acid residues Ser78, Ser80, and Lys82.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, e.g., Flatman et al., *J. Chromatogr. B* 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 Daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ, and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

A "blocking antibody" or an "antagonist antibody" is one that inhibits or reduces a biological activity of the antigen it binds. In some embodiments, blocking antibodies or antagonist antibodies substantially or completely inhibit the biological activity of the antigen. The anti-TIGIT antibodies of the invention may block signaling through PVR, PVRL2, and/or PVRL3 so as to restore a functional response by T-cells (e.g., proliferation, cytokine production, target cell killing) from a dysfunctional state to antigen stimulation.

An "agonist antibody" or "activating antibody" is one that enhances or initiates signaling by the antigen to which it binds. In some embodiments, agonist antibodies cause or activate signaling without the presence of the natural ligand. The OX40 agonist antibodies of the invention may increase memory T cell proliferation, increase cytokine production by memory T cells, inhibit Treg cell function, and/or inhibit Treg cell suppression of effector T cell function, such as effector T cell proliferation and/or cytokine production.

An "epitope" is the portion of the antigen to which the antibody specifically binds. For a polypeptide antigen, the epitope is generally a peptide portion of about 4-15 amino acid residues, which may be contiguous or non-contiguous.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

By "paratope" is meant the part of an antibody which selectively binds the epitope of an antigen. The paratope typically includes amino acids from the antibody's VH and VL chains, and, in particular, from the antibody's HVR region(s).

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci.*

USA 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see. e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technoogy* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen-binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest.* 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest,* 5$^{th}$ Ed. Public Health Service, National Institutes of Health. Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences: EVQLVES-GGGLVQPGGSLRLSCAAS (HC-FR1) (SEQ ID NO: 229); WVRQAPGKGLEWV (HC-FR2) (SEQ ID NO: 230); RFTISADTSKNTAYLQMNSLRAEDTAVYYCAR (HC-FR3) (SEQ ID NO: 232); and WGQGTLVTVSA (HC-FR4) (SEQ ID NO: 232).

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences: DIQMTQSPSSLSAS-VGDRVTITC (LC-FR1) (SEQ ID NO: 233); WYQQKPG-KAPKLLIY (LC-FR2) (SEQ ID NO: 234); GVPSRF-SGSGSGTDFTLTISSLQPEDFATYYC (LC-FR3) (SEQ ID NO: 235); and FGQGTKVEIKR (LC-FR4) (SEQ ID NO: 236).

An "amino-acid modification" at a specified position, for example, of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

"Affinity" refers to the strength of the sum total of non-covalent interactions between a single binding site of a molecule (e.g., an antibody) and its binding partner (e.g., an antigen, e.g., TIGIT). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by VH- and VL-domain shuffling. Random mutagenesis of HVR and/or framework residues is described by, for example: Barbas et al. *Proc Nat. Acad. Sci USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding. The term as used herein can be exhibited, for example, by a molecule having a Kd for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a Kd in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and Kd values are inversely related. A high affinity for an antigen is measured by a low Kd value. In one embodiment, the term "specific binding" refers to binding where a molecule binds to a particular polypeptide or epitope on a particular polypeptide without substantially binding to any other polypeptide or polypeptide epitope.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins for combination therapy herein include polypeptides that comprise the extracellular or OX40 binding portions of OX40L or the extracellular or OX40L binding portions of OX40, fused to a constant domain of an immunoglobulin sequence, such as a OX40 ECD-Fc or a OX40L ECD-Fc. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker but are in reading frame with each other.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

"Human effector cells" refer to leukocytes that express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

The term "antagonist" is used in the broadest sense, and includes any molecule that partially or fully blocks, inhibits, or neutralizes a biological activity of a native polypeptide disclosed herein. In a similar manner, the term "agonist" is used in the broadest sense and includes any molecule that mimics a biological activity of a native polypeptide disclosed herein. Suitable agonist or antagonist molecules specifically include agonist or antagonist antibodies or antibody fragments, fragments or amino acid sequence variants of native polypeptides, peptides, antisense oligonucleotides, small organic molecules, etc. Methods for identifying agonists or antagonists of a polypeptide may comprise contacting a polypeptide with a candidate agonist or antagonist molecule and measuring a detectable change in one or more biological activities normally associated with the polypeptide.

As used herein, an "antagonist antibody" of a target molecule refers to an antibody that interferes with the normal functioning of the target molecule, either by decreasing transcription or translation of the target molecule-encoding nucleic acid, or by inhibiting or blocking the target molecule activity, or both. For example, an antagonist antibody of TIGIT may be considered an antibody, or anti-TIGIT binding fragment thereof, that interferes with the normal functioning of TIGIT, either by decreasing transcription or translation of TIGIT-encoding nucleic acid, or by inhibiting or blocking TIGIT polypeptide activity, or both. It will be understood by one of ordinary skill in the art that in some instances, an antagonist antibody of TIGIT may antagonize one TIGIT activity without affecting another TIGIT activity. For example, a desirable antagonist antibody of TIGIT for use in certain methods herein is an antagonist antibody of TIGIT that antagonizes TIGIT activity in response to one of PVR interaction, PVRL3 interaction, or PVRL2 interaction, e.g., without affecting or minimally affecting any of the other TIGIT interactions.

The terms "TIGIT antagonist" and "antagonist of TIGIT activity or TIGIT expression" are used interchangeably and refer to a compound that interferes with the normal functioning of TIGIT, either by decreasing transcription or translation of TIGIT-encoding nucleic acid, or by inhibiting or blocking TIGIT polypeptide activity, or both. Examples of TIGIT antagonists include, but are not limited to, antisense polynucleotides, interfering RNAs, catalytic RNAs, RNA-DNA chimeras, TIGIT-specific aptamers, anti-TIGIT antibodies, TIGIT-binding fragments of anti-TIGIT antibodies, TIGIT-binding small molecules, TIGIT-binding peptides, and other polypeptides that specifically bind TIGIT (including, but not limited to, TIGIT-binding fragments of one or more TIGIT ligands, optionally fused to one or more additional domains), such that the interaction between the TIGIT antagonist and TIGIT results in a reduction or cessation of TIGIT activity or expression. It will be understood by one of ordinary skill in the art that in some instances, a TIGIT antagonist may antagonize one TIGIT activity without affecting another TIGIT activity. For example, a desirable TIGIT antagonist for use in certain of the methods herein is a TIGIT antagonist that antagonizes TIGIT activity in response to one of PVR interaction, PVRL3 interaction, or PVRL2 interaction, e.g., without affecting or minimally affecting any of the other TIGIT interactions.

The terms "PVR antagonist" and "antagonist of PVR activity or PVR expression" are used interchangeably and refer to a compound that interferes with the normal functioning of PVR, either by decreasing transcription or translation of PVR-encoding nucleic acid, or by inhibiting or blocking PVR polypeptide activity, or both. Examples of PVR antagonists include, but are not limited to, antisense polynucleotides, interfering RNAs, catalytic RNAs, RNA-DNA chimeras, PVR-specific aptamers, anti-PVR antibodies, PVR-binding fragments of anti-PVR antibodies, PVR-binding small molecules, PVR-binding peptides, and other polypeptides that specifically bind PVR (including, but not limited to, PVR-binding fragments of one or more PVR ligands, optionally fused to one or more additional domains), such that the interaction between the PVR antagonist and PVR results in a reduction or cessation of PVR activity or expression. It will be understood by one of ordinary skill in the art that in some instances, a PVR antagonist may antagonize one PVR activity without affecting another PVR activity. For example, a desirable PVR antagonist for use in certain of the methods herein is a PVR antagonist that antagonizes PVR activity in response to TIGIT interaction without impacting the PVR-CD96 and/or PVR-CD226 interactions.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis—with a result being to restore or enhance T-cell function (e.g., proliferation, cytokine production, target cell killing). As used herein, a PD-1 axis binding antagonist includes a PD-1 binding antagonist, a PD-L1 binding antagonist and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab) described herein. In another specific aspect, a PD-1 binding antagonist is MK-3475 (lambrolizumab) described herein. In another specific aspect, a PD-1 binding antagonist is CT-011 (pidilizumab) described herein. In another specific aspect, a PD-1 binding antagonist is MEDI-0680 (AMP-514) described herein. In another specific aspect, a PD-1 binding antagonist is PDR001 described herein. In another specific aspect, a PD-1 binding antagonist is REGN2810 described herein. In another specific aspect, a PD-1 binding antagonist is BGB-108 described herein.

The term "PD-L1 binding antagonist" refers to a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein. In still another specific aspect, an anti-PD-L1 antibody is MPDL3280A (atezolizumab) described herein. In still another specific aspect, an anti-PD-L1 antibody is MEDI4736 (durvalumab) described herein. In still another specific aspect, an anti-PD-L1 antibody is YW243.55.S70 described herein. In still another specific aspect, an anti-PD-L1 antibody is MSB0010718C (avelumab) described herein.

The term "PD-L2 binding antagonist" refers to a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

The term "OX40," as used herein, refers to any native OX40 from any vertebrate source, including mammals such as primates (e.g., humans) and rodents (e.g., mice and rats), unless otherwise indicated. The term encompasses "full-length," unprocessed OX40 as well as any form of OX40 that results from processing in the cell. The term also encompasses naturally occurring variants of OX40, for example, splice variants or allelic variants. The amino acid sequence of an exemplary human OX40 is set forth in SEQ ID NO: 354.

"OX40 activation" refers to activation of the OX40 receptor. Generally, OX40 activation results in signal transduction.

The term "aptamer" refers to a nucleic acid molecule that is capable of binding to a target molecule, such as a polypeptide. For example, an aptamer of the invention can specifically bind to a TIGIT polypeptide, or to a molecule in a signaling pathway that modulates the expression of TIGIT. The generation and therapeutic use of aptamers are well established in the art. See, for example, U.S. Pat. No. 5,475,096, and the therapeutic efficacy of MACUGEN® (Eyetech, New York) for treating age-related macular degeneration.

The term "dysfunction," in the context of immune dysfunction, refers to a state of reduced immune responsiveness to antigenic stimulation.

The term "dysfunctional," as used herein, also includes refractory or unresponsive to antigen recognition, specifically, impaired capacity to translate antigen recognition into downstream T-cell effector functions, such as proliferation, cytokine production (e.g., gamma interferon) and/or target cell killing.

"Antibody-dependent cell-mediated cytotoxicity" or "ADCC" refers to a form of cytotoxicity in which secreted immunoglobulin bound onto Fc receptors (FcRs) present on certain cytotoxic cells (e.g., NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS (USA)* 95:652-656 (1998). An exemplary assay for assessing ADCC activity is provided in the examples herein.

The term "anergy" refers to the state of unresponsiveness to antigen stimulation resulting from incomplete or insufficient signals delivered through the T-cell receptor (e.g., increase in intracellular $Ca^{2+}$ in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of interleukin-2 (IL-2). Anergic T-cells do not undergo clonal expansion and/or acquire effector functions.

"Enhancing T cell function" means to induce, cause or stimulate an effector or memory T cell to have a renewed, sustained or amplified biological function. Examples of enhancing T-cell function include: increased secretion of γ-interferon from $CD8^+$ effector T cells, increased secretion of γ-interferon from CD4+ memory and/or effector T-cells, increased proliferation of CD4+ effector and/or memory T cells, increased proliferation of CD8+ effector T-cells, increased antigen responsiveness (e.g., clearance), relative to such levels before the intervention. In one embodiment, the level of enhancement is at least 50%, alternatively 60%, 70%, 80%, 90%, 100%, 120%, 150%, 200%. The manner of measuring this enhancement is known to one of ordinary skill in the art.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from $CD8^+$ T-cells, increased proliferation, increased antigen responsiveness (e.g., viral, pathogen, or tumor clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate decreased signaling through OX40 and/or OX40L. In another embodiment, a T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection, and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage, and tumor clearance.

"Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include but are not limited to treatment with an OX40 binding agonist (e.g., anti-OX40 agonist antibodies) and a TIGIT inhibitor (e.g., anti-TIGIT blocking antibodies).

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein. "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, the term "reducing or inhibiting cancer relapse" means to reduce or inhibit tumor or cancer relapse or tumor or cancer progression.

As used herein, "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, myeloma, lymphoma, blastoma, sarcoma, and leukemia. More particular examples of such cancers include multiple myeloma (MM), squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma, various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia), chronic lymphocytic leukemia (CLL), acute lymphoblastic leukemia (ALL), Hairy cell leukemia, chronic myeloblastic leukemia, and post-transplant lymphoproliferative disorder (PTLD), as well as abnormal vascular proliferation associated with phakomatoses, edema (such as that associated with brain tumors), and Meigs' syndrome.

The term "tumor" refers to all neoplastic cell growth and proliferation, whether malignant or benign, and all precancerous and cancerous cells and tissues. The terms "cancer," "cancerous," "cell proliferative disorder," "proliferative disorder" and "tumor" are not mutually exclusive as referred to herein.

As used herein, "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

As used herein, "subject" or "individual" is meant a mammal, including, but not limited to, a human or non-human mammal, such as a bovine, equine, canine, ovine, or feline. Preferably, the subject is a human. Patients are also subjects herein.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline). Lonafamib (SCH 66336), sorafenib (NEXAVAR®, Bayer Labs), gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (ii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone), panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor, PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN Bio-Therapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., At211, I131, I125, Y90, Re186, Re188, Sm153, Bi212, P32, Pb212 and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyl-transferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-1α, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The phrase "pharmaceutically acceptable" indicates that the substance or composition must be compatible chemically and/or toxicologically, with the other ingredients comprising a formulation, and/or the mammal being treated therewith.

As used herein, "administering" is meant a method of giving a dosage of a compound (e.g., an anti-TIGIT antibody of the invention or a nucleic acid encoding an anti-TIGIT antibody of the invention) or a composition (e.g., a pharmaceutical composition, e.g., a pharmaceutical composition including an anti-TIGIT antibody of the invention) to a subject. The compositions utilized in the methods described herein can be administered, for example, intravenously, intramuscularly, intravitreally (e.g., by intravitreal injection), by eye drop, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors" or "expression vectors"). In general, expression vectors of utility in recombinant DNA techniques are often in the form of plasmids. In the present specification, "plasmid" and "vector" may be used interchangeably.

The term "about" as used herein refers to the usual error range for the respective value readily known to the skilled person in this technical field. Reference to "about" a value or parameter herein includes (and describes) embodiments that are directed to that value or parameter per se.

III. Exemplary Anti-TIGIT Antibodies

The invention provides anti-TIGIT antibodies useful for treating or delaying the progression of cancer or an immune-related disease (e.g., a T cell dysfunctional disorder) in a subject (e.g., a human).

In one example, the anti-TIGIT antibodies bind to an epitope on human TIGIT including one or more amino acid residues (e.g., 1, 2, or 3 amino acid residues) selected from the group consisting of Ser78, Ser80, and Lys82 of human TIGIT. For example, in some instances, the anti-TIGIT antibodies bind to an epitope on human TIGIT including amino acid residues Ser80 and Lys82. In some instances, the anti-TIGIT antibodies bind to an epitope on human TIGIT including amino acid residues Ser78 and Ser80. In some instances, the anti-TIGIT antibodies bind to an epitope on human TIGIT including amino acid residues Ser78 and Lys82. In some instances, the anti-TIGIT antibodies bind to an epitope on human TIGIT including amino acid residues Ser78, Ser80, and Lys82.

In some instances, the anti-TIGIT antibodies bind to an epitope on human TIGIT that includes, in addition to Ser78, Ser80, and/or Lys82, residue Ala67 of human TIGIT. In some instances, the anti-TIGIT antibodies bind to an epitope on human TIGIT including Ser78 and Ala67; Ser80 and Ala67; Lys82 and Ala67; Ser78, Ser80, and Ala67; Ser78, Lys82, and Ala67; Ser80, Lys82, and Ala67; or Ser78, Ser80, Lys82, and Ala67.

In some instances, the anti-TIGIT antibodies bind to an epitope on human TIGIT that includes, in addition to Ser78, Ser80, and/or Lys82, one or more additional amino acid residues (e.g., 1, 2, or 3 amino acid residues) selected from the group consisting of Glu60, Leu65, and Ile68 of human TIGIT. In some instances, the anti-TIGIT antibodies bind to an epitope on human TIGIT that includes Ser78 and Glu60; Ser80 and Glu60; Lys82 and Glu60; Ser78 and Leu65; Ser80 and Leu65; Lys82 and Leu65; Ser78 and Ile68; Ser80 and Ile68; Lys82 and Ile68. In some instances, the anti-TIGIT antibodies bind to an epitope on human TIGIT that includes Ser78, Ser80, and Glu60; Ser78, Ser80, and Leu65; Ser78, Ser80, and Ile68; Ser80, Lys82, and Glu60; Ser80, Lys82, and Leu65; Ser80, Lys82, and Ile68; Ser78, Lys82, and Glu60; Ser78, Lys82, and Leu65; Ser78, Lys82, and Ile68. In some instances, the anti-TIGIT antibodies bind to an epitope on human TIGIT that includes Glu60, Leu65, and Ser78; Glu60, Leu65, and Ser80; Glu60, Leu65, and Lys82; Leu65, Ile68, and Ser78; Leu65, Ile68, and Ser80; Leu65, Ile68, and Lys82; Glu60, Ile68, and Ser78; Glu60, Ile68, and Ser80; Glu60, Ile68, and Lys82. In some instances, the anti-TIGIT antibodies bind to an epitope on human TIGIT that includes Glu60, Leu65, Ile68, and Ser78; Glu60, Leu65, Ile68, and Ser80; Glu60, Leu65, Ile68, and Lys82. In some instances, the anti-TIGIT antibodies bind to an epitope on human TIGIT that includes Glu60, Leu65, Ser78, and Ser80; Glu60, Leu65, Ser78, and Lys82; Glu60, Leu65, Ser80, and Lys82; Leu65, Ile68, Ser78, and Ser80; Leu65, Ile68, Ser78, and Lys82; Leu65, Ile68, Ser80, and Lys82; Leu65, Glu60, Ser78, and Ser80; Leu65, Glu60, Ser78, and Lys82; Leu65, Glu60, Ser80, and Lys82. In some instances, the anti-TIGIT antibodies bind to an epitope on human TIGIT that includes Glu60, Leu65, Ser78, Ser80, and Lys82; Leu65, Ile68, Ser78, Ser80, and Lys82; Glu60, Leu65, Ser78, Ser80, and Lys82. In some instances, the anti-TIGIT antibodies bind to an epitope on human TIGIT that includes Ser78, Ser80, Glu60, Leu65, and Ile68; Ser78, Lys82, Glu60, Leu65, and Ile68; Ser80, Lys82, Glu60, Leu65, and Ile68. In some instances, the anti-TIGIT antibodies bind to an epitope on human TIGIT that includes Ser78, Ser80, Lys82, Glu60, Leu65, and Ile68.

In some instances, the anti-TIGIT antibodies bind to an epitope on human TIGIT that includes, in addition to Ser78, Ser80, and Lys82, one or more additional amino acid residues (e.g., 1, 2, 3, or 4 amino acid residues) selected from the group consisting of Gln56, Asn70, Leu73, and His111 of human TIGIT. In some instances, the anti-TIGIT antibodies bind to an epitope on human TIGIT that includes Ser78, Ser80, Lys82, and Gln56; Ser78, Ser80, Lys82, and Asn70; Ser78, Ser80, Lys82, and Leu73; Ser78, Ser80, Lys82, and His111. In some instances, the anti-TIGIT antibodies bind to an epitope on human TIGIT that includes Ser78, Ser80, Lys82, Gln56, and Asn70; Ser78, Ser80, Lys82, Gln56, and Leu73; Ser78, Ser80, Lys82, Gln56, and His111; Ser78, Ser80, Lys82, Asn70, and Leu73; Ser78, Ser80, Lys82, Asn70, and His111; Ser78, Ser80, Lys82, Leu73, and His111. In some instances, the anti-TIGIT antibodies bind to an epitope on human TIGIT that includes Ser78, Ser80, Lys82, Gln56, Asn70, and Leu73; Ser78, Ser80, Lys82, Gln56, Asn70, and His111; Ser78, Ser80, Lys82, Gln56, Leu73, and His111; Ser78, Ser80, Lys82, Asn70, Leu73, and His111. In some instances, the anti-TIGIT antibodies bind to an epitope on human TIGIT that includes Ser78, Ser80, Lys82, Gln56, Asn70, Leu73, and His111. In some instances, the anti-TIGIT antibodies bind to an epitope on human TIGIT that includes, in addition to Ser78, Ser80, and/or Lys82, one or more additional amino acid residues (e.g., 1, 2, or 3 amino acid residues) selected from the group consisting of Thr55, Asn58, Asp63, Gln64, His76, Ile77, and Pro79 of human TIGIT.

In some instances, the anti-TIGIT antibodies bind to an epitope on human TIGIT that includes amino acid residues Thr55, Gln56, Asn58, Glu60, Asp63, Gln64, Leu65, Ala67, Ile68, Asn70, Leu73, His76, Ile77, Ser78, Pro79, Ser80, Lys82, and His111 of human TIGIT. In some instances, the anti-TIGIT antibodies bind to an epitope on human TIGIT that consists of amino acid residues Thr55, Gln56, Asn58, Glu60, Asp63, Gln64, Leu65, Ala67, Ile68, Asn70, Leu73, His76, Ile77, Ser78, Pro79, Ser80, Lys82, and His111 of human TIGIT.

In another example, the anti-TIGIT antibodies bind to an epitope on human TIGIT including one or more amino acid residues (e.g., 1, 2, or 3 amino acid residues) selected from the group consisting of Thr55, Ser80, and Lys82 of human TIGIT. For example, in some instances, the anti-TIGIT antibodies bind to an epitope on human TIGIT including amino acid residue Lys82. In some instances, the anti-TIGIT antibodies bind to an epitope on human TIGIT including amino acid residues Ser80 and Lys82. In some instances, the anti-TIGIT antibodies bind to an epitope on human TIGIT including amino acid residues Thr55 and Ser80. In some instances, the anti-TIGIT antibodies bind to an epitope on human TIGIT including amino acid residues Thr55 and Lys82. In some instances, the anti-TIGIT antibodies bind to an epitope on human TIGIT including amino acid residues Thr55. Ser80, and Lys82.

In some instances, the anti-TIGIT antibodies bind to an epitope on human TIGIT that includes, in addition to Thr55, Ser80, and/or Lys82, residue Gln56 of human TIGIT. In some instances, the anti-TIGIT antibodies bind to an epitope on human TIGIT including Thr55 and Gln56; Ser80 and Gln56; Lys82 and Gln56; Thr55. Ser80, and Gln56; Thr55, Lys82, and Gln56; Ser80, Lys82, and Gln56; or Thr55, Ser80, Lys82, and Gln56.

In some instances, the anti-TIGIT antibodies bind to an epitope on human TIGIT that includes, in addition to Thr55, Ser80, and/or Lys82, one or more additional amino acid residues (e.g., 1, 2, or 3 amino acid residues) selected from the group consisting of Asn58, Glu60, Ile77, and Pro79 of human TIGIT. In some instances, the anti-TIGIT antibodies bind to an epitope on human TIGIT that includes Thr55 and Asn58; Thr55 and Glu60; Ser80 and Asn58; Ser80 and Glu60; Lys82 and Asn58; Lys82 and Glu60; Thr55 and Ile77; Ser80 and Ile77; Lys82 and Ile77; Thr55 and Pro79; Ser80 and Pro79; Lys82 and Pro79. In some instances, the anti-TIGIT antibodies bind to an epitope on human TIGIT that includes Thr55, Ser80, and Asn58; Thr55, Ser80, and Glu60; Thr55, Ser80, and Ile77; Thr55, Ser80, and Pro79; Ser80, Lys82, and Asn58; Ser80, Lys82, and Glu60; Ser80, Lys82, and Ile77; Ser80, Lys82, and Pro79; Thr55, Lys82, and Asn58; Thr55, Lys82, and Glu60; Thr55, Lys82, and Ile77; Thr55, Lys82, and Pro79. In some instances, the anti-TIGIT antibodies bind to an epitope on human TIGIT that includes Thr55, Ser80, Lys82, and Asn58; Thr55, Ser80, Lys82, and Glu60; Thr55, Ser80, Lys82, and Ile77; Thr55, Ser80, Lys82, and Pro79. In some instances, the anti-TIGIT antibodies bind to an epitope on human TIGIT that includes Asn58, Ile77, and Thr55; Glu60, Ile77, and Thr55; Asn58, Ile77, and Ser80; Glu60, Ile77, and Ser80; Asn58, Ile77, and Lys82; Glu60, Ile77, and Lys82; Ile77, Pro79, and Thr55; Ile77, Pro79, and Ser80; Ile77, Pro79, and Lys82; Glu60, Pro79, and Thr55; Asn58, Pro79, and Ser80; Glu60, Pro79, and Ser80; Asn58, Pro79, and Lys82; Glu60, Pro79, and Lys82. In some instances, the anti-TIGIT antibodies bind to an epitope on human TIGIT that includes Asn58, Ile77, Pro79, and Thr55; Glu60, Ile77, Pro79, and Thr55; Asn58, Ile77, Pro79, and Ser80; Glu60, Ile77, Pro79, and Ser80; Asn58, Ile77, Pro79, and Lys82; Glu60, Ile77, Pro79, and Lys82. In some instances, the anti-TIGIT antibodies bind to an epitope on human TIGIT that includes Asn58, Ile77, Thr55, and Ser80; Glu60, Ile77, Thr55, and Ser80; Asn58, Ile77, Thr55, and Lys82; Glu60, Ile77, Thr55, and Lys82; Asn58, Ile77, Ser80, and Lys82; Glu60, Ile77, Ser80, and Lys82; Ile77, Pro79, Thr55, and Ser80; Ile77, Pro79, Thr55, and Lys82; Ile77, Pro79, Ser80, and Lys82; Ile77, Asn58, Thr55, and Ser80; Ile77, Glu60, Thr55, and Ser80; Ile77, Asn58, Thr55, and Lys82; Ile77, Asn58, Thr55, and Lys82; Ile77, Glu60, Thr55, and Lys82; Ile77, Asn58, Ser80, and Lys82; Ile77, Glu60, Ser80, and Lys82. In some instances, the anti-TIGIT antibodies bind to an epitope on human TIGIT that includes Asn58, Ile77, Thr55, Ser80, and Lys82; Glu60, Ile77, Thr55, Ser80, and Lys82; Ile77, Pro79, Thr55, Ser80, and Lys82; Asn58, Ile77, Thr55, Ser80, and Lys82; Glu60, Ile77, Thr55, Ser80, and Lys82. In some instances, the anti-TIGIT antibodies bind to an epitope on human TIGIT that includes Thr55, Ser80, Asn58, Ile77, and Pro79; Thr55, Ser80, Glu60, Ile77, and Pro79; Thr55, Lys82, Asn58, Ile77, and Pro79; Thr55, Lys82, Glu60, Ile77, and Pro79; Ser80, Lys82, Asn58, Ile77, and Pro79; and Ser80, Lys82, Glu60, Ile77, and Pro79. In some instances, the anti-TIGIT antibodies bind to an epitope on human TIGIT that includes Thr55, Ser80, Lys82, Glu60, Ile77, and Pro79. In some instances, the anti-TIGIT antibodies bind to an epitope on human TIGIT that includes Thr55, Ser80, Lys82, Asn58, Ile77, and Pro79. In some instances, the anti-TIGIT antibodies bind to an epitope on human TIGIT that includes Thr55, Asn58, Glu60, Ile77, Pro79, Ser80, and Lys82.

In some instances, the anti-TIGIT antibodies bind to an epitope on human TIGIT that includes, in addition to Thr55, Ser80, and Lys82, one or more additional amino acid residues (e.g., 1, 2, 3, 4, 5, or 6 amino acid residues) selected from the group consisting of Leu65, Ile68, Leu73, His76, Ser78, and His111 of further comprises amino acid residues Leu65, Ile68, Leu73, His76, Ser78, and His111 of human TIGIT.

In some instances, the anti-TIGIT antibodies bind to an epitope on human TIGIT that includes amino acid residues Thr55, Gln56, Asn58, Glu60, Leu65, Ile68, Leu73, His76, Ile77, Ser78, Pro79, Ser80, Lys82, and His111 of human TIGIT. In some instances, the anti-TIGIT antibodies bind to an epitope on human TIGIT that consists of amino acid residues Thr55, Gln56, Asn58, Glu60, Leu65, Ile68, Leu73, His76, Ile77, Ser78, Pro79, Ser80, Lys82, and His111 of human TIGIT.

In some instances, any of the anti-TIGIT antibodies described above may include a paratope that includes one or more amino acid residues (e.g., 1, 2, 3, 4, 5, 6, 7, 8, 9, 10, 11, or 12 amino acid residues) selected from the group consisting of heavy chain variable region amino acid residues Asn32, Tyr52, Arg52b, Phe53, Lys54, Tyr56, Asp58, Tyr99, Asp100, Leu100a, Leu100b, and Ala100c and/or one or more amino acid residues (e.g., 1, 2, 3, 4, or 5 amino acid residues) selected from the group consisting of light chain variable region amino acid residues Tyr27d, Tyr92, Ser93, Thr94, and Phe96.

In some instances, the anti-TIGIT antibodies may include a paratope that consists of heavy chain variable region amino acid residues Asn32, Tyr52, Arg52b, Phe53, Lys54, Tyr56, Asp58, Tyr99, Asp100, Leu100a, Leu100b, and Ala100c and light chain variable region amino acid residues Tyr27d, Tyr92, Ser93, Thr94, and Phe96.

In certain embodiments, the anti-TIGIT antibody of the invention makes unique contacts with amino acids of human TIGIT at a distance of 4.5 Angstroms, 3.7 Angstroms, 3.5 Angstroms, 3.25 Angstroms, 3.00 Angstroms, 2.75 Angstroms, or less. In certain embodiments, an antibody is provided that binds to an epitope consisting of one, two, three, four, or five amino acids of human TIGIT at a distance of 4.5 Angstroms, 3.7 Angstroms, 3.5 Angstroms, 3.25 Angstroms, 3.00 Angstroms, 2.75 Angstroms or less. In one embodiment, the anti-TIGIT antibody of the invention makes unique contacts with amino acids of human TIGIT at a distance of 3.7 Angstroms or less. In certain embodiments, an antibody is provided that binds to an epitope consisting of one, two, three, four, or five amino acids of human TIGIT at a distance of 3.7 Angstroms or less.

In some instances, any of the above anti-TIGIT antibodies includes at least one, two, three, four, five, or six HVRs selected from (a) an HVR-H1 comprising the amino acid sequence of SNSAAWN (SEQ ID NO: 1); (b) an HVR-H2 comprising the amino acid sequence of KTYYRFKWYS-DYAVSVKG (SEQ ID NO: 2); (c) an HVR-H3 comprising the amino acid sequence of ESTTYDLLAGPFDY (SEQ ID NO: 3); (d) an HVR-L1 comprising the amino acid sequence of KSSQTVLYSSNNKKYLA (SEQ ID NO: 4); (e) an HVR-L2 comprising the amino acid sequence of WASTRES (SEQ ID NO: 5); and/or (f) an HVR-L3 comprising the amino acid sequence of QQYYSTPFT (SEQ ID NO: 6), or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 1-6. In some instances, any of the above anti-TIGIT antibodies includes (a) an HVR-H1 comprising the amino acid sequence of SNSAAWN (SEQ ID NO: 1); (b) an HVR-H2 comprising the amino acid sequence of KTYYRFKWYS-DYAVSVKG (SEQ ID NO: 2); (c) an HVR-H3 comprising the amino acid sequence of ESTTYDLLAGPFDY (SEQ ID NO: 3); (d) an HVR-L1 comprising the amino acid sequence of KSSQTVLYSSNNKKYLA (SEQ ID NO: 4); (e) an HVR-L2 comprising the amino acid sequence of WASTRES (SEQ ID NO: 5); and (f) an HVR-L3 comprising the amino acid sequence of QQYYSTPFT (SEQ ID NO: 6), such as possessed by the anti-TIGIT antibody 4.1D3 and derivatives thereof (e.g., 4.1D3.Q1E). In some instances, the anti-TIGIT antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 34 or 35 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36. In some instances, the anti-TIGIT antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 34 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36. In a particular instance, the anti-TIGIT antibody can be 4.1D3.Q1E, or a derivative or clonal relative thereof. In some instances, the anti-TIGIT antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 35 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 36. In a particular instance, the anti-TIGIT antibody can be 4.1D3, or a derivative or clonal relative thereof.

In some instances, the antibody further comprises at least one, two, three, or four of the following light chain variable region framework regions (FRs): an FR-L1 comprising the amino acid sequence of DIVMTQSPDSLAVSLGERATINC (SEQ ID NO: 7); an FR-L2 comprising the amino acid sequence of WYQQKPGQPPNLLIY (SEQ ID NO: 8); an FR-L3 comprising the amino acid sequence of GVPDRFSGSGSGTDFTLTISSLQAEDVAVYYC (SEQ ID NO: 9); and/or an FR-L4 comprising the amino acid sequence of FGPGTKVEIK (SEQ ID NO: 10), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 7-10. In some instances, for example, the antibody further comprises an FR-L1 comprising the amino acid sequence of DIVMTQSPDSLAVSLGERATINC (SEQ ID NO: 7); an FR-L2 comprising the amino acid sequence of WYQQKPGQPPNLLIY (SEQ ID NO: 8); an FR-L3 comprising the amino acid sequence of GVPDRFSGSGSGTDFTLTISSLQAEDVAVYYC (SEQ ID NO: 9): and an FR-L4 comprising the amino acid sequence of FGPGTKVEIK (SEQ ID NO: 10), such as possessed by the anti-TIGIT antibodies 4.1D3.Q1E and 4.1D3.

In some instances, the antibody further comprises at least one, two, three, or four of the following heavy chain variable region FRs: an FR-H1 comprising the amino acid sequence of $X_1$VQLQQSGPGLVKPSQTLSLTCAISGDSVS (SEQ ID NO: 11), wherein $X_1$ is Q or E; an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and/or an FR-H4 comprising the amino acid sequence of WGQGTLVTVSS (SEQ ID NO: 14), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 11-14. The anti-TIGIT antibody may further include, for example, at least one, two, three, or four of the following heavy chain variable region FRs: an FR-H1 comprising the amino acid sequence of EVQLQQSGPGLVKPSQTLSLTCAISGDSVS (SEQ ID NO: 15); an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and/or an FR-H4 comprising the amino acid sequence of WGQGTLVTVSS (SEQ ID NO: 14), or a combination of one or more of the above FRs and one or more variants thereof having at least about 90% sequence identity (e.g., 90%, 91%, 92%, 93%, 94%, 95%, 96%, 97%, 98%, or 99% sequence identity) to any one of SEQ ID NOs: 12-15. In some instances, the anti-TIGIT antibody includes an FR-H1 comprising the amino acid sequence of EVQLQQSGPGLVKPSQTLSLTCAISGDSVS (SEQ ID NO: 15); an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and an FR-H4 comprising the amino acid sequence of WGQGTLVTVSS (SEQ ID NO: 14), such as possessed by the 4.1D3.Q1E antibody. In another instance, for example, the anti-TIGIT antibody may further include at least one, two, three, or four of the following heavy chain variable region FRs: an FR-H1 comprising the amino acid sequence of QVQLQQSGPGLVKPSQTLSLTCAISGDSVS (SEQ ID NO: 16); an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and/or an FR-H4 comprising the amino acid sequence of WGQGTLVTVSS (SEQ ID NO: 14), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 12-14 and 16. In some instances, the anti-TIGIT antibody includes an FR-H1 comprising the amino acid sequence of QVQLQQSGPGLVKPSQTLSLTCAISGDSVS (SEQ ID NO: 16); an FR-H2 comprising the amino acid sequence of WIRQSPSRGLEWLG (SEQ ID NO: 12); an FR-H3 comprising the amino acid sequence of RITINPDTSKNQFSLQLNSVTPEDTAVFYCTR (SEQ ID NO: 13); and an FR-H4 comprising the amino acid sequence of WGQGTLVTVSS (SEQ ID NO: 14), such as possessed by the 4.1D3 antibody.

In another example, the invention provides anti-TIGIT antibodies that bind to an epitope on human TIGIT including one or more amino acid residues (e.g., 1, 2, or 3 amino acid residues) selected from the group consisting of Gln53, His111, and Tyr113 of human TIGIT. For example, in some instances, the anti-TIGIT antibodies bind to an epitope on human TIGIT including amino acid residues His111 and Tyr113. In some instances, the anti-TIGIT antibodies bind to an epitope on human TIGIT including amino acid residues Gln53 and His111. In some instances, the anti-TIGIT antibodies bind to an epitope on human TIGIT including amino acid residues Gln53 and Tyr113. In some instances, the anti-TIGIT antibodies bind to an epitope on human TIGIT including amino acid residues Gln53, His111, and Tyr113.

In some instances, the anti-TIGIT antibodies bind to an epitope on human TIGIT that includes, in addition to Gln53, His111, and/or Tyr113, residue Gln56 of human TIGIT. In some instances, the anti-TIGIT antibodies bind to an epitope on human TIGIT including Gln53 and Gln56; His111 and Gln56; Tyr113 and Gln56; Gln53, His111, and Gln56; Gln53, Tyr113, and Gln56; His111, Tyr113, and Gln56; or Gln53, His111, Tyr113, and Gln56.

In some instances, the anti-TIGIT antibodies bind to an epitope on human TIGIT that includes, in addition Gln53, His111, Tyr113, and/or Gln56, and one or more additional amino acid residues (e.g., 1, 2, 3, 4, 5, or 6 amino acid residues) selected from the group consisting of Glu60, Leu65, Ile68, Asn70, Leu73, and His76 of human TIGIT. For example, in some instances, the anti-TIGIT antibodies bind to an epitope on human TIGIT including Gln53, His111, Tyr113, Gln56, and Glu60; Gln53, His111, Tyr113, Gln56, and Leu65; Gln53, His111, Tyr113, Gln56, and Ile68; Gln53, His111, Tyr113, Gln56, and Asn70; Gln53, His111, Tyr113, Gln56, and Leu73; Gln53, His111, Tyr113, Gln56, and His76. In some instances, the anti-TIGIT antibodies bind to an epitope on human TIGIT including Gln53, His111, Tyr113, Gln56, Glu60, and Leu65; Gln53, His111, Tyr113, Gln56, Glu60, and Ile68; Gln53, His111, Tyr113, Gln56, Glu60, and Asn70; Gln53, His111, Tyr113, Gln56, Glu60, and Leu73; Gln53, His111, Tyr113, Gln56, Glu60, and His76. In some instances, the anti-TIGIT antibodies bind to an epitope on human TIGIT including Gln53, His111, Tyr113, Gln56, Glu60, Leu65, and Ile68; Gln53, His111, Tyr113, Gln56, Glu60, Leu65, and Asn70; Gln53, His111, Tyr113, Gln56, Glu60, Leu65, and Leu73; Gln53, His111, Tyr113, Gln56, Glu60, Leu65, and His76. In some instances, the anti-TIGIT antibodies bind to an epitope on human TIGIT including Gln53, His111, Tyr113, Gln56, Glu60, Ile68, and Asn70; Gln53, His111, Tyr113, Gln56, Glu60, Ile68, and Leu73; Gln53, His111, Tyr113, Gln56, Glu60, Ile68, and His76. In some instances, the anti-TIGIT antibodies bind to an epitope on human TIGIT including Gln53, His111, Tyr113, Gln56, Glu60, Asn70, and Leu73; Gln53, His111, Tyr113, Gln56, Glu60, Asn70, and His76. In some instances, the anti-TIGIT antibodies bind to an epitope on human TIGIT including Gln53, His111, Tyr113, Gln56, Glu60, Leu73, and His76. In some instances, the anti-TIGIT antibodies bind to an epitope on human TIGIT including Gln53, His111, Tyr113, Gln56, Glu60, Leu65, Ile68, and Asn70; Gln53, His111, Tyr113, Gln56, Glu60, Leu65, Ile68, and Leu73; Gln53, His111, Tyr113, Gln56, Glu60, Leu65, Ile68, and His76. In some instances, the anti-TIGIT antibodies bind to an epitope on human TIGIT including Gln53, His111, Tyr113, Gln56, Glu60, Ile68, Asn70, and Leu73; Gln53, His111, Tyr113, Gln56, Glu60, Ile68, Asn70, and His76. In some instances, the anti-TIGIT antibodies bind to an epitope on human TIGIT including Gln53, His111, Tyr113, Gln56, Glu60, Leu65, Ile68, Asn70, and Leu73; Gln53, His111, Tyr113, Gln56, Glu60, Leu65, Ile68, Asn70, and His76; Gln53, His111, Tyr113, Gln56, Glu60, Ile68, Asn70, Leu73 and His76. In some instances, the anti-TIGIT antibodies bind to an epitope on human TIGIT including Gln53, His111, Tyr113, Gln56, Glu60, Leu65, Ile68, Asn70, Leu73, and His76.

In some instances, the anti-TIGIT antibodies bind to an epitope on human TIGIT including Gln53, His111, Tyr113, Gln56, Leu65, and Ile68; Gln53, His111, Tyr113, Gln56, Leu65, and Asn70; Gln53, His111, Tyr113, Gln56, Leu65, and Leu73; Gln53, His111, Tyr113, Gln56, Leu65, and His76. In some instances, the anti-TIGIT antibodies bind to an epitope on human TIGIT including Gln53, His111, Tyr113, Gln56, Leu65, Ile68, and Asn70; Gln53, His111, Tyr113, Gln56, Leu65, Ile68, and Leu73; Gln53, His111, Tyr113, Gln56, Leu65, Ile68, and Asn70; Gln53, His111, Tyr113, Gln56, Leu65, Ile68, and His76. In some instances, the anti-TIGIT antibodies bind to an epitope on human TIGIT including Gln53, His111, Tyr113, Gln56, Leu65, Asn70, and Leu73; Gln53, His111, Tyr113, Gln56, Leu65, Asn70, and His76. In some instances, the anti-TIGIT antibodies bind to an epitope on human TIGIT including Gln53, His111, Tyr113, Gln56, Leu65, Leu73, and His76. In some instances, the anti-TIGIT antibodies bind to an epitope on human TIGIT including Gln53, His111, Tyr113, Gln56, Leu65, Ile68, Asn70, and Leu73; Gln53, His111, Tyr113, Gln56, Leu65, Ile68, Asn70, and His76. In some instances, the anti-TIGIT antibodies bind to an epitope on human TIGIT including Gln53, His111, Tyr113, Gln56, Leu65, Asn70, Leu73, and His76. In some instances, the anti-TIGIT antibodies bind to an epitope on human TIGIT including Gln53, His111, Tyr113, Gln56, Leu65, Asn70, Leu73, and His76.

In some instances, the anti-TIGIT antibodies bind to an epitope on human TIGIT including Gln53, His111, Tyr113, Gln56, Ile68, and Asn70; Gln53, His111, Tyr113, Gln56, Ile68, and Leu73; Gln53, His111, Tyr113, Gln56, Ile68, and His76. In some instances, the anti-TIGIT antibodies bind to an epitope on human TIGIT including Gln53, His111, Tyr113, Gln56, Ile68, Asn70, and Leu73; Gln53, His111, Tyr113, Gln56, Ile68, Asn70, and His76; Gln53, His111, Tyr113, Gln56, Ile68, Leu73, and His76. In some instances, the anti-TIGIT antibodies bind to an epitope on human TIGIT including Gln53, His111, Tyr113, Gln56, Ile68, Asn70, Leu73, and His76.

In some instances, the anti-TIGIT antibodies bind to an epitope on human TIGIT including Gln53, His111, Tyr113, Gln56, Asn70, and Leu73; Gln53, His111, Tyr113, Gln56, Asn70, and His76. In some instances, the anti-TIGIT antibodies bind to an epitope on human TIGIT including Gln53, His111, Tyr113, Gln56, Asn70, Leu73, and His76. In some instances, the anti-TIGIT antibodies bind to an epitope on human TIGIT including Gln53, His111, Tyr113, Gln56, Leu73, and His76.

In some instances, any of the anti-TIGIT antibodies of the preceding example includes at least one, two, three, four, five, or six HVRs selected from (a) an HVR-H1 comprising the amino acid sequence of SYPMN (SEQ ID NO: 17); (b) an HVR-H2 comprising the amino acid sequence of WINTNTGNPTYVQGFTG (SEQ ID NO: 18); (c) an HVR-H3 comprising the amino acid sequence of TGGHTYDSYAFDV (SEQ ID NO: 19); (d) an HVR-L1 comprising the amino acid sequence of RASQVISSSLA (SEQ ID NO: 20); (e) an HVR-L2 comprising the amino acid sequence of AASTLQS (SEQ ID NO: 21); and/or (f) an HVR-L3 comprising the amino acid sequence of QHLHGYPX$_1$N (SEQ ID NO: 22), wherein X$_1$ is C or S, or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 17-22. In some instances, any of the above anti-TIGIT antibodies of the preceding example may include, for example, (a) an HVR-H1 comprising the amino acid sequence of SYPMN (SEQ ID NO: 17); (b) an HVR-H2 comprising the amino acid sequence of WINTNTGNPTYVQGFTG (SEQ ID NO: 18); (c) an HVR-H3 comprising the amino acid sequence of TGGHTYDSYAFDV (SEQ ID NO: 19); (d) an HVR-L1 comprising the amino acid sequence of RASQVISSSLA (SEQ ID NO: 20); (e) an HVR-L2 comprising the amino acid sequence of AASTLQS (SEQ ID NO: 21); and (f) an HVR-L3 comprising the amino acid sequence of QHLHGYPX$_1$N (SEQ ID NO: 22), such as possessed by the anti-TIGIT antibody 7.4A3 and derivatives thereof (e.g., 7.4A3.C96S.Q1E). In some instances, the anti-TIGIT antibody may include (a) an HVR-H1 comprising the amino acid sequence of SYPMN (SEQ ID NO: 17); (b) an HVR-H2 comprising the amino acid sequence of WINTNTGNPTYVQGFTG (SEQ ID NO: 18); (c) an HVR-H3 comprising the amino acid sequence of TGGHTYDSYAFDV (SEQ ID NO: 19); (d) an HVR-L1 comprising the amino acid sequence of RASQVISSSLA (SEQ ID NO: 20); (e) an HVR-L2 comprising the amino acid sequence of AASTLQS (SEQ ID NO: 21); and (f) an HVR-L3 comprising the amino acid sequence of QHLHGYPSN (SEQ ID NO: 23), such as possessed by the anti-TIGIT antibody 7.4A3.C96S.Q1E. In other instances, the anti-TIGIT antibody may include (a) an HVR-H1 comprising the amino acid sequence of SYPMN (SEQ ID NO: 17); (b) an HVR-H2 comprising the amino acid sequence of WINTNTGNPTYVQGFTG (SEQ ID NO:

18); (c) an HVR-H3 comprising the amino acid sequence of TGGHTYDSYAFDV (SEQ ID NO: 19); (d) an HVR-L1 comprising the amino acid sequence of RASQVISSSLA (SEQ ID NO: 20); (e) an HVR-L2 comprising the amino acid sequence of AASTLQS (SEQ ID NO: 21); and (f) an HVR-L3 comprising the amino acid sequence of QHLH-GYPCN (SEQ ID NO: 28), such as possessed by the anti-TIGIT antibody 7.4A3.

In some instances, the anti-TIGIT antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 37 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 38. In a particular instance, the anti-TIGIT antibody can be 7.4A3.C96S.Q1E, or a derivative or clonal relative thereof. In some instances, the anti-TIGIT antibody may have a VH domain comprising an amino acid sequence having at least at least 90% sequence identity (e.g., at least 91%, 92%, 93%, 94%, 95%, 96%, 97%, 98%, or 99% sequence identity) to, or the sequence of, SEQ ID NO: 39 and/or a VL domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 40. In a particular instance, the anti-TIGIT antibody can be 7.4A3, or a derivative or clonal relative thereof.

In some instances, the antibody further comprises at least one, two, three, or four of the following light chain variable region framework regions (FRs): an DIQLTQSPTFLSAS-VGDRVTITC (SEQ ID NO: 30); an FR-L2 comprising the amino acid sequence of WYQQNPGKAPKLLIY (SEQ ID NO: 31); an FR-L3 comprising the amino acid sequence of GVPSRFSGSGSGTEFTLTISSLQPEDFVTYYC (SEQ ID NO: 32); and/or an FR-L4 comprising the amino acid sequence of FGQGTKVEIK (SEQ ID NO: 33), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 30-33, such as possessed by the anti-TIGIT antibody 7.4A3 and derivatives thereof (e.g., 7.4A3.C96S.Q1E).

In some instances, the antibody further comprises at least one, two, three, or four of the following heavy chain variable region FRs: an FR-H1 comprising the amino acid sequence of EVQLVQSGSDLKKPGASVRVSCKASGYTFT (SEQ ID NO: 24) or the amino acid sequence of QVQLVQSGS-DLKKPGASVRVSCKASGYTFT (SEQ ID NO: 29); an FR-H2 comprising the amino acid sequence of WVRQAPGHGLEWMG (SEQ ID NO: 25); an FR-H3 comprising the amino acid sequence of RFVFSLDTSVN-TAYLQISSLKAEDTAVYFCAR (SEQ ID NO: 26); and/or an FR-H4 comprising the amino acid sequence of WGQGT-MVTVSS (SEQ ID NO: 27), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 24-27 and 29. The anti-TIGIT antibody may further include, for example, at least one, two, three, or four of the following heavy chain variable region FRs: an FR-H1 comprising the amino acid sequence of EVQLVQSGSDLKKPGASVRVSCKAS-GYTFT (SEQ ID NO: 24); an FR-H2 comprising the amino acid sequence of WVRQAPGHGLEWMG (SEQ ID NO: 25); an FR-H3 comprising the amino acid sequence of RFVFSLDTSVNTAYLQISSLKAEDTAVYFCAR (SEQ ID NO: 26); and/or an FR-H4 comprising the amino acid sequence of WGQGTMVTVSS (SEQ ID NO: 27), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 24-27. In some instances, the anti-TIGIT antibody includes an FR-H1 comprising the amino acid sequence of EVQLVQSGSDLK-KPGASVRVSCKASGYTFT (SEQ ID NO: 24); an FR-H2 comprising the amino acid sequence of WVRQAPGH-GLEWMG (SEQ ID NO: 25); an FR-H3 comprising the amino acid sequence of RFVFSLDTSVNTAYLQISSL-KAEDTAVYFCAR (SEQ ID NO: 26); and an FR-H4 comprising the amino acid sequence of WGQGTMVTVSS (SEQ ID NO: 27), such as possessed by the 7.4A3.C96S.Q1E antibody. In another instance, for example, the anti-TIGIT antibody may further include at least one, two, three, or four of the following heavy chain variable region FRs: an FR-H1 comprising the amino acid sequence of QVQLVQSGSDLKKPGASVRVSCKAS-GYTFT (SEQ ID NO: 29); an FR-H2 comprising the amino acid sequence of WVRQAPGHGLEWMG (SEQ ID NO: 25); an FR-H3 comprising the amino acid sequence of RFVFSLDTSVNTAYLQISSLKAEDTAVYFCAR (SEQ ID NO: 26); and/or an FR-H4 comprising the amino acid sequence of WGQGTMVTVSS (SEQ ID NO: 27), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 25-27 and 29. In some instances, the anti-TIGIT antibody includes an FR-H1 comprising the amino acid sequence of QVQLVQSGSDLKKPGASVRVSCKASGYTFT (SEQ ID NO: 29); an FR-H2 comprising the amino acid sequence of WVRQAPGHGLEWMG (SEQ ID NO: 25); an FR-H3 comprising the amino acid sequence of RFVFSLDTSVN-TAYLQISSLKAEDTAVYFCAR (SEQ ID NO: 26); and an FR-H4 comprising the amino acid sequence of WGQGTM-VTVSS (SEQ ID NO: 27), such as possessed by the 7.4A3 anti-TIGIT antibody.

In another example, the invention provides anti-TIGIT antibodies that include at least one, two, three, four, five, or six HVRs selected from (a) an HVR-H1 comprising the amino acid sequence of NYPMN (SEQ ID NO: 41); (b) an HVR-H2 comprising the amino acid sequence of WINTNTGSPAYAQDFTE (SEQ ID NO: 42); (c) an HVR-H3 comprising the amino acid sequence of TAITSVYHFDY (SEQ ID NO: 43); (d) an HVR-L1 comprising the amino acid sequence of RASQGISSYLA (SEQ ID NO: 44); (e) an HVR-L2 comprising the amino acid sequence of GATTLQS (SEQ ID NO: 45); and/or (f) an HVR-L3 comprising the amino acid sequence of QKLNSHPX$_1$S (SEQ ID NO: 46), wherein X$_1$ is C, S, or Y, or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 41-46. In some instances, any of the above anti-TIGIT antibodies of the preceding example may include, for example, (a) an HVR-H1 comprising the amino acid sequence of NYPMN (SEQ ID NO: 41); (b) an HVR-H2 comprising the amino acid sequence of WINTNTG-SPAYAQDFTE (SEQ ID NO: 42); (c) an HVR-H3 comprising the amino acid sequence of TAITSVYHFDY (SEQ ID NO: 43); (d) an HVR-L1 comprising the amino acid sequence of RASQGISSYLA (SEQ ID NO: 44); (e) an HVR-L2 comprising the amino acid sequence of GATTLQS (SEQ ID NO: 45); and (f) an HVR-L3 comprising the amino acid sequence of QKLNSHPX$_1$S (SEQ ID NO: 46), wherein X$_1$ is C, S, or Y, such as possessed by the anti-TIGIT antibody 4.1A4 and derivatives thereof (e.g., 4.1A4.C96S.Q1E and 4.1A4.C96Y.Q1E). In some instances, the anti-TIGIT antibody may include (a) an HVR-H1 comprising the amino acid sequence of NYPMN (SEQ ID NO: 41); (b) an HVR-H2 comprising the amino acid sequence of WINTNTGSPAYAQDFTE (SEQ ID NO: 42); (c) an HVR-H3 comprising the amino acid sequence of TAITSVYHFDY (SEQ ID NO: 43); (d) an HVR-L1 comprising the amino acid sequence of RASQGISSYLA (SEQ ID NO: 44); (e) an HVR-L2 comprising the amino acid sequence of GATTLQS (SEQ ID NO: 45); and (f) an HVR-L3 comprising the amino acid sequence of QKLNSHPCS (SEQ ID NO: 47), such as possessed by the anti-TIGIT antibody 4.1A4. In other instances, the anti-TIGIT antibody may include (a) an HVR-H1 comprising the amino acid sequence of NYPMN (SEQ ID NO: 41); (b) an HVR-H2 comprising the amino acid sequence of WINTNTGSPAYAQDFTE (SEQ ID NO: 42); (c) an HVR-H3 comprising the amino acid sequence of TAITSVYHFDY (SEQ ID NO: 43); (d) an HVR-L1 comprising the amino acid sequence of RASQGISSYLA (SEQ ID NO: 44); (e) an HVR-L2 comprising the amino acid sequence of GATTLQS (SEQ ID NO: 45); and (f) an HVR-L3 comprising the amino acid sequence of QKLNSHPSS (SEQ ID NO: 48), such as possessed by the anti-TIGIT antibody 4.1A4.C96S.Q1E. In other instances, the anti-TIGIT antibody may include (a) an HVR-H1 comprising the amino acid sequence of NYPMN (SEQ ID NO: 41); (b) an HVR-H2 comprising the amino acid sequence of WINTNTGSPAYAQDFTE (SEQ ID NO: 42): (c) an HVR-H3 comprising the amino acid sequence of TAITSVYHFDY (SEQ ID NO: 43); (d) an HVR-L1 comprising the amino acid sequence of RASQGISSYLA (SEQ ID NO: 44); (e) an HVR-L2 comprising the amino acid sequence of GATTLQS (SEQ ID NO: 45); and (f) an HVR-L3 comprising the amino acid sequence of QKLNSHPYS (SEQ ID NO: 49), such as possessed by the anti-TIGIT antibody 4.1A4.C96Y.Q1E.

In some instances, the antibody further comprises at least one, two, three, or four of the following light chain variable region framework regions (FRs): an FR-L1 comprising the amino acid sequence of DIQLTQSPSFLSASVGDRVTITC (SEQ ID NO: 56); an FR-L2 comprising the amino acid sequence of WYQQKPGKAPRVLIY (SEQ ID NO: 57); an FR-L3 comprising the amino acid sequence of GVPSRFSGSESGTEFTLTISSLQPEDLATYYC (SEQ ID NO: 58); and/or an FR-L4 comprising the amino acid sequence of FGQGTKVEIK (SEQ ID NO: 59), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 56-59, such as possessed by the anti-TIGIT antibody 4.1A4 and derivatives thereof (e.g., 1A4.C96S.Q1E and 1A4.C96Y.Q1E).

In some instances, the antibody further comprises at least one, two, three, or four of the following heavy chain variable region FRs: an FR-H1 comprising the amino acid sequence of X$_1$VQLVQSGSELKKPGASVKVSCKASGYTLT (SEQ ID NO: 50), wherein X$_1$ is E or Q; an FR-H2 comprising the amino acid sequence of WVRQAPGRGLEWMG (SEQ ID NO: 51); an FR-H3 comprising the amino acid sequence of RFVFSLDTSVTTAYLQISSLKAEDTAVYYCAR (SEQ ID NO: 52); and/or an FR-H4 comprising the amino acid sequence of WGQGTLVTVSS (SEQ ID NO: 53), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 50-53. The anti-TIGIT antibody may further include, for example, at least one, two, three, or four of the following heavy chain variable region FRs: an FR-H1 comprising the amino acid sequence of QVQLVQSGSELKKPGASVKVSCKASGYTLT (SEQ ID NO: 54); an FR-H2 comprising the amino acid sequence of WVRQAPGRGLEWMG (SEQ ID NO: 51); an FR-H3 comprising the amino acid sequence of RFVFSLDTSVTTAYLQISSLKAEDTAVYYCAR (SEQ ID NO: 52); and/or an FR-H4 comprising the amino acid sequence of WGQGTLVTVSS (SEQ ID NO: 53), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 51-54, such as possessed by the anti-TIGIT antibody 4.1A4. In some instances, the anti-TIGIT antibody includes an FR-H1 comprising the amino acid sequence of EVQLVQSGSELKKPGASVKVSCKASGYTLT (SEQ ID NO: 55); an FR-H2 comprising the amino acid sequence of WVRQAPGRGLEWMG (SEQ ID NO: 51); an FR-H3 comprising the amino acid sequence of RFVFSLDTSVTTAYLQISSLKAEDTAVYYCAR (SEQ ID NO: 52); and/or an FR-H4 comprising the amino acid sequence of WGQGTLVTVSS (SEQ ID NO: 53), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 51-53 and 55, such as possessed by the anti-TIGIT antibody 1A4.C96S.Q1E or 1A4.C96Y.Q1E.

In another example, the invention provides anti-TIGIT antibodies that include at least one, two, three, four, five, or six HVRs selected from (a) an HVR-H1 comprising the amino acid sequence of TYGMGVS (SEQ ID NO: 68); (b) an HVR-H2 comprising the amino acid sequence of SIWWNGNTYYNPSLKS (SEQ ID NO: 69); (c) an HVR-H3 comprising the amino acid sequence of TGGAVITWFAY (SEQ ID NO: 70); (d) an HVR-L1 comprising the amino acid sequence of KASQSVGKNIA (SEQ ID NO: 71); (e) an HVR-L2 comprising the amino acid sequence of YASNRYT (SEQ ID NO: 72); and/or (f) an HVR-L3 comprising the amino acid sequence of QHIYNSPYP (SEQ ID NO: 73), or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 68-73. In some instances, any of the above anti-TIGIT antibodies of the preceding example may include, for example, (a) an HVR-H1 comprising the amino acid sequence of TYGMGVS (SEQ ID NO: 68); (b) an HVR-H2 comprising the amino acid sequence of SIWWNGNTYYNPSLKS (SEQ ID NO: 69); (c) an HVR-H3 comprising the amino acid sequence of TGGAVITWFAY (SEQ ID NO: 70); (d) an HVR-L1 comprising the amino acid sequence of KASQSVGKNIA (SEQ ID NO: 71); (e) an HVR-L2 comprising the amino acid sequence of YASNRYT (SEQ ID NO: 72); and (f) an HVR-L3 comprising the amino acid sequence of QHIYNSPYP (SEQ ID NO: 73), such as possessed by the anti-TIGIT antibody rat6B2 and derivatives thereof (e.g., h6B2.L1H1, h6B2.L2H1, h6B2.L1H2, h6B2.L1H3, h6B2.L1H4, h6B2.L1H5, and h6B2.L2H5).

In some instances, the antibody further comprises at least one, two, three, or four of the following light chain variable region framework regions (FRs): an FR-L1 comprising the amino acid sequence of X$_1$IX$_2$MTQSPX$_3$SX$_4$SX$_5$SVGDRVTX$_6$X$_7$C (SEQ ID NO:

88), wherein $X_1$ is D or N; $X_2$ is Q or V; $X_3$ is K or S; $X_4$ is L or M; $X_5$ is A or I; $X_6$ is I or M; and $X_7$ is N or T; an FR-L2 comprising the amino acid sequence of WYQQKPGX$_1$X$_2$PKLLIY (SEQ ID NO: 89), wherein $X_1$ is K or Q and $X_2$ is A or S; an FR-L3 comprising the amino acid sequence of GVPX$_1$RFX$_2$GX$_3$GSGTDFTX4TIX$_5$X$_6$X$_7$QX$_8$EDX$_9$AX$_{10}$X$_{11}$YC (SEQ ID NO: 90), wherein $X_1$ is D or S; $X_2$ is S or T; $X_3$ is G or S; $X_4$ is F or L; $X_5$ is N or S; $X_6$ is S or T; $X_7$ is L or V; $X_8$ is A or P; $X_9$ is A or I; $X_{10}$ is F or T; and $X_{11}$ is F or Y; and/or an FR-L4 comprising the amino acid sequence of FGX$_1$GTKX$_2$EIK (SEQ ID NO: 91), wherein $X_1$ is Q or T and $X_2$ is L or V, or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 88-91, such as possessed by the anti-TIGIT antibody rat6B2 and derivatives thereof (e.g., h6B2.L1H1, h6B2.L2H1, h6B2.L1H2, h6B2.L1H3, h6B2.L1H4, h6B2.L1H5, and h6B2.L2H5). The anti-TIGIT antibody may further include, for example, at least one, two, three, or four of the following light chain variable region FRs: an FR-L1 comprising the amino acid sequence of NIVMTQSPKSMSISVGDRVTMNC (SEQ ID NO: 92); an FR-L2 comprising the amino acid sequence of WYQQKPGQSPKLLIY (SEQ ID NO: 93); an FR-L3 comprising the amino acid sequence of GVPDRFTGGGSGTDFTLTINTVQAEDAAFFYC (SEQ ID NO: 94); and/or an FR-L4 comprising the amino acid sequence of FGTGTKLEIK (SEQ ID NO: 95), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 92-65, such as possessed by the anti-TIGIT antibody rat6B2. In some instances, the anti-TIGIT antibody includes an FR-L1 comprising the amino acid sequence of DIQMTQSPSSLSASVGDRVTITC (SEQ ID NO: 96); an FR-L2 comprising the amino acid sequence of WYQQKPGKSPKLLIY (SEQ ID NO: 97); an FR-L3 comprising the amino acid sequence of GVPSRFSGSGSGTDFTFTISSLQPEDIATYYC (SEQ ID NO: 99); and/or an FR-L4 comprising the amino acid sequence of FGQGTKVEIK (SEQ ID NO: 100), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 96-97 and 99-100, such as possessed by the anti-TIGIT antibodies h6B2.L1H1, h6B2.L1H2, h6B2.L1H3, h6B2.L1H4, and h6B2.L1H5. In some instances, the anti-TIGIT antibody includes an FR-L1 comprising the amino acid sequence of DIQMTQSPSSLSASVGDRVTITC (SEQ ID NO: 96); an FR-L2 comprising the amino acid sequence of WYQQKPGKAPKLLIY (SEQ ID NO: 98); an FR-L3 comprising the amino acid sequence of GVPSRFSGSGSGTDFTFTISSLQPEDIATYYC (SEQ ID NO: 99); and/or an FR-L4 comprising the amino acid sequence of FGQGTKVEIK (SEQ ID NO: 100), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 96 and 98-100, such as possessed by the anti-TIGIT antibodies h6B2.L2H1 and h6B2.L2H5.

In some instances, the antibody further comprises at least one, two, three, or four of the following heavy chain variable region FRs: an FR-H1 comprising the amino acid sequence of X$_1$VX$_2$LKESGPX$_3$X$_4$X$_5$X$_6$PX$_7$X$_8$TLX$_9$LTCX$_{10}$FSGFSLS (SEQ ID NO: 74), wherein $X_1$ is E or Q; $X_2$ is S or T; $X_3$ is A or G; $X_4$ is I or L; $X_5$ is L or V; $X_6$ is K or Q; $X_7$ is S or T; $X_8$ is H or Q; $X_9$ is S or T; and $X_{10}$ is S or T; an FR-H2 comprising the amino acid sequence of WIRQPX$_1$X$_2$KX$_3$LEWLA (SEQ ID NO: 75), wherein $X_1$ is P or S; $X_2$ is E or G; and $X_3$ is A or G; an FR-H3 comprising the amino acid sequence of RLTX$_1$X$_2$KDX$_3$SX$_4$X$_5$QX$_6$X$_7$LX$_8$X$_9$TX$_{10}$X$_{11}$DX$_{12}$X$_{13}$DTATYYCAH (SEQ ID NO: 76), wherein $X_1$ is I or V; $X_2$ is S or T; $X_3$ is A or T; $X_4$ is K or N; $X_5$ is D or N; $X_6$ is A or V; $X_7$ is F or V; $X_8$ is N or T; $X_9$ is M or V; $X_{10}$ is N or S; $X_{11}$ is M or V; $X_{12}$ is P or T; and $X_{13}$ is T or V; and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 74-77, such as possessed by the anti-TIGIT antibody rat6B2 and derivatives thereof (e.g., h6B2.L1H1, h6B2.L2H1, h6B2.L1H2, h6B2.L1H3, h6B2.L1H4, h6B2.L1H5, and h6B2.L2H5). The anti-TIGIT antibody may further include, for example, at least one, two, three, or four of the following heavy chain variable region FRs: an FR-H1 comprising the amino acid sequence of QVSLKESGPGILQPSHTLSLTCSFSGFSLS (SEQ ID NO: 78); an FR-H2 comprising the amino acid sequence of WIRQPSEKGLEWLA (SEQ ID NO: 79); an FR-H3 comprising the amino acid sequence of RLTVSKDASNDQAFLNVTSVDTTDTATYYCAH (SEQ ID NO: 80); and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 77-80, such as possessed by the anti-TIGIT antibody rat6B2. In some instances, the anti-TIGIT antibody includes an FR-H1 comprising the amino acid sequence of EVTLKESGPALVKPTQTLTLTCTFSGFSLS (SEQ ID NO: 81); an FR-H2 comprising the amino acid sequence of WIRQPPGKALEWLA (SEQ ID NO: 82); an FR-H3 comprising the amino acid sequence of RLTVTKDASKNQAVLTMTNMDPVDTATYYCAH (SEQ ID NO: 83); and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 77 and 81-83, such as possessed by the anti-TIGIT antibodies h6B2.L1H1 and h6B2.L2H1. In some instances, the anti-TIGIT antibody includes an FR-H1 comprising the amino acid sequence of EVTLKESGPALVKPTQTLTLTCTFSGFSLS (SEQ ID NO: 81); an FR-H2 comprising the amino acid sequence of WIRQPPGKALEWLA (SEQ ID NO: 82); an FR-H3 comprising the amino acid sequence of RLTITKDASKNQAVLTMTNMDPVDTATYYCAH (SEQ ID NO: 84); and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 77, 81-82, and 84, such as possessed by the anti-TIGIT antibody h6B2.L1H2. In some instances, the anti-TIGIT antibody includes an FR-H1 comprising the amino acid sequence of EVTLKES- GPALVKPTQTLTLTCTFSGFSLS (SEQ ID NO: 81); an FR-H2 comprising the amino acid sequence of WIRQPPGKALEWLA (SEQ ID NO: 82); an FR-H3 comprising the amino acid sequence of RLTVTKDTSKNQAVLTMTNMDPVDTATYYCAH (SEQ ID NO: 85); and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 77, 81-82, and 85, such as possessed by the anti-TIGIT antibody h6B2.L1H3. In some instances, the anti-TIGIT antibody includes an FR-H1 comprising the amino acid sequence of EVTLKESGPALVKPTQTLTLTCTFSGFSLS (SEQ ID NO: 81); an FR-H2 comprising the amino acid sequence of WIRQPPGKALEWLA (SEQ ID NO: 82); an FR-H3 comprising the amino acid sequence of RLTVTKDASKNQVVLTMTNMDPVDTATYYCAH (SEQ ID NO: 86); and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 77, 81-82, and 85, such as possessed by the anti-TIGIT antibody h6B2.L1H4. In some instances, the anti-TIGIT antibody includes an FR-H1 comprising the amino acid sequence of EVTLKESGPALVKPTQTLTLTCTFSGFSLS (SEQ ID NO: 81); an FR-H2 comprising the amino acid sequence of WIRQPPGKALEWLA (SEQ ID NO: 82); an FR-H3 comprising the amino acid sequence of RLTITKDTSKNQWLTMTNMDPVDTATYYCAH (SEQ ID NO: 87); and/or an FR-H4 comprising the amino acid sequence of WGQGTLVTVSS (SEQ ID NO: 77), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 77, 81-82, and 87, such as possessed by the anti-TIGIT antibodies h6B2.L1H5 and h6B2.L2H5.

In another example, the invention provides anti-TIGIT antibodies that include at least one, two, three, four, five, or six HVRs selected from (a) an HVR-H1 comprising the amino acid sequence of TYGMGVS (SEQ ID NO: 110); (b) an HVR-H2 comprising the amino acid sequence of SIWWNGNTYYNPSLRS (SEQ ID NO: 111); (c) an HVR-H3 comprising the amino acid sequence of TGGAVITWFAY (SEQ ID NO: 112); (d) an HVR-L1 comprising the amino acid sequence of KASQSVGKNIA (SEQ ID NO: 113); (e) an HVR-L2 comprising the amino acid sequence of YASNRYT (SEQ ID NO: 114); and/or (f) an HVR-L3 comprising the amino acid sequence of QHIYNSPYP (SEQ ID NO: 115), or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 110-115. In some instances, any of the above anti-TIGIT antibodies of the preceding example may include, for example, (a) an HVR-H1 comprising the amino acid sequence of TYGMGVS (SEQ ID NO: 110); (b) an HVR-H2 comprising the amino acid sequence of SIWWNGN-TYYNPSLRS (SEQ ID NO: 111); (c) an HVR-H3 comprising the amino acid sequence of TGGAVITWFAY (SEQ ID NO: 112); (d) an HVR-L1 comprising the amino acid sequence of KASQSVGKNIA (SEQ ID NO: 113); (e) an HVR-L2 comprising the amino acid sequence of YASNRYT (SEQ ID NO: 114); and (f) an HVR-L3 comprising the amino acid sequence of QHIYNSPYP (SEQ ID NO: 115), such as possessed by the anti-TIGIT antibody rat10A5 and derivatives thereof (e.g., h10A5.L1H1; h10A5.L2H1; h10A5.L3H1; h10A5.L4H1; h10A5.L1H2; h10A5.L1H3; h10A5.L1H4; and h10A5.L4H4).

In some instances, the antibody further comprises at least one, two, three, or four of the following light chain variable region framework regions (FRs): an FR-L1 comprising the amino acid sequence of $X_1$IVMTQSPX$_2$X$_3$X$_4$SX$_5$SX$_6$GX$_7$RX$_8$TX$_9$X$_{10}$C (SEQ ID NO: 129), wherein $X_1$ is E or N; $X_2$ is A or K; $X_3$ is S or T; $X_4$ is L or M; $X_5$ is I or V; $X_6$ is I or P; $X_7$ is D or E; $X_8$ is A or V; $X_9$ is L or M; and $X_{10}$ is N or S; an FR-L2 comprising the amino acid sequence of WYQQKX$_1$GQX$_2$PX$_3$LLIY (SEQ ID NO: 130), wherein $X_1$ is P or T; $X_2$ is A or S; and $X_3$ is Q or R; an FR-L3 comprising the amino acid sequence of GX$_1$PX$_2$RFX$_3$GX$_4$GSGTX$_5$FTLTIX$_6$SX$_7$QX$_8$EDX$_9$AX$_{10}$X$_{11}$YC (SEQ ID NO: 131), wherein $X_1$ is I or V; $X_2$ is A or D; $X_3$ is S or T; $X_4$ is G or S; $X_5$ is D or E; $X_6$ is N or S; $X_7$ is L or V; $X_8$ is A or S; $X_9$ is A or F; $X_{10}$ is F or V; and $X_{11}$ is F or Y; and/or an FR-L4 comprising the amino acid sequence of FGX$_1$GTKX$_2$EIK (SEQ ID NO: 132), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 129-132, such as possessed by the anti-TIGIT antibody rat10A5 and derivatives thereof (e.g., h10A5.L1H1; h10A5.L2H1; h10A5.L3H1; h10A5.L4H1; h10A5.L1H2; h10A5.L1H3; h10A5.L1H4; and h10A5.L4H4). The anti-TIGIT antibody may further include, for example, at least one, two, three, or four of the following light chain variable region FRs: an FR-L1 comprising the amino acid sequence of NIVMTQSPKSMSISIGDRVTMNC (SEQ ID NO: 133); an FR-L2 comprising the amino acid sequence of WYQQKTGQSPQLLIY (SEQ ID NO: 134); an FR-L3 comprising the amino acid sequence of GVPDRFTGGGSGTDFTLTINSVQAEDAAFFYC (SEQ ID NO: 135); and/or an FR-L4 comprising the amino acid sequence of FGTGTKLEIK (SEQ ID NO: 136), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 133-136, such as possessed by the anti-TIGIT antibody rat10A5. In some instances, the anti-TIGIT antibody includes an FR-L1 comprising the amino acid sequence of EIVMTQSPATLSVSPGERATLSC (SEQ ID NO: 137); an FR-L2 comprising the amino acid sequence of WYQQKPGQSPRLLIY (SEQ ID NO: 138); an FR-L3 comprising the amino acid sequence of GVPARFSGSGSGTEFTLTISSLQSEDFAVYYC (SEQ ID NO: 140); and/or an FR-L4 comprising the amino acid sequence of FGQGTKVEIK (SEQ ID NO: 142), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 137-138, 140, and 142, such as possessed by the anti-TIGIT antibodies h10A5.L1H1, h10A5.L1H2, h10A5.L1H3, and h10A5.L1H4. In some instances, the anti-TIGIT antibody includes an FR-L1 comprising the amino acid sequence of EIVMTQSPATLSVSPGERATLSC (SEQ ID NO: 137); an FR-L2 comprising the amino acid sequence of WYQQKPGQAPRLLIY (SEQ ID NO: 139); an FR-L3 comprising the amino acid sequence of GVPARFSGSGSGTEFTLTISSLQSEDFAVYYC (SEQ ID NO: 140); and/or an FR-L4 comprising the amino acid sequence of FGQGTKVEIK (SEQ ID NO: 142), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 137, 139-140, and 142, such as possessed by the anti-TIGIT antibody h10A5.L2H1. In some instances, the anti-TIGIT antibody includes an FR-L1 comprising the amino acid sequence of EIVMTQSPATLSVSPGERATLSC (SEQ ID NO: 137); an FR-L2 comprising the amino acid sequence of WYQQKPGQSPRLLIY (SEQ ID NO: 138); an FR-L3 comprising the amino acid sequence of GIPARFSGSGS-GTEFTLTISSLQSEDFAVYYC (SEQ ID NO: 141); and/or an FR-L4 comprising the amino acid sequence of FGQGT-KVEIK (SEQ ID NO: 142), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 137-138 and 141-142, such as possessed by the anti-TIGIT antibodies h10A5.L3H1. In some instances, the anti-TIGIT antibody includes an FR-L1 comprising the amino acid sequence of EIVMTQSPATLS-VSPGERATLSC (SEQ ID NO: 137); an FR-L2 comprising the amino acid sequence of WYQQKPGQAPRLLIY (SEQ ID NO: 139); an FR-L3 comprising the amino acid sequence of GIPARFSGSGSGTEFTLTISSLQSEDFAVYYC (SEQ ID NO: 141); and/or an FR-L4 comprising the amino acid sequence of FGQGTKVEIK (SEQ ID NO: 142), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 137, 139, and 141-142, such as possessed by the anti-TIGIT antibodies h10A5.L4H1 and h10A5.L4H4.

In some instances, the antibody further comprises at least one, two, three, or four of the following heavy chain variable region FRs: FR-H1 comprising the amino acid sequence of $X_1VX_2LKESGPX_3X_4X_5X_6PX_7X_8TLX_9LTCX_{10}FSGFSLT$ (SEQ ID NO: 116), wherein $X_1$ is E or Q; $X_2$ is S or T; $X_3$ is A or G; $X_4$ is I or L; $X_5$ is L or V; $X_6$ is K or Q; $X_7$ is S or T; $X_8$ is H or Q; $X_9$ is S or T; and $X_{10}$ is S or T; an FR-H2 comprising the amino acid sequence of WIRQPX$_1$X$_2$KX$_3$LEWLA (SEQ ID NO: 117), wherein $X_1$ is P or S; $X_2$ is E or G; and $X_3$ is A or G; an FR-H3 comprising the amino acid sequence of RLTX$_1$X$_2$KDTSX$_3$X$_4$QX$_5$X$_6$LX$_7$X$_8$TX$_9$X$_{10}$DX$_{11}$X$_{12}$DTATYYCAH (SEQ ID NO: 118), wherein $X_1$ is I or V; $X_2$ is S or T; $X_3$ is K or N; $X_4$ is D or N; $X_5$ is A or V; $X_6$ is F or V; $X_7$ is N or T; $X_8$ is M or V; $X_9$ is N or S; $X_{10}$ is M or V; $X_{11}$ is P or T; and $X_{12}$ is T or V; and/or an FR-H4 comprising the amino acid sequence of WGQGTLVTVSS (SEQ ID NO: 119), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 116-119, such as possessed by the anti-TIGIT antibody rat10A5 and derivatives thereof (e.g., h10A5.L1H1; h10A5.L2H1; h10A5.L3H1; h10A5.L4H1; h10A5.L1H2; h10A5.L1H3; h10A5.L1H4; and h10A5.L4H4). The anti-TIGIT antibody may further include, for example, at least one, two, three, or four of the following heavy chain variable region FRs: an FR-H1 comprising the amino acid sequence of QVSLKES-GPGILQPSHTLSLTCSFSGFSLT (SEQ ID NO: 120); an FR-H2 comprising the amino acid sequence of WIRQPSEK-GLEWLA (SEQ ID NO: 121); an FR-H3 comprising the amino acid sequence of RLTVSKDTSNDQAFLNVTS-VDTTDTATYYCAH (SEQ ID NO: 122); and/or an FR-H4 comprising the amino acid sequence of WGQGTLVTVSS (SEQ ID NO: 119), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 119-122, such as possessed by the anti-TIGIT antibody rat10A5. In some instances, the anti-TIGIT antibody includes an FR-H1 comprising the amino acid sequence of EVTLKESGPALVKPTQTLTLTCTFSGFSLT (SEQ ID NO: 123); an FR-H2 comprising the amino acid sequence of WIRQPPGKALEWLA (SEQ ID NO: 124); an FR-H3 comprising the amino acid sequence of RLTVT-KDTSKNQAVLTMTNMDPVDTATYYCAH (SEQ ID NO: 125); and/or an FR-H4 comprising the amino acid sequence of WGQGTLVTVSS (SEQ ID NO: 119), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 119 and 123-125, such as possessed by the anti-TIGIT antibodies h10A5.L1H1, h10A5.L2H1, h10A5.L3H1, and h10A5.L4H1. In some instances, the anti-TIGIT antibody includes an FR-H1 comprising the amino acid sequence of EVTLKES-GPALVKPTQTLTLTCTFSGFSLT (SEQ ID NO: 123); an FR-H2 comprising the amino acid sequence of WIRQPPG-KALEWLA (SEQ ID NO: 124); an FR-H3 comprising the amino acid sequence of RLTITKDTSKNQAVLTMTNMD-PVDTATYYCAH (SEQ ID NO: 126); and/or an FR-H4 comprising the amino acid sequence of WGQGTLVTVSS (SEQ ID NO: 119), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 119, 123-124, and 126, such as possessed by the anti-TIGIT antibody h10A5.L1H2. In some instances, the anti-TIGIT antibody includes an FR-H1 comprising the amino acid sequence of EVTLKES-GPALVKPTQTLTLTCTFSGFSLT (SEQ ID NO: 123); an FR-H2 comprising the amino acid sequence of WIRQPPG-KALEWLA (SEQ ID NO: 124); an FR-H3 comprising the amino acid sequence of RLTVTKDTSKNQVVLTMTNM-DPVDTATYYCAH (SEQ ID NO: 127); and/or an FR-H4 comprising the amino acid sequence of WGQGTLVTVSS (SEQ ID NO: 119), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 119, 123-124, and 127, such as possessed by the anti-TIGIT antibody h10A5.L1H3. In some instances, the anti-TIGIT antibody includes an FR-H1 comprising the amino acid sequence of EVTLKES-GPALVKPTQTLTLTCTFSGFSLT (SEQ ID NO: 123); an FR-H2 comprising the amino acid sequence of WIRQPPG-KALEWLA (SEQ ID NO: 124); an FR-H3 comprising the amino acid sequence of RLTITKDTSKNQWLTMTNMD-PVDTATYYCAH (SEQ ID NO: 128); and/or an FR-H4 comprising the amino acid sequence of WGQGTLVTVSS (SEQ ID NO: 119), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 119, 123-124, and 128, such as possessed by the anti-TIGIT antibodies h10A5.L1H4 and h10A5.L4H4.

In another example, the invention provides anti-TIGIT antibodies that include at least one, two, three, four, five, or six HVRs selected from (a) an HVR-H1 comprising the amino acid sequence of EYSIY (SEQ ID NO: 153); (b) an HVR-H2 comprising the amino acid sequence of RIDPKN-GRTYYVDKFKN (SEQ ID NO: 154); (c) an HVR-H3 comprising the amino acid sequence of IYGFYFDF (SEQ ID NO: 155); (d) an HVR-L1 comprising the amino acid sequence of KGSQNVNKYLV (SEQ ID NO: 156); (e) an HVR-L2 comprising the amino acid sequence of NTDNLQS (SEQ ID NO: 157); and/or (f) an HVR-L3 comprising the amino acid sequence of YQYNNGFT (SEQ ID NO: 158), or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 153-158. In some instances, any of the above anti-TIGIT antibodies of the preceding example may include, for example, (a) an HVR-H1 comprising the amino acid sequence of EYSIY (SEQ ID NO: 153); (b) an HVR-H2 comprising the amino acid sequence of RIDPKNGRTYYVDKFKN (SEQ ID NO: 154); (c) an HVR-H3 comprising the amino acid sequence of IYGFYFDF (SEQ ID NO: 155); (d) an HVR-L1 comprising the amino acid sequence of KGSQNVNKYLV (SEQ ID NO: 156); (e) an HVR-L2 comprising the amino acid sequence of NTDNLQS (SEQ ID NO: 157); and (f) an HVR-L3 comprising the amino acid sequence of YQYNNGFT (SEQ ID NO: 158) such as possessed by the anti-TIGIT antibody rat7E7 and derivatives thereof (e.g., h7E7.L1H1, h7E7.L2H1, h7E7.L3H1, h7E7.L4H1, h7E7.L5H1, h7E7.L1H2, h7E7.L1H3, h7E7.L1H4, h7E7.L1H5, h7E7.L1H6, h7E7.L1H7, h7E7.L1H8, h7E7.L1H9, h7E7.L5H9, and 7E7.L5aH9a).

In some instances, the antibody further comprises at least one, two, three, or four of the following light chain variable region framework regions (FRs): an FR-L1 comprising the amino acid sequence of $X_1IX_2LTQSPSX_3LSASVGDRVTX_4X_5C$ (SEQ ID NO: 180), wherein $X_1$ is D or N; $X_2$ is H or Q; $X_3$ is F or L; $X_4$ is I or L; and $X_5$ is S or T; an FR-L2 comprising the amino acid sequence of $WYQQKX_1GX_2APKLLIY$ (SEQ ID NO: 181), wherein $X_1$ is L or P; and $X_2$ is E or K; an FR-L3 comprising the amino acid sequence of $GX_1PSRFSGSGSGTX_2X_3TLTISSLQPEDX_4ATYX_5C$ (SEQ ID NO: 182), wherein $X_1$ is I or V; $X_2$ is D or E; $X_3$ is F or Y; $X_4$ is A or F; and $X_5$ is F or Y; and/or an FR-L4 comprising the amino acid sequence of $FGX_1GTKX_2EIK$ (SEQ ID NO: 183), wherein $X_1$ is Q or S; and $X_2$ is L or V or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 180-183, such as possessed by the anti-TIGIT antibody rat7E7 and derivatives thereof (e.g., h7E7.L1H1, h7E7.L2H1, h7E7.L3H1, h7E7.L4H1, h7E7.L5H1, h7E7.L1H2, h7E7.L1H3, h7E7.L1H4, h7E7.L1H5, h7E7.L1H6, h7E7.L1H7, h7E7.L1H8, h7E7.L1H9, h7E7.L5H9, and 7E7.L5aH9a). The anti-TIGIT antibody may further include, for example, at least one, two, three, or four of the following light chain variable region FRs: an FR-L1 comprising the amino acid sequence of NIHLTQSPSLLSASVGDRVTLSC (SEQ ID NO: 184); an FR-L2 comprising the amino acid sequence of WYQQKLGEAPKLLIY (SEQ ID NO: 185); an FR-L3 comprising the amino acid sequence of GIPSRFSGSGSGTDYTLTISSLQPEDAATYFC (SEQ ID NO: 186); and/or an FR-L4 comprising the amino acid sequence of FGSGTKLEIK (SEQ ID NO: 187), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 184-187, such as possessed by the anti-TIGIT antibody rat7E7. In some instances, the anti-TIGIT antibody includes an FR-L1 comprising the amino acid sequence of DIQLTQSPSFLSASVGDRVTITC (SEQ ID NO: 188); an FR-L2 comprising the amino acid sequence of WYQQKPGKAPKLLIY (SEQ ID NO: 189); an FR-L3 comprising the amino acid sequence of GIPSRFSGSGSGTEYTLTISSLQPEDFATYFC (SEQ ID NO: 190); and/or an FR-L4 comprising the amino acid sequence of FGQGTKVEIK (SEQ ID NO: 196), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 188-190 and 196, such as possessed by the anti-TIGIT antibodies h7E7.L1H1, h7E7.L1H2, h7E7.L1H3, h7E7.L1H4, h7E7.L1H5, h7E7.L1H6, h7E7.L1H7, h7E7.L1H8, and h7E7.L1H9. In some instances, the anti-TIGIT antibody includes an FR-L1 comprising the amino acid sequence of DIQLTQSPSFLSASVGDRVTITC (SEQ ID NO: 188); an FR-L2 comprising the amino acid sequence of WYQQKPGKAPKLLIY (SEQ ID NO: 189); an FR-L3 comprising the amino acid sequence of GVPSRFSGSGSGTEYTLTISSLQPEDFATYFC (SEQ ID NO: 191); and/or an FR-L4 comprising the amino acid sequence of FGQGTKVEIK (SEQ ID NO: 196), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 188-189, 191 and 196, such as possessed by the anti-TIGIT antibody h7E7.L2H1. In some instances, the anti-TIGIT antibody includes an FR-L1 comprising the amino acid sequence of DIQLTQSPSFLSASVGDRVTITC (SEQ ID NO: 188); an FR-L2 comprising the amino acid sequence of WYQQKPGKAPKLLIY (SEQ ID NO: 189); an FR-L3 comprising the amino acid sequence of GIPSRFSGSGSGTEFTLTISSLQPEDFATYFC (SEQ ID NO: 192); and/or an FR-L4 comprising the amino acid sequence of FGQGTKVEIK (SEQ ID NO: 196), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 188-189, 192 and 196, such as possessed by the anti-TIGIT antibodies h7E7.L3H1. In some instances, the anti-TIGIT antibody includes an FR-L1 comprising the amino acid sequence of DIQLTQSPSFLSASVGDRVTITC (SEQ ID NO: 188); an FR-L2 comprising the amino acid sequence of WYQQKPGKAPKLLIY (SEQ ID NO: 189); an FR-L3 comprising the amino acid sequence of GIPSRFSGSGSGTEYTLTISSLQPEDFATYYC (SEQ ID NO: 193); and/or an FR-L4 comprising the amino acid sequence of FGQGTKVEIK (SEQ ID NO: 196), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 188-189, 193 and 196, such as possessed by the anti-TIGIT antibodies h7E7.L4H1. In some instances, the anti-TIGIT antibody includes an FR-L1 comprising the amino acid sequence of DIQLTQSPSFLSASVGDRVTITC (SEQ ID NO: 188); an FR-L2 comprising the amino acid sequence of WYQQKPGKAPKLLIY (SEQ ID NO: 189); an FR-L3 comprising the amino acid sequence of GVPSRFSGSGSGTEFTLTISSLQPEDFATYYC (SEQ ID NO: 194); and/or an FR-L4 comprising the amino acid sequence of FGQGTKVEIK (SEQ ID NO: 196), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 188-189, 194 and 196, such as possessed by the anti-TIGIT antibodies h7E7.L5H1 and h7E7.L5H9. In some instances, the anti-TIGIT antibody includes an FR-L1 comprising the amino acid sequence of DIQLTQSPSFLSASVGDRVTITC (SEQ ID NO: 188); an FR-L2 comprising the amino acid sequence of WYQQK-PGKAPKLLIY (SEQ ID NO: 189); an FR-L3 comprising the amino acid sequence of GVPSRFSGSGSGTEYTLTISS-LQPEDFATYYC (SEQ ID NO: 195); and/or an FR-L4 comprising the amino acid sequence of FGQGTKVEIK (SEQ ID NO: 196), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 188-189 and 195-196, such as possessed by the anti-TIGIT antibodies 7E7.L5aH9a.

In some instances, the antibody further comprises at least one, two, three, or four of the following heavy chain variable region FRs: an FR-H1 comprising the amino acid sequence of EVQLX$_1$QSGX$_2$EX$_3$X$_4$X$_5$PGASVKX$_6$SCKAX$_7$GYTFT (SEQ ID NO: 159), wherein X$_1$ is Q or V; X$_2$ is A or P; X$_3$ is L or V; X$_4$ is K or Q; X$_5$ is K or R; X$_6$ is L or V; and X$_7$ is S or T; an FR-H2 comprising the amino acid sequence of WVX$_1$QX$_2$PX$_3$QX$_4$LEX$_5$X$_6$G (SEQ ID NO: 160), wherein X$_1$ is K or R; X$_2$ is A or R; X$_3$ is G or K; X$_4$ is R or S; X$_5$ is I or W; and X$_6$ is I or M; an FR-H3 comprising the amino acid sequence of RX$_1$TX$_2$TX$_3$DTSX$_4$X$_5$TAYMX$_6$LSSLX$_7$TSEDTAX$_8$ YX$_9$CX$_{10}$R (SEQ ID NO: 161), wherein X$_1$ is A or V; X$_2$ is I or L; X$_3$ is A or R; X$_4$ is A or S; X$_5$ is N or S; X$_6$ is E or Q; X$_7$ is R or T; X$_8$ is T or V; X$_9$ is F or Y; and X$_{10}$ is A or T; and/or an FR-H4 comprising the amino acid sequence of WGQGX$_1$X$_2$VTX$_3$SS (SEQ ID NO: 162), wherein X$_1$ is T or V; X$_2$ is L or M; and X$_3$ is A or V, or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 159-162, such as possessed by the anti-TIGIT antibody rat7E7 and derivatives thereof (e.g., h7E7.L1H1, h7E7.L2H1, h7E7.L3H1, h7E7.L4H1, h7E7.L5H1, h7E7.L1H2, h7E7.L1H3, h7E7.L1H4, h7E7.L1H5, h7E7.L1H6, h7E7.L1H7, h7E7.L1H8, h7E7.L1H9, h7E7.L5H9, and 7E7.L5aH9a). The anti-TIGIT antibody may further include, for example, at least one, two, three, or four of the following heavy chain variable region FRs: an FR-H1 comprising the amino acid sequence of EVQLQQSGPELQRPGAS-VKLSCKATGYTFT (SEQ ID NO: 163); an FR-H2 comprising the amino acid sequence of WVKQRPKQSLEIIG (SEQ ID NO: 164); an FR-H3 comprising the amino acid sequence of RATLTADTSSNTAYMQLSSLTSEDTATY-FCTR (SEQ ID NO: 165); and/or an FR-H4 comprising the amino acid sequence of WGQGVMVTASS (SEQ ID NO: 166), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 163-166, such as possessed by the anti-TIGIT antibody rat7E7. In some instances, the anti-TIGIT antibody includes an FR-H1 comprising the amino acid sequence of EVQLVQSGAEVKKPGASVKVSCKASGYTFT (SEQ ID NO: 167); an FR-H2 comprising the amino acid sequence of WVRQAPGQRLEIIG (SEQ ID NO: 168); an FR-H3 comprising the amino acid sequence of RATLTADTSAS-TAYMELSSLRSEDTAVYFCTR (SEQ ID NO: 172); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167-138, 172, and 179, such as possessed by the anti-TIGIT antibodies h7E7.L1H1, h7E7.L2H1, h7E7.L3H1, h7E7.L4H1, and h7E7.L5H1. In some instances, the anti-TIGIT antibody includes an FR-H1 comprising the amino acid sequence of EVQLVQSGAEVK-KPGASVKVSCKASGYTFT (SEQ ID NO: 167); an FR-H2 comprising the amino acid sequence of WVRQAPGQR-LEWIG (SEQ ID NO: 169); an FR-H3 comprising the amino acid sequence of RATLTADTSASTAYMELSSL-RSEDTAVYFCTR (SEQ ID NO: 172); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167, 169, 172, and 179, such as possessed by the anti-TIGIT antibody h7E7.L1H2. In some instances, the anti-TIGIT antibody includes an FR-H1 comprising the amino acid sequence of EVQLVQSGAEVKKPGASVK-VSCKASGYTFT (SEQ ID NO: 167); an FR-H2 comprising the amino acid sequence of WVRQAPGQRLEIMG (SEQ ID NO: 170); an FR-H3 comprising the amino acid sequence of RATLTADTSASTAYMELSSLRSEDTAVYFCTR (SEQ ID NO: 172); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167, 170, 172, and 179, such as possessed by the anti-TIGIT antibody h7E7.L1H3. In some instances, the anti-TIGIT antibody includes an FR-H1 comprising the amino acid sequence of EVQLVQSGAEVKKPGASVKVSCKASGYTFT (SEQ ID NO: 167); an FR-H2 comprising the amino acid sequence of WVRQAPGQRLEIIG (SEQ ID NO: 168); an FR-H3 comprising the amino acid sequence of RVTLTADTSAS-TAYMELSSLRSEDTAVYFCTR (SEQ ID NO: 173); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167-168, 173, and 179, such as possessed by the anti-TIGIT antibody h7E7.L1H4. In some instances, the anti-TIGIT antibody includes an FR-H1 comprising the amino acid sequence of EVQLVQS-GAEVKKPGASVKVSCKASGYTFT (SEQ ID NO: 167); an FR-H2 comprising the amino acid sequence of WVRQAPGQRLEIIG (SEQ ID NO: 168); an FR-H3 comprising the amino acid sequence of RATITADTSAS-TAYMELSSLRSEDTAVYFCTR (SEQ ID NO: 174); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167-168, 174, and 179, such as possessed by the anti-TIGIT antibody h7E7.L1H5. In some instances, the anti-TIGIT antibody includes an FR-H1 comprising the amino acid sequence of EVQLVQS-GAEVKKPGASVKVSCKASGYTFT (SEQ ID NO: 167); an FR-H2 comprising the amino acid sequence of WVRQAPGQRLEIIG (SEQ ID NO: 168); an FR-H3 comprising the amino acid sequence of RATLTRDTSAS- TAYMELSSLRSEDTAVYFCTR (SEQ ID NO: 175); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167-168, 175, and 179, such as possessed by the anti-TIGIT antibody h7E7.L1H6. In some instances, the anti-TIGIT antibody includes an FR-H1 comprising the amino acid sequence of EVQLVQS-GAEVKKPGASVKVSCKASGYTFT (SEQ ID NO: 167); an FR-H2 comprising the amino acid sequence of WVRQAPGQRLEIIG (SEQ ID NO: 168); an FR-H3 comprising the amino acid sequence of RATLTADTSAS-TAYMELSSLRSEDTAVYYCTR (SEQ ID NO: 176); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167-168, 176, and 179, such as possessed by the anti-TIGIT antibody h7E7.L1H7. In some instances, the anti-TIGIT antibody includes an FR-H1 comprising the amino acid sequence of EVQLVQS-GAEVKKPGASVKVSCKASGYTFT (SEQ ID NO: 167); an FR-H2 comprising the amino acid sequence of WVRQAPGQRLEIIG (SEQ ID NO: 168); an FR-H3 comprising the amino acid sequence of RATLTADTSAS-TAYMELSSLRSEDTAVYFCAR (SEQ ID NO: 177); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167-168, 177, and 179, such as possessed by the anti-TIGIT antibody h7E7.L1H8. In some instances, the anti-TIGIT antibody includes an FR-H1 comprising the amino acid sequence of EVQLVQS-GAEVKKPGASVKVSCKASGYTFT (SEQ ID NO: 167); an FR-H2 comprising the amino acid sequence of WVRQAPGQRLEWMG (SEQ ID NO: 171); an FR-H3 comprising the amino acid sequence of RVTITRDTSAS-TAYMELSSLRSEDTAVYYCAR (SEQ ID NO: 178); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167, 171, and 178-179, such as possessed by the anti-TIGIT antibodies h7E7.L1H9 and h7E7.L5H9. In some instances, the anti-TIGIT antibody includes an FR-H1 comprising the amino acid sequence of EVQLVQSGAEVKKPGASVKVSCKASGYTFT (SEQ ID NO: 167); an FR-H2 comprising the amino acid sequence of WVRQAPGQRLEIMG (SEQ ID NO: 170); an FR-H3 comprising the amino acid sequence of RVTITRDTSAS-TAYMELSSLRSEDTAVYYCAR (SEQ ID NO: 178); and/or an FR-H4 comprising the amino acid sequence of WGQGTLVTVSS (SEQ ID NO: 179), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 167, 170, and 178-179, such as possessed by the anti-TIGIT antibody 7E7.L5aH9a.

In another example, the invention provides anti-TIGIT antibodies that include at least one, two, three, four, five, or six HVRs selected from (a) an HVR-H1 comprising the amino acid sequence of EHSIY (SEQ ID NO: 215); (b) an HVR-H2 comprising the amino acid sequence of RIDPKN-GRTYFVDKFKN (SEQ ID NO: 216); (c) an HVR-H3 comprising the amino acid sequence of IDGFYFDF (SEQ ID NO: 217); (d) an HVR-L1 comprising the amino acid sequence of KGSQNVNKYLV (SEQ ID NO: 218); (e) an HVR-L2 comprising the amino acid sequence of STDNLQS (SEQ ID NO: 219); and/or (f) an HVR-L3 comprising the amino acid sequence of YQYNNGFT (SEQ ID NO: 220), or a combination of one or more of the above HVRs and one or more variants thereof having at least about 90% sequence identity (e.g., 90%, 91%, 92%, 93%, 94%, 95%, 96%, 97%, 98%, or 99% identity) to any one of SEQ ID NOs: 215-220. In some instances, any of the above anti-TIGIT antibodies of the preceding example may include, for example, (a) an HVR-H1 comprising the amino acid sequence of EHSIY (SEQ ID NO: 215); (b) an HVR-H2 comprising the amino acid sequence of RIDPKNGRTYFVDKFKN (SEQ ID NO: 216); (c) an HVR-H3 comprising the amino acid sequence of IDGFYFDF (SEQ ID NO: 217); (d) an HVR-L1 comprising the amino acid sequence of KGSQNVNKYLV (SEQ ID NO: 218); (e) an HVR-L2 comprising the amino acid sequence of STDNLQS (SEQ ID NO: 219); and (f) an HVR-L3 comprising the amino acid sequence of YQYNNGFT (SEQ ID NO: 220), such as possessed by the anti-TIGIT antibody rat15C8 and derivatives thereof (e.g., h15C8.L1H1, h15C8.L2H1, h15C8.L3H1, h15C8.L4H1, h15C8.L5H1, h15C8.L1H2, h15C8.L1H3, h15C8.L1H4, h15C8.L1H5, h15C8.L1H6, h15C8.L1H7, h15C8.L1H8, h15C8.L1H9, h15C8.L5H9, and 5C8.L5aH9a).

In some instances, the antibody further comprises at least one, two, three, or four of the following light chain variable region framework regions (FRs): an FR-L1 comprising the amino acid sequence of $X_1IX_2LTQSPSX_3LSASVGDRVTX_4X_5C$ (SEQ ID NO: 243), wherein $X_1$ is D or N; $X_2$ is H or Q; $X_3$ is F or L; $X_4$ is I or L; and $X_5$ is S or T; an FR-L2 comprising the amino acid sequence of $WYQQKX_1GX_2APKLLIY$ (SEQ ID NO: 244), wherein $X_1$ is L or P and $X_2$ is E or K; an FR-L3 comprising the amino acid sequence of $GX_1PSRFSGSGSGTX_2X_3TLTISSLQPEDX_4ATYX_5C$ (SEQ ID NO: 245), wherein $X_1$ is I or V; $X_2$ is D or E; $X_3$ is F or Y; $X_4$ is A or F; and $X_5$ is F or Y; and/or an FR-L4 comprising the amino acid sequence of $FGX_1GTKX_2EIK$ (SEQ ID NO: 246), wherein $X_1$ is Q or S and $X_2$ is L or V, or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 243-246, such as possessed by the anti-TIGIT antibody rat15C8 and derivatives thereof (e.g., h15C8.L1H1, h15C8.L2H1, h15C8.L3H1, h15C8.L4H1, h15C8.L5H1, h15C8.L1H2, h15C8.L1H3, h15C8.L1H4, h15C8.L1H5, h15C8.L1H6, h15C8.L1H7, h15C8.L1H8, h15C8.L1H9, h15C8.L5H9, and 5C8.L5aH9a). The anti-TIGIT antibody may further include, for example, at least one, two, three, or four of the following light chain variable region FRs: an FR-L1 comprising the amino acid sequence of NIHLTQSPSLLSAS-VGDRVTLSC (SEQ ID NO: 247); an FR-L2 comprising the amino acid sequence of WYQQKLGEAPKLLIY (SEQ ID NO: 248); an FR-L3 comprising the amino acid sequence of GIPSRFSGSGSGTDYTLTISSLQPEDAATYFC (SEQ ID NO: 249); and/or an FR-L4 comprising the amino acid sequence of FGSGTKLEIK (SEQ ID NO: 250), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 247-250, such as possessed by the anti-TIGIT antibody rat15C8. In some instances, the anti-TIGIT antibody includes an FR-L1 comprising the amino acid sequence of DIQLTQSPSFLSAS-VGDRVTITC (SEQ ID NO: 251); an FR-L2 comprising the amino acid sequence of WYQQKPGKAPKLLIY (SEQ ID NO: 252); an FR-L3 comprising the amino acid sequence of GIPSRFSGSGSGTEYTLTISSLQPEDFATYFC (SEQ ID NO: 253); and/or an FR-L4 comprising the amino acid sequence of FGQGTKVEIK (SEQ ID NO: 259), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 251-253 and 259, such as possessed by the anti-TIGIT antibodies h15C8.L1H1, h15C8.L1H2, h15C8.L1H3, h15C8.L1H4, h15C8.L1H5, h15C8.L1H6, h15C8.L1H7, h15C8.L1H8, and h15C8.L1H9. In some instances, the anti-TIGIT antibody includes an FR-L1 comprising the amino acid sequence of DIQLTQSPSFLSASVGDRVTITC (SEQ ID NO: 251); an FR-L2 comprising the amino acid sequence of WYQQKPGKAPKLLIY (SEQ ID NO: 252); an FR-L3 comprising the amino acid sequence of GVPSRFSGSGS-GTEYTLTISSLQPEDFATYFC (SEQ ID NO: 254); and/or an FR-L4 comprising the amino acid sequence of FGQGT-KVEIK (SEQ ID NO: 259), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 251-252, 254, and 259, such as possessed by the anti-TIGIT antibody h15C8.L2H1. In some instances, the anti-TIGIT antibody includes an FR-L1 comprising the amino acid sequence of DIQLTQSPSFLSAS-VGDRVTITC (SEQ ID NO: 251); an FR-L2 comprising the amino acid sequence of WYQQKPGKAPKLLIY (SEQ ID NO: 252); an FR-L3 comprising the amino acid sequence of GIPSRFSGSGSGTEFTLTISSLQPEDFATYFC (SEQ ID NO: 255); and/or an FR-L4 comprising the amino acid sequence of FGQGTKVEIK (SEQ ID NO: 259), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 251-252, 255, and 259, such as possessed by the anti-TIGIT antibodies h15C8.L3H1. In some instances, the anti-TIGIT antibody includes an FR-L1 comprising the amino acid sequence of DIQLTQSPSFLSASVGDRVTITC (SEQ ID NO: 251); an FR-L2 comprising the amino acid sequence of WYQQKPGKAPKLLIY (SEQ ID NO: 252); an FR-L3 comprising the amino acid sequence of GIPSRFSGSGS-GTEYTLTISSLQPEDFATYYC (SEQ ID NO: 256); and/or an FR-L4 comprising the amino acid sequence of FGQGT-KVEIK (SEQ ID NO: 259), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 251-252, 256, and 259, such as possessed by the anti-TIGIT antibodies h15C8.L4H1. In some instances, the anti-TIGIT antibody includes an FR-L1 comprising the amino acid sequence of DIQLTQSPSFL-SASVGDRVTITC (SEQ ID NO: 251); an FR-L2 comprising the amino acid sequence of WYQQKPGKAPKLLIY (SEQ ID NO: 252); an FR-L3 comprising the amino acid sequence of GVPSRFSGSGSGTEFTLTISSLQPEDFA-TYYC (SEQ ID NO: 257); and/or an FR-L4 comprising the amino acid sequence of FGQGTKVEIK (SEQ ID NO: 259), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 251-252, 257, and 259, such as possessed by the anti-TIGIT antibodies h15C8.L5H1 and h15C8.L5H9. In some instances, the anti-TIGIT antibody includes an FR-L1 comprising the amino acid sequence of DIQLTQSPSFLSASVGDRVTITC (SEQ ID NO: 251); an FR-L2 comprising the amino acid sequence of WYQQKPGKAPKLLIY (SEQ ID NO: 252); an FR-L3 comprising the amino acid sequence of GVPSRF-SGSGSGTEYTLTISSLQPEDFATYYC (SEQ ID NO: 258); and/or an FR-L4 comprising the amino acid sequence of FGQGTKVEIK (SEQ ID NO: 259), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 251-252, and 258-259, such as possessed by the anti-TIGIT antibodies 5C8.L5aH9a.

In some instances, the antibody further comprises at least one, two, three, or four of the following heavy chain variable region FRs: FR-H1 comprising the amino acid sequence of EVQLX$_1$QSGX$_2$EX$_3$X$_4$X$_5$PGASVKX$_6$SCKASGYTFT (SEQ ID NO: 221), wherein X$_1$ is Q or V; X$_2$ is A or P; X$_3$ is L or V; X$_4$ is K or Q; X$_5$ is K or R; and X$_6$ is L or V; an FR-H2 comprising the amino acid sequence of WX$_1$X$_2$QX$_3$PX$_4$QX$_5$LEX$_6$X$_7$G (SEQ ID NO: 222), wherein X$_1$ is L or V; X$_2$ is K or R; X$_3$ is A or R; X$_4$ is G or K; X$_5$ is R or S; X$_6$ is I or W; and X$_7$ is I or M; an FR-H3 comprising the amino acid sequence of RX$_1$TX$_2$TX$_3$X$_4$TSX$_5$X$_6$TAYMX$_7$LSSLX$_8$SEDTAX$_9$YX$_{10}$CAR (SEQ ID NO: 223), wherein X$_1$ is A or V; X$_2$ is I or L; X$_3$ is R or T; X$_4$ is D or N; X$_5$ is A or S; X$_6$ is N or S; X$_7$ is E or Q; X$_8$ is R or T; X$_9$ is I or V; and X$_{10}$ is F or Y; and/or an FR-H4 comprising the amino acid sequence of WGQGX$_1$X$_2$VTX$_3$SS (SEQ ID NO: 224), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 221-224, such as possessed by the anti-TIGIT antibody rat15C8 and derivatives thereof (e.g., h15C8.L1H1, h15C8.L2H1, h15C8.L3H1, h15C8.L4H1, h15C8.L5H1, h15C8.L1H2, h15C8.L1H3, h15C8.L1H4, h15C8.L1H5, h15C8.L1H6, h15C8.L1H7, h15C8.L1H8, h15C8.L1H9, h15C8.L5H9, and 5C8.L5aH9a). The anti-TIGIT antibody may further include, for example, at least one, two, three, or four of the following heavy chain variable region FRs: an FR-H1 comprising the amino acid sequence of EVQLQQS-GPELQRPGASVKLSCKASGYTFT (SEQ ID NO: 225); an FR-H2 comprising the amino acid sequence of WLKQRP-KQSLEIIG (SEQ ID NO: 226); an FR-H3 comprising the amino acid sequence of RATLTTNTSSNTAYMQLSSLT-SEDTAIYFCAR (SEQ ID NO: 227); and/or an FR-H4 comprising the amino acid sequence of WGQGVMVTASS (SEQ ID NO: 228), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 225-228, such as possessed by the anti-TIGIT antibody rat15C8. In some instances, the anti-TIGIT antibody includes an FR-H1 comprising the amino acid sequence of EVQLVQSGAEVKKPGASVKVSCKAS-GYTFT (SEQ ID NO: 229); an FR-H2 comprising the amino acid sequence of WLRQAPGQRLEIIG (SEQ ID NO: 230); an FR-H3 comprising the amino acid sequence of RATLTTDTSASTAYMELSSLRSEDTAVYFCAR (SEQ ID NO: 235); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229-230, 235, and 242, such as possessed by the anti-TIGIT antibodies h15C8.L1H1, h15C8.L2H1, h15C8.L3H1, h15C8.L4H1, and h15C8.L5H1. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WVRQAPGQRLEIIG (SEQ ID NO: 231); an FR-H3 comprising the amino acid sequence of RATLTTDTSASTAYMELSSLRSEDTAVYFCAR (SEQ ID NO: 235); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229, 231, 235, and 242, such as possessed by the anti-TIGIT antibody h15C8.L1H2. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEWIG (SEQ ID NO: 232); an FR-H3 comprising the amino acid sequence of RATLTTDTSASTAYMELSSLRSEDTAVYFCAR (SEQ ID NO: 235); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229, 232, 235, and 242, such as possessed by the anti-TIGIT antibody h15C8.L1H3. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEIMG (SEQ ID NO: 233); an FR-H3 comprising the amino acid sequence of RATLTTDTSASTAYMELSSLRSEDTAVYFCAR (SEQ ID NO: 235); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229, 233, 235, and 242, such as possessed by the anti-TIGIT antibody h15C8.L1H4. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEIIG (SEQ ID NO: 230); an FR-H3 comprising the amino acid sequence of RVTLTTDTSASTAYMELSSLRSEDTAVYFCAR (SEQ ID NO: 236); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229-230, 236, and 242, such as possessed by the anti-TIGIT antibody h15C8.L1H5. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEIIG (SEQ ID NO: 230); an FR-H3 comprising the amino acid sequence of RATITTDTSASTAYMELSSLRSEDTAVYFCAR (SEQ ID NO: 237); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229-230, 237, and 242, such as possessed by the anti-TIGIT antibody h15C8.L1H6. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEIIG (SEQ ID NO: 230); an FR-H3 comprising the amino acid sequence of RATLTRDTSASTAYMELSSLRSEDTAVYFCAR (SEQ ID NO: 238); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229-230, 238, and 242, such as possessed by the anti-TIGIT antibody h15C8.L1H7. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEIIG (SEQ ID NO: 230); an FR-H3 comprising the amino acid sequence of RATLTTDTSASTAYMELSSLRSEDTAVYYCAR (SEQ ID NO: 239); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229-230, 239, and 242, such as possessed by the anti-TIGIT antibody h15C8.L1H8. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WVRQAPGQRLEWMG (SEQ ID NO: 234); an FR-H3 comprising the amino acid sequence of RVTITRDTSASTAYMELSSLRSEDTAVYYCAR (SEQ ID NO: 240); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229, 234, 240, and 242, such as possessed by the anti-TIGIT antibodies h15C8.L1H9 and h15C8.L5H9. In some instances, the anti-TIGIT antibody includes an FR-H1 comprising the amino acid sequence of EVQLVQSGAEVKKPGASVKVSCKASGYTFT (SEQ ID NO: 229); an FR-H2 comprising the amino acid sequence of WLRQAPGQRLEIMG (SEQ ID NO: 233); an FR-H3 comprising the amino acid sequence of RATITTDTSASTAYMELSSLRSEDTAVYYCAR (SEQ ID NO: 241); and/or an FR-H4 comprising the amino acid sequence of WGQGTLVTVSS (SEQ ID NO: 242), or a combination of one or more of the above FRs and one or more variants thereof having at least about 90% sequence identity (e.g., 90%, 91%, 92%, 93%, 94%, 95%, 96%, 97%, 98%, or 99% identity) to any one of SEQ ID NOs: 229, 233, and 241-242, such as possessed by the anti-TIGIT antibody 5C8.L5aH9a.

Anti-TIGIT antibodies are also provided that include a heavy chain variable region having at least 90% (e.g., 91%, 92%, 93%, or 94%), or at least 95% (e.g., 96%, 97%, 98%, or 99%) sequence identity to, or the sequence of, SEQ ID NO: 60, 62, 66, 101, 103, 104, 105, 106, 107, 145, 146, 147, 148, 197, 199, 200, 201, 202, 203, 204, 205, 206, 207, 213, 260, 262, 263, 264, 265, 266, 267, 268, 269, 270, or 276. Also provided are anti-TIGIT antibodies that include a light chain variable region having at least 90% (e.g., 91%, 92%, 93%, or 94%), or at least 95% (e.g., 96%, 97%, 98%, or 99%) sequence identity to, or the sequence of, SEQ ID NO: 61, 63, 64, 67, 102, 108, 109, 144, 149, 150, 151, 152, 198, 208, 209, 210, 211, 212, 214, 261, 271, 272, 273, 274, 275, or 277.

In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 60, and a light chain variable region having at least 90% (e.g., 91%, 92%, 93%, or 94%), or at least 95% (e.g., 96%, 97%, 98%, or 99%) sequence identity to, or the sequence of, SEQ ID NO: 61. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 62, and a light chain variable region having at least 90% (e.g., 91%, 92%, 93%, or 94%), or at least 95% (e.g., 96%, 97%, 98%, or 99%) sequence identity to, or the sequence of, SEQ ID NO: 63. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 62, and a light chain variable region having at least 90% (e.g., 91%, 92%, 93%, or 94%), or at least 95% (e.g., 96%, 97%, 98%, or 99%) sequence identity to, or the sequence of, SEQ ID NO: 64. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 66, and a light chain variable region having at least 90% (e.g., 91%, 92%, 93%, or 94%), or at least 95% (e.g., 96%, 97%, 98%, or 99%) sequence identity to, or the sequence of, SEQ ID NO: 67. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 101, and a light chain variable region having at least 90% (e.g., 91%, 92%, 93%, or 94%), or at least 95% (e.g., 96%, 97%, 98%, or 99%) sequence identity to, or the sequence of, SEQ ID NO: 102. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 103, and a light chain variable region having at least 90% (e.g., 91%, 92%, 93%, or 94%), or at least 95% (e.g., 96%, 97%, 98%, or 99%) sequence identity to, or the sequence of, SEQ ID NO: 108. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 104, and a light chain variable region having at least 90% (e.g., 91%, 92%, 93%, or 94%), or at least 95% (e.g., 96%, 97%, 98%, or 99%) sequence identity to, or the sequence of, SEQ ID NO: 108. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 105, and a light chain variable region having at least 90% (e.g., 91%, 92%, 93%, or 94%), or at least 95% (e.g., 96%, 97%, 98%, or 99%) sequence identity to, or the sequence of, SEQ ID NO: 108. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 106, and a light chain variable region having at least 90% (e.g., 91%, 92%, 93%, or 94%), or at least 95% (e.g., 96%, 97%, 98%, or 99%) sequence identity to, or the sequence of, SEQ ID NO: 108. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 107, and a light chain variable region having at least 90% (e.g., 91%, 92%, 93%, or 94%), or at least 95% (e.g., 96%, 97%, 98%, or 99%) sequence identity to, or the sequence of, SEQ ID NO: 109. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 143, and a light chain variable region having at least 90% (e.g., 91%, 92%, 93%, or 94%), or at least 95% (e.g., 96%, 97%, 98%, or 99%) sequence identity to, or the sequence of, SEQ ID NO: 144. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 145, and a light chain variable region having at least 90% (e.g., 91%, 92%, 93%, or 94%), or at least 95% (e.g., 96%, 97%, 98%, or 99%) sequence identity to, or the sequence of, SEQ ID NO: 149. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 145, and a light chain variable region having at least 90% (e.g., 91%, 92%, 93%, or 94%), or at least 95% (e.g., 96%, 97%, 98%, or 99%) sequence identity to, or the sequence of, SEQ ID NO: 150. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 145, and a light chain variable region having at least 90% (e.g., 91%, 92%, 93%, or 94%), or at least 95% (e.g., 96%, 97%, 98%, or 99%) sequence identity to, or the sequence of, SEQ ID NO: 151. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 145, and a light chain variable region having at least 90% (e.g., 91%, 92%, 93%, or 94%), or at least 95% (e.g., 96%, 97%, 98%, or 99%) sequence identity to, or the sequence of, SEQ ID NO: 152. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 147, and a light chain variable region having at least 90% (e.g., 91%, 92%, 93%, or 94%), or at least 95% (e.g., 96%, 97%, 98%, or 99%)

sequence identity to, or the sequence of, SEQ ID NO: 149. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 148, and a light chain variable region having at least 90% (e.g., 91%, 92%, 93%, or 94%), or at least 95% (e.g., 96%, 97%, 98%, or 99%) sequence identity to, or the sequence of, SEQ ID NO: 149. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 148, and a light chain variable region having at least 90% (e.g., 91%, 92%, 93%, or 94%), or at least 95% (e.g., 96%, 97%, 98%, or 99%) sequence identity to, or the sequence of, SEQ ID NO: 152. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 197, and a light chain variable region having at least 90% (e.g., 91%, 92%, 93%, or 94%), or at least 95% (e.g., 96%, 97%, 98%, or 99%) sequence identity to, or the sequence of, SEQ ID NO: 198. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 199, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 200, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 201, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 202, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 203, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 204, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 205, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 206, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 207, and a light chain variable region having at least 90% (e.g., 91%, 92%, 93%, or 94%), or at least 95% (e.g., 96%, 97%, 98%, or 99%) sequence identity to, or the sequence of, SEQ ID NO: 208. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 207, and a light chain variable region having at least 90% (e.g., 91%, 92%, 93%, or 94%), or at least 95% (e.g., 96%, 97%, 98%, or 99%) sequence identity to, or the sequence of, SEQ ID NO: 212. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 199, and a light chain variable region having at least 90% (e.g., 91%, 92%, 93%, or 94%), or at least 95% (e.g., 96%, 97%, 98%, or 99%) sequence identity to, or the sequence of, SEQ ID NO: 209. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 199, and a light chain variable region having at least 90% (e.g., 91%, 92%, 93%, or 94%), or at least 95% (e.g., 96%, 97%, 98%, or 99%) sequence identity to, or the sequence of, SEQ ID NO: 210. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 199, and a light chain variable region having at least 90% (e.g., 91%, 92%, 93%, or 94%), or at least 95% (e.g., 96%, 97%, 98%, or 99%) sequence identity to, or the sequence of, SEQ ID NO: 211. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 199, and a light chain variable region having at least 90% (e.g., 91%, 92%, 93%, or 94%), or at least 95% (e.g., 96%, 97%, 98%, or 99%) sequence identity to, or the sequence of, SEQ ID NO: 212. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 213, and a light chain variable region having at least 90% (e.g., 91%, 92%, 93%, or 94%), or at least 95% (e.g., 96%, 97%, 98%, or 99%) sequence identity to, or the sequence of, SEQ ID NO: 214. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 260, and a light chain variable region having at least 90% (e.g., 91%, 92%, 93%, or 94%), or at least 95% (e.g., 96%, 97%, 98%, or 99%) sequence identity to, or the sequence of, SEQ ID NO: 261. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 262, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 263, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 264, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 265, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 266, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 267, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 268, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 269, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 270, and a light chain variable region having at least 90% (e.g., 91%, 92%, 93%, or 94%), or at least 95% (e.g., 96%, 97%, 98%, or 99%) sequence identity to, or the sequence of, SEQ ID NO: 271. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 270, and a light chain variable region having at least 90% (e.g., 91%, 92%, 93%, or 94%), or at least 95% (e.g., 96%, 97%, 98%, or 99%) sequence identity to, or the sequence of, SEQ ID NO: 275. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 262, and a light chain variable region having at least 90% (e.g., 91%, 92%, 93%, or 94%), or at least 95% (e.g., 96%, 97%, 98%, or 99%) sequence identity to, or the sequence of, SEQ ID NO: 272. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 262, and a light chain variable region having at least 90% (e.g., 91%, 92%, 93%, or 94%), or at least 95% (e.g., 96%, 97%, 98%, or 99%) sequence identity to, or the sequence of, SEQ ID NO: 273. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 262, and a light chain variable region having at least 90% (e.g., 91%, 92%, 93%, or 94%), or at least 95% (e.g., 96%, 97%, 98%, or 99%) sequence identity to, or the sequence of, SEQ ID NO: 274. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 262, and a light chain variable region having at least 90% (e.g., 91%, 92%, 93%, or 94%), or at least 95% (e.g., 96%, 97%, 98%, or 99%) sequence identity to, or the sequence of, SEQ ID NO: 275. In some instances, the anti-TIGIT antibody includes a heavy chain variable region having at least 90% (e.g., 91%, 92%, 93%, or 94%), or at least 95% (e.g., 96%, 97%, 98%, or 99%) sequence identity to, or the sequence of, SEQ ID NO: 276, and a light chain variable region having at least 90% (e.g., 91%, 92%, 93%, or 94%), or at least 95% (e.g., 96%, 97%, 98%, or 99%) sequence identity to, or the sequence of, SEQ ID NO: 277.

In another aspect, an anti-TIGIT antibody is provided, wherein the antibody comprises a VH as in any of the embodiments provided above, and a VL as in any of the embodiments provided above, wherein one or both of the variable domain sequences include post-translational modifications.

In some instances, any one of the anti-TIGIT antibodies described above may be capable of binding to rabbit TIGIT, in addition to human TIGIT. In some instances, any one of the anti-TIGIT antibodies described above may be capable of binding to both human TIGIT and cynomolgus monkey (cyno) TIGIT. In some instances, any one of the anti-TIGIT antibodies described above may be capable of binding to human TIGIT, cyno TIGIT, and rabbit TIGIT. In some instances, any one of the anti-TIGIT antibodies described above (e.g., 4.1D3 or a derivative thereof) may be capable of binding to human TIGIT, cyno TIGIT, and rabbit TIGIT, but not murine TIGIT.

In some instances, the anti-TIGIT antibody binds human TIGIT with a Kd of about 10 nM or lower and cyno TIGIT with a Kd of about 10 nM or lower (e.g., binds human TIGIT with a Kd of about 0.1 nM to about 1 nM and cyno TIGIT with a Kd of about 0.5 nM to about 1 nM. e.g., binds human TIGIT with a Kd of about 0.1 nM or lower and cyno TIGIT with a Kd of about 0.5 nM or lower).

In some embodiments, the anti-TIGIT antibody is an antagonist antibody. The antagonist antibody may specifically bind TIGIT and inhibit or block TIGIT interaction with poliovirus receptor (PVR) (e.g., the antagonist antibody inhibits intracellular signaling mediated by TIGIT binding to PVR). In some instances, the antagonist antibody inhibits or blocks binding of human TIGIT to human PVR with an IC50 value of 10 nM or lower (e.g., 1 nM to about 10 nM). In some instances, the antagonist antibody inhibits or blocks binding of cyno TIGIT to cyno PVR with an IC50 value of 50 nM or lower (e.g., 1 nM to about 50 nM, e.g., 1 nM to about 5 nM).

In other embodiments, the anti-TIGIT antibody can be an agonist antibody. The agonist antibody can specifically bind TIGIT and stimulate the interaction of PVR with CD226 or CD96. For example, the agonist antibody can specifically bind TIGIT and stimulate the interaction of PVR with CD226 and CD96 (e.g., binds human TIGIT and stimulates the interaction of human PVR with human CD226 and human CD96 and/or binds cyno TIGIT and stimulates the interaction of cyno PVR with cyno CD226 and cyno CD96).

In a further aspect, the invention provides an isolated antibody that competes for binding to TIGIT with any of the anti-TIGIT antibodies described above. In yet a further aspect, the invention provides an isolated antibody that binds to the same epitope as an anti-TIGIT antibody described above.

An anti-TIGIT antibody according to any of the above embodiments is a monoclonal antibody, comprising a chimeric, humanized, or human antibody. In one embodiment, an anti-TIGIT antibody is an antibody fragment, for example, a Fv, Fab, Fab', scFv, diabody, or F(ab')$_2$ fragment. In another embodiment, the antibody is a full-length antibody, e.g., an intact IgG antibody (e.g., an intact IgG1 antibody) or other antibody class or isotype as defined herein.

In a further aspect, an anti-TIGIT antibody according to any of the above embodiments may incorporate any of the features, singly or in combination, as described in Sections 1-7 below.

1. Antibody Affinity

In certain embodiments, an antibody (e.g., an anti-TIGIT antibody) provided herein has a dissociation constant (Kd) of ≤1 µM, ≤100 nM, ≤10 nM, ≤1 nM, ≤0.1 nM, ≤0.01 nM, or ≤0.001 nM (e.g., $10^{-8}$M or less, e.g., from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIACORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., *J. Mol. Biol.* 293:865-881 (1999). If the on-rate exceeds $10^6 M^{-1}s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S.

Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al. Nat. Med. 9:129-134 (2003); and Hollinger et al. Proc. Natl. Acad. Sci. USA 90: 6444-6448 (1993). Triabodies and tetrabodies are also described in Hudson et al. Nat. Med. 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. E. coli or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al. Proc. Natl. Acad. Sci. USA, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, Front. Biosci. 13:1619-1633 (2008), and are further described, e.g., in Riechmann et al., Nature 332:323-329 (1988); Queen et al., Proc. Nat'l Acad. Sci. USA 86:10029-10033 (1989); U.S. Pat. Nos. 5,821,337, 7,527,791, 6,982,321, and 7,087,409; Kashmiri et al., Methods 36:25-34 (2005) (describing specificity determining region (SDR) grafting); Padlan, Mol. Immunol. 28:489-498 (1991) (describing "resurfacing"); Dall'Acqua et al., Methods 36:43-60 (2005) (describing "FR shuffling"); and Osbourn et al., Methods 36:61-68 (2005) and Klimka et al., Br. J. Cancer, 83:252-260 (2000) (describing the "guided selection" approach to FR shuffling).

Human framework regions that may be used for humanization include but are not limited to: framework regions selected using the "best-fit" method (see, e.g., Sims et al. J. Immunol. 151:2296 (1993)); framework regions derived from the consensus sequence of human antibodies of a particular subgroup of light or heavy chain variable regions (see, e.g., Carter et al. Proc. Natl. Acad. Sci. USA, 89:4285 (1992); and Presta et al. J. Immunol., 151:2623 (1993)); human mature (somatically mutated) framework regions or human germline framework regions (see, e.g., Almagro and Fransson, Front. Biosci. 13:1619-1633 (2008)); and framework regions derived from screening FR libraries (see, e.g., Baca et al., J. Biol. Chem. 272:10678-10684 (1997) and Rosok et al., J. Biol. Chem. 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, Curr. Opin. Pharmacol. 5: 368-74 (2001) and Lonberg, Curr. Opin. Immunol. 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci. USA, 103:3557-3582 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J*, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In any one of the above aspects, the anti-TIGIT antibodies (e.g., 4.1D3 or a variant thereof, e.g., 4.1D3.Q1E) provided herein can be multispecific antibodies, for example, bispecific antibodies. Multispecific antibodies can be monoclonal antibodies that have binding specificities for at least two different sites. In certain embodiments, bispecific antibodies may bind to two different epitopes on TIGIT. In certain embodiments, one of the binding specificities is for TIGIT and the other is for any other antigen (e.g., a second biological molecule, e.g., a cell surface antigen, e.g., a tumor antigen). Accordingly, a bispecific anti-TIGIT antibody may have binding specificities for TIGIT and a second biological molecule, such as a PD-1, PD-L1, PD-L2, OX40, PD-1, CTLA-4, LAG3, TIM3, BTLA, VISTA, B7H4, or CD96. Bispecific antibodies can also be prepared as full-length antibodies or antibody fragments.

In other embodiments, bispecific antibodies may bind to two different epitopes of TIGIT, OX40, PD-1, PD-L1, PD-L2. In certain embodiments, one of the binding specificities is for TIGIT and the other is for any other antigen (e.g., a second biological molecule, such as OX40). In other embodiments, the bispecific antibody may have binding specificity for TIGIT and PD-L1; TIGIT and PD-L2; TIGIT and PD-1; TIGIT and CTLA-4; TIGIT and LAG3; TIGIT and TIM3; TIGIT and BTLA; TIGIT and VISTA; TIGIT and B7H4; or TIGIT and CD96, wherein the bispecific antibody is preferably an antagonist antibody for TIGIT and an antagonist antibody for its second target. In other embodiments, the bispecific antibody may have binding specificity for TIGIT and CD226; TIGIT and CD28; TIGIT and CD27; TIGIT and CD137; TIGIT and HVEM; TIGIT and GITR; TIGIT and MICA; TIGIT and ICOS; TIGIT and NKG2D; or TIGIT and 2B4, wherein the bispecific antibody is preferably an antagonist antibody for TIGIT and for its second target. In other embodiments, the bispecific antibody may have binding specificity for TIGIT that is not antagonistic in nature (i.e., the bispecific antibody does not have act as a TIGIT antagonist).

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). "Knob-in-hole" engineering of multispecific antibodies may be utilized to generate a first arm containing a knob and a second arm containing the hole into which the knob of the first arm may bind. The knob of the multispecific antibodies of the invention may be an anti-TIGIT arm in one embodiment. Alternatively, the knob of the multispecific antibodies of the invention may be an anti-TIGIT arm in one embodiment. Multispecific antibodies may also be engineered using immunoglobulin crossover (also known as Fab domain exchange or CrossMab format) technology (see e.g., WO2009/080253; Schaefer et al., *Proc. Natl. Acad. Sci. USA*, 108:11187-11192 (2011)). Multispecific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bispecific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g. US 2006/0025576A1).

The antibodies, or antibody fragments thereof, may also include a "Dual Acting FAb" or "DAF" comprising an antigen binding site that binds to TIGIT as well as another, different antigen (e.g., a second biological molecule) (see, e.g., US 2008/0069820).

7. Antibody Variants

In certain embodiments, amino acid sequence variants of the anti-TIGIT antibodies of the invention are contemplated. As described in detail herein, anti-TIGIT antibodies may be optimized based on desired structural and functional properties. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen-binding.

I. Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, Methods Mol. Biol. 207:179-196 (2008)), and/or residues that contact antigen, with the resulting variant VH or VL being tested for binding affinity. Affinity maturation by constructing and reselecting from secondary libraries has been described, e.g., in Hoogenboom et al. in Methods in Molecular Biology 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) Science, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

II. Glycosylation Variants

In certain embodiments, anti-TIGIT antibodies of the invention (e.g., 4.1D3 or a variant thereof, e.g., 4.1D3.Q1E) can be altered to increase or decrease the extent to which the antibody is glycosylated. Addition or deletion of glycosylation sites to anti-TIGIT antibody of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, anti-TIGIT antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta. L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-TIGIT antibodies variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

III. Fc Region Variants

In certain embodiments, one or more amino acid modifications may be introduced into the Fc region of an anti-TIGIT antibody of the invention (e.g., 4.1D3 or a variant thereof, e.g., 4.1D3.Q1E), thereby generating an Fc region variant (see e.g., US 2012/0251531). The Fc region variant may comprise a human Fc region sequence (e.g., a human IgG1, IgG2, IgG3 or IgG4 Fc region) comprising an amino acid modification (e.g., a substitution) at one or more amino acid positions.

In certain embodiments, the invention contemplates an anti-TIGIT antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al. *J. Immunol. Methods* 202:163 (1996); Cragg, M. S. et al. *Blood.* 101:1045-1052 (2003); and Cragg, M. S, and M. J. Glennie *Blood.* 103:2738-2743 (2004)). FcRn binding and in vivo clearance/half life determinations can also be performed using methods known in the art (see, e.g., Petkova, S. B. et al. *Int'l. Immunol.* 18(12):1759-1769 (2006)).

Antibodies with reduced effector function include those with substitution of one or more of Fc region residues 238, 265, 269, 270, 297, 327 and 329 (U.S. Pat. Nos. 6,737,056 and 8,219,149). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. Nos. 7,332,581 and 8,219,149).

In certain embodiments, the proline at position 329 of a wild-type human Fc region in the antibody is substituted with glycine or arginine or an amino acid residue large enough to destroy the proline sandwich within the Fc/Fc.gamma. receptor interface that is formed between the proline 329 of the Fc and tryptophan residues Trp 87 and Trp 110 of FcgRIII (Sondermann et al.: Nature 406, 267-273 (20 Jul. 2000)). In certain embodiments, the antibody comprises at least one further amino acid substitution. In one embodiment, the further amino acid substitution is S228P, E233P, L234A, L235A, L235E, N297A, N297D, or P331 S, and still in another embodiment the at least one further amino acid substitution is L234A and L235A of the human IgG1 Fc region or S228P and L235E of the human IgG4 Fc region (see e.g., US 2012/0251531), and still in another embodiment the at least one further amino acid substitution is L234A and L235A and P329G of the human IgG1 Fc region.

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

In some aspects the anti-TIGIT antibody (e.g., 4.1D3 or a variant thereof, e.g., 4.1D3.Q1E) comprises an Fc region comprising an N297G mutation.

In some embodiments, the anti-TIGIT antibody (e.g., 4.1D3 or a variant thereof, e.g., 4.1D3.Q1E) comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some instances, at least one of the one or more heavy chain constant domains is paired with another heavy chain constant domain. In some instances, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some instances, the $CH3_1$ and $CH3_2$ domains meet at an interface between said protuberance and cavity. In some instances, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In other instances, the $CH2_1$ and $CH2_2$ domains meet at an interface between said protuberance and cavity. In some instances, the anti-TIGIT antibody is an IgG1 antibody.

IV. Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, for example, in U.S. Pat. No. 7,521,541.

V. Antibody Derivatives

In certain embodiments, an anti-TIGIT antibody of the invention (e.g., 4.1D3 or a variant thereof, e.g., 4.1D3.Q1E) provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

IV. Recombinant Methods and Compositions

Anti-TIGIT antibodies of the invention (e.g., 4.1D3 or a variant thereof, e.g., 4.1D3.Q1E) may be produced using recombinant methods and compositions, for example, as described in U.S. Pat. No. 4,816,567, which is incorporated herein by reference in its entirety. In one embodiment, isolated nucleic acid encoding an anti-TIGIT antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-TIGIT antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-TIGIT antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells.

Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

V. Immunoconjugates

The invention also provides immunoconjugates comprising an anti-TIGIT antibody of the invention (e.g., 4.1D3 or a variant thereof, e.g., 4.1D3.Q1E) conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an anti-TIGIT antibody as described herein (e.g., 4.1D3 or a variant thereof, e.g., 4.1D3.Q1E) conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, cumin, crotin, *sapaonaria officinalis* inhibitor, gelonin, mitogellin, restrictocin, phenomycin, enomycin, and the tricothecenes.

In another embodiment, an immunoconjugate comprises an anti-TIGIT antibody as described herein (e.g., 4.1D3 or a variant thereof, e.g., 4.1D3.Q1E) conjugated to a radioactive atom to form a radioconjugate. A variety of radioactive isotopes are available for the production of radioconjugates. Examples include $At^{211}$, $I^{131}$, $I^{125}$, $Y^{90}$, $Re^{18}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

VI. Methods and Compositions for Diagnostics and Detection

In certain embodiments, any of the anti-TIGIT antibodies of the invention (e.g., 4.1D3 or a variant thereof, e.g., 4.1D3.Q1E) is useful for detecting the presence of TIGIT in a biological sample. The term "detecting" as used herein encompasses quantitative or qualitative detection. In certain embodiments, a biological sample comprises a cell or tissue.

In one embodiment, an anti-TIGIT antibody for use in a method of diagnosis or detection is provided. In a further aspect, a method of detecting the presence of TIGIT in a biological sample is provided. In certain embodiments, the method comprises contacting the biological sample with an anti-TIGIT antibody as described herein under conditions permissive for binding of the anti-TIGIT antibody to TIGIT, and detecting whether a complex is formed between the anti-TIGIT antibody and TIGIT. Such method may be an in vitro or in vivo method.

In certain embodiments, labeled anti-TIGIT antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

VII. Pharmaceutical Compositions

Pharmaceutical compositions of an anti-TIGIT antibody of the invention (e.g., 4.1D3 or a variant thereof, e.g., 4.1D3.Q1E) are prepared by mixing such an antibody having the desired degree of purity with one or more optional pharmaceutically acceptable carriers (*Remington's Pharmaceutical Sciences* 16th edition. Osol, A. Ed. (1980)), in the form of lyophilized compositions or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

In some instances, a pharmaceutical composition including an anti-TIGIT antibody provided herein may further include a PD-1 axis binding antagonist, such as a PD-1 binding antagonist, a PD-L1 binding antagonist, and a PD-L2 binding antagonist.

In some instances, a pharmaceutical composition including an anti-TIGIT antibody provided herein may further include an OX40 binding agonist, such as an OX40 agonist antibody, an OX40L agonist fragment, an OX40 oligomeric receptor, and an OX40 immunoadhesin.

In some instances, a pharmaceutical composition including an anti-TIGIT antibody provided herein may further include an additional therapeutic agent, such as a chemotherapeutic agent or an agent that decreases or inhibits one or more additional immune co-inhibitory receptors (e.g., PD-1, CTLA-4, LAG3, TIM3, BTLA, VISTA, B7H4, and/or CD96).

In other embodiments, a pharmaceutical composition including an anti-TIGIT antibody may further include (a) a PD-1 axis binding antagonist and an OX40 binding agonist; (b) a PD-1 axis binding antagonist and an additional therapeutic agent (e.g., a chemotherapeutic agent); (c) a PD-1 axis binding antagonist and an agent that decreases or inhibits one or more additional immune co-inhibitory receptors (e.g., PD-1, CTLA-4, LAG3, TIM3, BTLA, VISTA, B7H4, and/or CD96); (d) an OX40 binding agonist and an additional therapeutic agent (e.g., a chemotherapeutic agent); (e) an OX40 binding agonist and an agent that decreases or inhibits one or more additional immune co-inhibitory receptors (e.g., PD-1, CTLA-4, LAG3, TIM3, BTLA, VISTA, B7H4, and/or CD96); (f) an additional therapeutic agent (e.g., a chemotherapeutic agent) and an agent that decreases or inhibits one or more additional immune co-inhibitory receptors (e.g., PD-1, CTLA-4, LAG3, TIM3, BTLA, VISTA, B7H4, and/or CD96); or (g) a PD-1 axis binding antagonist, an OX40 binding agonist, and an agent that decreases or inhibits one or more additional immune co-inhibitory receptors (e.g., PD-1, CTLA-4, LAG3, TIM3, BTLA, VISTA, B7H4, and/or CD96). Optionally, the pharmaceutical composition will include one or more pharmaceutically acceptable carriers, excipients, or diluent.

Exemplary lyophilized antibody compositions are described in U.S. Pat. No. 6,267,958. Aqueous antibody compositions include those described in U.S. Pat. No. 6,171,586 and WO2006/044908, the latter compositions including a histidine-acetate buffer.

The composition herein may also contain more than one active ingredients as necessary for the particular indication being treated, preferably those with complementary activities that do not adversely affect each other. For example, it may be desirable to further provide an additional therapeutic agent (e.g., a chemotherapeutic agent, a cytotoxic agent, a growth inhibitory agent, and/or an anti-hormonal agent, such as those recited herein above). Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, for example, films, or microcapsules.

The compositions to be used for in vivo administration are generally sterile. Sterility may be readily accomplished, e.g., by filtration through sterile filtration membranes.

VIII. Therapeutic Methods

Any of the anti-TIGIT antibodies of the invention (e.g., 4.1D3 or a variant thereof, e.g., 4.1D3.Q1E) may be used in therapeutic methods.

In one aspect, an anti-TIGIT antibody for use as a medicament is provided. In further aspects, an anti-TIGIT antibody described herein (e.g., 4.1D3 or a variant thereof, e.g., 4.1D3.Q1E) for use in treating or delaying progression of an immune-related disease in a subject is provided. In certain embodiments, the invention provides an anti-TIGIT antibody for use in a method of treating a subject having an immune-related disease that is associated with a T cell dysfunctional disorder. In other embodiments, the immune-related disease is a viral infection. In certain embodiments, the viral infection is a chronic viral infection. In some embodiments, T cell dysfunctional disorder is characterized by decreased responsiveness to antigenic stimulation. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the T cell dysfunctional disorder includes unresolved acute infection, chronic infection and tumor immunity.

In another aspect, an anti-TIGIT antibody described herein (e.g., 4.1D3 or a variant thereof, e.g., 4.1D3.Q1E) for treating or delaying progression of a cancer in a subject is provided. In certain embodiments, the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphomas, a myeloma (e.g., multiple myeloma (MM)), mycoses fungoides, a merkel cell cancer, and a hematologic malignancy. Thus, a variety of cancers may be treated, or their progression may be delayed. In some embodiments, the individual may have breast cancer (e.g., triple-negative breast cancer). In other embodiments, the individual may have pancreatic cancer (e.g., pancreatic ductal adenocarcinoma (PDAC)). In some embodiments, the individual has non-small cell lung cancer. The non-small cell lung cancer may be at early stage or at late stage. In some embodiments, the individual has small cell lung cancer. The small cell lung cancer may be at early stage or at late stage. In some embodiments, the individual has renal cell cancer. The renal cell cancer may be at early stage or at late stage. In some embodiments, the individual has colorectal cancer. The colorectal cancer may be at early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has pancreatic cancer. The pancreatic cancer may be at early stage or at late stage. In some embodiments, the individual has gastric carcinoma. The gastric carcinoma may be at early stage or at late stage. In some embodiments, the individual has bladder cancer. The bladder cancer may be at early stage or at late stage. In some embodiments, the individual has esophageal cancer. The esophageal cancer may be at early stage or at late stage. In some embodiments, the individual has mesothelioma. The mesothelioma may be at early stage or at late stage. In some embodiments, the individual has melanoma. The melanoma may be at early stage or at late stage. In some embodiments, the individual has head and neck cancer. The head and neck cancer may be at early stage or at late stage. In some embodiments, the individual has thyroid cancer. The thyroid cancer may be at early stage or at late stage. In some embodiments, the individual has sarcoma. The sarcoma may be at early stage or late stage. In some embodiments, the individual has prostate cancer. The prostate cancer may be at early stage or at late stage. In some embodiments, the individual has glioblastoma. The glioblastoma may be at early stage or at late stage. In some embodiments, the individual has cervical cancer. The cervical cancer may be at early stage or at late stage. In some embodiments, the individual has thymic carcinoma. The thymic carcinoma may be at early stage or at late stage. In some embodiments, the individual has leukemia. The leukemia may be at early stage or at late stage. In some embodiments, the individual has lymphomas. The lymphoma may be at early stage or at late stage. In some embodiments, the individual has a myeloma (e.g., MM). The myeloma (e.g., MM) may be at early stage or at late stage. In some embodiments, the individual has mycoses fungoides. The mycoses fungoides may be at early stage or at late stage. In some embodiments, the individual has merkel cell cancer. The merkel cell cancer may be at early stage or at late stage. In some embodiments, the individual has hematologic malignancies. The hematological malignancies may be early stage or late stage.

In another aspect, an anti-TIGIT antibody described herein (e.g., 4.1D3 or a variant thereof, e.g., 4.1D3.Q1E) for use in increasing, enhancing, or stimulating an immune response or function in a subject in need thereof is provided. In some embodiments, the immune response or function is increased, enhanced, and/or stimulated by activating effector cells (e.g., T cells, e.g., CD8+ and/or CD4+ T cells), expanding (increasing) an effector cell population, and/or killing target cells (e.g., target tumor cells) in the subject. In some embodiments, the CD4 and/or CD8 T cells in the individual have increased or enhanced priming, activation, proliferation, cytokine release and/or cytolytic activity relative to prior to the administration of the combination. In some embodiments, the number of CD4 and/or CD8 T cells is elevated relative to prior to administration of the combination. In some embodiments, the number of activated CD4 and/or CD8 T cells is elevated relative to prior to administration of the combination. In some embodiments, the activated CD4 and/or CD8 T cells is characterized by γ-IFN+ producing CD4 and/or CD8 T cells and/or enhanced cytolytic activity relative to prior to the administration of the combination. In some embodiments, the CD4 and/or CD8 T cells exhibit increased release of cytokines selected from the group consisting of IFN-γ, TNF-α and interleukins. In some embodiments of the methods of this invention, the CD4 and/or CD8 T cell is an effector memory T cell. In some embodiments, the CD4 and/or CD8 effector memory T cell is characterized by γ-IFN+ producing CD4 and/or CD8 T cells and/or enhanced cytolytic activity. In some embodiments, the CD4 and/or CD8 effector memory T cell is characterized by having the expression of $CD44^{high}$ $CD62L^{low}$. In some embodiments, the cancer has elevated levels of T cell infiltration.

In any of the above aspects, the anti-TIGIT antibody may be for use in combination with a different TIGIT antagonist, a PD-1 axis binding antagonist, a OX40 binding agonist, an agent that decreases or inhibits one or more additional immune co-inhibitory receptors, and/or an additional therapeutic agent, such as a chemotherapeutic agent, as described in detail herein.

In another aspect, the invention provides for the use of an anti-TIGIT antibody described herein (e.g., 4.1D3 or a variant thereof, e.g., 4.1D3.Q1E) in the manufacture or preparation of a medicament. In one embodiment, the medicament is for treating or delaying progression of a cancer. In a further embodiment, the medicament is for treating or delaying progression of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, mycoses fungoides, a merkel cell cancer, or a hematologic malignancy. Thus, a variety of cancers may be treated, or their progression may be delayed. In some embodiments, the individual may have breast cancer (e.g., triple-negative breast cancer). In other embodiments, the individual may have pancreatic cancer (e.g., pancreatic ductal adenocarcinoma (PDAC)). In some embodiments, the individual has non-small cell lung cancer. The non-small cell lung cancer may be at early stage or at late stage. In some embodiments, the individual has small cell lung cancer. The small cell lung cancer may be at early stage or at late stage. In some embodiments, the individual has renal cell cancer. The renal cell cancer may be at early stage or at late stage. In some embodiments, the individual has colorectal cancer. The colorectal cancer may be at early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has pancreatic cancer. The pancreatic cancer may be at early stage or at late stage. In some embodiments, the individual has gastric carcinoma. The gastric carcinoma may be at early stage or at late stage. In some embodiments, the individual has bladder cancer. The bladder cancer may be at early stage or at late stage. In some embodiments, the individual has esophageal cancer. The esophageal cancer may be at early stage or at late stage. In some embodiments, the individual has mesothelioma. The mesothelioma may be at early stage or at late stage. In some embodiments, the individual has melanoma. The melanoma may be at early stage or at late stage. In some embodiments, the individual has head and neck cancer. The head and neck cancer may be at early stage or at late stage. In some embodiments, the individual has thyroid cancer. The thyroid cancer may be at early stage or at late stage. In some embodiments, the individual has sarcoma. The sarcoma may be at early stage or late stage. In some embodiments, the individual has prostate cancer. The prostate cancer may be at early stage or at late stage. In some embodiments, the individual has glioblastoma. The glioblastoma may be at early stage or at late stage. In some embodiments, the individual has cervical cancer. The cervical cancer may be at early stage or at late stage. In some embodiments, the individual has thymic carcinoma. The thymic carcinoma may be at early stage or at late stage. In some embodiments, the individual has leukemia. The leukemia may be at early stage or at late stage. In some embodiments, the individual has lymphomas. The lymphoma may be at early stage or at late stage. In some embodiments, the individual has a myeloma (e.g., MM). The myeloma (e.g., MM) may be at early stage or at late stage. In some embodiments, the individual has mycoses fungoides. The mycoses fungoides may be at early stage or at late stage. In some embodiments, the individual has merkel cell cancer. The merkel cell cancer may be at early stage or at late stage. In some embodiments, the individual has hematologic malignancies. The hematological malignancies may be early stage or late stage.

In another aspect, the invention provides for the use of an anti-TIGIT antibody described herein (e.g., 4.1D3 or a variant thereof, e.g., 4.1D3.Q1E) in the manufacture of a medicament for treating or delaying progression of an immune-related disease. In some embodiments, the immune-related disease is associated with T cell dysfunctional disorder. In some embodiments, the immune-related disease is a viral infection. In certain embodiments, the viral infection is a chronic viral infection. In some embodiments. T cell dysfunctional disorder is characterized by decreased responsiveness to antigenic stimulation. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the T cell dysfunctional disorder includes unresolved acute infection, chronic infection and tumor immunity.

In another aspect, an anti-TIGIT antibody described herein (e.g., 4.1D3 or a variant thereof, e.g., 4.1D3.Q1E) in the manufacture of a medicament for use in increasing, enhancing, or stimulating an immune response or function in a subject in need thereof is provided. In some embodiments, the immune response or function is increased, enhanced, and/or stimulated by activating effector cells (e.g., T cells, e.g., CD8+ and/or CD4+ T cells), expanding (increasing) an effector cell population, and/or killing target cells (e.g., target tumor cells) in the subject. In some embodiments, the CD4 and/or CD8 T cells in the individual have increased or enhanced priming, activation, proliferation, cytokine release and/or cytolytic activity relative to prior to the administration of the combination. In some embodiments, the number of CD4 and/or CD8 T cells is elevated relative to prior to administration of the combination. In some embodiments, the number of activated CD4 and/or CD8 T cells is elevated relative to prior to administration of the combination. In some embodiments, the activated CD4 and/or CD8 T cells is characterized by γ-IFN+ producing CD4 and/or CD8 T cells and/or enhanced cytolytic activity relative to prior to the administration of the combination. In some embodiments, the CD4 and/or CD8 T cells exhibit increased release of cytokines selected from the group consisting of IFN-γ, TNF-α and interleukins. In some embodiments of the methods of this invention, the CD4 and/or CD8 T cell is an effector memory T cell. In some embodiments, the CD4 and/or CD8 effector memory T cell is characterized by γ-IFN+ producing CD4 and/or CD8 T cels and/or enhanced cytolytic activity. In some embodiments, the CD4 and/or CD8 effector memory T cell is characterized by having the expression of $CD44^{high}$ $CD62L^{low}$. In some embodiments, the cancer has elevated levels of T cell infiltration.

In any of the above aspects, the medicament may be formulated for use in combination with a different TIGIT antagonist, a PD-1 axis binding antagonist, an OX40 binding agonist, an agent that decreases or inhibits one or more additional immune co-inhibitory receptors, and/or an additional therapeutic agent, such as a chemotherapeutic agent, as described in detail herein.

In another aspect, the invention provides a method for treating or delaying progression of a cancer in a subject, the method comprising administering to the subject an effective amount of an anti-TIGIT antibody described herein (e.g., 4.1D3 or a variant thereof, e.g., 4.1D3.Q1E), thereby treating or delaying the progression of the cancer in the subject. In certain embodiments, the cancer is selected from the group consisting of a non-small cell lung cancer, a small cell lung cancer, a renal cell cancer, a colorectal cancer, an ovarian cancer, a breast cancer, a pancreatic cancer, a gastric carcinoma, a bladder cancer, an esophageal cancer, a mesothelioma, a melanoma, a head and neck cancer, a thyroid cancer, a sarcoma, a prostate cancer, a glioblastoma, a cervical cancer, a thymic carcinoma, a leukemia, a lymphoma, a myeloma, mycoses fungoides, a merkel cell cancer, and a hematologic malignancy. Thus, a variety of cancers may be treated, or their progression may be delayed. In some embodiments, the individual may have breast cancer (e.g., triple-negative breast cancer). In other embodiments, the individual may have pancreatic cancer (e.g., pancreatic ductal adenocarcinoma (PDAC)). In some embodiments, the individual has non-small cell lung cancer. The non-small cell lung cancer may be at early stage or at late stage. In some embodiments, the individual has small cell lung cancer. The small cell lung cancer may be at early stage or at late stage. In some embodiments, the individual has renal cell cancer. The renal cell cancer may be at early stage or at late stage. In some embodiments, the individual has colorectal cancer. The colorectal cancer may be at early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has pancreatic cancer. The pancreatic cancer may be at early stage or at late stage. In some embodiments, the individual has gastric carcinoma. The gastric carcinoma may be at early stage or at late stage. In some embodiments, the individual has bladder cancer. The bladder cancer may be at early stage or at late stage. In some embodiments, the individual has esophageal cancer. The esophageal cancer may be at early stage or at late stage. In some embodiments, the individual has mesothelioma. The mesothelioma may be at early stage or at late stage. In some embodiments, the individual has melanoma. The melanoma may be at early stage or at late stage. In some embodiments, the individual has head and neck cancer. The head and neck cancer may be at early stage or at late stage. In some embodiments, the individual has thyroid cancer. The thyroid cancer may be at early stage or at late stage. In some embodiments, the individual has sarcoma. The sarcoma may be at early stage or late stage. In some embodiments, the individual has prostate cancer. The prostate cancer may be at early stage or at late stage. In some embodiments, the individual has glioblastoma. The glioblastoma may be at early stage or at late stage. In some embodiments, the individual has cervical cancer. The cervical cancer may be at early stage or at late stage. In some embodiments, the individual has thymic carcinoma. The thymic carcinoma may be at early stage or at late stage. In some embodiments, the individual has leukemia. The leukemia may be at early stage or at late stage. In some embodiments, the individual has lymphomas. The lymphoma may be at early stage or at late stage. In some embodiments, the individual has a myeloma (e.g., MM). The myeloma (e.g., MM) may be at early stage or at late stage. In some embodiments, the individual has mycoses fungoides. The mycoses fungoides may be at early stage or at late stage. In some embodiments, the individual has merkel cell cancer. The merkel cell cancer may be at early stage or at late stage. In some embodiments, the individual has hematologic malignancies. The hematological malignancies may be early stage or late stage.

In another aspect, the invention provides a method for treating or delaying progression of an immune-related disease in a subject, the method comprising administering to the subject an effective amount of an anti-TIGIT antibody described herein (e.g., 4.1D3 or a variant thereof, e.g., 4.1D3.Q1E), thereby treating or delaying the progression of the immune-related disease in the subject. In some embodiments, the immune-related disease is associated with T cell dysfunctional disorder. In some embodiments, the immune-related disease is a viral infection. In certain embodiments, the viral infection is a chronic viral infection. In some embodiments, T cell dysfunctional disorder is characterized by decreased responsiveness to antigenic stimulation. In some embodiments, the T cell dysfunctional disorder is characterized by T cell anergy or decreased ability to secrete cytokines, proliferate or execute cytolytic activity. In some embodiments, the T cell dysfunctional disorder is characterized by T cell exhaustion. In some embodiments, the T cells are CD4+ and CD8+ T cells. In some embodiments, the T cell dysfunctional disorder includes unresolved acute infection, chronic infection and tumor immunity.

In another aspect, the invention provides a method of increasing, enhancing, or stimulating an immune response or function in a subject, the comprising administering to the subject an effective amount of an anti-TIGIT antibody described herein (e.g., 4.1D3 or a variant thereof, e.g., 4.1D3.Q1E), thereby increasing, enhancing, or stimulating an immune response or function in the subject. In some embodiments, the immune response or function is increased, enhanced, and/or stimulated by activating effector cells (e.g., T cells, e.g., CD8+ and/or CD4+ T cells), expanding (increasing) an effector cell population, and/or killing target cells (e.g., target tumor cells) in the subject. In some embodiments of the methods of this invention, the CD4 and/or CD8 T cells in the individual have increased or enhanced priming, activation, proliferation, cytokine release and/or cytolytic activity relative to prior to the administration of the combination. In some embodiments of the methods of this invention, the number of CD4 and/or CD8 T cells is elevated relative to prior to administration of the combination. In some embodiments of the methods of this invention, the number of activated CD4 and/or CD8 T cells is elevated relative to prior to administration of the combination. In some embodiments of the methods of this invention, the activated CD4 and/or CD8 T cells is characterized by γ-IFN$^+$ producing CD4 and/or CD8 T cells and/or enhanced cytolytic activity relative to prior to the administration of the combination. In some embodiments of the methods of this invention, the CD4 and/or CD8 T cells exhibit increased release of cytokines selected from the group consisting of IFN-γ, TNF-α and interleukins. In some embodiments of the methods of this invention, the CD4 and/or CD8 T cell is an effector memory T cell. In some embodiments of the methods of this invention, the CD4 and/or CD8 effector memory T cell is characterized by γ-IFN$^+$ producing CD4 and/or CD8 T cells and/or enhanced cytolytic activity. In some embodiments of the methods of this invention, the CD4 and/or CD8 effector memory T cell is characterized by having the expression of CD44$^{high}$ CD62L$^{low}$. In some embodiments of the methods of this invention, the cancer has elevated levels of T cell infiltration.

In any of the above aspects, the anti-TIGIT antibody may be for administration in combination with a different TIGIT antagonist, a PD-1 axis binding antagonist, an OX40 binding agonist, an agent that decreases or inhibits one or more additional immune co-inhibitory receptors, and/or an additional therapeutic agent, such as a chemotherapeutic agent, as described in detail herein.

In some embodiments, the different (second) TIGIT antagonist can be an antagonist of TIGIT expression and/or activity, such as a small molecule inhibitor, an inhibitory antibody or antigen-binding fragment thereof, an aptamer, an inhibitory nucleic acid, and an inhibitory polypeptide. In some embodiments, the TIGIT antagonist is a different anti-TIGIT antibody or antigen-binding fragment thereof (e.g., one that binds to a different epitope on TIGIT that is either non-overlapping or only partially overlapping with the epitope recognized by the anti-TIGIT antibody of the invention that is used). In some embodiments, the TIGIT antagonist is an inhibitory nucleic acid selected from an antisense polynucleotide, an interfering RNA, a catalytic RNA, and an RNA-DNA chimera.

In some embodiments, TIGIT antagonist can be an agent that modulates the CD226 expression and/or activity. For example, an agent that modulates the CD226 expression and/or activity that is capable of increasing and/or stimulating CD226 expression and/or activity; increasing and/or stimulating the interaction of CD226 with PVR, PVRL2, and/or PVRL3; and increasing and/or stimulating the intracellular signaling mediated by CD226 binding to PVR, PVRL2, and/or PVRL3. As used herein, an agent that is capable of increasing and/or stimulating CD226 expression and/or activity includes, without limitation, agents that increase and/or stimulate CD226 expression and/or activity. As used herein, an agent that is capable of increasing and/or stimulating the interaction of CD226 with PVR, PVRL2, and/or PVRL3 includes, without limitation, agents that increase and/or stimulate the interaction of CD226 with PVR, PVRL2, and/or PVRL3. As used herein, an agent that is capable of increasing and/or stimulating the intracellular signaling mediated by CD226 binding to PVR, PVRL2, and/or PVRL3 includes, without limitation, agents that increase and/or stimulate the intracellular signaling mediated by CD226 binding to PVR, PVRL2, and/or PVRL3.

In some embodiments, the agent that modulates the CD226 expression and/or activity is selected from an agent that inhibits and/or blocks the interaction of CD226 with TIGIT, an antagonist of PVR expression and/or activity, an agent that inhibits and/or blocks the interaction of TIGIT with PVR, an agent that inhibits and/or blocks the interaction of TIGIT with PVRL2, an agent that inhibits and/or blocks the interaction of TIGIT with PVRL3, an agent that inhibits and/or blocks the intracellular signaling mediated by TIGIT binding to PVR, an agent that inhibits and/or blocks the intracellular signaling mediated by TIGIT binding to PVRL2, an agent that inhibits and/or blocks the intracellular signaling mediated by TIGIT binding to PVRL3, and combinations thereof.

In some embodiments, the agent that inhibits and/or blocks the interaction of CD226 with TIGIT is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of CD226 with TIGIT is an anti-TIGIT antibody or antigen-binding fragment thereof (e.g., one that binds to a different epitope on TIGIT that is either non-overlapping or only partially overlapping with the epitope recognized by the anti-TIGIT antibody of the invention that is used). In some embodiments, the agent that inhibits and/or blocks the interaction of CD226 with TIGIT is an inhibitory nucleic acid selected from an antisense polynucleotide, an interfering RNA, a catalytic RNA, and an RNA-DNA chimera.

In some embodiments, the antagonist of PVR expression and/or activity is a small molecule inhibitor, an inhibitory antibody or antigen-binding fragment thereof, an aptamer, an inhibitory nucleic acid, and an inhibitory polypeptide. In some embodiments, the antagonist of PVR expression and/or activity is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the interaction of TIGIT with PVR is a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVR is selected from a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVRL2 is selected from a small molecule inhibitor, an inhibitory antibody or antigen-binding fragment thereof, an aptamer, an inhibitory nucleic acid, and an inhibitory polypeptide. In some embodiments, the agent that inhibits and/or blocks the interaction of TIGIT with PVRL3 is selected from a small molecule inhibitor, an inhibitory antibody or antigen-binding fragment thereof, an aptamer, an inhibitory nucleic acid, and an inhibitory polypeptide.

In some embodiments, the agent that inhibits and/or blocks the intracellular signaling mediated by TIGIT binding to PVR is a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVR is selected from a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVRL2 is selected from a small molecule inhibitor, an inhibitory antibody or antigen-binding fragment thereof, an aptamer, an inhibitory nucleic acid, and an inhibitory polypeptide. In some embodiments, the agent that inhibits and/or blocks the intracellular signaling mediated by TIGIT binding to PVRL3 is selected from a small molecule inhibitor, an inhibitory antibody or antigen-binding fragment thereof, an aptamer, an inhibitory nucleic acid, and an inhibitory polypeptide.

Other TIGIT antagonists that can be used in combination with the anti-TIGIT antibodies of the invention include the anti-TIGIT antibodies and compositions containing such antibodies described in WO 2009/126688, which is incorporated by reference herein in its entirety.

In some instances, the methods provided herein include administration of an effective amount of a PD-1 axis binding antagonist, prior to, subsequent to, or concurrently with an anti-TIGIT antibody of the invention (and, optionally, one or more additional agents, such as a second, different TIGIT antagonist, an OX40 binding agonist, a chemotherapeutic agent, etc.). The PD-1 axis bidning antagonist can be selected from the group consisting of a PD-1 binding antagonist, a PD-L1 binding antagonist, and a PD-L2 binding antagonist.

In some embodiments of the above aspect, the PD-1 axis binding antagonist is a PD-1 binding antagonist. In some embodiments, the PD-1 binding antagonist inhibits the binding of PD-1 to its ligand binding partners. In some embodiments, the PD-1 binding antagonist inhibits the binding of PD-1 to PD-L1. In some embodiments, the PD-1 binding antagonist inhibits the binding of PD-1 to PD-L2. In some embodiments, the PD-1 binding antagonist inhibits the binding of PD-1 to both PD-L1 and PD-L2. In some embodiments, the PD-1 binding antagonist is an antibody. In some embodiments, the PD-1 binding antagonist is selected from the group consisting of MDX 1106 (nivolumab). MK-3475 (pembrolizumab), CT-011 (pidilizumab), MEDI-0680 (AMP-514), PDR001, REGN2810, and BGB-108.

In other embodiments of the above aspect, the PD-1 axis binding antagonist is a PD-L1 binding antagonist. In some embodiments, the PD-L1 binding antagonist inhibits the binding of PD-L1 to PD-1. In some embodiments, the PD-L1 binding antagonist inhibits the binding of PD-L1 to B7-1. In some embodiments, the PD-L1 binding antagonist inhibits the binding of PD-L1 to both PD-1 and B7-1. In some embodiments, the PD-L1 binding antagonist is an antibody. In some embodiments, the antibody is selected from the group consisting of: MPDL3280A (atezolizumab), YW243.55.S70, MDX-1105, MEDI4736 (durvalumab), and MSB0010718C (avelumab).

In other embodiments of the above aspect, the PD-1 axis binding antagonist is a PD-L2 binding antagonist. In some embodiments, the PD-L2 binding antagonist is an antibody. In some embodiments, the PD-L2 binding antagonist is an immunoadhesin.

As a general proposition, the therapeutically effective amount of a PD-1 axis binding antagonist (e.g., an anti-PD-L1 antibody) may be administered to a human will be in the range of about 0.01 to about 50 mg/kg of patient body weight whether by one or more administrations. In some embodiments, for example, the antagonist (e.g., anti-PD-L1 antibody) is administered in a dose of about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In some embodiments, the antagonist (e.g., anti-PD-L1 antibody) is administered at 15 mg/kg. However, other dosage regimens may be useful. In one embodiment, a PD-1 axis binding antagonist (e.g., anti-PD-L1 antibody) is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, or about 1500 mg. In some embodiments, a PD-1 axis binding antagonist (e.g., anti-PD-L1 antibody) is administered at a dose of about 800 mg to about 850 mg every two weeks. In some embodiments, a PD-1 axis binding antagonist (e.g., anti-PD-L1 antibody) is administered at a dose of about 840 mg every two weeks. The dose may be administered as a single dose or as multiple doses (e.g., 2 or 3 doses), such as infusions. The dose of the antibody administered in a combination treatment may be reduced as compared to a single treatment. In some embodiments, for example, the method for treating or delaying progression of locally advanced or metastatic breast cancer in an individual comprises a dosing regimen comprising treatment cycles, wherein the individual is administered, on days 1 and 15 of each cycle, a human PD-1 axis binding antagonist (e.g., anti-PD-L1 antibody) at a dose of about 840 mg, wherein each cycle is 28 days (i.e., each cycle is repeated every 28 days). The progress of this therapy is easily monitored by conventional techniques.

In some embodiments, the OX40 binding agonist includes, for example, an OX40 agonist antibody (e.g., an anti-human OX40 agonist antibody), an OX40L agonist fragment, an OX40 oligomeric receptor, and an OX40 immunoadhesin.

In some embodiments, the OX40 agonist antibody depletes cells that express human OX40 (e.g., CD4+ effector T cells, CD8+ T cells, and/or Treg cells), for example, by ADCC and/or phagocytosis. In some embodiments, the OX40 agonist antibody binds human OX40 with an affinity of less than or equal to about 1 nM (e.g., less than or equal to about 0.5 nM, e.g., less than or equal to about 0.45 nM, e.g., less than or equal to about 0.4 nM, e.g., less than or equal to about 0.3 nM). In some embodiments, the binding affinity of the OX40 agonist antibody is determined using radioimmunoassay.

In some embodiments, the OX40 agonist antibody binds human OX40 and cynomolgus OX40. In further embodiments, binding to human OX40 and cynomolgus OX40 is determined using a FACS assay. In some embodiments, binding to human OX40 has an EC50 of less than or equal to about 1 µg/ml (e.g., less than or equal to about 0.7 µg/ml, e.g., less than or equal to about 0.5 µg/ml, e.g., less than or equal to about 0.4 µg/ml, e.g., less than or equal to about 0.3 µg/ml, e.g., less than or equal to about 0.2 µg/ml, e.g., less than or equal to about 0.1 µg/ml). In some embodiments, binding to cynomolgus OX40 has an EC50 of less than or equal to 3 µg/ml (e.g., less than or equal to about 2 µg/ml, e.g., less than or equal to about 1.7 µg/ml, e.g., less than or equal to about 1.5 µg/ml, e.g., less than or equal to about 1.4 µg/ml, e.g., less than or equal to about 1.3 µg/ml, e.g., less than or equal to about 1.2 µg/ml, e.g., less than or equal to about 1.1 µg/ml, e.g., less than or equal to about 1.0 µg/ml).

In some embodiments, the OX40 agonist antibody increases CD4+ effector T cell proliferation and/or increases cytokine production by the CD4+ effector T cell as compared to proliferation and/or cytokine production prior to treatment with the OX40 agonist antibody. In some embodiments, the cytokine is IFN-γ.

In some embodiments, the OX40 agonist antibody increases memory T cell proliferation and/or increasing cytokine production by the memory cell. In some embodiments, the cytokine is IFN-γ.

In some embodiments, the OX40 agonist antibody inhibits Treg suppression of effector T cell function. In some embodiments, effector T cell function is effector T cell proliferation and/or cytokine production. In some embodiments, the effector T cell is a CD4+ effector T cell.

In some embodiments, the OX40 agonist antibody increases OX40 signal transduction in a target cell that expresses OX40. In some embodiments, OX40 signal transduction is detected by monitoring NFkB downstream signaling.

In some embodiments, the OX40 agonist antibody is stable after treatment at 40° C. for one to four weeks, e.g., one week, two weeks, three weeks, or four weeks. In some embodiments, the OX40 agonist antibody is stable after treatment at 40° C. for two weeks.

In some embodiments, the OX40 agonist antibody comprises a variant IgG1 Fc polypeptide comprising a mutation that eliminates binding to human effector cells has diminished activity relative to the OX40 agonist antibody comprising a native sequence IgG1 Fc portion. In some embodiments, the OX40 agonist antibody comprises a variant Fc portion comprising a DANA mutation.

In some embodiments, antibody cross-linking is required for anti-human OX40 antagonist antibody function.

In some embodiments, the OX40 agonist antibody comprises (a) a VH domain comprising (i) a HVR-H1 comprising the amino acid sequence of SEQ ID NO: 278, 279, or 280. (ii) a HVR-H2 comprising the amino acid sequence of SEQ ID NO: 281, 282, 283, 284, 285, or 286, and (iii) a HVR-H3 comprising an amino acid sequence selected from SEQ ID NO: 287, 288, or 289; and (b) a VL domain comprising (i) a HVR-L1 comprising the amino acid sequence of SEQ ID NO: 290, (ii) a HVR-L2 comprising the amino acid sequence of SEQ ID NO: 291, and (iii) a HVR-L3 comprising the amino acid sequence of SEQ ID NO: 292, 293, 294, 295, 296, 297, 298, or 299. For example, in some embodiments, the OX40 agonist antibody comprises (a) HVR-H1 comprising the amino acid sequence of SEQ ID NO: 278; (b) HVR-H2 comprising the amino acid sequence of SEQ ID NO: 281; (c) HVR-H3 comprising the amino acid sequence of SEQ ID NO: 287; (d) HVR-L1 comprising the amino acid sequence of SEQ ID NO: 290; (e) HVR-L2 comprising the amino acid sequence of SEQ ID NO: 291; and (t) HVR-L3 comprising an amino acid sequence selected from SEQ ID NO: 292. In some embodiments, the OX40 agonist antibody comprises (a) HVR-H1 comprising the amino acid sequence of SEQ ID NO: 278; (b) HVR-H2 comprising the amino acid sequence of SEQ ID NO: 281; (c) HVR-H3 comprising the amino acid sequence of SEQ ID NO: 287; (d) HVR-L1 comprising the amino acid sequence of SEQ ID NO: 290; (e) HVR-L2 comprising the amino acid sequence of SEQ ID NO: 291; and (f) HVR-L3 comprising an amino acid sequence selected from SEQ ID NO: 297. In some embodiments, the OX40 agonist antibody comprises (a) HVR-H1 comprising the amino acid sequence of SEQ ID NO: 278; (b) HVR-H2 comprising the amino acid sequence of SEQ ID NO: 281; (c) HVR-H3 comprising the amino acid sequence of SEQ ID NO: 287; (d) HVR-L1 comprising the amino acid sequence of SEQ ID NO: 290; (e) HVR-L2 comprising the amino acid sequence of SEQ ID NO: 291; and (t) HVR-L3 comprising an amino acid sequence selected from SEQ ID NO: 298.

In other embodiments, the OX40 agonist antibody comprises a VH sequence having at least 90% sequence identity to the amino acid sequence of any one of SEQ ID NOs: 300-325. For example, the OX40 agonist antibody comprises a VH sequence having at least 90% sequence identity to the amino acid sequence of SEQ ID NO: 300 (e.g., wherein a total of 1 to 10 amino acids have been substituted, inserted, and/or deleted in SEQ ID NO: 300). Thus, in some embodiments, the OX40 agonist antibody comprises a VH comprising one, two, or three HVRs selected from: (a) HVR-H1 comprising the amino acid sequence of SEQ ID NO: 278, (b) HVR-H2 comprising the amino acid sequence of SEQ ID NO: 281, and (c) HVR-H3 comprising the amino acid sequence of SEQ ID NO: 287.

In other embodiments, the OX40 agonist antibody comprises a VL sequence having at least 90% sequence identity to the amino acid sequence of any one of SEQ ID NOs: 326-351. For example, the OX40 agonist antibody comprises a VL having at least 90% sequence identity to the amino acid sequence of SEQ ID NO: 326 (e.g., wherein a total of 1 to 10 amino acids have been substituted, inserted, and/or deleted in SEQ ID NO: 326). Thus, in some embodiments, the OX40 agonist antibody comprises a VL comprising one, two, or three HVRs selected from (a) HVR-L1 comprising the amino acid sequence of SEQ ID NO: 290; (b)

HVR-L2 comprising the amino acid sequence of SEQ ID NO: 291; and (c) HVR-L3 comprising the amino acid sequence of SEQ ID NO: 292.

In some embodiments, the OX40 agonist antibody comprises (a) a VH sequence of SEQ ID NO: 300; (b) a VL sequence of SEQ ID NO: 326; or (c) a VH sequence as in (a) and a VL sequence as in (b).

In some embodiments, the OX40 agonist antibody comprises (a) a VH sequence of SEQ ID NO: 319; (b) a VL sequence of SEQ ID NO: 345; or (c) a VH sequence as in (a) and a VL sequence as in (b).

In some embodiments, the OX40 agonist antibody comprises (a) a VH sequence of SEQ ID NO: 320; (b) a VL sequence of SEQ ID NO: 346; or (c) a VH sequence as in (a) and a VL sequence as in (b).

Also specifically contemplated are OX40 agonist antibodies, such as an antibody sharing the same or substantially the same HVR sequences and/or VH and VL sequences of the anti-OX40 antibodies disclosed in U.S. Pat. No. 7,550,140 and International Pub. Nos. WO 2014/148895 and WO 2013/038191, which are incorporated herein by reference in their entirety.

In some embodiments, the OX40 agonist antibody is L106 BD (Pharmingen Product #340420). In some embodiments, the antibody comprises at least one, two, three, four, five, or six hypervariable region (HVR) sequences of antibody L106 (BD Pharmingen Product #340420). In some embodiments, the antibody comprises a heavy chain variable region sequence and/or a light chain variable region sequence of antibody L106 (BD Pharmingen Product #340420).

In some embodiments the OX40 agonist antibody is ACT35 (Santa Cruz Biotechnology, Catalog #20073). In some embodiments, the antibody comprises at least one, two, three, four, five, or six hypervariable region (HVR) sequences of antibody ACT35 (Santa Cruz Biotechnology, Catalog #20073). In some embodiments, the antibody comprises a heavy chain variable region sequence and/or a light chain variable region sequence of antibody ACT35 (Santa Cruz Biotechnology, Catalog #20073).

In some embodiments, the OX40 agonist antibody is MEDI6469. In some embodiments, the antibody comprises at least one, two, three, four, five, or six hypervariable region (HVR) sequences of antibody MEDI6469. In some embodiments, the antibody comprises a heavy chain variable region sequence and/or a light chain variable region sequence of antibody MEDI6469.

In some embodiments, the OX40 agonist antibody is MEDI0562. In some embodiments, the antibody comprises at least one, two, three, four, five, or six hypervariable region (HVR) sequences of antibody MEDI0562. In some embodiments, the antibody comprises a heavy chain variable region sequence and/or a light chain variable region sequence of antibody MEDI0562.

In some embodiments, the OX40 agonist antibody is an agonist antibody that binds to the same epitope as any one of the OX40 agonist antibodies set forth above.

In any of the above embodiments, the OX40 agonist antibody can be a full-length antibody (e.g., IgG1 antibody) or an antibody fragment.

OX40 agonists useful for the methods described herein are in no way intended to be limited to antibodies. Non-antibody OX40 agonists are contemplated and well known in the art.

As described above. OX40L (also known as CD134L) serves as a ligand for OX40. As such, agonists that present part or all of OX40L may serve as OX40 agonists. In some embodiments, an OX40 agonist may include one or more extracellular domains of OX40L. Examples of extracellular domains of OX40L may include OX40-binding domains. In some embodiments, an OX40 agonist may be a soluble form of OX40L that includes one or more extracellular domains of OX40L but lacks other, insoluble domains of the protein, e.g., transmembrane domains. In some embodiments, an OX40 agonist is a soluble protein that includes one or more extracellular domains of OX40L able to bind OX40L. In some embodiments, an OX40 agonist may be linked to another protein domain, e.g., to increase its effectiveness, half-life, or other desired characteristics. In some embodiments, an OX40 agonist may include one or more extracellular domains of OX40L linked to an immunoglobulin Fc domain.

In some embodiments, an OX40 agonist may be an oligomeric or multimeric molecule. For example, an OX40 agonist may contain one or more domains (e.g., a leucine zipper domain) that allows proteins to oligomerize. In some embodiments, an OX40 agonist may include one or more extracellular domains of OX40L linked to one or more leucine zipper domains.

In some embodiments, an OX40 agonist may be any one of the OX40 agonists described in European Patent No. EP0672141 B1.

In some embodiments, an OX40 agonist may be a trimeric OX40L fusion protein. For example, an OX40 agonist may include one or more extracellular domains of OX40L linked to an immunoglobulin Fc domain and a trimerization domain (including without limitation an isoleucine zipper domain).

In some embodiments, an OX40 agonist may be any one of the OX40 agonists described in International Publication No. WO2006/121810, such as an OX40 immunoadhesin. In some embodiments, the OX40 immunoadhesin may be a trimeric OX40-Fc protein. In some embodiments, the OX40 agonist is MEDI6383.

Such combination therapies noted above encompass combined administration, whereby the anti-TIGIT antibody and the one or more agents (e.g., PD-1 axis binding antagonist, OX40 binding agonist, agent that decreases or inhibits one or more additional immune co-inhibitory receptors, and/or additional therapeutic agent) are included in the same or separate formulations, and separate administration, whereby administration of the anti-TIGIT antibody of the invention can occur prior to, simultaneously, and/or following, administration of the one or more agents (e.g., PD-1 axis binding antagonist, OX40 binding agonist, agent that decreases or inhibits one or more additional immune co-inhibitory receptors, and/or additional therapeutic agent). In one embodiment, administration of the anti-TIGIT antibody and administration of one or more of the agents occur within about one month, or within about one, two or three weeks, or within about one, two, three, four, five, or six days, of each other. Anti-TIGIT antibodies of the invention (e.g., 4.1D3 or a variant thereof, e.g., 4.1D3.Q1E) can also be used in combination with radiation therapy.

An anti-TIGIT antibody of the invention (and/or any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. In some embodiments, the antibody is administered by subcutaneous administration. In some embodiments, an anti-TIGIT antibody administered by subcutaneous injection exhibits a less toxic response in a patient than the same anti-TIGIT antibody administered by intravenous injection. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein.

Anti-TIGIT antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an anti-TIGIT antibody of the invention (e.g., 4.1D3 or a variant thereof, e.g., 4.1D3.Q1E), when used alone or in combination with one or more other additional agents (e.g., PD-1 axis binding antagonist, OX40 binding agonist, agent that decreases or inhibits one or more additional immune co-inhibitory receptors, and/or additional therapeutic agent), will depend on the type of disease to be treated, the type of antibody used, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

As a general proposition, the therapeutically effective amount of the anti-TIGIT antibody administered to human will be in the range of about 0.01 to about 100 mg/kg of patient body weight whether by one or more administrations. In some embodiments, the antibody used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, an anti-TIGIT antibody described herein is administered to a human at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg, or 10 mg/kg (or any combination thereof) may be administered to the patient. Such doses may be administered intermittently, for example, every week or every three weeks (e.g., such that the patient receives from about two to about twenty, or, for example, about six doses of the anti-TIGIT antibody). An initial higher loading dose, followed by one or more lower doses may be administered. The progress of this therapy is easily monitored by conventional techniques and assays.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

IX. Articles of Manufacture

In another aspect of the invention, an article of manufacture or a kit containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an anti-TIGIT antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In one embodiment, provided is a kit including an anti-TIGIT antibody of the invention (e.g., 4.1D3 or a variant thereof, e.g., 4.1D3.Q1E) and a package insert comprising instructions for using the anti-TIGIT antibody for treating or delaying progression of cancer in a subject or for treating or delaying progression of an immune-related disease in a subject. In a related embodiment, the invention features a kit including an anti-TIGIT antibody of the invention (e.g., 4.1D3 or a variant thereof, e.g., 4.1D3.Q1E), a PD-1 axis binding antagonist (e.g., a PD-1 binding antagonist, a PD-L1 binding antagonist, and a PD-L2 binding antagonist), and a package insert comprising instructions for using the anti-TIGIT antibody for treating or delaying progression of cancer in a subject or for treating or delaying progression of an immune-related disease in a subject. In a related embodiment, the invention features a kit including an anti-TIGIT antibody of the invention (e.g., 4.1D3 or a variant thereof, e.g., 4.1D3.Q1E), an OX40 binding agonist (e.g., an OX40 agonist antibody, an OX40L agonist fragment, an OX40 oligomeric receptor, and an OX40 immunoadhesin), and a package insert comprising instructions for using the anti-TIGIT antibody for treating or delaying progression of cancer in a subject or for treating or delaying progression of an immune-related disease in a subject. In a related embodiment, the invention features a kit including an anti-TIGIT antibody of the invention (e.g., 4.1D3 or a variant thereof, e.g., 4.1D3.Q1E), a PD-1 axis binding antagonist (e.g., a PD-1 binding antagonist, a PD-L1 binding antagonist, and a PD-L2 binding antagonist), an OX40 binding agonist (e.g., an OX40 agonist antibody, an OX40L agonist fragment, an OX40 oligomeric receptor, and an OX40 immunoadhesin), and a package insert comprising instructions for using the anti-TIGIT antibody for treating or delaying progression of cancer in a subject or for treating or delaying progression of an immune-related disease in a subject. In any of the above embodiments, the subject may, for example, be a human. It is specifically contemplated that any of the anti-TIGIT antibodies, OX40 binding agonists, and PD-1 axis binding antagonists described herein may be included in the kit.

In yet another embodiment, provided is a kit including an anti-TIGIT antibody of the invention (e.g., 4.1D3 or a variant thereof, e.g., 4.1D3.Q1E) and a package insert comprising instructions for increasing, enhancing, or stimulating an immune response or function in a subject. In a related embodiment, the invention features a kit including an anti-TIGIT antibody of the invention (e.g., 4.1D3 or a variant thereof, e.g., 4.1D3.Q1E), a PD-1 axis binding antagonist (e.g., a PD-1 binding antagonist, a PD-L1 binding antagonist, and a PD-L2 binding antagonist), and a package insert comprising instructions for increasing, enhancing, or stimulating an immune response or function in a subject. In a related embodiment, the invention features a kit including an anti-TIGIT antibody of the invention (e.g., 4.1D3 or a variant thereof, e.g., 4.1D3.Q1E), an OX40 binding agonist (e.g., an OX40 agonist antibody, an OX40L agonist fragment, an OX40 oligomeric receptor, and an OX40 immunoadhesin), and a package insert comprising instructions for using the anti-TIGIT antibody for increasing, enhancing, or stimulating an immune response or function in a subject. In a related embodiment, the invention features a kit including an anti-TIGIT antibody of the invention (e.g., 4.1D3 or a variant thereof, e.g., 4.1D3.Q1E), a PD-1 axis binding antagonist (e.g., a PD-1 binding antagonist, a PD-L1 binding antagonist, and a PD-L2 binding antagonist), an OX40 binding agonist (e.g., an OX40 agonist antibody, an OX40L agonist fragment, an OX40 oligomeric receptor, and an OX40 immunoadhesin), and a package insert comprising instructions for using the anti-TIGIT antibody for increasing, enhancing, or stimulating an immune response or function in a subject. In any of the above embodiments, the subject may, for example, be a human. It is specifically contemplated that any of the anti-TIGIT antibodies, OX40 binding agonists, and PD-1 axis binding antagonists described herein may be included in the kit.

EXAMPLES

The invention can be further understood by reference to the following examples, which are provided by way of illustration and are not meant to be limiting.

Example 1. Generation of Anti-TIGIT Antibodies

Either Sprague Dawley rats or OMT transgenic rats (Open Monoclonal Technology, Palo Alto, Calif.) were co-immunized with an initial dose subcutaneously of 50 µg human TIGIT protein (Genentech, Inc.) and 50 µg cynomolgus monkey (cyno) TIGIT protein (Genentech, Inc.) mixed with Complete Freund's Adjuvant (BD, Franklin Lakes, N.J.), followed by 25 µg human TIGIT protein and 25 µg cyno TIGIT protein diluted in PBS in multiple sites subcutaneously and intraperitoneally every two weeks.

Multiple lymph nodes were harvested three days after the last immunization. B cells from these rats were enriched using negative selection with biotinlyated antibodies targeting rat non-B cells (BD; eBioscience, San Diego, Calif.) and streptavidin-coated magnetic beads (Miltenyi, San Diego, Calif.). The resulting B cell population was fused with P3X63-Ag8U.1 mouse myeloma cells (American Type Culture Collection, Rockville, Md.) via electrofusion (Harvard Apparatus, Holliston, Mass.). Fused cells were incubated at 37° C., 7% $CO_2$, overnight in Medium C (StemCell Technologies, Vancouver, BC, Canada), before resuspension in semi-solid Medium D (StemCell Technologies) with anti-rat IgG-FITC (Sigma-Aldrich, St. Louis, Mo.) and plating into Omniwell trays (Thermo Fisher Scientific, Rochester, N.Y.). Seven days after plating, fluorescent colonies were selected and transferred into 96-well culture plates (BD) containing Medium E (StemCell Technologies) using a Clonepix FL (Molecular Devices, Sunnyvale, Calif.). Supernatants were screened by ELISA against human TIGIT protein seven days after colony picking, 384-well plates (Greiner Microlon, Greiner Bio-One, Monroe, N.C.) were coated with 1 µg/ml of protein diluted in 0.05 M sodium carbonate buffer, pH 9.6, and incubated overnight at 4° C. Then wells were blocked with 100 µl of PBS containing 0.5% BSA and 0.5% Tween-20 for one hour at room temperature. After washing, supernatants and/or sera were added at 50 µl and shaken for 30 minutes at room temperature. For detection of specific antibodies, horseradish peroxidase-conjugated anti-rat IgG antibodies (Bethyl Laboratories, Montgomery, Tex.) were diluted to an optimized concentration in PBS containing 0.5% BSA and 0.5% Tween-20 and added at 50 µl per well after washing, and plates were shaken for 30 minutes at room temperature. Plates were washed three times with 100 µl PBS containing 0.05% Tween-20. 50 µl TMB Substrate (BioFX, Owings Mills, Md.) was added and plates were incubated for five minutes at room temperature, followed by the addition of 50 µl stop solution (BioFX), then read at 630 nm. Human TIGIT-binding hybridoma cell lines were expanded and cultured for two to four days, then screened by ELISA against human TIGIT, cyno TIGIT, and mouse TIGIT proteins (Genentech, Inc.). Supernatant from human and cyno cross-reactive cell lines was harvested and purified by protein G (Protein G Sepharose 4 Fast Flow, GE Healthcare, Pittsburgh, Pa.). Approximately 500 clones were screened. From the screening, clones 4.1D3, 7.4A3, and 4.1A4 were identified from the immunization of OMT rats, and clones 1.6B2, 1.10A5, 1.7E7, and 1.15C8 were identified from the immunization of Sprague Dawley rats.

Example 2. Optimization of Anti-TIGIT Antibodies

A. OMT Rat-Derived Anti-TIGIT Human Monoclonal Antibody Polishing

To prevent unwanted pyroglutamate formation for clones 4.1A4, 4.1D3, and 7.4A3 (also referred to as 1A4, 1D3, and 4A3, respectively) and to resolve the issue of unpaired cysteine residues for clones 4.1A4 and 7.4A3, the following optimized anti-TIGIT antibody variants were generated: 4.1A4.C96S.Q1E, 4.1A4.C96Y.Q1E, 4.1D3.Q1E, 7.4A3.C96S.Q1E, and 7.4A3.C96Y.Q1E (also referred to as 1A4.C96S.Q1E, 1A4.C96Y.Q1E, 1D3.Q1E, 4A3.C96S.Q1E, and 4A3.C96Y.Q1E, respectively). As described below in Table 2, the affinities of these five optimized variants for human and cynomolgus monkey (cyno) TIGIT were then determined by Surface Plasmon Resonance (SRP) (BIACORE™ analysis) and compared to that of their respective parental clones.

Briefly, a series S CM5 biosensor chip was activated with N-ethyl-N'-(3-dimethylaminopropyl)-carbodiimide hydrochloride (EDC) and N-hydroxysuccinimide (NHS) reagents according to the supplier's (GE Healthcare Biosciences, Piscataway, N.J.) instructions, and a human antibody capture kit was applied to couple goat anti-human Fc IgGs in order to achieve approximately 10,000 response units (RU) on each flow cell, followed by blocking un-reacted groups with 1M ethanolamine.

For kinetics measurements, each clone was captured to achieve approximately 250 RU and 5-fold serial dilutions of TIGIT antigen (1.23 nM to 300 nM) were injected in HBS-P buffer (0.01M HEPES pH 7.4, 0.15M NaCl, 0.005% surfactant P20) at 25° C. (flow rate: 30 μl/min) with no regeneration between injections. The sensorgrams were recorded and evaluated by BIAcore™ T200 Evaluation Software (version 2.0) after subtraction of reference cell signal. Association rates ($k_{on}$) and dissociation rates ($k_{off}$) were calculated using a simple one-to-one Langmuir binding model. The equilibrium dissociation constant ($K_D$) was calculated as the ratio $k_{off}/k_{on}$.

TABLE 3

4.1D3.Q1E is capable of cross-reacting with human, cyno, and rabbit TIGIT

| | | BIAcore Kinetics Analysis | | |
|---|---|---|---|---|
| | | Human TIGIT | Cyno TIGIT | Rabbit TIGIT |
| Source | Clone | Monovalent Affinity (nM) | | |
| oMT | 4.1D3.Q1E | 0.56 | 3.2 | 4.9 |
| | 7.4A3.Q1E.C96S | 2.97 | 2.01 | >500 |
| Mouse | h1A5.L2H8 | 5.76 | >500 | >500 |

B. Humanization of SD Rat-Derived Anti-TIGIT Monoclonal Antibodies

Monoclonal antibodies 1.6B2, 1.10A5, 1.7E7, and 1.15C8 (as referred to herein as 6B2, 10A5, 7E7, and 15C8, respectively) were humanized as described below. Residue numbers are according to Kabat et al. (*Sequences of Proteins of Immunological Interest*. 5th Ed., Public Health Service, National Institutes of Health, Bethesda, Md. (1991)).

For 6B2 antibody humanization, hypervariable regions from the rat 6B2 (rat6B2) antibody were engineered into its closest human acceptor frameworks to generate humanized 6B2 (h6B2.L1H1). Specifically, from the rat6B2 VL domain, positions 24-34 (L1), 50-56 (L2), and 89-97 (L3) were grafted into human germline IGKV1-33*01. From the rat6B2 VH domain, positions 26-35 (H1), 50-65 (H2), and 95-102 (H3) were grafted into human germline IGHV2-5*08. In addition, position 43 in framework II of VL and positions 69, 73, 78 in framework III of VH were retained from the rat sequence in h6B2.L1H1. Those residues were found to be part of the framework residues acting as "Vernier" zone, which may adjust CDR/HVR structure and fine-tune the antigen fit. See, e.g., Foote and Winter, *J. Mol. Biol.* 224: 487-499 (1992). These CDR/HVR definitions include positions defined by their sequence hypervariability (Wu, T. T. & Kabat, E. A. (1970)), their structural location (Chothia, C. & Lesk. A. M. (1987)) and their involvement in antigen-antibody contacts (MacCallum et al. *J. Mol. Biol.* 262: 732-745 (1996)).

TABLE 2

BIACORE™ affinity measurements for OMT rat-derived 1A4, 1D3, and 4A3 antibody variants against human and cyno TIGIT

| | Human TIGIT | | | Cyno TIGIT | | |
|---|---|---|---|---|---|---|
| xTIGIT mAbs | Kon ($10^5$ M$^{-1}$ s$^{-1}$) | Koff ($10^{-4}$ s$^{-1}$) | KD (nM) | Kon ($10^5$ M$^{-1}$ s$^{-1}$) | Koff ($10^{-4}$ s$^{-1}$) | KD (nM) |
| 1A4 | 3.42 | 12.2 | 3.57 | 2.66 | 6.43 | 2.42 |
| 1A4.C96S.Q1E | 12.5 | 367.9 | 29.4 | 13.4 | 169.1 | 12.6 |
| 1A4.C96Y.Q1E | — | — | >100 | — | — | >100 |
| 1D3 | 38.4 | 16.4 | 0.43 | 6.21 | 20.7 | 3.33 |
| 1D3.Q1E | 17.2 | 9.7 | 0.56 | 4.78 | 15.4 | 3.22 |
| 4A3 | 3.02 | 10.4 | 3.44 | 3.34 | 6.99 | 2.09 |
| 4A3.C96S.Q1E | 2.88 | 8.56 | 2.97 | 2.76 | 5.56 | 2.01 |
| 4A3.C96Y.Q1E | 3.72 | 364.7 | 98.0 | 3.95 | 140.5 | 35.6 |

The clones 4.1A4.C96S.Q1E, 7.4A3.C96S.Q1E, and 4.1D3.Q1E were considered as final molecules with similar and acceptable binding affinity to both human and cyno TIGIT by comparison with the parental clones. Additional BIACORE™ analyses revealed that the 4.1D3.Q1E clone, in particular, was able to cross-react and bind to rabbit TIGIT with low nanomolar affinity (Table 3).

Additional humanized 6B2 variants were generated by engineering each rat residue of h6B2.L1H1 at Vernier zone back to human germline residue and these variants are h6B2.L2H1 (VL: S43A), h6B2.L1H2 (VH: V69I), h6B2.L1H3 (VH: A73T), h6B2.L1H4 (VH: A78V), h6B2.L1H5 (VH: V69I, A73T, A78V), and h6B2.L2H5 (VL: S43A, VH: V69I, A73T, A78V; a fully humanized version).

For 10A5 antibody humanization, hypervariable regions from the rat 10A5 (rat10A5) antibody were engineered into its closest human acceptor frameworks to generate humanized 10A5 (h10A5.L1H1). Specifically, from the rat10A5 VL domain, positions 24-34 (L1), 50-56 (L2), and 89-97 (L3) were grafted into human germline IGKV3-15*01. From the rat10A5 VH domain, positions 26-35 (H1), 50-65 (H2) and 95-102 (H3) were grafted into human germline IGHV2-5*08. In addition, position 43 in framework II and position 58 in framework III of VL and positions 69 and 78 in framework III of VH were retained from the rat sequence in h10A5.L1H1. Those residues were found to be part of the framework residues acting as "Vernier" zone as described above.

Additional humanized 10A5 variants were generated by engineering each rat residue of h10A5.L1H1 at Vernier zone back to human germline residue and these variants are h10A5.L2H1 (VL: S43A), h10A5.L3H1 (VL: V58I), h10A5.L4H1 (VL: S43A, V58I), h10A5.L1H2 (VH: V69I), h10A5.L1H3 (VH: A78V), h10A5.L1H4 (VH: V69I, A78V), and h10A5.L4H4 (VL: S43A, V58I, VH: V69I, A78V; a fully humanized version)

For 7E7 antibody humanization, hypervariable regions from the rat 7E7 (rat7E7) antibody were engineered into its closest human acceptor frameworks to generate humanized 7E7 (h7E7.L1H1). Specifically, from the rat7E7 VL domain, positions 24-34 (L1), 50-56 (L2), and 89-97 (L3) were grafted into human germline IGKV1-9*01. From the rat7E7 VH domain, positions 26-35 (H1), 50-65 (H2), and 95-102 (H3) were grafted into human germline IGHV1-3*01. In addition, positions 58, 71, and 87 in framework III of VL, positions 47, 48 in framework II of VH and positions 67, 69, 71, 91, and 93 in framework III of VH were retained from the rat sequence in h7E7.L1H1. Those residues were found to be part of the framework residues acting as "Vernier" zone as described above.

Additional humanized 7E7 variants were generated by engineering each rat residue of h7E7.L1H1 at Vernier zone back to human germline residue and these variants are h7E7.L2H1 (VL: I58V), h7E7.L3H1 (VL: Y71F), h7E7.L4H1 (VL: F87Y), h7E7.L5H1 (VL: I58V, Y71F, F87Y), h7E7.L1H2 (VH: I47W), h7E7.L1H3 (VH: I48M), h7E7.L1H4 (VH: A67V), h7E7.L1H5 (VH: L69I), h7E7.L1H6 (VH: A71R), h7E7.L1H7 (VH: F91Y), h7E7.L1H8 (VH: T93A), h7E7.L1H9 (VH: I47W, I48M, A67V, L69I, A71R, F91Y, T93A), and h7E7.L5H9 (VL: I58V, Y71F, F87Y, VH: I47W, I48M, A67V, L69I, A71R, F91Y, T93A; a fully humanized version).

For 15C8 antibody humanization, hypervariable regions from the rat 15C8 (rat15C8) antibody were engineered into its closest human acceptor frameworks to generate humanized 15C8 (h15C8.L1H1). Specifically, from the rat15C8 VL domain, positions 24-34 (L1), 50-56 (L2), and 89-97 (L3) were grafted into human germline IGKV1-9*01. From the rat15C8 VH domain, positions 26-35 (H1), 50-65 (H2), and 95-102 (H3) were grafted into human germline IGHV1-3*01. In addition, positions 58, 71, and 87 in framework III of VL, positions 37, 47, and 48 in framework II of VH, and positions 67, 69, 71 and 91 in framework III of VH were retained from the rat sequence in h15C8.L1H1. Those residues were found to be part of the framework residues acting as "Vernier" zone as described above.

Additional humanized 15C8 variants were generated by engineering each rat residue of h15C8.L1H1 at Vernier zone back to human germline residue and these variants are h15C8.L2H1 (VL: I58V), h15C8.L3H1 (VL: Y71F), h15C8.L4H1 (VL: F87Y), h15C8.L5H1 (VL: I58V, Y71F, F87Y), h15C8.L1H2 (VH: L37V), h15C8.L1H3 (VH: I47W), h15C8.L1H4 (VH: I48M), h15C8.L1H5 (VH: A67V), h15C8.L1H6 (VH: L69I), h15C8.L1H7 (VH: T71R), h15C8.L1H8 (VH: F91Y), h15C8.L1H9 (VH: L37V, I47W, I48M, A67V, L69I, T71R, F91Y), and h7E7.L5H9 (VL: I58V, Y71F, F87Y, VH: L37V, I47W, I48M, A67V, L69I, T71R, F91Y; a fully humanized version).

The first humanized versions, h6B2, L1H1, h10A5.L1H1, h7E7, L1H1, and h15C8.L1H1, which contain both rat CDRs and framework residues at Vernier positions, and the fully humanized versions, h6B2.L2H5, h10A5.L4H4, h7E7.L5H9, and h15C8.L5H9, which contain only rat CDRs were subject to BIAcore affinity measurement by comparison with original rat antibodies, rat6B2, rat10A5, rat7E7 and rat 15C8. For binding affinity determinations of TIGIT antibodies against human TIGIT, cynomolgus monkey TIGIT and human alanine-scanned TIGIT mutants by single-cycle kinetics, Surface Plasmon Resonance (SRP) measurement with a BIACORE™-T200 instrument was used, as described above. The BIACORE™ results in Table 4, below, indicate that all the humanized variants exhibit a drop in binding affinity (i.e., an increase in $K_D$) of about 5- to 10-fold against both human and cyno TIGIT. The fully humanized versions of h6B2.L2H5 and h10A5.L4H4 surprisingly show similar binding affinity as the first humanized versions of h6B2.L1H1 and h10A5.L1H1, suggesting that rat6B2 and rat10A5 framework residues at Vernier positions do not contribute to human and cyno TIGIT binding. Therefore, both h6B2.L2H5 and h10A5.L4H4 represent the final humanized version for rat6B2 and rat10A5, respectively. By contrast, the fully humanized versions of h7E7.L5H9 and h15C8.L5H9 lost the ability to bind human and cyno TIGIT.

To further elucidate which rat framework residues at Vernier positions for the first humanized antibodies h7E7, L1H1, and h15C8.L1H1 are crucial for binding, all the framework polishing variants were subject to BIAcore affinity measurement. For 7E7 framework polishing, variants of h7E7.L1H2, h7E7.L1H9, and h7E7.L5H9 containing VH: I47W substitution show human and cyno TIGIT binding affinity drop more than 100-fold, and variants of h7E7.L3H1 and h7E7.L5H1, containing VL: Y71F substitution, show cyno TIGIT binding affinity drop about 2-3 fold. Therefore, both VH: I47 and VL: Y71 rat framework residues were kept in the final 7E7 humanized version, called h7E7.L5aH9a, to retain human and cyno TIGIT binding. For 15C8 framework polishing, variants of h15C8.L1H3, h15C8.L1H9, and h15C8.L5H9, containing VH: I47W, substitution show human and cyno TIGIT binding affinity drop more than 100-fold, and variants of h15C8.L3H1 and h15C8.L5H1 containing VL: Y71F substitution show human and cyno TIGIT binding affinity drop about 2-3 fold. Other variants, h15C8.L1H2, h15C8.L1H5, and h15C8.L1H7, contain VH: L37V, A67V. and T71R substitution, respectively, also show human TIGIT binding affinity drop about 2-3 fold. Therefore, all five VH: I47, L37, A67, T71 and VL: Y71 rat framework residues were kept in the final 15C8 humanized version, called h15C8.L5aH9a, to retain human and cyno TIGIT binding.

TABLE 4

BiACORE ™ affinity measurements summary for humanized SD rat-derived 6B2, 10A5, 7E7, and 15C8 antibody variants against human and cyno TIGIT

| | Human TIGIT | | | Cyno TIGIT | | |
|---|---|---|---|---|---|---|
| xTIGIT mAbs | Kon ($10^5$ $M^{-1}$ $s^{-1}$) | Koff ($10^{-4}$ $s^{-1}$) | KD (nM) | Kon ($10^5$ $M^{-1}$ $s^{-1}$) | Koff ($10^{-4}$ $s^{-1}$) | KD (nM) |
| rat6B2 | 9.97 | 0.35 | 0.04 | 6.88 | 2.02 | 0.29 |
| h6B2.L1H1 | 46.7 | 25.3 | 0.54 | 12.3 | 11.8 | 0.96 |
| h6B2.L2H5 | 48.5 | 22.2 | 0.48 | 12.8 | 12.4 | 0.97 |
| rat10A5 | 9.05 | 0.84 | 0.09 | 6.78 | 2.81 | 0.41 |
| h10A5.L1H1 | 45.7 | 23.8 | 0.52 | 14.7 | 12.7 | 0.86 |
| h10A5.L4H4 | 52.1 | 22.7 | 0.44 | 15.2 | 12.9 | 0.85 |
| rat7E7 | 5.68 | 0.18 | 0.03 | 3.99 | 0.27 | 0.07 |
| h7E7.L1H1 | 20.6 | 4.76 | 0.23 | 4.18 | 1.52 | 0.36 |
| h7E7.L2H1 | 20.6 | 5.04 | 0.24 | 4.93 | 1.79 | 0.36 |
| h7E7.L3H1 | 9.2 | 2.18 | 0.24 | 12.8 | 12.2 | 0.95 |
| h7E7.L4H1 | 29.5 | 7.96 | 0.27 | 6.29 | 2.74 | 0.44 |
| h7E7.L5H1 | 32.1 | 10.4 | 0.32 | 5.75 | 3.24 | 0.56 |
| h7E7.L1H2 | — | — | >100 | — | — | >100 |
| h7E7.L1H3 | 28.2 | 10.7 | 0.38 | 9.08 | 3.81 | 0.42 |
| h7E7.L1H4 | 27.9 | 7.49 | 0.27 | 6.01 | 2.43 | 0.40 |
| h7E7.L1H5 | 32.4 | 12.9 | 0.40 | 8.98 | 3.59 | 0.40 |
| h7E7.L1H6 | 18.5 | 6.48 | 0.35 | 6.41 | 2.84 | 0.44 |
| h7E7.L1H7 | 27.4 | 8.49 | 0.31 | 6.64 | 2.86 | 0.43 |
| h7E7.L1H8 | 27.8 | 10.1 | 0.36 | 8.45 | 3.31 | 0.39 |
| h7E7.L1H9 | — | — | >100 | — | — | >100 |
| h7E7.L5H9 | — | — | >100 | — | — | >100 |
| h7E7.L5aH9a | 12.8 | 3.63 | 0.28 | 5.91 | 1.82 | 0.31 |
| rat15C8 | 5.22 | 0.18 | 0.03 | 3.81 | 0.96 | 0.25 |
| h15C8.L1H1 | 9.22 | 3.57 | 0.39 | 4.93 | 4.64 | 0.94 |
| h15C8.L2H1 | 7.71 | 5.06 | 0.66 | 5.02 | 5.02 | 1.00 |
| h15C8.L3H1 | 6.31 | 5.33 | 0.84 | 3.36 | 5.88 | 1.75 |
| h15C8.L4H1 | 9.55 | 6.11 | 0.64 | 4.85 | 5.59 | 1.15 |
| h15C8.L5H1 | 6.74 | 5.62 | 0.83 | 2.81 | 7.52 | 2.68 |
| h15C8.L1H2 | 10.4 | 10.7 | 1.03 | 3.82 | 8.06 | 2.1 |
| h15C8.L1H3 | — | — | >100 | — | — | >100 |
| h15C8.L1H4 | 8.41 | 4.98 | 0.59 | 5.32 | 5.58 | 1.05 |
| h15C8.L1H5 | 7.98 | 5.67 | 0.71 | 4.84 | 5.58 | 1.15 |
| h15C8.L1H6 | 13.8 | 7.56 | 0.55 | 6.63 | 5.56 | 0.84 |
| h15C8.L1H7 | 6.1 | 5.97 | 0.98 | 2.19 | 2.06 | 0.94 |
| h15C8.L1H8 | 6.2 | 3.81 | 0.61 | 2.91 | 1.19 | 0.41 |
| h15C8.L1H9 | — | — | >100 | — | — | >100 |
| h15C8.L5H9 | — | — | >100 | — | — | >100 |
| h15C8.L5aH9a | 11.2 | 4.21 | 0.38 | 5.96 | 6.13 | 1.03 |

Example 3. In Vitro Binding and Blocking Studies of Anti-TIGIT Antibodies

A. In Vitro Binding Characterization of Anti-TIGIT Antibodies

The OMT- and SD-derived anti-TIGIT antibodies were characterized in vitro for their ability to bind to TIGIT and to block poliovirus receptor (PVR) binding to TIGIT. Binding to human and cyno TIGIT was tested by BIACORE™ analysis, as described above, in the context of both monovalent and bivalent affinity, and compared to a mouse-derived anti-TIGIT antibody (1A5) and a chimeric hamster-derived anti-TIGIT antibody (10A7; see, e.g., U.S. Pub. No. 2009/0258013, which is incorporated herein by reference in its entirety). The results of the BIACORE™ analysis, depicted in Table 5, indicate that numerous OMT-derived anti-TIGIT clone variants, such as 4.1D3.Q1E and 7.4A3.C96S.Q1E, and SD-derived anti-TIGIT clone variants were capable of binding to both human and cyno TIGIT, each with a high and similar affinity. Such properties are desirable for therapeutic anti-TIGIT antibodies as they allow for facile toxicity testing using cynomolgus monkey (*Macaca fascicularis*) as a non-clinical toxicology species. Additional cross-reactivity of the 4.1D3.Q1E clone with rabbit may provide an additional toxicology species.

TABLE 5

BIACORE™ analysis of optimized OMT- and SD-derived anti-TIGIT clones

| | | BIAcore Kinetics Analysis | | | |
|---|---|---|---|---|---|
| | | Human TIGIT Monovalent Affinity (nM) | Cyno TIGIT Monovalent Affinity (nM) | Human TIGIT Bivalent Affinity (nM) | Cyno TIGIT Bivalent Affinity (nM) |
| Source | Clone | | | | |
| OMT Rat | 4.1A4.Q1.C96 | 4.9 | 2.6 | 0.31 | 0.035 |
| | 4.1A4.Q1E.C96 | 3.6 | 2.4 | | |
| | 4.1A4.Q1E.C96S | 29.4 | 12.6 | | |
| | 4.1A4.Q1E.C96Y | >100 | >100 | | |
| | 4.1D3.Q1 | 0.61 | 3.4 | ≤0.019 | 0.36 |
| | 4.1D3.Q1E | 0.57 | 3.2 | | |
| | 7.4A3.Q1.C96 | 3.60 | 1.6 | 0.098 | ≤0.05 |
| | 7.4A3.Q1E.C96 | 3.45 | 2.09 | | |
| | 7.4A3.Q1E.C96S | 2.97 | 2.02 | | |
| | 7.4A3.Q1E.C96Y | 98.1 | 35.5 | | |
| SD Rat | Chimeric 1.6B2 | 0.035 | 0.29 | ≤0.027 | 0.091 |
| | h1.6B2.L1H1 | 0.54 | 0.96 | | |
| | Chimeric 1.10A5 | 0.093 | 0.41 | ≤0.003 | 0.013 |
| | h1.10A5.L1H1 | 0.52 | 0.86 | | |
| | Chimeric 1.7E7 | ≤0.018 | 0.067 | ≤0.004 | ≤0.009 |
| | h1.7E7.L1H1 | 0.33 | 0.51 | | |

TABLE 5-continued

BIACORE™ analysis of optimized OMT-
and SD-derived anti-TIGIT clones

| | | BIAcore Kinetics Analysis | | | |
|---|---|---|---|---|---|
| | | Human TIGIT Monovalent Affinity (nM) | Cyno TIGIT Monovalent Affinity (nM) | Human TIGIT Bivalent Affinity (nM) | Cyno TIGIT Bivalent Affinity (nM) |
| Source | Clone | | | | |
| | Chimeric 1.15C8 | 0.034 | 0.25 | ≤0.007 | ≤0.013 |
| | h1.15C8.L1H1 | 0.58 | 1.39 | | |
| Mouse | h1A5.L2H8 | 5.76 | >500 | 0.26 | 7.77 |
| Hamster | c10A7 (to human) | 24 | | 0.54 | 8.22 |
| | c10A7 (to murine) | 0.24 | | | |

Additional in vitro binding studies of the OMT- and SD-derived anti-TIGIT antibody clones were conducted. The OMT- and SD-derived anti-TIGIT clones were tested for binding to human and cyno TIGIT expressed on the surface of CHO cells by FACS analysis. CHO cells were transfected with full-length human TIGIT (CHO-hTIGIT) or cynomologous TIGIT (CHO-cyTIGIT). The TIGIT-expressing CHO cells were incubated with each anti-TIGIT antibody at the indicated concentrations and then detected via a FITC-labeled anti-hIgG antibody (see FIG. 1A) using standard methods. The results, shown in Table 6 and FIGS. 1B-1E, corroborate the results from the BIACORE™ analysis, described above.

The OMT- and SD-derived anti-TIGIT clones were also tested for binding to human primary T cells by FACS analysis. Human PBMC were activated for with plate-bound anti-CD3 (5 µg/ml) and soluble anti-CD28 (2 µg/ml) for 2 days as described in Yu et al. *Nature Immunology*. 10: 48-57, 2009, which is incorporated herein by reference in its entirety. Cells were then washed and incubated with incubated with each anti-TIGIT antibody at the indicated concentrations and then detected via a FITC-labeled anti-hIgG antibody. Cells were also stained with anti-CD4, anti-CD8, and anti-CD25 (BD bioscience). Human CD4+ (CD25+CD4+) and human CD8+ (CD25+CD8+) T cells were assessed for binding by the anti-TIGIT clones by FACS. All samples were acquired on LSR-II or LSR-Fortessa instruments (BD Biosciences) and analyzed using FlowJo software (Treestar). As described in Table 6 and FIGS. 2A-2D, the clones exhibited approximately equivalent binding to their target TIGIT.

TABLE 6

Summary of CHO-TIGIT and human T cell binding of
optimized OMT- and SD-derived anti-TIGIT clones

| Assay | 10A7 (mu TIGIT) & 1A5 (hu TIGIT) | | OMT clones (hu TIGIT) | | SD clones (hu TIGIT) | |
|---|---|---|---|---|---|---|
| CHO-TIGIT binding (EC50) | 10A7 | 0.54 nM | 4.1A4.C96S.Q1E | 0.90 nM | 1.6B2 | 0.52 nM |
| | 1A5 | 0.14 nM | 4.1D3.Q1E | 1.04 nM | 1.7E7 | 0.10 nM |
| | | | 7.4A3.C96S.Q1E | 3.04 nM | | |
| Human T cell binding (EC50) | 10A7 | 0.63 nM | 4.1A4.C96S.Q1E | 0.38 nM | 1.6B2 | 0.09 nM |
| | 1A5 | 0.14 nM | 4.1D3.Q1E | 1.36 nM | 1.7E7 | 0.11 nM |
| | | | 7.4A3.C96S.Q1E | 2.63 nM | | |

B. In Vitro Blocking Characterization of Anti-TIGIT Antibodies

The OMT- and SD-derived anti-TIGIT antibody clones were also tested for their ability to block TIGIT-PVR and TIGIT-CD226 interactions.

To test for the ability of the clones to block the TIGIT-PVR interaction, a blocking ELISA assay was used. Briefly, recombinant human PVR-Fc fusion protein, cynomolgus monkey PVR-Fc fusion protein, or mouse PVR-Fc fusion protein was coated at 4 µg/ml at 25 µl/well in phosphate-buffered saline (PBS, pH 7.0) onto 384-well Maxisorp microtiter plates (NUNC, Denmark) and incubated overnight at 4° C. The coating solution was then discarded and the plate was blocked using 0.5% bovine serum albumin (BSA) in PBS at 80 µl/well and incubated with gentle agitation for 1 hour. Titration curves of anti-TIGIT and Fab isotype control antibodies were diluted in assay buffer (PBS, 0.5% BSA, 0.05% Tween 20) using 12 serial 2.5-fold dilutions (40000-1.7 ng/mL). Equal volumes of either human TIGIT-AviFlag-biotin (1 µg/mL), cynomolgus TIGIT-AviFlag-biotin (150 ng/mL), or mouse TIGIT-His (1 µg/mL) were added to these titration curves and incubated at room temperature for 1 hour with gentle agitation. The blocked plate was washed 3× with wash buffer (PBS, 0.05% Tween 20, pH 7.4) using an ELx405 automated microtiter plate washer (BioTek Instruments, Vermont) and the antibody/ligand-biotin or ligand-His mixture was added at 25 µl/well and incubated for 1 hour at room temperature with gentle agitation. The plate was then washed 6× with wash buffer and bound human TIGIT-AviFlag-biotin, cyno TIGIT-AviFlag-biotin, or mouse TIGIT-His was detected by adding 25 µl/well of horseradish peroxidase-conjugated streptavidin (1:10000, Amersham, UK) or horseradish peroxidase-conjugated mouse anti-His (1:2500, Qiagen, Germany) diluted in assay buffer. After a 30 minute or 1 hour incubation, the plate was washed 6× with wash buffer and 100 µl/well of 3,3',5,5'-tetramethyl benzidine (TMB) substrate (KPL, Inc., Gaithersburg, Md. USA) was added to allow color to develop. The reaction was quenched by addition of 1 M phosphoric acid. Absorbance was read at 450 nm on a MULTISKAN ASCENT® microtiter plate reader (Thermo Labsystems, Helsinki, Finland). Fit curves were plotted from the resulting optical density values from the ELISA plates and IC50s were calculated using Genedata Screener software (Genedata, Switzerland). As shown below in FIGS. 3A-3D, these assays demonstrated the cross-reactivity and blocking ability of 4.1D3.Q1E for human TIGIT and cyno TIGIT, which distinguishes 4.1D3.Q1E from the hamster-derived anti-TIGIT antibody, 10A7, which cross-reacts with mouse TIGIT, but not cyno TIGIT. The data indicate that 4.1D3.Q1E strongly blocks the binding of cyno TIGIT to cyno PVR. The data also indicate that 4.1D3.Q1E is a stronger blocker of human TIGIT to human PVR than the 10A7 hamster-derived anti-TIGIT antibody done.

Figures 4A, 4B, 4C:
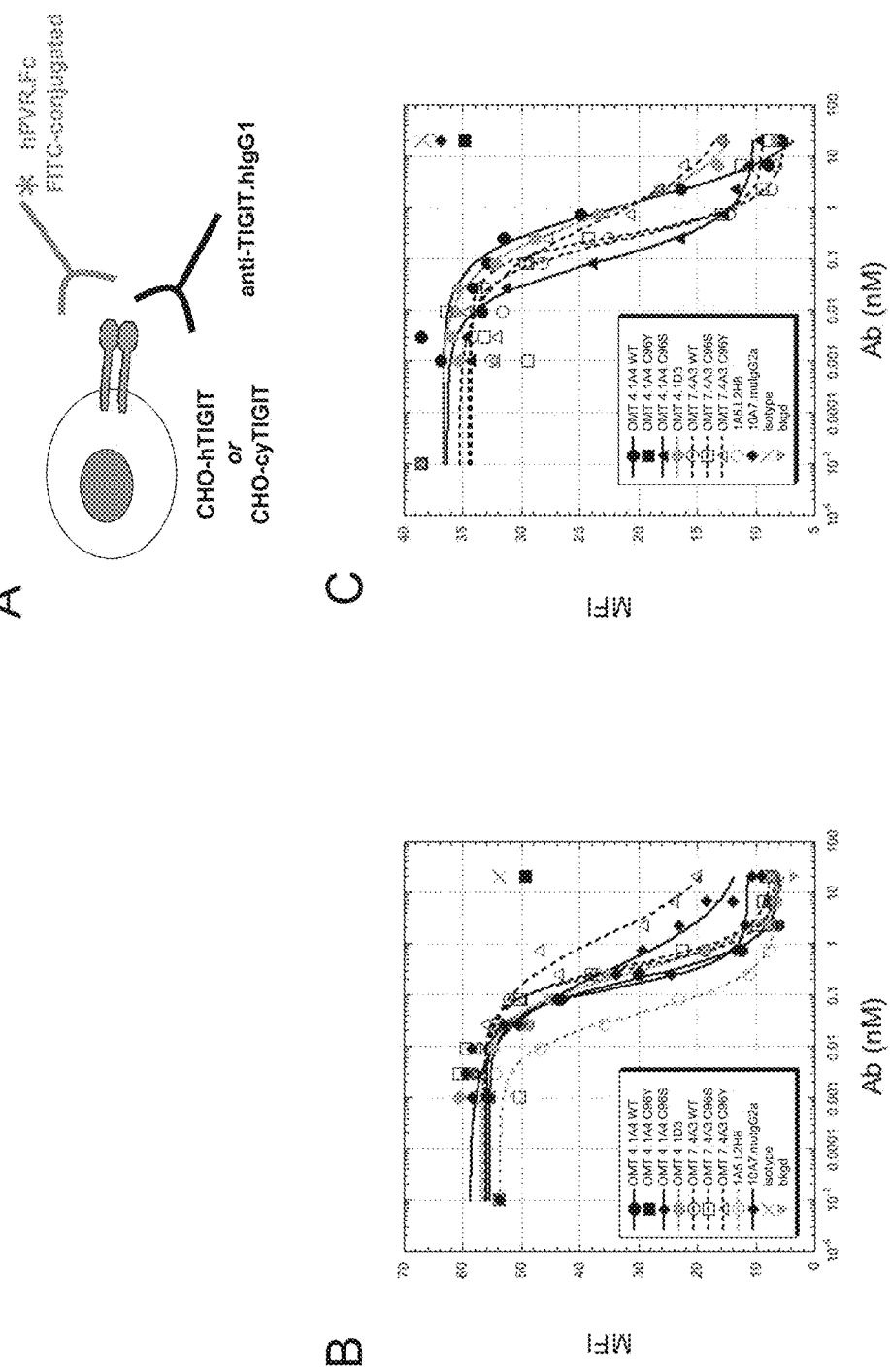
FIG. 4A is a schematic diagram of a CHO-TIGIT PVR blocking assay.
FIG. 4B is a graph showing the results of the CHO-TIGIT PVR blocking assay depicted in FIG. 4A using human TIGIT-expressing CHO cells and the indicated OMT-derived anti-TIGIT antibodies at varying concentrations, as analyzed by FACS.
FIG. 4C is a graph showing the results of the CHO-TIGIT PVR blocking assay depicted in FIG. 4A using cyno TIGIT-expressing CHO cells and the indicated OMT-derived anti-TIGIT antibodies at varying concentrations, as analyzed by FACS.
Figure 4D:
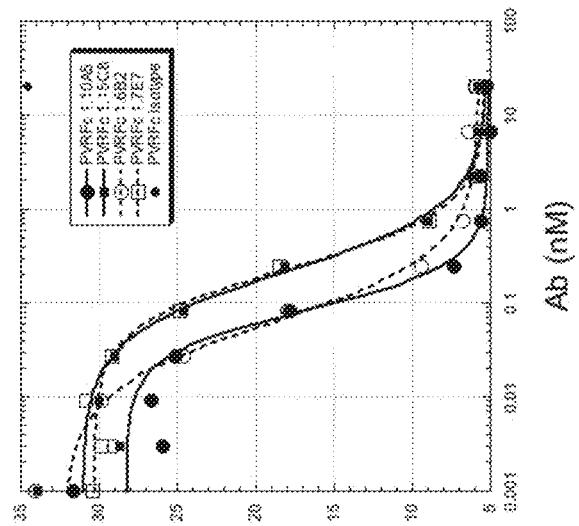
FIG. 4D is a graph showing the results of the CHO-TIGIT PVR blocking assay depicted in FIG. 4A using human TIGIT-expressing CHO cells and the indicated SD-derived anti-TIGIT antibodies at varying concentrations, as analyzed by FACS.
Figure 4E:
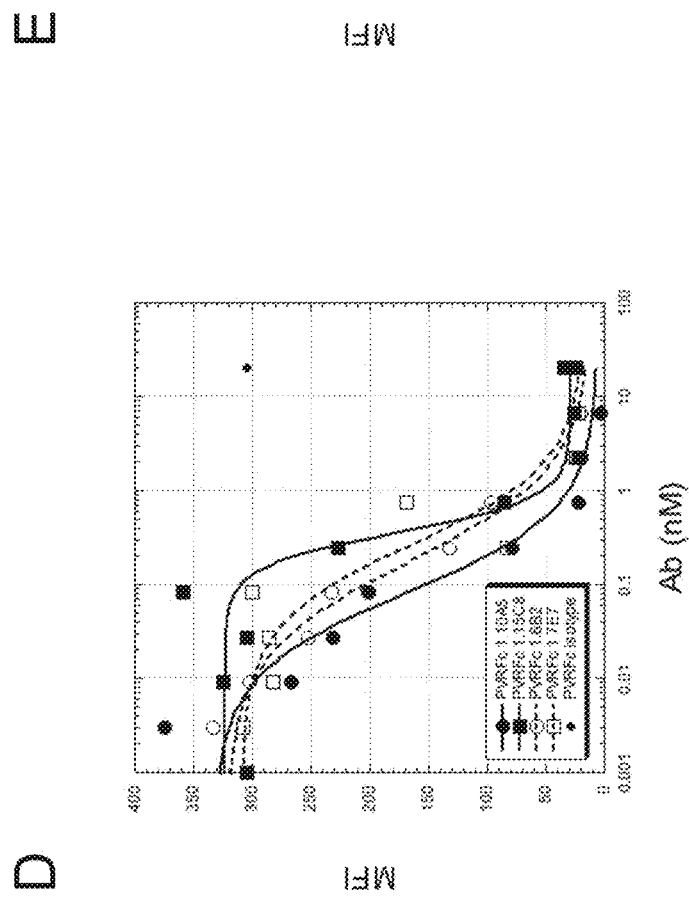
FIG. 4E is a graph showing the results of the CHO-TIGIT PVR blocking assay depicted in FIG. 4A using cyno TIGIT-expressing CHO cells and the indicated SD-derived anti-TIGIT antibodies at varying concentrations, as analyzed by FACS.

These studies were further validated in CHO-TIGIT PVR blocking experiments in which TIGIT-expressing CHO cells were incubated with labeled PVR-Fc fusion protein in the presence of anti-TIGIT antibody or an human IgG1 control (FIG. 4A). As shown in Table 7 and FIGS. 4B-4E, incubation with 10 μg/ml of OMT-derived anti-TIGIT antibody (FIGS. 4B and 4C) or SD-derived anti-TIGIT antibody (FIGS. 4D and 4E) resulted in blocking of TIGIT-PVR binding for both huTIGIT-huPVR and cyTIGIT-cyPVR, with IC50 values in the nanomolar and subnanomolar range.

To test for the ability of the clones to block the TIGIT-CD226 interaction, TR-FRET (Time-resolved Fluorescence Resonance Energy Transfer) was used. First, human SNAP-tagged (ST) CD226 with non-permeant donor and acceptor fluorophores was expressed and labeled using CHO cells. The human ST-CD226 was co-expressed with HA-tagged TIGIT, in the presence or the absence of the OMT- and SD-derived anti-TIGIT antibody clones. The addition of each of the tested clones to the cell cultures significantly reduced the ability of TIGIT and CD226 to associate (Table 7). These data suggested that anti-TIGIT treatment with the identified anti-TIGIT antibodies can limit TIGIT's interaction with CD226, indicating that these antibodies may be favorable therapeutics based on their ability to activate T cell activity by releasing TIGIT-mediated suppression of CD226 activity and preventing subsequent $CD8^+$ T cell exhaustion.

receiving h10A7.K4G3 and the second group receiving 4.1D3. Both anti-TIGIT antibodies were administered at a dose level of 10 mg/kg (dose volume of 5 ml/kg; dose concentration of 2 mg/ml) by slow bolus intravenous injection. Blood samples (0.5 ml) were collected at 0 hour (pre-dose), 0.25 hour, 2 hours, 8 hours, 1 day, 3 days, and 7 days post-dose in accordance with the following collection windows:

| Postdose Time Point | Collection Window |
|---|---|
| 0 to 15 minutes | +/−1 minute |
| 16 to 30 minutes | +/−2 minutes |
| 31 to 45 minutes | +/−3 minutes |
| 46 to 60 minutes | +/−4 minutes |
| 61 minutes to 2 hours | +/−5 minutes |
| >2 to 8 hours | +/−10 minutes |
| >8 to 24 hours | +/−20 minutes |

TABLE 7

Summary of TIGIT-PVR blocking and TIGIT-CD226 blocking of optimized OMT- and SD- derived anti-TIGIT clones

| Assay | 10A7 (mu TIGIT) & 1A5 (hu TIGIT) | | OMT clones (hu TIGIT) | | SD clones (hu TIGIT) | |
|---|---|---|---|---|---|---|
| TIGIT-PVR blocking (IC50) | 10A7 | 0.07 nM | 4.1A4.C96S.Q1E | 0.14 nM | 1.6B2 | 0.08 nM |
| | 1A5 | 0.18 nM | 4.1D3.Q1E | 0.29 nM | 1.7E7 | 0.04 nM |
| | | | 7.4A3.C96S.Q1E | 0.38 nM | | |
| TIGIT-CD226 FRET (IC50) | 10A7 | 17.6 nM | 4.1A4.C96S.Q1E | 25.2 nM | | |
| | 1A5 | 13.7 nM | 4.1D3.Q1E | 45.0 nM | | |
| | | | 7.4A3.C96S.Q1E | 19.3 nM | | |

Example 4. Pharmacokinetic Characterization of Anti-TIGIT Antibodies

Figure 5A:
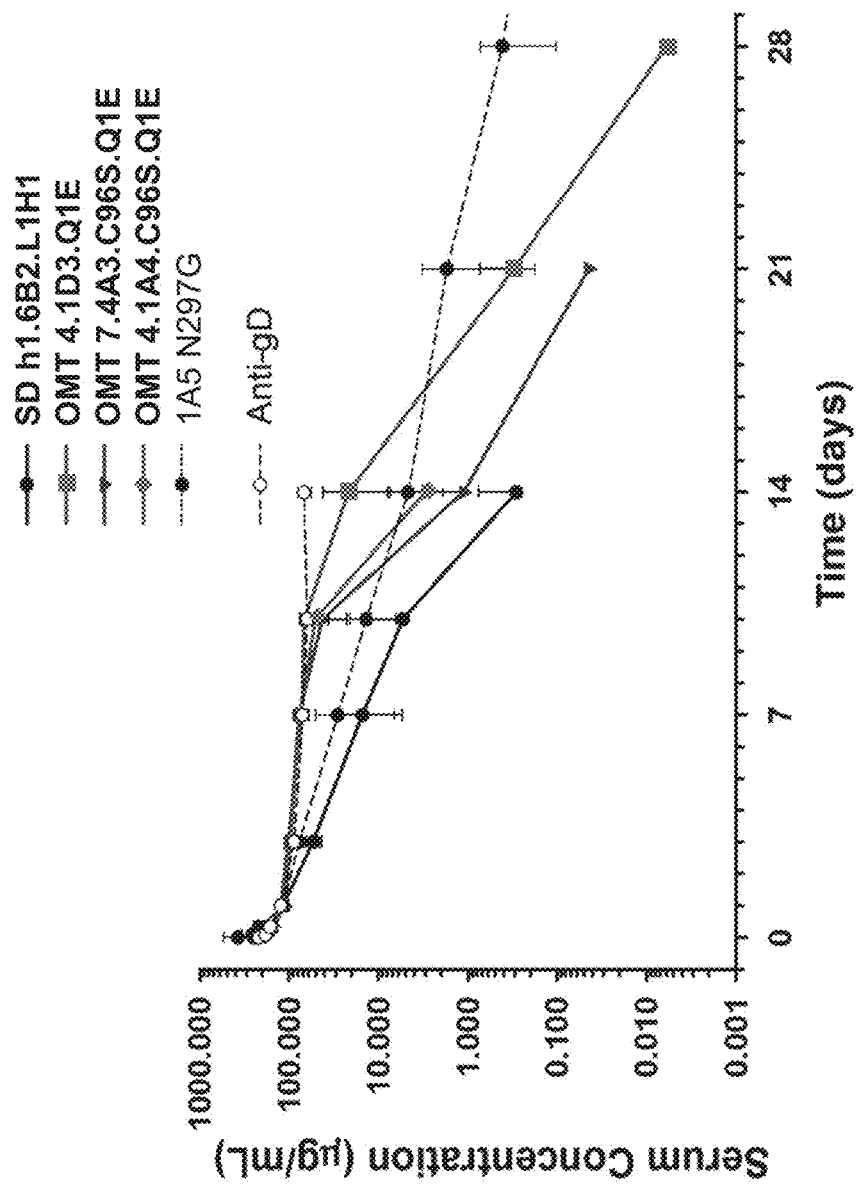
FIG. 5A is a graph showing the pharmacokinetic clearance of the indicated anti-TIGIT antibodies in cyno following 10 mg/kg intravenous administration as a function of serum concentration (μg/ml) over time (days).

Next, the pharmacokinetic (PK) properties of OMT- and SD-derived anti-TIGIT antibody clones were tested in cynomogus monkeys as compared to the mouse-derived anti-TIGIT antibody bearing an N297G aglycosylation mutation (1A5 N297G) and an anti-gD control antibody. In these experiments, serum concentration of the antibodies was measured over the span of 28 days following 10 mg/kg intravenous administrations in cynomolgus monkeys. The PK studies revealed that the SD-derived h1.6B2 variant exhibited the fastest clearance, at approximately 20 ml/day/kg (FIGS. 5A and 5B). The tested 1A5 variant also exhibited fast clearance, at approximately 15 ml/day/kg (FIGS. 5A and 5B). In contrast to these anti-TIGIT variants, the tested OMT variants (4.1D3.Q1E, 7.4A3.C96S.Q1E, and 4.1A4.C96S.Q1E) exhibited a clearance of approximately 8-10 ml/day/kg (FIGS. 5A and 5B), which is on the high end of the historically accepted cyno range of approximately 4-8 ml/day/kg. The PK profiles of the OMT variants were similar to the control anti-gD antibody through d10, at which time target-mediated drug disposition (TMDD) and/or anti-therapeutic antibody (ATA) effects convolute the estimates.

The OMT-derived anti-TIGIT antibody 4.1D3, which exhibited favorable PK properties, was also compared to humanized 10A7 (h10A7.K4G3) in a 7-day PK study. In this experiment, eight female cynomolgus monkeys were binned into two groups of four monkeys, with the first group using gel serum separator tubes. The blood was maintained at ambient temperature and allowed to clot for at least 20 minutes prior to centrifugation. Samples were centrifuged (approximately 10 to 15 minutes at approximately 1500 to 2000×g [force], 2° C. to 8° C.) within 1 hour of collection. Serum was harvested within 30 minutes of the start of centrifugation and transferred into 0.5-mL 2D bar-coded screw top tubes (Thermofisher Scientific catalog #3744 or equivalent). The serum sample was labeled with the animal number, species, dose group, day of collection, sample type (i.e., PK-serum), and study numbers. The serum samples were then analyzed for concentrations of h10A7.K4G3 or 4.1D3. As shown in FIGS. 5C and 5D, this PK study revealed that h10A7.K4G3 exhibited a faster clearance (lower AUC) than 4.1D3, and that the clearance of h10A7.K4G3 (>9 ml/day/kg) is faster than recommended for monoclonal antibody selection in cynomolgus monkey. The estimated clearance was based on data from day 0 through day 7 and calculated by Winnonlin using NCA.

Example 5. Molecular Analysis of Anti-TIGIT Antibodies

OMT-derived (4.1D3, 7.4A3.C96S, and 4.1A4.C96S) and SD-derived (h1.6B2.L1H1, h1.10A5.L1H1, h1.7E7.L1H1, and h1.15C8.L1H1) anti-TIGIT antibody clones were also tested in molecular assessment (MA) analyses for stable cell line properties. Briefly, the anti-TIGIT antibodies (1 mg/ml) were tested for stress under chemical conditions with AAPH (2,2-azobis(2-amidinopropane) dihydrochloride), a small molecule known to generate free radicals, as well as under thermal conditions at varying pH (a two-week thermal stress test at 40° C., at either pH 5.5 or pH 7.4). As shown in Tables 8 and 9, below, 4.1A4.C96S was determined to be unstable, showing unacceptable main peak loss and increased deamidation in the MA studies. Similarly, h1.7E7.L1H1 and h1.15C8.L1H1 showed high initial deamidation (>30%). On the other hand, the anti-TIGIT antibodies 4.1D3, 7.4A3.C96S, h1.6B2.L1H1, and h1.10A5.L1H1 were found to possess acceptable stability properties in the MA studies.

TABLE 8

MA stability summary for OMT-derived anti-TIGIT antibody clones

| | 4.1A4.C96S | 4.1D3 | 7.4A3.C96S |
|---|---|---|---|
| AAPH Stress | M in CDR-H1 is stable<br>W in CDR-H2 is stable | W in CDR-H1 is stable<br>W in CDR-H2 is stable<br>W in CDR-L2 is stable | M in CDR-H1 is stable<br>W in CDR-H2 is stable |
| Thermal Stress pH 5.5 (2 weeks) Peptide map analysis Size Charge LC/MS | NY in CDR-H1 is stable<br>N(52)T in CDR-H2 are stable<br>N(54)T in CDR-H2 are stable<br>DY in CDR-H3 is stable<br>NS in CDR-L3 is unstable - 15.7% increase in deamidation<br>Monomer loss (0.5%) is acceptable<br>Main peak loss (16.7%) is unacceptable<br>Masses are as expected | DS in CDR-H1 is stable<br>NS in CDR-H1 is stable<br>DY in CDR-H2 is stable<br>DY in CDR-H3 is stable<br>NN in CDR-L1 is stable<br><br>Monomer loss (0.6%) is acceptable<br>Main peak loss (11.1%) is acceptable<br>Masses are as expected | N(52)T in CDR-H2 is stable<br>N(54)T in CDR-H2 is stable<br>NP in CDR-H2 is stable<br>DS in CDR-H3 is stable<br><br><br>Monomer loss (1.1%) is acceptable<br>Main peak loss (7.3%) is acceptable<br>Masses are as expected |
| Thermal Stress pH 7.4 (2 weeks) Peptide map analysis Size Charge LC/MS | NY in CDR-H1 no change<br>N(52)T & N(54)T in CDR-H2 no change<br>DY in CDR-H3 no change<br>NS in CDR-L3 9.4% increase in deamidation<br>Monomer loss (2.7%)<br>Main peak loss (21.9%)<br>Masses are as expected | DS CDR-H1 2.8% increase in isomerization<br>NS CDR-H1 no change<br>DY in CDR-H2 no change<br>DY in CDR-H3 2.7% increase in isomerization<br>NN in CDR-L1 no change<br>Monomer loss (0.9%)<br>Main peak loss (27.7%)<br>Masses are as expected | N(52)T in CDR-H2 no change<br>N(54)T in CDR-H2 no change<br>NP in CDR-H2 no change<br>DS in CDR-H3 no change<br><br><br>Monomer loss (2.3%)<br>Main peak loss (15.7%)<br>Masses are as expected |

TABLE 9-1

MA stability summary for SD-derived anti-TIGIT antibody clones

| | h7E7.L1H1 | h15C8.L1H1 |
|---|---|---|
| AAPH Stress<br>Thermal Stress pH 5.5 (2 weeks) Peptide map analysis Size Charge LC/MS | No oxidation hotspots<br>DP in CDR-H2 is stable<br>NG in CDR-H2 is stable<br>NT in CDR-L2 is stable<br>NL in CDR-L2 is stable<br>N(92)N(93)G in CDR-L3 is stable - high initial deamidation 31.5% | No oxidation hotspots<br>DP in CDR-H2 is stable<br>NG in CDR-H2 is stable<br>DG in CDR-H3 is unstable (14.7% increase in isomerization (3.8% to 18.5%))<br>N(92)N(93)G in CDR-L3 is stable - high initial deamidation 39.2% |
| (2 weeks) Peptide map analysis Size Charge LC/MS | Monomer loss (0.8%) is acceptable<br>Main peak loss (6.2%) is acceptable<br>Masses are as expected | Monomer loss (0.9%) is acceptable<br>Main peak loss (10.3%) is acceptable<br>Masses are as expected |
| Thermal Stress pH 7.4 | DP in CDR-H2 no change<br>NG in CDR-H2 1.9% increase in deamidation | DP in CDR-H2 no change<br>NG in CDR-H2 3.3% increase in deamidation |
| (2 weeks) Peptide map analysis Size Charge LC/MS | NT in CDR-L2 no change<br>NL in CDR-L2 no change<br>N(92)N(93)G in CDR-L3 - 24.3% increase in deamidation<br>Monomer loss (0.5%)<br>Main peak loss (16.7%)<br>Masses are as expected | DG in CDR-H3 7.0% increase in isomerization<br>N(92)N(93)G in CDR-L3 - 15.5% increase in deamidation<br>Monomer loss (1.5%)<br>Main peak loss (25.2%)<br>Masses are as expected |

TABLE 9-2

MA stability summary for SD-derived anti-TIGIT antibody clones

|  | h6B2.L1H1 | h10A5.L1H1 |
|---|---|---|
| AAPH Stress | M in CDR-H1 is stable<br>W(52) and W(53) in CDR-H2 are stable<br>W in CDR-H3 is stable | M in CDR-H1 is stable<br>W(52) and W(53) in CDR-H2 are stable<br>W in CDR-H3 is stable |
| Thermal Stress pH 5.5 (2 weeks) Peptide map analysis | NG in CDR-H2 is stable<br>NT in CDR-H2 is stable<br>NP in CDR-H2 is stable<br>NS is CDR-L3 is stable<br>Monomer loss (0.2%) is acceptable | NG in CDR-H2 is stable<br>NT in CDR-H2 is stable<br>NP in CDR-H2 is stable<br>NS is CDR-L3 is stable<br>Monomer loss (0.1%) is acceptable |
| Size Charge | Main peak loss (2.4%) is acceptable | Main peak loss (6.3%) is acceptable |
| LC/MS | Masses are as expected | Masses are as expected |
| Thermal Stress pH 7.4 (2 weeks) Peptide map analysis | NG in CDR-H2 5.6% increase in deamidation<br>NT in CDR-H2 no change<br>NP in CDR-H2 no change<br>NS is CDR-L3 no change<br>Monomer loss (0.0%) | NG in CDR-H2 4.8% increase in deamidation<br>NT in CDR-H2 no change<br>NP in CDR-H2 no change<br>NS is CDR-L3 no change<br>Monomer loss (0.2%) |
| Size Charge | Main peak loss (9.9%) | Main peak loss (14.5%) |
| LC/MS | Masses are as expected | Masses are as expected |

Example 6. Structural and Functional TIGIT Epitope Mapping

To better understand how the 4.1D3 anti-TIGIT antibody and its optimized variants (e.g., 4.1D3.Q1E), in particular, are capable of exemplary cross-reactivity (e.g., cross-reactivity between human, cyno, and rabbit TIGIT), high affinity for TIGIT, and robust blocking of TIGIT-PVR and TIGIT-CD226 interaction/function while exhibiting pharmacokinetic and molecular assessment properties, the crystal structure of 4.1D3 in complex with TIGIT was determined and compared to the crystal structures of mouse-derived anti-TIGIT antibody 1A5 bound to TIGIT and a hamster-derived anti-TIGIT antibody 10A7 bound to TIGIT, as described in detail below. Alanine scanning mutagenesis experiments of the TIGIT interface were also performed to identify functional epitopic residues.

A. TIGIT and Fab Expression, Purification, and Crystallization

Human TIGIT residues 23-128 was expressed and purified as described (see, e.g., Stengel et al. *PNAS.* 109(14): 5399-5404, 2012). Fab fragments including heavy and light chains were expressed and purified as described (see, e.g., Carter et al. *Nat. Biotech.* 1992). Purified TIGIT was mixed with an excess of purified Fab fragment to generate the TIGIT/Fab complex. The complex was then further purified on a size exclusion column equilibrated in HEPES buffered saline (10 mM HEPES, pH 7.5 and 100 mM NaCl) to generate a sample containing only 1:1 complexes of TIGIT and Fab. Each of the TIGIT/Fab complexes were then concentrated for crystallization and subjected to standard techniques of high throughput vapor diffusion crystallization screening. For the TIGIT/10A7 complex, the sample was concentrated to approximately 25 mg/mL and found to crystallize in 0.1 M HEPES pH 7.5, 20% PEG 4000, and 10% isopropanol. For the TIGIT/1A5 complex, the sample was concentrated to approximately 25 mg/mL and found to crystallize in 0.05 M HEPES pH 7.0, 12% PEG3350, and 1% Tryptone. For the TIGIT/4.1D3 complex, the sample was concentrated to approximately 25 mg/mL and found to crystallize in 0.1 M HEPES pH 7.5, 10% PEG 6000, and 5% MPD. Crystals were cryoprotected with glycerol and flash frozen in liquid nitrogen according to standard techniques for data collection.

B. Data Collection and Structure Solution

X-ray diffraction data was collected under cryo cooled conditions at 100 Kelvin using various synchotron X-ray radiation at the Advanced Light Source (Berkeley, Calif.) or Advanced Photon Source (Argonne, Ill.) according to standard methods. Diffraction images were processed and reduced using the data processing software XDS (Kabsch W. *Acta Cryst. D. Biol. Crystl.* 66: 125-132, 2010). Models were generated using the molecular replacement technique with the program PHASER. The structure of human TIGIT (Stengel et al PNAS 2012) and Fab antibody model (Nakamura et al Cell Host Microbe 2013) were used as search models. The structures underwent iterative rounds of model adjustment using the program COOT and refinement using the Phenix.refine or BUSTER programs. Models were refined to acceptable R and R free values and Ramachandran statistics (calculated by Molprobity). Data processing and refinement statistics can be found in Table 10.

TABLE 10

Data Collection and Refinement Statistics
Data collection and refinement statistics

|  | TIGIT/10A7 | TIGIT/1A5 | TIGIT/1D3 |
|---|---|---|---|
| Data collection | ALS 5.0.2 | APS LS-CAT 21ID-G | APS 22ID-D |
| Space group | P21 | P1 | I4 |
| Cell dimensions |  |  |  |
| a, b, c (Å) | 53.02, 76.99, 136.91 | 74.60, 88.78, 101.10 | 212.39, 212.39, 66.52 |
| $\alpha, \beta, \gamma$ (°) | 90, 90.6, 90 | 101.1, 101.5, 110.5 | 90, 90, 90 |

TABLE 10-continued

Data Collection and Refinement Statistics
Data collection and refinement statistics

|  | TIGIT/10A7 | TIGIT/1A5 | TIGIT/1D3 |
|---|---|---|---|
| Resolution (Å) | 136.90-1.84 (1.94-1.84)* | 81.11-2.77 (2.92-2.77)* | 106.19-1.91 (2.01-1.91)* |
| $R_{sym}$ or $R_{merge}$ | 0.063 (0.512) | 0.062 (0.558) | 0.089 (0.973) |
| I/σI | 12.7 (2.4) | 12.1 (2.3) | 12.8 (1.8) |
| Completeness (%) | 96.4 (95.7) | 97.8 (97.1) | 93.8 (69.3) |
| Redundancy | 3.8 (3.8) | 2.2 (2.1) | 7.4 (6.6) |
| Refinement |  |  |  |
| Resolution (Å) | 136.9-1.85 | 81.11-2.77 | 27.96-1.91 |
| No. reflections | 90418 | 58936 | 107910 |
| $R_{work}/R_{free}$ | 17.8/21.8% | 19.9/27.1% | 18.6/21.6% |
| r.m.s. deviations |  |  |  |
| Bond lengths (Å) | 0.010 | 0.010 | 0.010 |
| Bond angles (°) | 1.16 | 1.26 | 1.13 |
| Ramachandran |  |  |  |
| Most favorable | 97.0% | 91.2% | 97.4% |
| Disallowed | 0.3% | 1.4% | 0.1% |

*Values in parentheses are for highest-resolution shell.

C. The Structure of 4.1D3 Bound to Human TIGIT

Figure 6A:
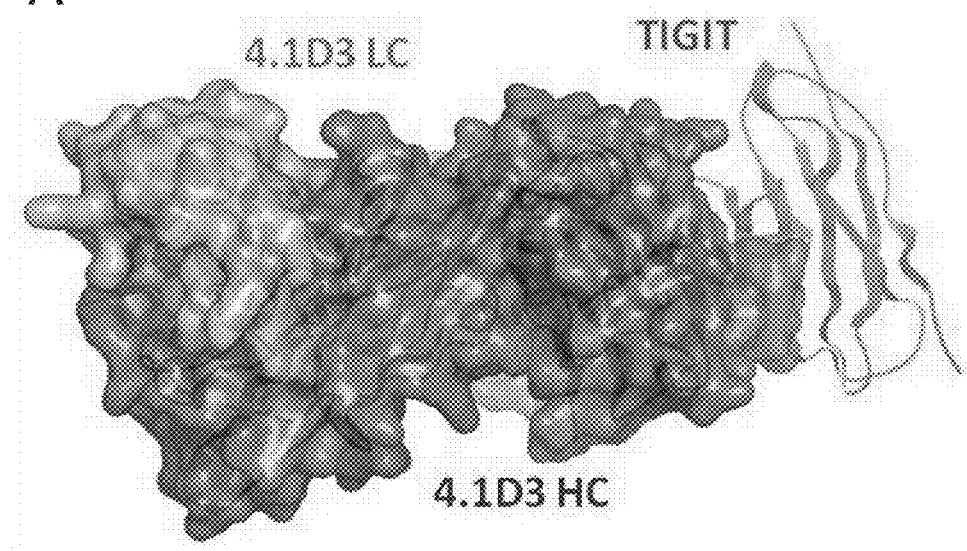
FIG. 6A is a rendering of the crystal structure of the 4.1D3 Fab bound to human TIGIT, with the 4.1D3 heavy chain (HC) and light chain (LC) regions indicated and distinguished by color.
Figure 6B:
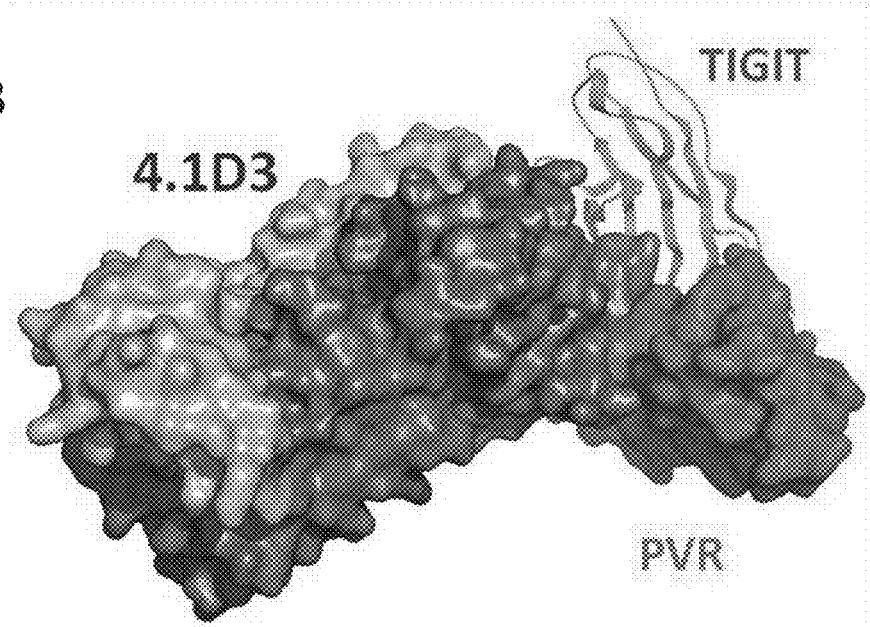
FIG. 6B is a rendering of the crystal structure of the 4.1D3 Fab bound to human TIGIT, superimposed with the known PVR-TIGIT structure (PDB 3UDW), showing that the 4.1D3 antibody and PVR have overlapping binding sites for TIGIT.
Figure 6C:
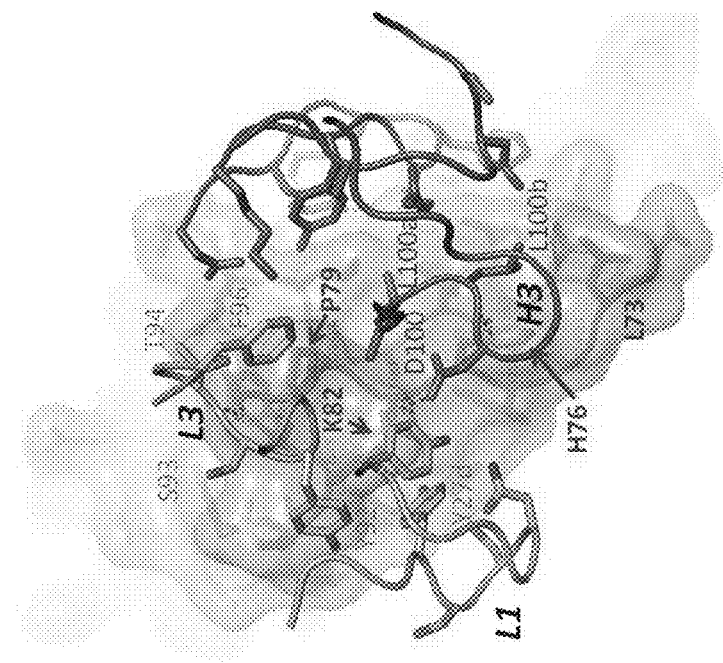
FIG. 6C is a rendering of the crystal structure of the 4.1D3 Fab bound to human TIGIT, with the relative location of the PVR binding site indicated. Also indicated is the relative location of the 72-79 loop of TIGIT.
Figure 6D:
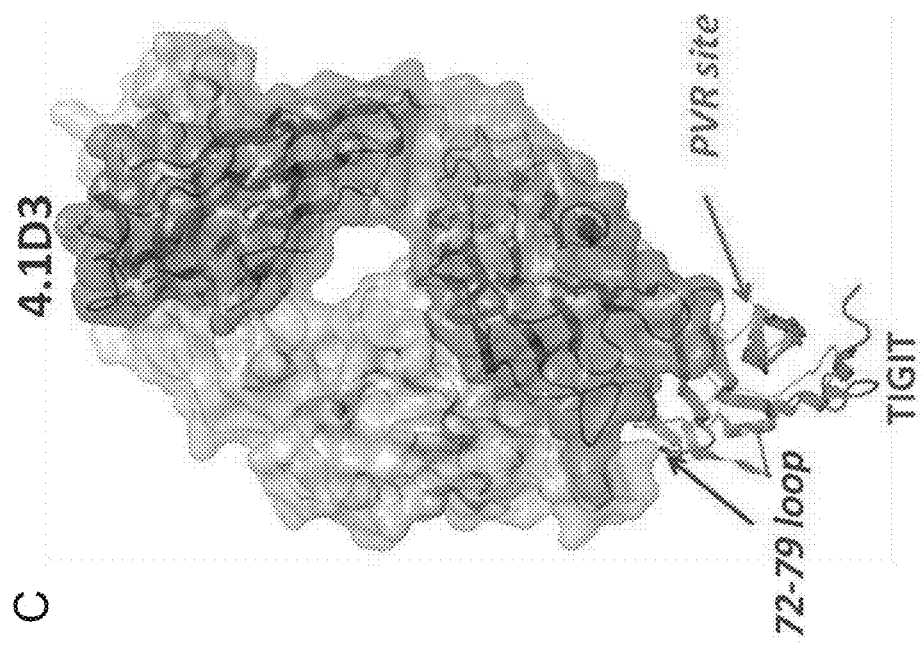
FIGS. 6D and 6E are renderings of the crystal structure of the 4.1D3 Fab bound to human TIGIT from different views, identifying certain key contact residues of 4.1D3 (paratope residues) and TIGIT (epitope residues). The boxed residues indicated in FIG. 6E were identified as functionally important epitopic residues by alanine scanning mutagenesis.
Figure 6E:
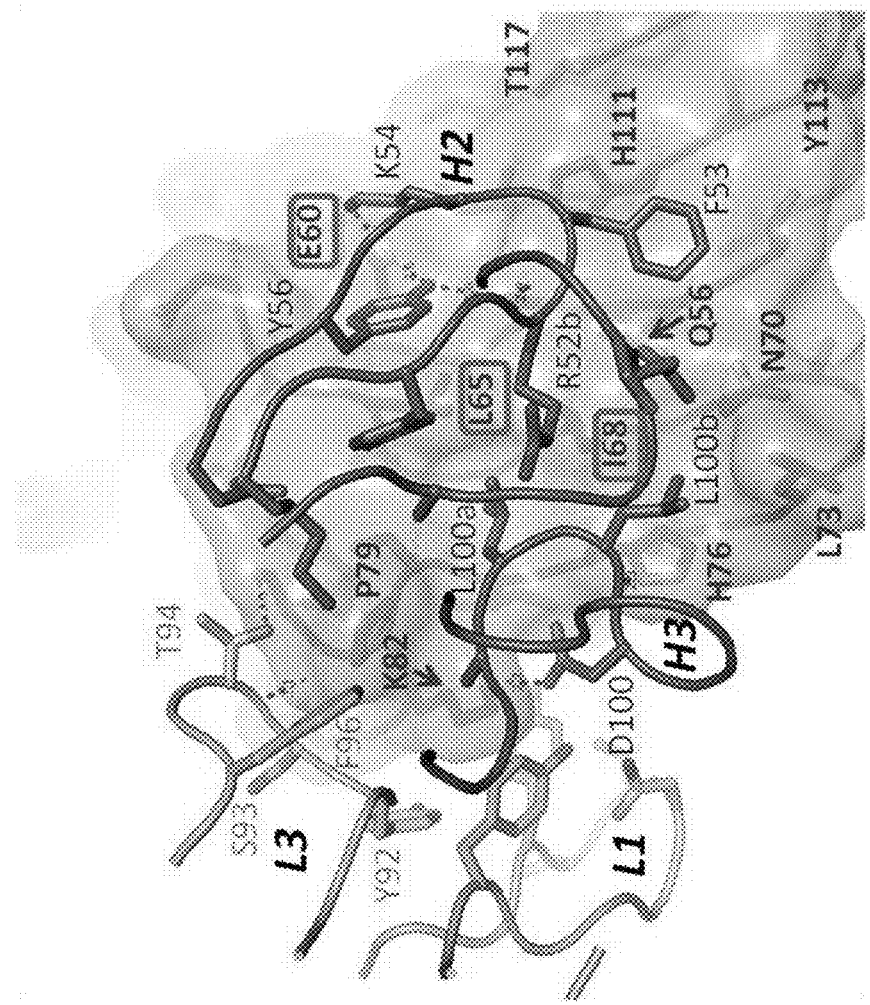

The 4.1D3 Fab in complex with TIGIT crystallized in the I4 space group, with two complexes in the asymmetric unit, and diffracted to 1.91 Å. Overlay of the two individual complexes in the asymmetric unit shows only minor changes in main chain positioning between the individual copies. The structure of 4.1D3 bound to human TIGIT (FIG. 6A) shows that 4.1D3 sterically interferes with PVR binding (FIGS. 6B and 6C). The buried surface area between 4.1D3 and TIGIT is approximately 1630 Å$^2$. 4.1D3 light chain interactions are clustered around TIGIT residues 77-82, with CDR L1 Tyr27d and CDR L3 Tyr92, Ser93, Thr94, and Phe96 contacting TIGIT residues Ile77, Pro79, Ser80, and Lys82. CDR L2 does not make any contact with TIGIT. 4.1D3 heavy chain interactions are primarily mediated by CDR H2 and H3 and make more extensive contact with TIGIT. 4.1D3 CDR H1 Asn32 contacts TIGIT Leu73. 4.1D3 CDR H2 Tyr52, Arg52b, Phe53, Lys54, Tyr56, and Asp58 contact TIGIT residues Thr55, Gln56, Asn58, Glu60, Asp63, Gln64, Leu65, Ile68, Asn70, Ser80, and His111. 4.1D3 CDR H3 residues Tyr99, Asp100, Leu100a Leu100b, and Ala100c contact TIGIT residues Leu65, Ala67, Ile68, Leu73, His76, Ile77, Ser78, Pro79, and Lys82. 4.1D3 interacts with TIGIT using a combination of non-polar and polar interactions. Light chain residue CDR L3 Thr94 forms polar contacts with TIGIT Pro79 and Ser80. Heavy chain CDR H2 residues Arg52b and Tyr56 form hydrogen bonds with TIGIT residues Asn58 and Glu60. Heavy chain CDR H3 residue Leu100a forms a hydrogen bond with TIGIT His76. Heavy chain CDR H2 residue Lys54 and CDR H3 residue Asp100 form salt bridges with TIGIT residues Glu60 and Lys82, respectively. See also FIGS. 6D and 6E.

Based on the crystal structure of the 4.1D3/TIGIT complex, the residues of TIGIT that are contacted by 4.1D3 (i.e., the epitopic residues of TIGIT bound by 4.1D3) and the residues of 4.1D3 that are contacted by TIGIT (i.e., the paratopic residues of 4.1D3 contacted by TIGIT) were determined. Tables 11 and 12, below, show the residues of TIGIT and the light or heavy chain residues of 4.1D3 to which they contact, as assessed using a contact distance stringency of 3.7 Å, a point at which van der Waals (non-polar) interaction forces are highest.

TABLE 11

Epitopic residues of TIGIT and their corresponding paratopic residues on the light chain of 4.1D3

| TIGIT | | 4.1D3 Light chain | |
|---|---|---|---|
| Ile | 77 | Tyr | 27d |
| Pro | 79 | Tyr | 92 |
|  |  | Ser | 93 |
|  |  | Thr | 94 |
| Ser | 80 | Thr | 94 |
| Lys | 82 | Tyr | 27d |

TABLE 12

Epitopic residues of TIGIT and their corresponding paratopic residues on the heavy chain of 4.1D3

| TIGIT | | 4.1D3 Heavy chain | |
|---|---|---|---|
| Thr | 55 | Phe | 53 |
| Gln | 56 | Phe | 53 |
| Asn | 58 | Arg | 52b |
|  |  | Tyr | 56 |
| Glu | 60 | Lys | 54 |
|  |  | Tyr | 58 |
| Leu | 65 | Leu | 100b |
| Ile | 68 | Leu | 100a |
| Leu | 73 | Leu | 100a |
| His | 76 | Tyr | 99 |
|  |  | Asp | 100 |
|  |  | Leu | 100a |
|  |  | Leu | 100b |
| Ser | 78 | Leu | 100b |
| Pro | 79 | Leu | 100b |
| Ser | 80 | Asp | 58 |
| Lys | 82 | Asp | 100 |
| His | 111 | Phe | 53 |

Figures 7C, 7D, 7E, 7F:
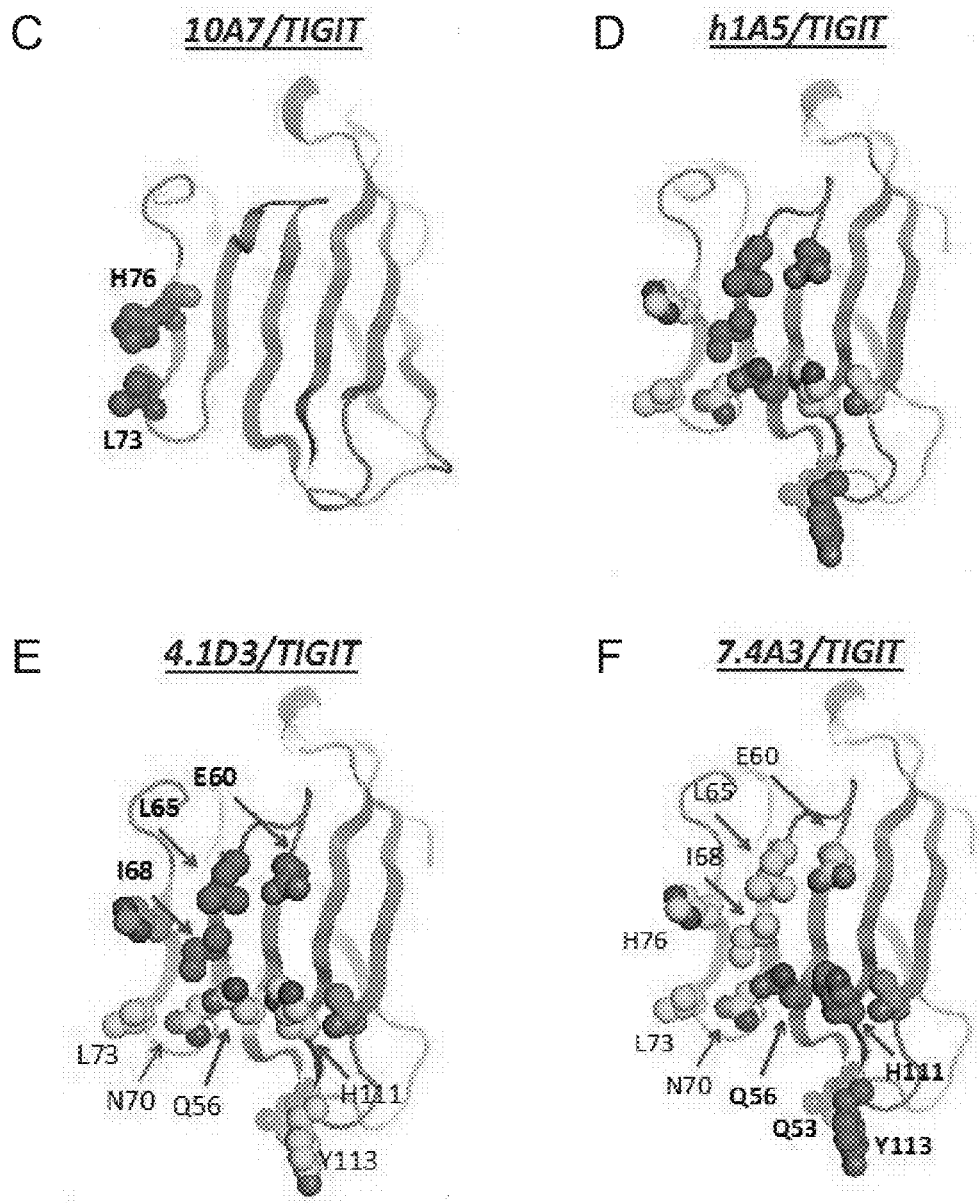
FIG. 7C is a ribbon rendering of the human TIGIT structure with residues identified as important for 10A7 recognition by alanine scanning mutagenesis indicated and represented as spheres.
FIG. 7D is a ribbon rendering of the human TIGIT structure with residues identified as important for h1A5 recognition by alanine scanning mutagenesis indicated and represented as spheres.
FIG. 7E is a ribbon rendering of the human TIGIT structure with residues identified as important for 4.1D3 recognition by alanine scanning mutagenesis indicated and represented as spheres.
FIG. 7F is a ribbon rendering of the human TIGIT structure with residues identified as important for 7.4A3 recognition by alanine scanning mutagenesis indicated and represented as spheres.
Figures 7G, 7H, 7I:
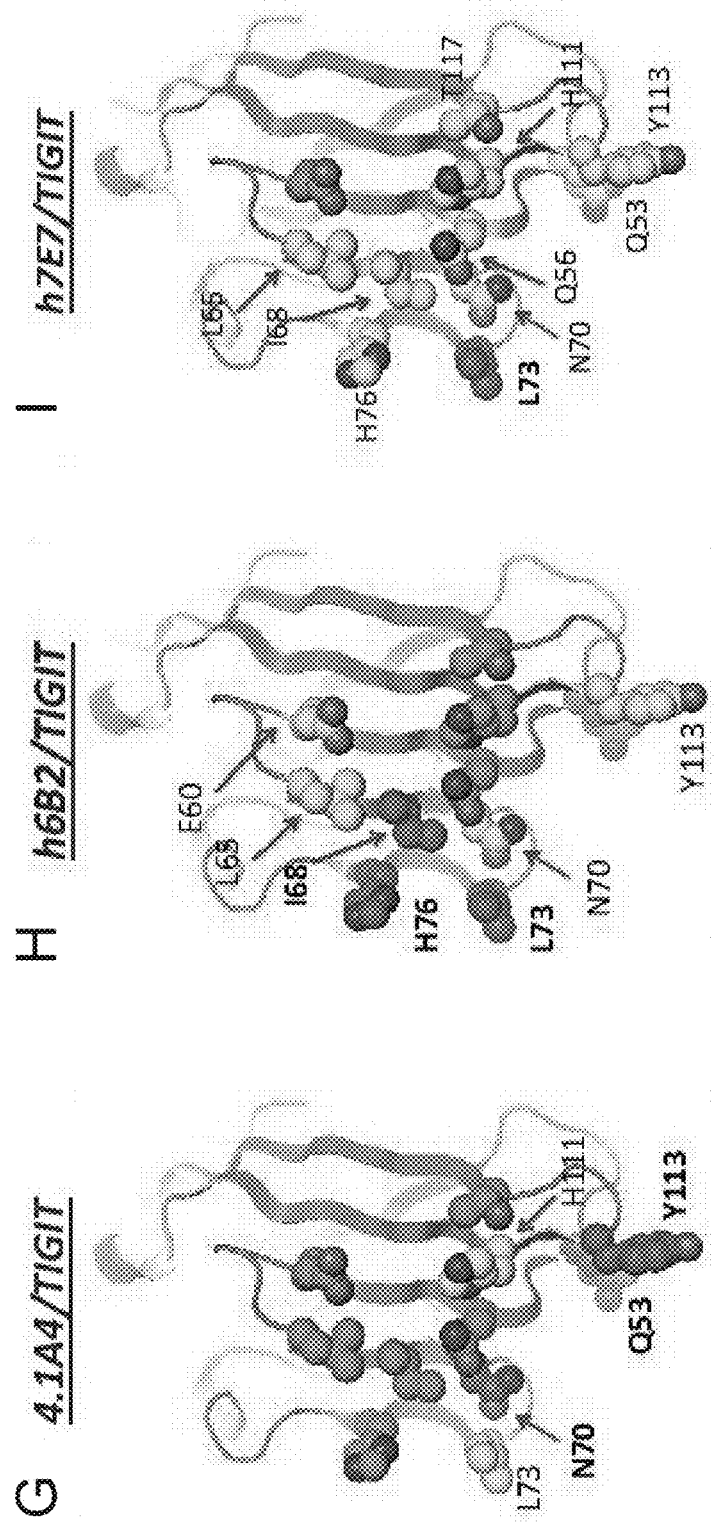
FIG. 7G is a ribbon rendering of the human TIGIT structure with residues identified as important for 4.1A4 recognition by alanine scanning mutagenesis indicated and represented as spheres.
FIG. 7H is a ribbon rendering of the human TIGIT structure with residues identified as important for h6B2 recognition by alanine scanning mutagenesis indicated and represented as spheres.
FIG. 7I is a ribbon rendering of the human TIGIT structure with residues identified as important for h7E7 recognition by alanine scanning mutagenesis indicated and represented as spheres.

Alanine scanning of the human TIGIT interface was also performed, with alanine mutations of TIGIT residues made for Gln53, Gln56, Glu60, Leu65, Ile68, Asn70, Leu73, His76, His111, Tyr113, and Thr117. These mutants, along with wild-type, were tested for binding to the 4.1D3 Fab fragment. In this experiment, mutation of TIGIT residues Glu60, Leu65, and Ile68 reduced 4.1D3 binding greater than 10 fold (FIGS. 7A, 7B, and 7E). Mutation of TIGIT residues Gln56, Asn70, Leu73, His111, and Tyr113 reduced 4.1D3 binding between 1 and 10 fold (FIGS. 7A, 7B, and 7E).

Mutation of TIGIT Gln53, His76, and Thr117 did not affect 4.1D3 binding (FIGS. 7A, 7B, and 7E). This analysis agreed with the crystal structure analysis, with the TIGIT residues that most affected 4.1D3 binding found to interact with 4.1D3 in the structure.

D. The Structure of 1A5 Bound to Human TIGIT

Figure 8:
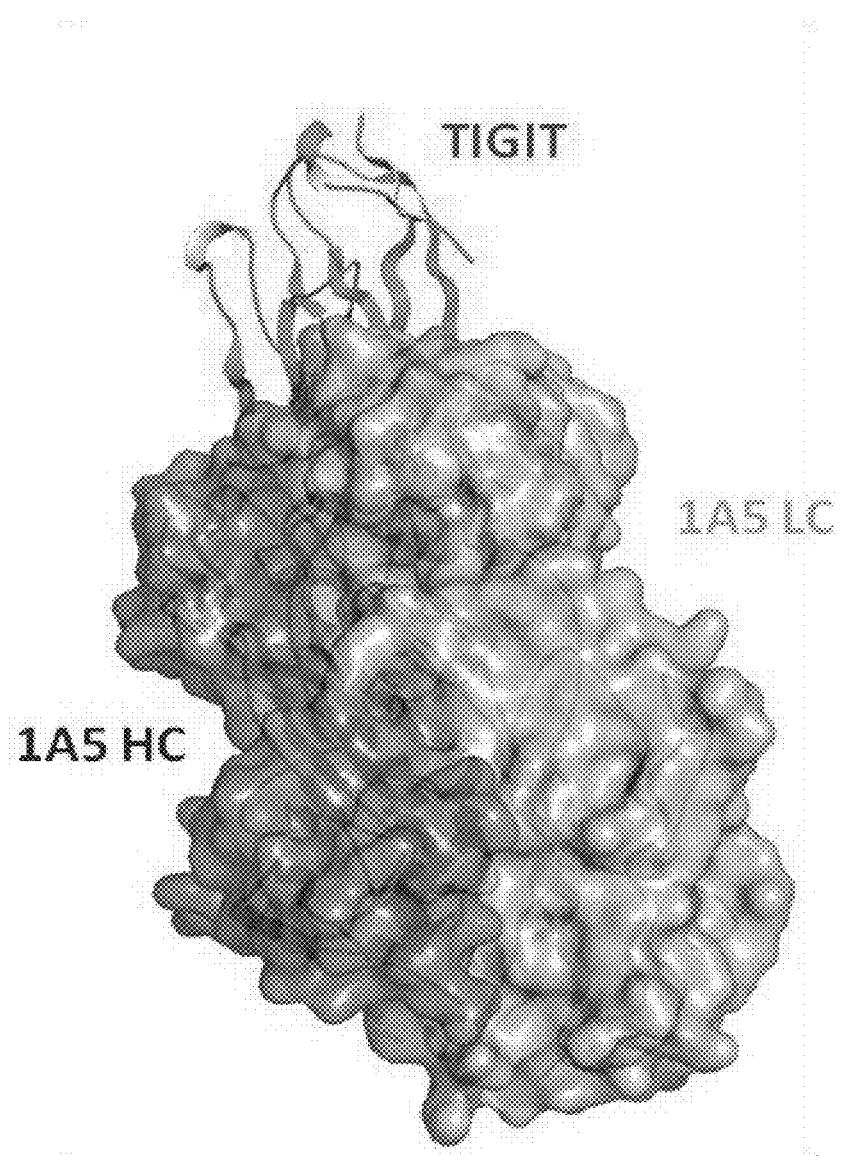
FIG. 8 is a rendering of the crystal structure of the 1A5 Fab bound to human TIGIT, with the 1A5 heavy chain (HC) and light chain (LC) regions indicated and distinguished by color.
Figure 9:
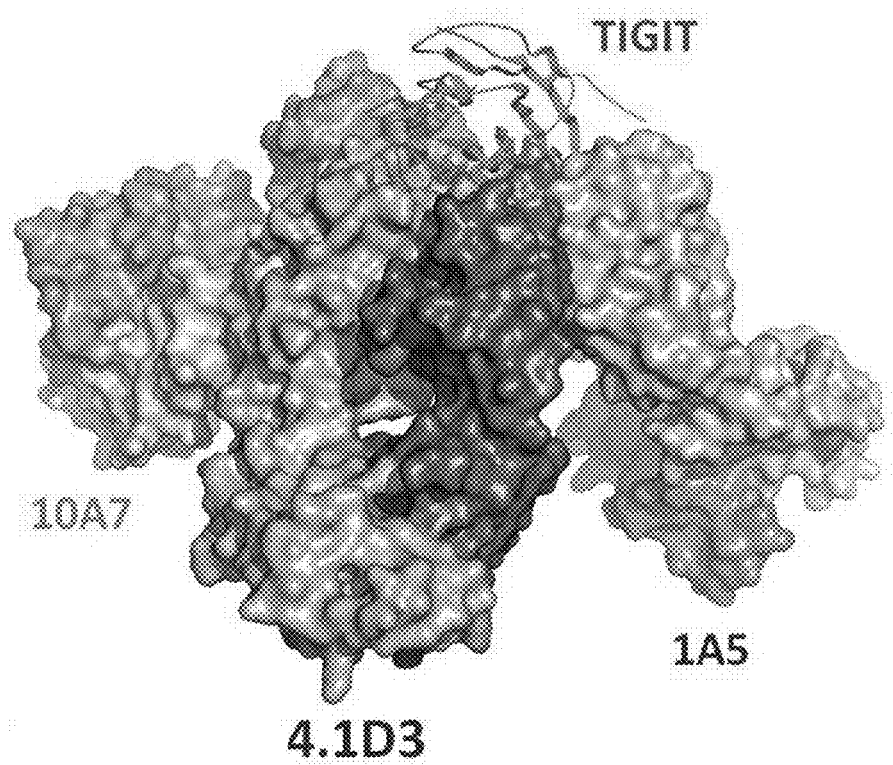
FIG. 9 is a rendering of the crystal structures of the 4.1D3-TIGIT, 1A5-TIGIT, and 10A7-TIGIT complexes, superimposed on one another with respect to TIGIT, showing that the three anti-TIGIT antibodies bind to human TIGIT at non-identical epitopes.

The 1A5 Fab complex with TIGIT crystallized in the P1 space group, with four complexes in the asymmetric unit, and diffracted to 2.77 Å. Overlay of the four individual complexes in the asymmetric unit shows only minor changes in main chain positioning between the individual copies. The structure of 1A5 bound to human TIGIT (FIG. 8) shows that 1A5 sterically interferes with PVR binding, but the epitope on human TIGIT to which 1A5 binds is not identical to that of 4.1D3 (FIG. 9). The buried surface area between 1A5 and TIGIT is approximately 1715 Å$^2$. 1A5 light chain interactions with TIGIT are primarily clustered between residues 109 and 119, with one outlying contact with Glu60. 1A5 light chain CDR L1 has a single contact residue, Trp32, that contacts TIGIT residues Ile109, Thr117, and Thr119. 1A5 CDR L2 residue Lys50 contacts TIGIT Glu60. 1A5 CDR L3 residues Gly91, Gln92, Ser93, and Tyr94 contact TIGIT residues Thr112, Tyr113, Pro114, Asp115, Gly116, and Thr117. For the 10A7 heavy chain, CDR H1 residues Thr30 and Asp31 make a contact with TIGIT residue Leu73. 10A7 CDR H2 residues Tyr52, Val53, Ser54, Tyr58, and Tyr59 make contact with TIGIT residues Gln53, Thr55, Asp72, Leu73, and Tyr113. 10A7 CDR H3 residues Phe97, Arg98, Pro100, and Trp100a make contact with TIGIT residues Gln56, Asn58, Glu60, Asp63, Gln64, Leu65, Ile68, Leu73, His76, and His111. Contacts between 1A5 and TIGIT are primarily non-polar in nature, with the two exceptions being a hydrogen bond between 1A5 CDR H2 residue Ser54 and TIGIT residue Asp72, and a salt bridge between 1A5 CDR H3 residue Arg98 and TIGIT residue Glu60.

Based on the crystal structure of the 1A5/TIGIT complex, the residues of TIGIT that are contacted by 1A5 (i.e., the epitopic residues of TIGIT bound by 1A5) and the residues of 1A5 that are contacted by TIGIT (i.e., the paratopic residues of 1A5 contacted by TIGIT) were determined. Tables 13 and 14, below, show the residues of TIGIT and the light or heavy chain residues of 1A5 to which they contact, as assessed using a contact distance stringency of 3.7 Å, a point at which van der Waals (non-polar) interaction forces are highest.

TABLE 13

Epitopic residues of TIGIT and their corresponding paratopic residues on the light chain of 1A5

| TIGIT | | 1A5 Light chain | |
|---|---|---|---|
| Thr | 112 | Tyr | 94 |
| Tyr | 113 | Tyr | 94 |
| Pro | 114 | Tyr | 94 |
| Gly | 116 | Gln | 92 |
| Thr | 117 | Trp | 32 |
| | | Gly | 91 |
| | | Gln | 92 |

TABLE 14

Epitopic residues of TIGIT and their corresponding paratopic residues on the heavy chain of 1A5

| TIGIT | | 1A5 Heavy chain | |
|---|---|---|---|
| Gln | 53 | Tyr | 58 |
| Thr | 55 | Tyr | 52 |
| | | Tyr | 58 |
| Gln | 56 | Phe | 97 |
| | | Arg | 98 |
| | | Pro | 100 |
| Asn | 58 | Arg | 98 |
| Glu | 60 | Arg | 98 |
| Leu | 65 | Arg | 98 |
| Asp | 72 | Tyr | 52 |
| | | Val | 53 |
| | | Ser | 54 |
| Leu | 73 | Thr | 30 |
| | | Asp | 31 |
| Tyr | 113 | Tyr | 58 |
| | | Tyr | 59 |

Alanine scanning of the TIGIT interface was also performed, with alanine mutations of TIGIT residues made for Gln53, Gln56, Glu60, Leu65, Ile68, Asn70, Leu73, His76, His111, Tyr113, and Thr117. These mutants, along with wild-type, were tested for binding to the 1A5 Fab fragment. In this experiment, mutation of TIGIT residues Gln56, Glu60, Leu65, Ile68, and Tyr113 reduced 1A5 binding greater than 10 fold (FIGS. 7A, 7B, and 7D). Mutation of TIGIT residues Leu73, His76, Asn70, His111, and Thr117 reduced 1A5 binding between 1 and 10 fold (FIGS. 7A, 7B, and 7D). Only mutation of TIGIT Gln53 did not affect 1A5 binding (FIGS. 7A, 7B, and 7D). This analysis agreed with the crystal structure analysis, with many of the TIGIT residues that most affected 1A5 binding found to interact with 1A5 in the structure.

E. the Structure of 10A7 Bound to Human TIGIT

Figure 10A:
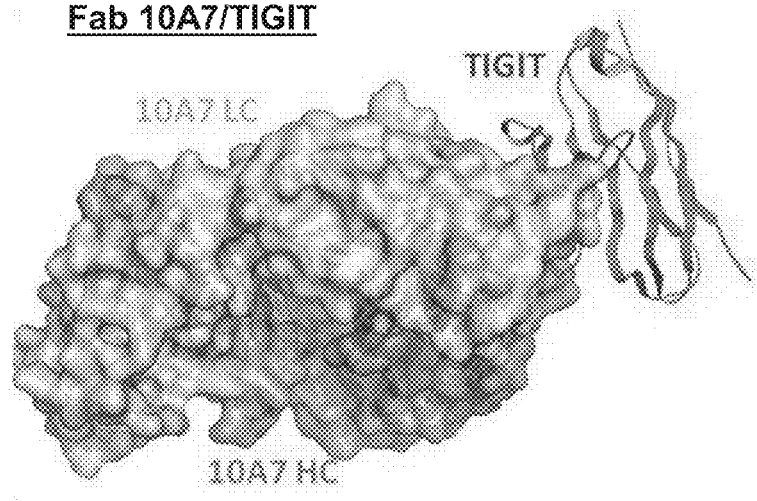
FIG. 10A is a rendering of the crystal structure of the 10A7 Fab bound to human TIGIT, with the 10A7 heavy chain (HC) and light chain (LC) regions indicated and distinguished by color.
Figure 10B:
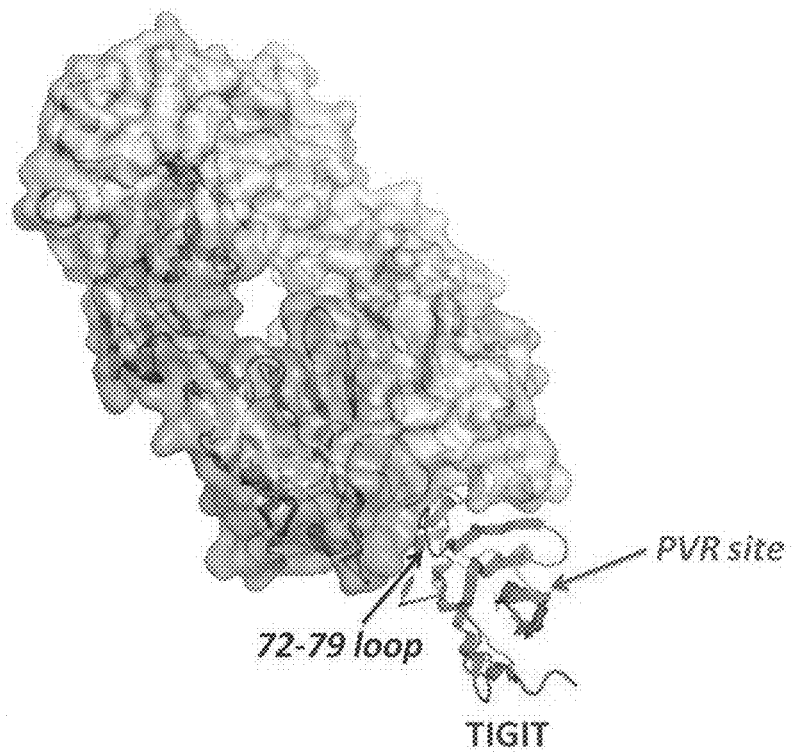
FIG. 10B is a rendering of the crystal structure of the 10A7 Fab bound to human TIGIT, with the relative location of the PVR binding site indicated. Also indicated is the relative location of the 72-79 loop of TIGIT.

The 10A7 Fab/TIGIT complex crystallized in the P21 space group, with two 10A7/TIGIT complexes in the asymmetric unit, and diffracted to 1.85 Å. Overlay of the two complexes shows only minor differences in main chain positioning for both TIGIT and 10A7. The structure of 10A7 bound to human TIGIT (FIG. 10A) shows that 10A7 sterically interferes with PVR binding (FIG. 10B), but the epitope on human TIGIT to which 10A7 binds is not identical to that of 4.1D3 or 1A5 (FIG. 9). The buried surface area between 10A7 and TIGIT is approximately 1420 Å$^2$. TIGIT contact residues cluster between Leu65 and Ile77, with two outlying 10A7 CDR contacts with TIGIT Gln56 and Pro87. The light chain CDR L1 has as six amino acid insertion and utilizes residues Tyr27d, Gly27f, Val28, Lys29, and Leu32 to make contacts with TIGIT residues Gln56, Leu65, Ile68, Asn70, Leu73, His76, Ser78, Ile77, and Pro79. CDR L2 only makes two contacts via Tyr50 and Ile53 with TIGIT His76, Ile77, and Pro79. CDR L3 Gly91, Ile92, Asn93, and Asn94 contact TIGIT residues Asp72, Leu73, and His76. For the heavy chain CDRs, no H1 residues contact TIGIT. For CDR H2, Phe50 and Arg52 contact Asn70, Ala71, Asp72, Leu73, and Gly74. For CDR H3, residues Arg95, Leu97, Gly98, His99, and Asn100 contact TIGIT residues Leu73, Gly74, Trp75, His76, Ile77, and Pro87. Overall the interactions between the 10A7 light chain and TIGIT were primarily hydrophobic in nature, with one hydrogen bond contact between CDR L2 Tyr50 hydroxyl group and the backbone carbonyl of Ile77. For the 10A7 heavy chain, polar contacts are found between Arg52 and the backbone carbonyl groups of TIGIT Ala71 and Asp72, as well as between Arg95 and the backbone carbonyl groups of Gly74 and Trp75.

Based on the crystal structure of the 10A7/TIGIT complex, the residues of TIGIT that are contacted by 10A7 (i.e., the epitopic residues of TIGIT bound by 10A7) and the residues of 10A7 that are contacted by TIGIT (i.e., the paratopic residues of 10A7 contacted by TIGIT) were determined. Tables 15 and 16, below, show the residues of TIGIT and the light or heavy chain residues of 10A7 to which they contact, as assessed using a contact distance stringency of 3.7 Å, a point at which van der Waals (non-polar) interaction forces are highest.

TABLE 15

Epitopic residues of TIGIT and their corresponding paratopic residues on the light chain of 10A7

| TIGIT | | 10A7 Light chain | |
|---|---|---|---|
| Asp | 72 | Asn | 94 |
| Leu | 73 | Gly | 91 |
| | | Ile | 92 |
| His | 76 | Tyr | 27d |
| | | Leu | 32 |
| | | Tyr | 50 |
| Ile | 77 | Tyr | 50 |
| Pro | 79 | Glu | 30 |
| | | Tyr | 50 |
| | | Ile | 53 |

TABLE 16

Epitopic residues of TIGIT and their corresponding paratopic residues on the heavy chain of 10A7

| TIGIT | | 10A7 Heavy chain | |
|---|---|---|---|
| Ala | 71 | Arg | 52 |
| | | Phe | 58 |
| Asp | 72 | Arg | 52 |
| Leu | 73 | Arg | 52 |
| | | Arg | 95 |
| | | Asn | 100 |
| Gly | 74 | Arg | 52 |
| Trp | 75 | Arg | 95 |
| | | Leu | 97 |
| | | Gly | 98 |
| | | His | 99 |
| His | 76 | Gly | 98 |
| | | Asn | 100 |
| Ile | 77 | Gly | 98 |
| Pro | 87 | Leu | 97 |

Alanine scanning of the TIGIT interface was also performed, with alanine mutations of TIGIT residues made for Gln53, Gln56, Glu60, Leu65, Ile68, Asn70, Leu73, His76, His111, Tyr113, and Thr117. These mutants, along with wild-type, were tested for binding to the 10A7 Fab fragment. In this experiment, only Leu73Ala and His76Ala mutations affected 10A7 binding greater than 10 fold (FIGS. 7A-7C). Mutation of the other residues listed did not significantly affect 10A7 binding (FIGS. 7A-7C). This agreed closely with the crystal structure of 10A7 bound to TIGIT, in which Leu73 and His76 were found directly in the epitope bound by 10A7.

Figure 11:
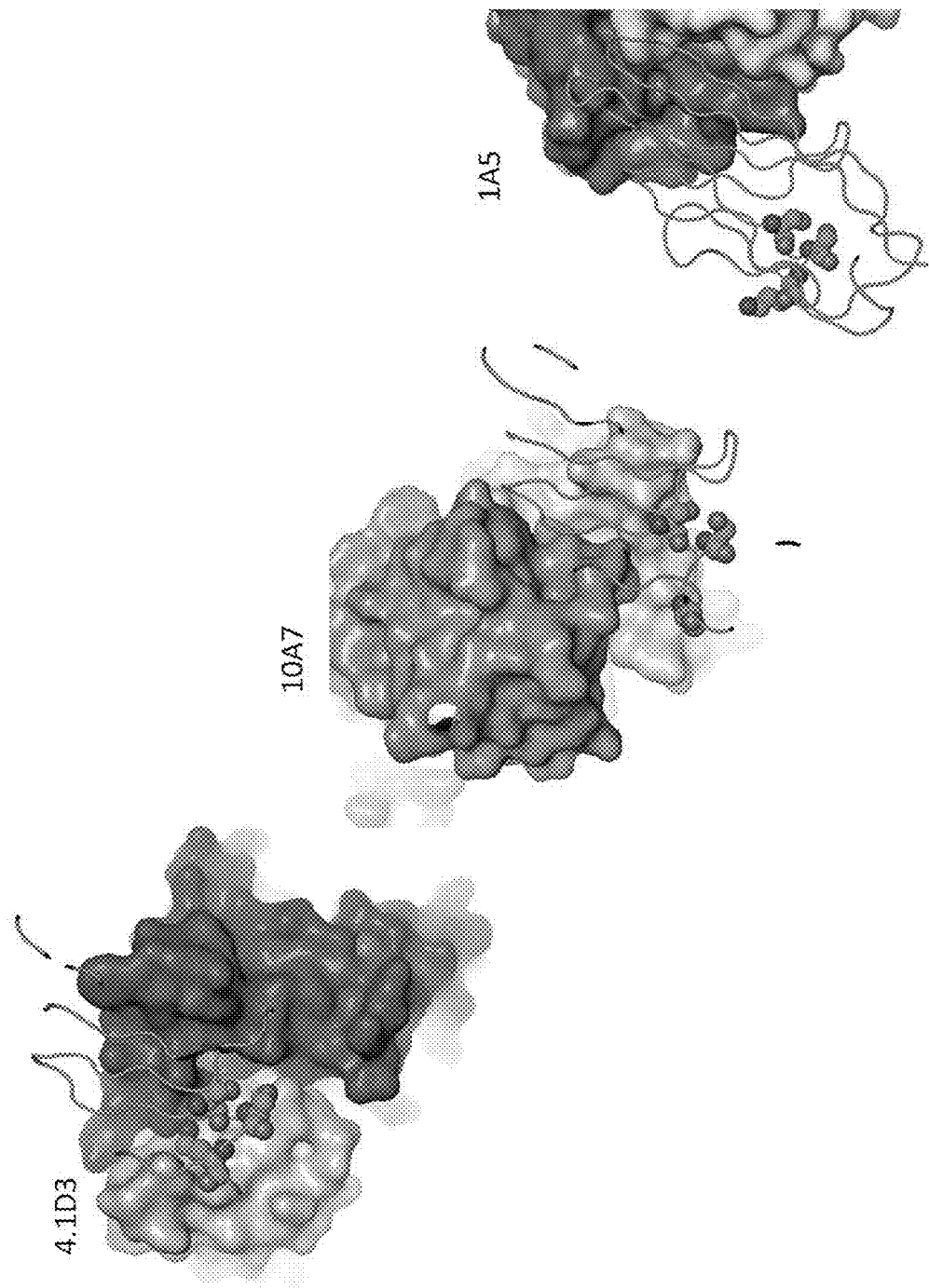
FIG. 11 is a series of renderings of the 4.1D3 (top left), 10A7 (center middle), and 1A5 (bottom right) antibodies and the relative location of the Ser78, Ser80, and Lys82 residues of human TIGIT. The structures indicate that the Ser78, Ser80, and Lys82 residues of human TIGIT are key epitopic residues for 4.1D3, but not for 10A7 or 1A5, where these three residues are located at a distance further from the antibody binding pocket.

F. the Anti-TIGIT Antibodies 4.1D3, 1A5, and 10A7 Recognize TIGIT at Unique Epitopes The structural studies described above demonstrate that the three anti-TIGIT antibodies 4.1D3, 1A5, and 10A7, recognize TIGIT at unique epitopes, which may explain their distinct functional properties and characteristics. As shown below in Table 17, for example, 4.1D3 binds to TIGIT at residues Ser78, Ser80, and Lys82, which are not bound by either the 1A5 or the 10A7 antibodies. FIG. 11 is a structural rendering, showing that residues Ser78, Ser80, and Lys82 of TIGIT are intimately contacted by 4.1D3, but not by 1A5 or 10A7.

TABLE 17

Epitopic residues of TIGIT within 3.7 Å for the 4.1D3, 1A5, and 10A7 anti-TIGIT antibodies

| 4.1D3 | 1A5 | 10A7 |
|---|---|---|
| | 53 | |
| 55 | 55 | |
| 56 | 56 | |
| 58 | 58 | |
| 60 | 60 | |
| 65 | 65 | |
| 68 | | |
| | | 71 |
| | 72 | 72 |
| 73 | 73 | 73 |
| | | 74 |
| | | 75 |
| 76 | | 76 |
| 77 | | 77 |
| 78 | | |
| 79 | | 79 |
| 80 | | |
| 82 | | |
| | | 87 |
| 111 | | |
| | 112 | |
| | 113 | |
| | 114 | |
| | 116 | |
| | 117 | |

Example 7. Characterization of TIGIT, PD-1, and CD226 Expression on Immune Cells Next, we characterized the expression of TIGIT, PD-1, and CD226 on CD4+ and CD8+ T cells from bone marrow specimens of multiple myeloma (MM) pateints using multicolor flow cytometry. Cells were isolated from frozen bone marrow procured from MM patients (n=10). Two of the MM patients tested had samples collected at diagnosis and again upon remission. Frozen bone marrow from healthy donors was used as a control (n=8). In these experiments, the bone marrow samples were stained with the following fluorescently conjugated monoclonal antibodies: BV605 (PD-1), Alexa Fluor 488 (FoxP3), PE-DNAM-1 (CD226), PE-Cy7 (CD45), BUV737 (CD8), PerCP-eF710 (CD4), APC (TIGIT), Brilliant Violet 421 (NKp46), Brilliant Violet 421 (CD56), Brilliant Violet 510 (CD3), Brilliant Violet 510 (CD38), PE-Cy7 (CD319), PE (CD19), and LIVE/DEAD FixableNear-IR Dead Cell Stain (Life Technologies, ThermoFisher).

Figure 12:
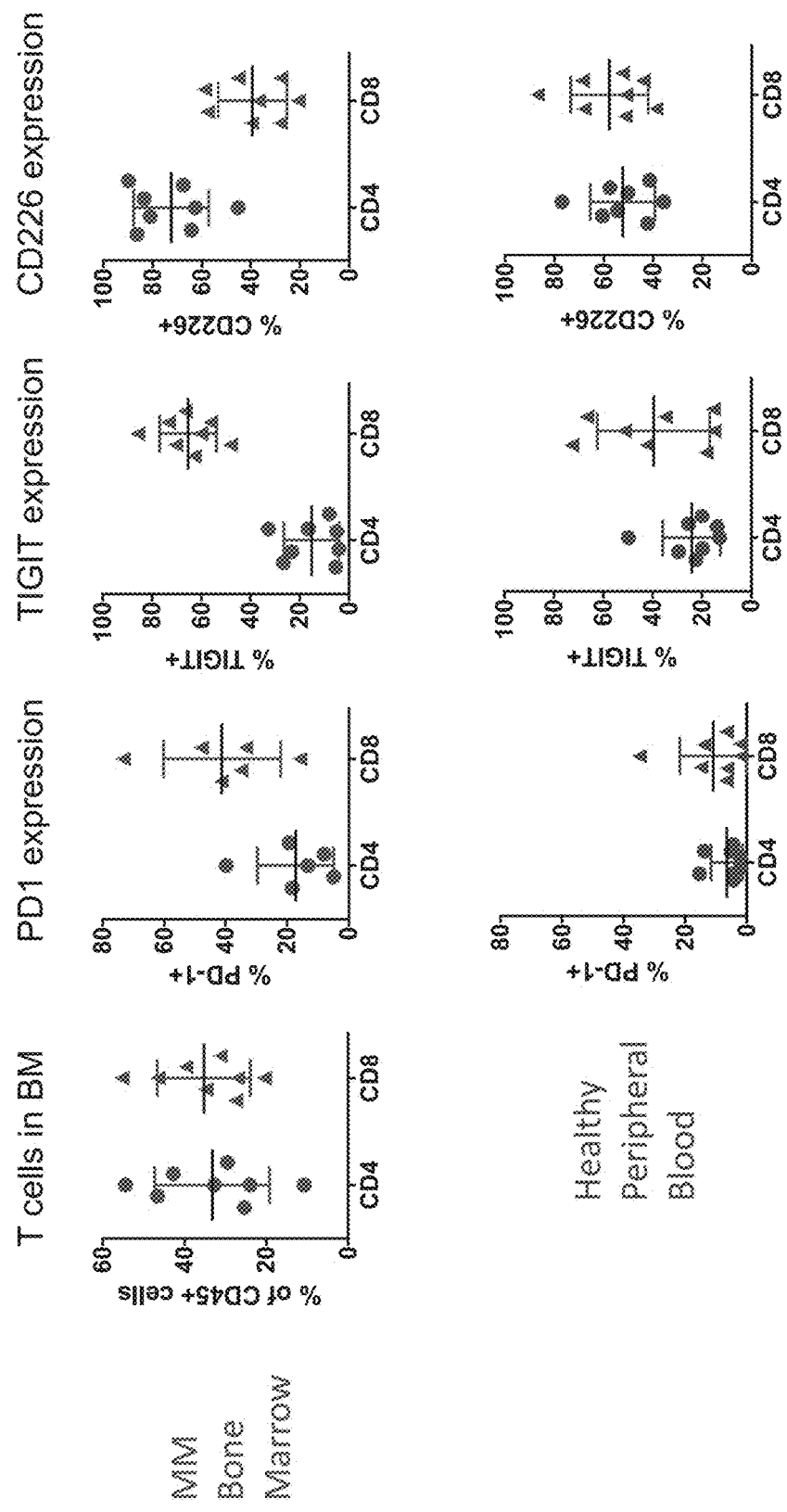
FIG. 12 is a series of graphs showing CD45, PD-1, TIGIT, and CD226 expression on CD4+ and CD8+ T cells isolated from the bone marrow of multiple myeloma (MM) patients (top row) and PD-1, TIGIT, and CD226 expression on CD4+ and CD8+ T cells isolated from the peripheral blood of healthy patients (bottom row), as assessed by multi-color flow cytometry.
Figure 13:
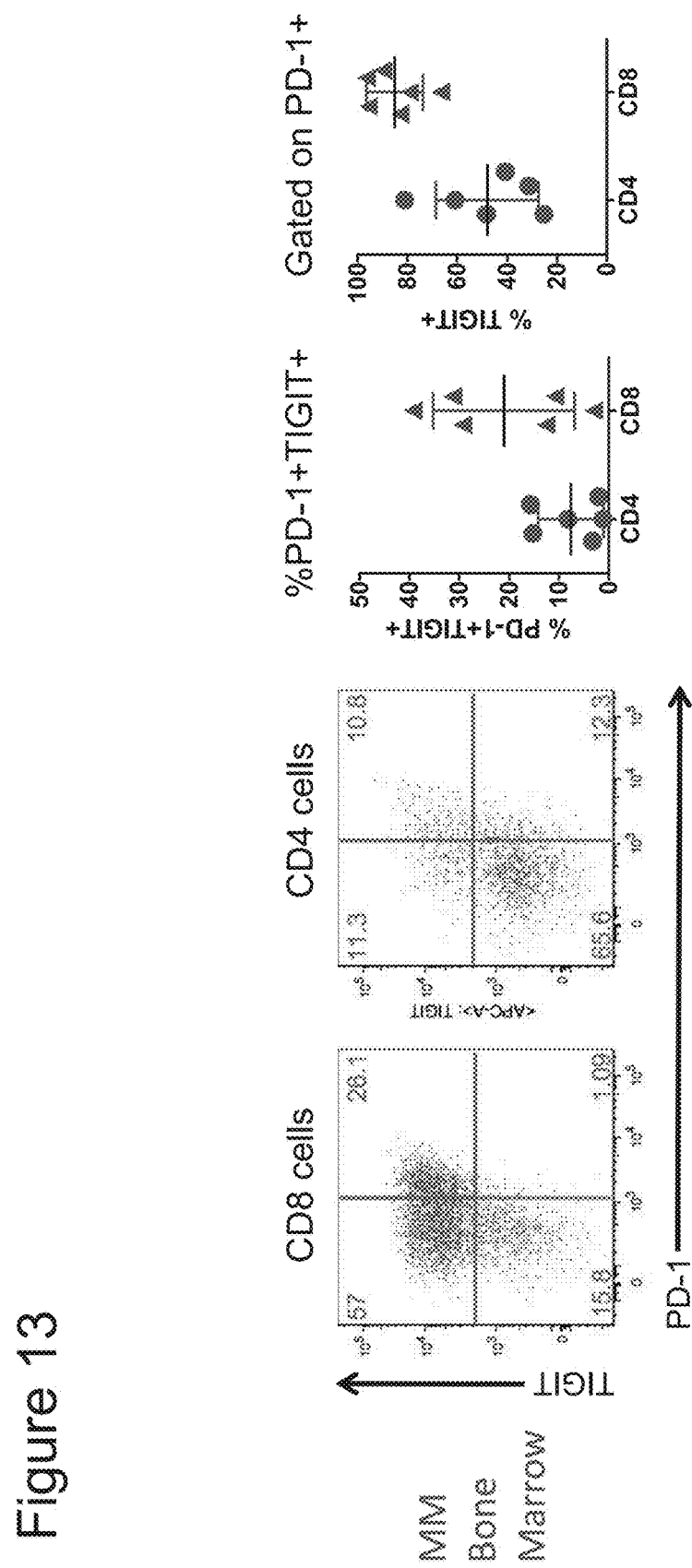
FIG. 13 is a series of flow cytometry graphs (left) and accompanying plots (right) showing that TIGIT and PD-1 are co-expressed on CD4+ and CD8+ T cells in bone marrow of MM patients.

TIGIT, PD-1, and CD226 were shown to be highly expressed on CD4+ and CD8+ T cells obtained from the bone marrow of MM patients compared to CD4+ and CD8+ T cells obtained from the peripheral blood of healthy patients (FIG. 12). CD4+ and CD8+ T cells obtained from the bone marrow of MM patients were also determined to co-express both TIGIT and PD-1 (FIG. 13). Given this expression pattern, the anti-TIGIT antibodies of the invention are useful for treating patients having an immune-related disease or cancer (e.g., a myeloma, e.g., MM), either as a monotherapy or in combination with an additional therapeutic agent, such as a PD-1 axis binding antagonist (e.g., a PD-L1 binding antagonist, e.g., an anti-PD-L1 antibody, e.g., MPDL3280A (atezolizumab)).

OTHER EMBODIMENTS

Although the foregoing invention has been described in some detail by way of illustration and example for purposes of clarity of understanding, the descriptions and examples should not be construed as limiting the scope of the invention. It is understood that various other embodiments may be practiced, given the general description provided above. The disclosures of all patent and scientific literature cited herein are expressly incorporated in their entirety by reference.

What is claimed is:

1. An antibody that specifically binds to human TIGIT, wherein the antibody comprises the following six hypervariable regions (HVRs):
   an HVR-H1 comprising the amino acid sequence of SNSAAWN (SEQ ID NO: 1);
   an HVR-H2 comprising the amino acid sequence of KTYYRFKWYSDYAVSVKG (SEQ ID NO: 2);
   an HVR-H3 comprising the amino acid sequence of ESTTYDLLAGPFDY (SEQ ID NO: 3);
   an HVR-L1 comprising the amino acid sequence of KSSQTVLYSSNNKKYLA (SEQ ID NO: 4);
   an HVR-L2 comprising the amino acid sequence of WASTRES (SEQ ID NO: 5); and
   an HVR-L3 comprising the amino acid sequence of QQYYSTPFT (SEQ ID NO: 6).

2. The antibody of claim 1, wherein the antibody further comprises the following light chain variable region framework regions (FRs):
   an FR-L1 comprising the amino acid sequence of DIVMTQSPDSLAVSLGERATINC (SEQ ID NO: 7);
   an FR-L2 comprising the amino acid sequence of WYQQKPGQPPNLLIY (SEQ ID NO: 8);
   an FR-L3 comprising the amino acid sequence of GVPDRFSGSGSGTDFTLTISSLQAEDVAVYYC (SEQ ID NO: 9); and
   an FR-L4 comprising the amino acid sequence of FGPGTKVEIK (SEQ ID NO: 10).

3. The antibody of claim 1, wherein the antibody further comprises the following heavy chain variable region FRs:
   an FR-H1 comprising the amino acid sequence of $X_1$VQLQQSGPGLVKPSQTLSLTCAISGDSVS (SEQ ID NO: 11), wherein $X_1$ is Q or E;
   an FR-H2 comprising the amino acid sequence of WIRQSPSRGLEWLG (SEQ ID NO: 12);
   an FR-H3 comprising the amino acid sequence of RITINPDTSKNQFSLQLNSVTPEDTAVFYCTR (SEQ ID NO: 13); and
   an FR-H4 comprising the amino acid sequence of WGQGTLVTVSS (SEQ ID NO: 14).

4. The antibody of claim 3, wherein $X_1$ is Q.

5. The antibody of claim 3, wherein $X_1$ is E.

6. The antibody of claim 1, wherein the antibody comprises a VH domain comprising an amino acid sequence having at least 95% sequence identity to the amino acid sequence of SEQ ID NO: 34 or 35 and a VL domain comprising an amino acid sequence having at least 95% sequence identity to the amino acid sequence of SEQ ID NO: 36.

7. The antibody of claim 1, wherein the antibody comprises a VH domain comprising an amino acid sequence having at least 96% sequence identity to the amino acid sequence of SEQ ID NO: 34 or 35 and a VL domain comprising an amino acid sequence having at least 96% sequence identity to the amino acid sequence of SEQ ID NO: 36.

8. The antibody of claim 1, wherein the antibody comprises a VH domain comprising an amino acid sequence having at least 97% sequence identity to the amino acid sequence of SEQ ID NO: 34 or 35 and a VL domain comprising an amino acid sequence having at least 97% sequence identity to the amino acid sequence of SEQ ID NO: 36.

9. The antibody of claim 1, wherein the antibody comprises a VH domain comprising an amino acid sequence having at least 98% sequence identity to the amino acid sequence of SEQ ID NO: 34 or 35 and a VL domain comprising an amino acid sequence having at least 98% sequence identity to the amino acid sequence of SEQ ID NO: 36.

10. The antibody of claim 1, wherein the antibody comprises a VH domain comprising an amino acid sequence having at least 99% sequence identity to the amino acid sequence of SEQ ID NO: 34 or 35 and a VL domain comprising an amino acid sequence having at least 99% sequence identity to the amino acid sequence of SEQ ID NO: 36.

11. The antibody of claim 1, wherein the antibody is a monoclonal antibody.

12. The antibody of claim 11, wherein the antibody is a human antibody.

13. The antibody of claim 1, wherein the antibody is a full-length antibody.

14. The antibody of claim 1, wherein the antibody is an antibody fragment that binds TIGIT selected from the group consisting of Fab, Fab', Fab'-SH, Fv, single chain variable fragment (scFv), and (Fab')$_2$ fragments.

15. The antibody of claim 1, wherein the antibody is an IgG class antibody.

16. The antibody of claim 15, wherein the IgG class antibody is an IgG1 subclass antibody.

17. An antibody that specifically binds to human TIGIT, wherein the antibody comprises a VH domain comprising the amino acid sequence of SEQ ID NO: 34 and a VL domain comprising the amino acid sequence of SEQ ID NO: 36.

18. The antibody of claim 17, wherein the antibody is a monoclonal antibody.

19. The antibody of claim 18, wherein the antibody is a human antibody.

20. The antibody of claim 17, wherein the antibody is a full-length antibody.

21. The antibody of claim 17, wherein the antibody is an antibody fragment that binds TIGIT selected from the group consisting of Fab, Fab', Fab'-SH, Fv, single chain variable fragment (scFv), and (Fab')$_2$ fragments.

22. The antibody of claim 17, wherein the antibody is an IgG class antibody.

23. The antibody of claim 22, wherein the IgG class antibody is an IgG1 subclass antibody.

24. An antibody that specifically binds to human TIGIT, wherein the antibody comprises a VH domain comprising the amino acid sequence of SEQ ID NO: 35 and a VL domain comprising the amino acid sequence of SEQ ID NO: 36.

25. The antibody of claim 12, wherein the antibody is a monoclonal antibody.

26. The antibody of claim 25, wherein the antibody is a human antibody.

27. The antibody of claim 12, wherein the antibody is a full-length antibody.

28. The antibody of claim 12, wherein the antibody is an antibody fragment that binds TIGIT selected from the group consisting of Fab, Fab', Fab'-SH, Fv, single chain variable fragment (scFv), and (Fab')$_2$ fragments.

29. The antibody of claim 12, wherein the antibody is an IgG class antibody.

30. The antibody of claim 29, wherein the IgG class antibody is an IgG1 subclass antibody.

* * * * *

UNITED STATES PATENT AND TRADEMARK OFFICE
CERTIFICATE OF CORRECTION

| | | |
|---|---|---|
| PATENT NO. | : 10,047,158 B2 | Page 1 of 1 |
| APPLICATION NO. | : 15/895741 | |
| DATED | : August 14, 2018 | |
| INVENTOR(S) | : Jane L. Grogan et al. | |

It is certified that error appears in the above-identified patent and that said Letters Patent is hereby corrected as shown below:

In the Specification

Column 8, Lines 28-29, replace "human.
 ¶ In another aspect," with
 --human.
 ¶ In another aspect, the invention features the use of an antibody described herein in the manufacture of a medicament for treating or delaying progression of an immune-related disease in a subject in need thereof. In some embodiments, the immune-related disease is associated with a T cell dysfunctional disorder. In some embodiments, the T cell dysfunctional disorder is characterized by T cell exhaustion. In some embodiments, the immune-related disease is selected from the group consisting of unresolved acute infection, chronic infection, and tumor immunity. In some embodiments, the medicament is formulated for administration subcutaneously, intravenously, intramuscularly, topically, orally, transdermally, intraperitoneally, intraorbitally, by implantation, by inhalation, intrathecally, intraventricularly, or intranasally. In some embodiments, the subject is a human.
 ¶ In another aspect,--.

Column 53, Line 7, replace "$TX_4TIX_5$" with --$TX_4TIX_5$--.

Column 61, Line 29, replace "$TSEDTAX_8$" with --$SEDTAX_8$--.

Column 89, Line 2, replace "$Re^{18}$," with --$Re^{186}$,--.

In the Claims

Column 331, Line 4, replace "claim 12" with --claim 24--;
 Line 8, replace "claim 12" with --claim 24--;
 Line 10, replace "claim 12" with --claim 24--;
 Line 14, replace "claim 12" with --claim 24--.

Signed and Sealed this
Twenty-eighth Day of January, 2020

Andrei Iancu
*Director of the United States Patent and Trademark Office*